United States Patent
Fehr et al.

(10) Patent No.: US 10,626,450 B2
(45) Date of Patent: *Apr. 21, 2020

(54) ASSAYS FOR SINGLE MOLECULE DETECTION AND USE THEREOF

(71) Applicant: Singular Bio, Inc., San Francisco, CA (US)

(72) Inventors: Adrian Nielsen Fehr, San Francisco, CA (US); Patrick James Collins, San Francisco, CA (US); Jill Lyndon Herschleb, San Francisco, CA (US); Hywel Bowden Jones, San Francisco, CA (US)

(73) Assignee: Singular Bio, Inc., San Francisco, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/675,234

(22) Filed: Aug. 11, 2017

(65) Prior Publication Data

US 2018/0179586 A1  Jun. 28, 2018

Related U.S. Application Data

(63) Continuation of application No. 14/949,097, filed on Nov. 23, 2015, now Pat. No. 9,758,814, which is a continuation of application No. 14/603,323, filed on Jan. 22, 2015, now Pat. No. 9,212,394, which is a continuation of application No. PCT/US2014/051763, filed on Aug. 19, 2014.

(60) Provisional application No. 61/867,559, filed on Aug. 19, 2013, provisional application No. 61/867,554, filed on Aug. 19, 2013.

(51) Int. Cl.
| | |
|---|---|
| *C12P 19/34* | (2006.01) |
| *C12Q 1/6827* | (2018.01) |
| *C12Q 1/6809* | (2018.01) |
| *C12Q 1/6825* | (2018.01) |
| *C12Q 1/6837* | (2018.01) |
| *C12Q 1/6876* | (2018.01) |

(52) U.S. Cl.
CPC ......... *C12Q 1/6827* (2013.01); *C12Q 1/6809* (2013.01); *C12Q 1/6825* (2013.01); *C12Q 1/6837* (2013.01); *C12Q 1/6876* (2013.01); C12Q 2600/156 (2013.01); C12Q 2600/158 (2013.01); C12Q 2600/16 (2013.01)

(58) Field of Classification Search
CPC ........ C12Q 2525/155; C12Q 2525/161; C12Q 2525/185; C12Q 2533/107; C12Q 2535/131; C12Q 2537/143; C12Q 1/6827; C12Q 1/6837; C12Q 2521/101; C12Q 2531/137; C12Q 2535/125; C12Q 2545/101; C12Q 2563/107; C12Q 2565/102; C12Q 2565/519; C12Q 2565/601; C12Q 1/6809; C12Q 1/6825; C12Q 1/6876; C12Q 2600/156; C12Q 2600/158; C12Q 2600/16

See application file for complete search history.

(56) References Cited

U.S. PATENT DOCUMENTS

| | | |
|---|---|---|
| 5,256,536 A | 10/1993 | Miyada et al. |
| 5,547,839 A | 8/1996 | Dower et al. |
| 6,268,146 B1 | 7/2001 | Shultz et al. |
| 6,706,473 B1 | 3/2004 | Edman et al. |
| 6,890,741 B2 | 5/2005 | Fan et al. |
| 6,913,884 B2 | 7/2005 | Stuelpnagel et al. |
| 7,582,420 B2 | 9/2009 | Oliphant et al. |
| 7,955,794 B2 | 6/2011 | Shen et al. |
| 8,288,103 B2 | 10/2012 | Oliphant et al. |
| 8,700,338 B2 | 4/2014 | Oliphant et al. |
| 8,906,626 B2 | 12/2014 | Oliphant et al. |
| 2002/0006617 A1 | 1/2002 | Fan et al. |
| 2005/0244863 A1 | 11/2005 | Mir |
| 2006/0019304 A1 | 1/2006 | Hardenbol et al. |
| 2007/0037152 A1 | 2/2007 | Drmanac |
| 2008/0138809 A1 | 6/2008 | Kapur et al. |
| 2010/0015626 A1 | 1/2010 | Oliphant et al. |
| 2012/0021919 A1 | 1/2012 | Scholl et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0077185 A1 | 3/2012 | Oliphant et al. |
| 2012/0164646 A1 | 6/2012 | Song et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0219950 A1 | 8/2012 | Oliphant et al. |
| 2013/0004950 A1 | 1/2013 | Sparks et al. |
| 2013/0040375 A1 | 2/2013 | Sparks et al. |
| 2013/0072390 A1 | 3/2013 | Wang et al. |

(Continued)

FOREIGN PATENT DOCUMENTS

| | | |
|---|---|---|
| CN | 1824786 A | 8/2006 |
| CN | 101864482 A | 10/2010 |

(Continued)

OTHER PUBLICATIONS

Office Action issued in corresponding Chinese Patent Application No. 201480057266.8 dated Sep. 5, 2017.

(Continued)

*Primary Examiner* — Cynthia B Wilder

(74) *Attorney, Agent, or Firm* — Morgan, Lewis & Bockius LLP

(57) ABSTRACT

The invention relates to methods of detecting a genetic variation in a genetic sample from a subject using labeled probes and counting the number of labels in the probes.

28 Claims, 51 Drawing Sheets

Specification includes a Sequence Listing.

(56) References Cited

U.S. PATENT DOCUMENTS

| | | | |
|---|---|---|---|
| 2013/0089863 A1 | 4/2013 | Oliphant et al. |
| 2013/0090250 A1 | 4/2013 | Sparks et al. |
| 2013/0122500 A1 | 5/2013 | Sparks et al. |
| 2013/0143213 A1 | 6/2013 | Oliphant et al. |
| 2013/0172211 A1 | 7/2013 | Oliphant et al. |
| 2013/0172212 A1 | 7/2013 | Oliphant et al. |
| 2013/0172213 A1 | 7/2013 | Oliphant et al. |
| 2013/0178371 A1 | 7/2013 | Oliphant et al. |
| 2013/0210640 A1 | 8/2013 | Sparks et al. |
| 2013/0261003 A1 | 10/2013 | Oliphant et al. |
| 2013/0275103 A1 | 10/2013 | Struble et al. |
| 2013/0288252 A1 | 10/2013 | Sparks et al. |
| 2013/0310262 A1 | 11/2013 | Zahn et al. |
| 2014/0024538 A1 | 1/2014 | Zahn et al. |
| 2014/0186827 A1 | 7/2014 | Pieprzyk et al. |
| 2014/0242582 A1 | 8/2014 | Oliphant et al. |
| 2014/0256572 A1 | 9/2014 | Struble et al. |
| 2014/0342940 A1 | 11/2014 | Oliphant et al. |
| 2014/0349859 A1 | 11/2014 | Oliphant et al. |

FOREIGN PATENT DOCUMENTS

| | | | |
|---|---|---|---|
| JP | 2009-232778 A | 10/2009 |
| WO | 89/10977 A1 | 11/1989 |
| WO | 92/10092 A1 | 6/1992 |
| WO | 96/27025 A1 | 9/1996 |
| WO | 00/06770 A1 | 2/2000 |
| WO | 00/36152 A1 | 6/2000 |
| WO | 00/79008 A2 | 12/2000 |
| WO | 01/23610 A2 | 4/2001 |
| WO | 01/57248 A3 | 8/2001 |
| WO | 01/57249 A1 | 8/2001 |
| WO | 2005/026329 A3 | 3/2005 |
| WO | 2011/142836 A2 | 11/2011 |
| WO | 2012/021749 A1 | 2/2012 |

OTHER PUBLICATIONS

International Search Report and the Written Opinion issued in related International Patent Application No. PCT/US2014/051763 dated Dec. 11, 2014.

Osborne et al., "Single-Molecule Analysis of DNA Immobilized on Microspheres," Analytical Chemistry, 72: 3678-3681 (2000).

Shalon et al., "A DNA Microarray System for Analyzing Complex DNA Samples Using Two-color Fluorescent Probe Hybridization," Genome Research, 6: 639-645 (1996).

Extended European Search Report issued in related European Patent Application No. 14172340.3 dated Oct. 14, 2014.

Liu et al, "Molecular Beacons for DNA Biosensors with Micrometer to Submicrometer Dimensions," Analytical Biochemistry, 283: 56-63 (2000).

Goodwin et al., "Single-Molecule Detection in Liquids by Laser-Induced Fluorescence," Accounts of Chemical Research, 29: 607-613 (1996).

International Preliminary Examination Report issued in related International Patent Application No. PCT/GB02/01245 dated Oct. 24, 2003.

Ampligase® Thermostable DNA Ligase, downloaded from internet (http://www.epibio.com/docs/default-source/protocols/ampligase-thermostable-dna-ligase.pdf?sfvrsn=4) in Jun. 2015.

Batool et al., Ligase Chain Reaction, http://www.slideshare.net/SHBZaidi/ligase-chain-reactionlcr# (Dec. 2102).

Battistella et al., "Genotyping beta-globin gene mutations on copolymer-coated glass slides with the ligation detection reaction," Clinical Chemistry, 54: 1657-1663 (2008).

Cheng et al., "Multiplexed profiling of candidate genes for CpG island methylation status using a flexible PCR/LDR/Universal Array assay," Genome Research, 16: 282-289 (2006).

Davis et al., "A comparison of ligase chain reaction to polymerase chain reaction in the detection of Chlamydia trachomatis endocervical infections," Infections Diseases in Obstetrics and Gynecology 6: 57-60 (1998).

Deng et al., "Oligonucleotide ligation assay-based DNA chip for multiplex detection of single nucleotide polymorphism," Biosensors and Bioelectronics, 19: 1277-1283 (2004).

Dille et al., "Amplification of Chlamydia trachomatis DNA by ligase chain reaction," Journal of Clinical Microbiology, 31: 729-731 (1993).

Eggerding, "A one-step coupled amplification and oligonucleotide ligation procedure for multiplex genetic typing," Genome Research, 4:337-345 (1995).

Fu et al., "Counting individual DNA molecules by the stochastic attachment of diverse labels," PNAS, 108: 9026-9031 (2011).

Grossman et al., "High-density multiplex detection of nucleic acid sequences: oligonucleotide ligation assay and sequence-coded separation," Nucleic Acids Research, 22: 4527-4534 (1994).

Hesse et al., "RNA expression profiling at the single molecule level," Genome Research, 16: 1041-1045 (2006).

Kuhn et al., "Template-independent ligation of single-stranded DNA by T4 DNA ligase," FEBS Journal, 272: 5991-6000 (2005).

Landergren, "A ligase mediated gene detection technique," Science, 241: 1077-1080 (1988).

Sullivan, Chapter 7: Nucleic Acid Amplification Techniques, downloaded from internet (http://www.austincc.edu/mlt/mdfund/mdfund_unit9Chapter7NucleicAcidAmplificationTechniques.ppt) in Jun. 2015.

Sample Protocol for Oligonucleotide Ligation Assay (OLA) and Hybridization to Magplex-Tag Microspheres—Washed Protocol, Luminex Corporation (Aug. 2010).

MacDonald, "Genotyping by Oligonucleotide Ligation Assay (OLA)," Cold Spring Harbor Protocols (2007).

Muresan et al., "Microarray analysis at single molecule resolution," IEEE Trans Nanobioscience, 9: 51-58 (2010).

Romppanen, "Oligonucleotide ligation assays for the diagnosis of inherited diseases," Chapter 4, Molecular Diagnostics, 31-40 (2005).

Stone et al., "Combined PCR-oligonucleotide ligation assay for rapid detection of Salmonella serovars," Journal of Clinical Microbiology, 33: 2888-2893 (1995).

Tobler et al., "Universal Detector Assay for Measuring DNA Copy Number Changes," American Society of Human Genetics (ASHG) Annual Meeting (2006).

Wiedmann et al., "Ligase chain reaction (LCR)—overview and applications," Genome Research, 3: S51-S64 (1994).

Supplementary European Search Report issued in corresponding European Patent Application No. 14838189 dated Feb. 27, 2017.

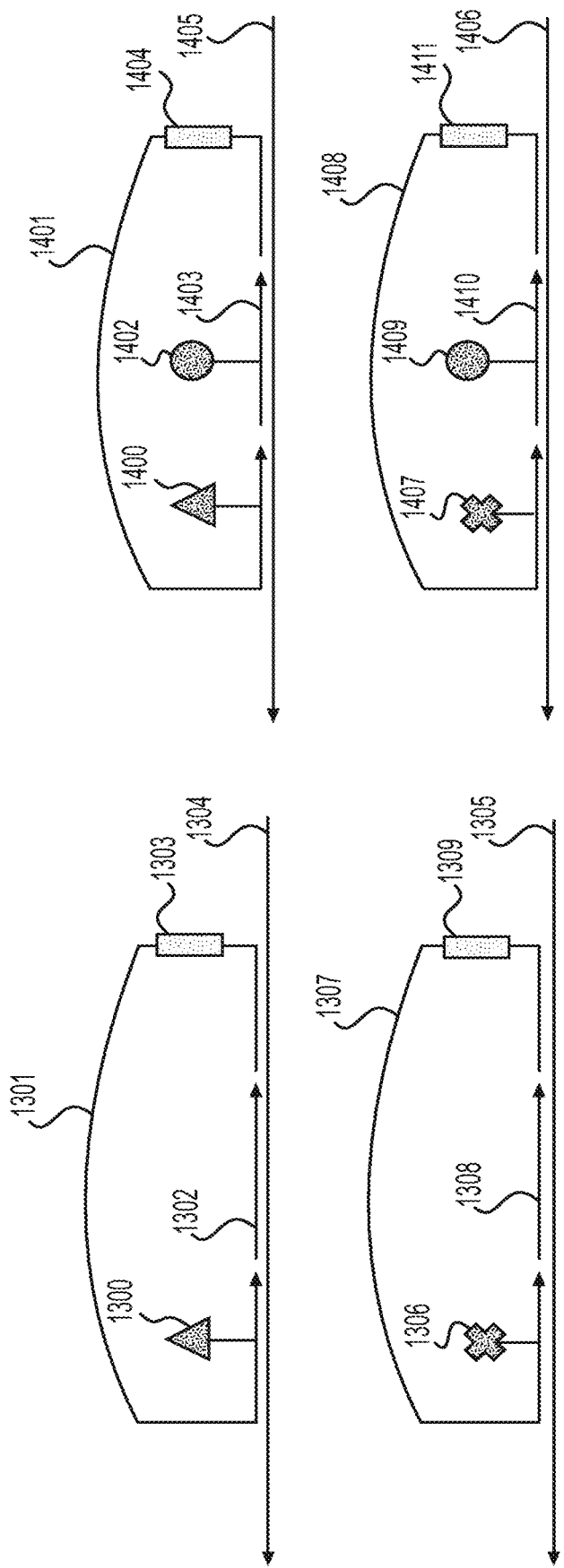

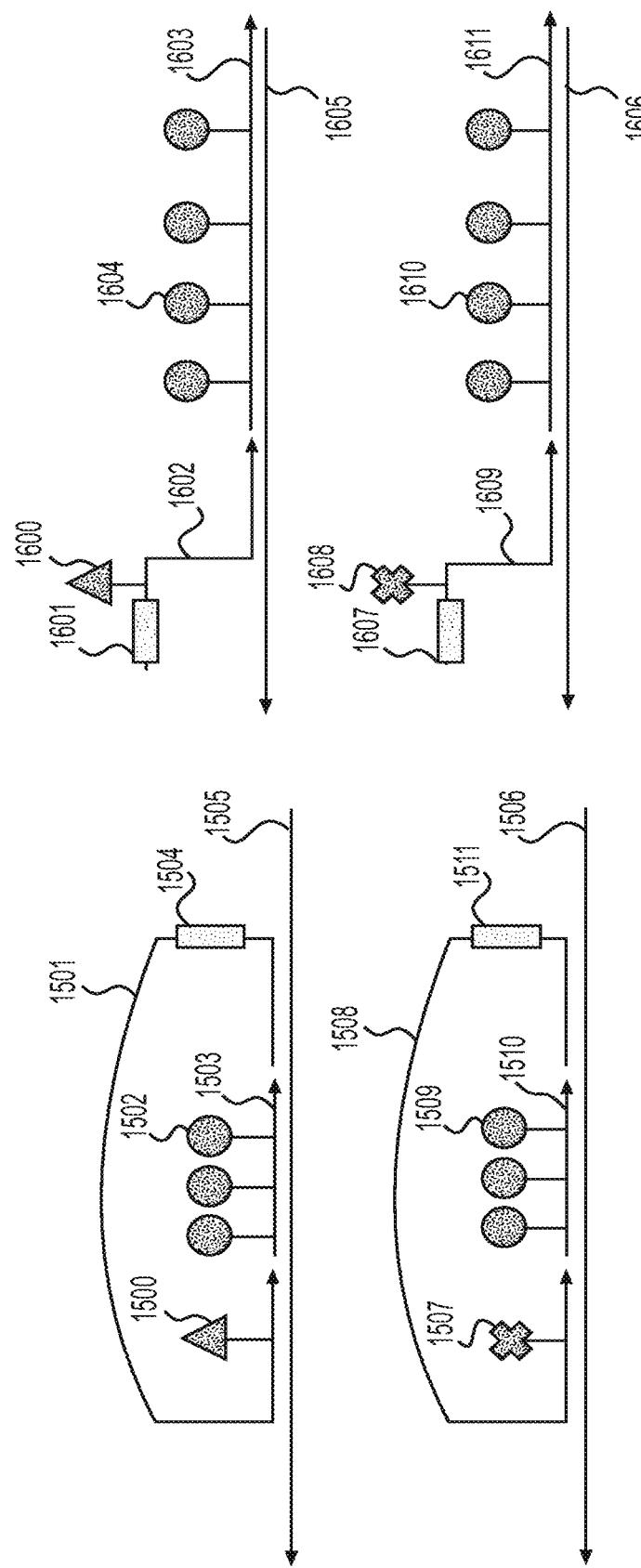

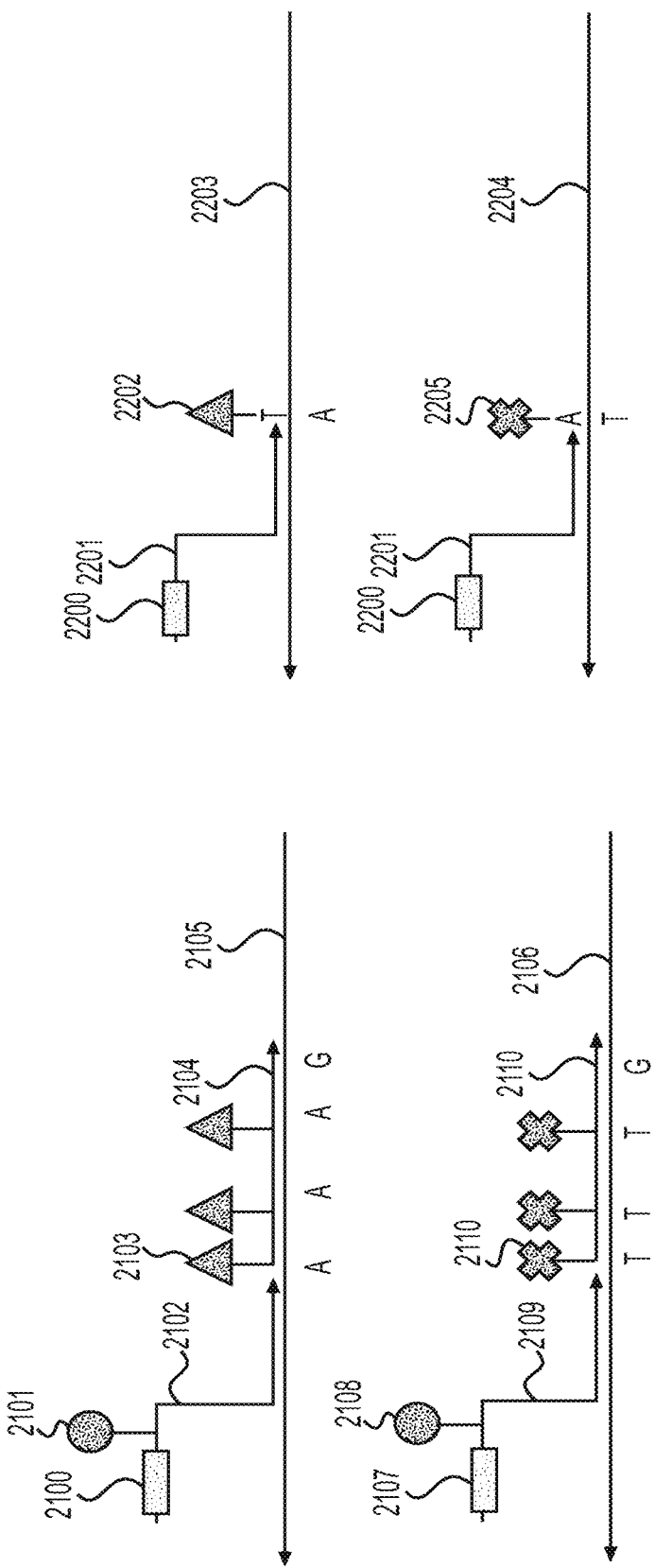

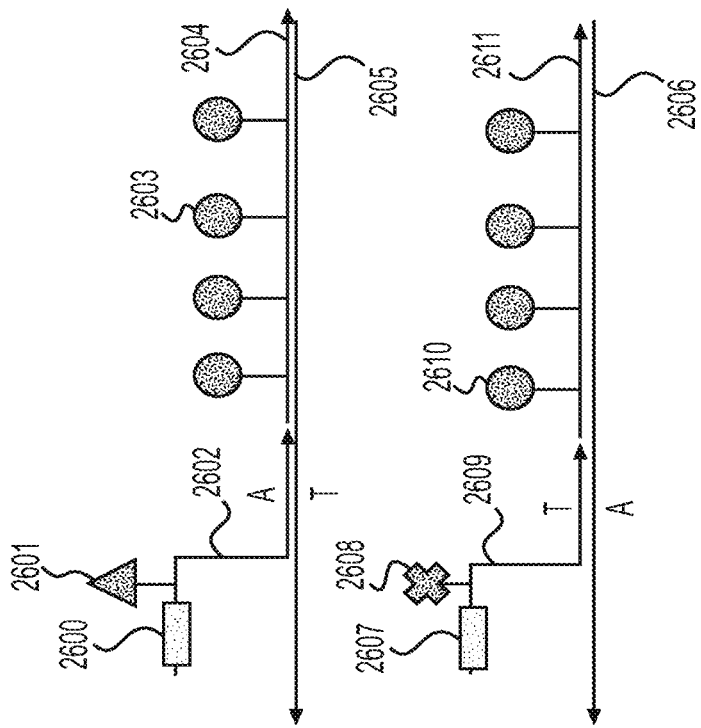
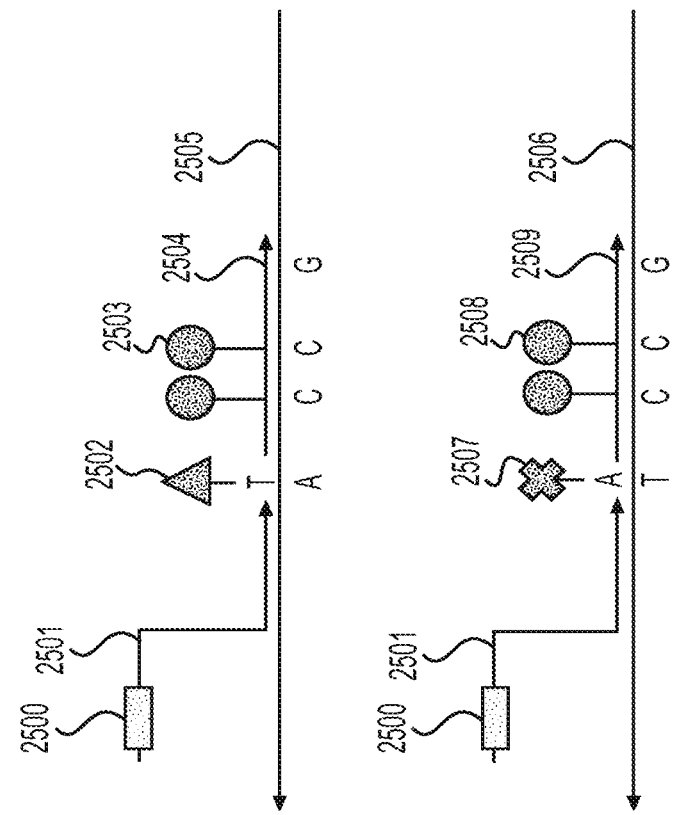
Figure 46
Figure 45

SEQUENCE LISTING

```
<160> NUMBER OF SEQ ID NOS: 369

<210> SEQ ID NO 1
<211> LENGTH: 60
<212> TYPE: DNA
<213> ORGANISM: Artificial Sequence
<220> FEATURE:
<223> OTHER INFORMATION: Synthetic sequence

<400> SEQUENCE: 1
gccctcatct tcttccctgc gttctcacca ccctcaccaa ggaagaagtg agggcttctc     60

<210> SEQ ID NO 2
<211> LENGTH: 60
<212> TYPE: DNA
<213> ORGANISM: Artificial Sequence
<220> FEATURE:
<223> OTHER INFORMATION: Synthetic sequence

<400> SEQUENCE: 2
gccctcatct tcttccctgc gttctcacca ccctcaccaa aaatcaaggt gaccagctcc     60

<210> SEQ ID NO 3
<211> LENGTH: 62
<212> TYPE: DNA
<213> ORGANISM: Artificial Sequence
<220> FEATURE:
<223> OTHER INFORMATION: Synthetic sequence

<400> SEQUENCE: 3
gccctcatct tcttccctgc gttctcacca ccctcaccaa tcatctgcca agacagaagt     60
tc                                                                   62

<210> SEQ ID NO 4
<211> LENGTH: 60
<212> TYPE: DNA
<213> ORGANISM: Artificial Sequence
<220> FEATURE:
```

<223> OTHER INFORMATION: Synthetic sequence

<400> SEQUENCE: 4
gccctcatct tcttccctgc gttctcacca ccctcaccaa gcaggagagt caaaggtctg    60

<210> SEQ ID NO 5
<211> LENGTH: 60
<212> TYPE: DNA
<213> ORGANISM: Artificial Sequence
<220> FEATURE:
<223> OTHER INFORMATION: Synthetic sequence

<400> SEQUENCE: 5
gccctcatct tcttccctgc gttctcacca ccctcaccaa gttgccatgg agattgttgc    60

<210> SEQ ID NO 6
<211> LENGTH: 60
<212> TYPE: DNA
<213> ORGANISM: Artificial Sequence
<220> FEATURE:
<223> OTHER INFORMATION: Synthetic sequence

<400> SEQUENCE: 6
gccctcatct tcttccctgc gttctcacca ccctcaccaa cagctcagtg atgtcattgc    60

<210> SEQ ID NO 7
<211> LENGTH: 61
<212> TYPE: DNA
<213> ORGANISM: Artificial Sequence
<220> FEATURE:
<223> OTHER INFORMATION: Synthetic sequence

<400> SEQUENCE: 7
gccctcatct tcttccctgc gttctcacca ccctcaccaa ccttgacctc tgctaatgtg    60
g                                                                   61

<210> SEQ ID NO 8
<211> LENGTH: 60
<212> TYPE: DNA
<213> ORGANISM: Artificial Sequence
<220> FEATURE:
<223> OTHER INFORMATION: Synthetic sequence

<400> SEQUENCE: 8
gccctcatct tcttccctgc gttctcacca ccctcaccaa cacctgtcca acagctacag    60

<210> SEQ ID NO 9
<211> LENGTH: 61
<212> TYPE: DNA
<213> ORGANISM: Artificial Sequence
<220> FEATURE:
<223> OTHER INFORMATION: Synthetic sequence

<400> SEQUENCE: 9
gccctcatct tcttccctgc gttctcacca ccctcaccaa agaatgtatc ttcaggcctg    60
c                                                                   61

<210> SEQ ID NO 10
<211> LENGTH: 60
<212> TYPE: DNA
<213> ORGANISM: Artificial Sequence
<220> FEATURE:
<223> OTHER INFORMATION: Synthetic sequence

<400> SEQUENCE: 10

```
gccctcatct tcttccctgc gttctcacca ccctcaccaa aagtaatcac tctgggtggc    60

<210> SEQ ID NO 11
<211> LENGTH: 60
<212> TYPE: DNA
<213> ORGANISM: Artificial Sequence
<220> FEATURE:
<223> OTHER INFORMATION: Synthetic sequence

<400> SEQUENCE: 11
gccctcatct tcttccctgc gttctcacca ccctcaccaa agctcacaga caaccttgtg    60

<210> SEQ ID NO 12
<211> LENGTH: 60
<212> TYPE: DNA
<213> ORGANISM: Artificial Sequence
<220> FEATURE:
<223> OTHER INFORMATION: Synthetic sequence

<400> SEQUENCE: 12
gccctcatct tcttccctgc gttctcacca ccctcaccaa gcaatagaca cctacaggcg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic sequence

<400> SEQUENCE: 13
gccctcatct tcttccctgc gttctcacca ccctcaccaa gcacattatc aaaggccacg    60

<210> SEQ ID NO 14
<211> LENGTH: 60
<212> TYPE: DNA
<213> ORGANISM: Artificial Sequence
<220> FEATURE:
<223> OTHER INFORMATION: Synthetic sequence

<400> SEQUENCE: 14
gccctcatct tcttccctgc gttctcacca ccctcaccaa caacgaccta aagcatgtgc    60

<210> SEQ ID NO 15
<211> LENGTH: 60
<212> TYPE: DNA
<213> ORGANISM: Artificial Sequence
<220> FEATURE:
<223> OTHER INFORMATION: Synthetic sequence

<400> SEQUENCE: 15
gccctcatct tcttccctgc gttctcacca ccctcaccaa gacatacatg gctttggcag    60

<210> SEQ ID NO 16
<211> LENGTH: 62
<212> TYPE: DNA
<213> ORGANISM: Artificial Sequence
<220> FEATURE:
<223> OTHER INFORMATION: Synthetic sequence

<400> SEQUENCE: 16
gccctcatct tcttccctgc gttctcacca ccctcaccaa gagatactgc cacttatgca    60
cg                                                                   62

<210> SEQ ID NO 17
```

```
<211> LENGTH: 40
<212> TYPE: DNA
<213> ORGANISM: Artificial Sequence
<220> FEATURE:
<223> OTHER INFORMATION: Synthetic sequence

<400> SEQUENCE: 17
cgtgctaata gtctcagggc ttcctccacc gaacgtgtct                     40

<210> SEQ ID NO 18
<211> LENGTH: 40
<212> TYPE: DNA
<213> ORGANISM: Artificial Sequence
<220> FEATURE:
<223> OTHER INFORMATION: Synthetic sequence

<400> SEQUENCE: 18
cgacgcttca ttgcttcatt ttcctccacc gaacgtgtct                     40

<210> SEQ ID NO 19
<211> LENGTH: 40
<212> TYPE: DNA
<213> ORGANISM: Artificial Sequence
<220> FEATURE:
<223> OTHER INFORMATION: Synthetic sequence

<400> SEQUENCE: 19
cttgcgccaa acaattgtcc ttcctccacc gaacgtgtct                     40

<210> SEQ ID NO 20
<211> LENGTH: 40
<212> TYPE: DNA
<213> ORGANISM: Artificial Sequence
<220> FEATURE:
<223> OTHER INFORMATION: Synthetic sequence

<400> SEQUENCE: 20
gctgcagagt ttgcattcat ttcctccacc gaacgtgtct                     40

<210> SEQ ID NO 21
<211> LENGTH: 41
<212> TYPE: DNA
<213> ORGANISM: Artificial Sequence
<220> FEATURE:
<223> OTHER INFORMATION: Synthetic sequence

<400> SEQUENCE: 21
catacacaca gaccgagagt cttcctccac cgaacgtgtc t                   41

<210> SEQ ID NO 22
<211> LENGTH: 40
<212> TYPE: DNA
<213> ORGANISM: Artificial Sequence
<220> FEATURE:
<223> OTHER INFORMATION: Synthetic sequence

<400> SEQUENCE: 22
ggatgtcagc cagcataagt ttcctccacc gaacgtgtct                     40

<210> SEQ ID NO 23
<211> LENGTH: 40
<212> TYPE: DNA
<213> ORGANISM: Artificial Sequence
<220> FEATURE:
<223> OTHER INFORMATION: Synthetic sequence

<400> SEQUENCE: 23
```

```
gcaagtgcca aacagttctc ttcctccacc gaacgtgtct                    40

<210> SEQ ID NO 24
<211> LENGTH: 41
<212> TYPE: DNA
<213> ORGANISM: Artificial Sequence
<220> FEATURE:
<223> OTHER INFORMATION: Synthetic sequence

<400> SEQUENCE: 24
gattccagca cacttgagtc tttcctccac cgaacgtgtc t                  41

<210> SEQ ID NO 25
<211> LENGTH: 40
<212> TYPE: DNA
<213> ORGANISM: Artificial Sequence
<220> FEATURE:
<223> OTHER INFORMATION: Synthetic sequence

<400> SEQUENCE: 25
ccgttgcagg tttaaatggc gccctattgc aagccctctt                    40

<210> SEQ ID NO 26
<211> LENGTH: 40
<212> TYPE: DNA
<213> ORGANISM: Artificial Sequence
<220> FEATURE:
<223> OTHER INFORMATION: Synthetic sequence

<400> SEQUENCE: 26
caagagtgct ttatgggcct gccctattgc aagccctctt                    40

<210> SEQ ID NO 27
<211> LENGTH: 41
<212> TYPE: DNA
<213> ORGANISM: Artificial Sequence
<220> FEATURE:
<223> OTHER INFORMATION: Synthetic sequence

<400> SEQUENCE: 27
gcactcaagg agatcagact ggccctattg caagccctct t                  41

<210> SEQ ID NO 28
<211> LENGTH: 41
<212> TYPE: DNA
<213> ORGANISM: Artificial Sequence
<220> FEATURE:
<223> OTHER INFORMATION: Synthetic sequence

<400> SEQUENCE: 28
ggctatcgaa ctacaaccac agccctattg caagccctct t                  41

<210> SEQ ID NO 29
<211> LENGTH: 41
<212> TYPE: DNA
<213> ORGANISM: Artificial Sequence
<220> FEATURE:
<223> OTHER INFORMATION: Synthetic sequence

<400> SEQUENCE: 29
gtagctgtct gtggtgtgat cgccctattg caagccctct t                  41

<210> SEQ ID NO 30
<211> LENGTH: 42
<212> TYPE: DNA
```

```
<213> ORGANISM: Artificial Sequence
<220> FEATURE:
<223> OTHER INFORMATION: Synthetic sequence

<400> SEQUENCE: 30
caagaaactt cgagccttag cagccctatt gcaagccctc tt                     42

<210> SEQ ID NO 31
<211> LENGTH: 40
<212> TYPE: DNA
<213> ORGANISM: Artificial Sequence
<220> FEATURE:
<223> OTHER INFORMATION: Synthetic sequence

<400> SEQUENCE: 31
gtgaaccagt ccgagtgaaa gccctattgc aagccctctt                       40

<210> SEQ ID NO 32
<211> LENGTH: 41
<212> TYPE: DNA
<213> ORGANISM: Artificial Sequence
<220> FEATURE:
<223> OTHER INFORMATION: Synthetic sequence

<400> SEQUENCE: 32
gcaaatgatg ttcagcacca cgccctattg caagccctct t                     41

<210> SEQ ID NO 33
<211> LENGTH: 20
<212> TYPE: DNA
<213> ORGANISM: Artificial Sequence
<220> FEATURE:
<223> OTHER INFORMATION: Synthetic sequence

<400> SEQUENCE: 33
gccctcatct tcttccctgc                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic sequence

<400> SEQUENCE: 34
gttctcacca ccctcaccaa                                             20

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence

<400> SEQUENCE: 35
ggaagaagtg agggcttctc                                             20

<210> SEQ ID NO 36
<211> LENGTH: 20
<212> TYPE: DNA
<213> ORGANISM: Artificial Sequence
<220> FEATURE:
<223> OTHER INFORMATION: Synthetic sequence

<400> SEQUENCE: 36
aaatcaaggt gaccagctcc                                             20
```

<210> SEQ ID NO 37
<211> LENGTH: 22
<212> TYPE: DNA
<213> ORGANISM: Artificial Sequence
<220> FEATURE:
<223> OTHER INFORMATION: Synthetic sequence

<400> SEQUENCE: 37
tcatctgcca agacagaagt tc                                              22

<210> SEQ ID NO 38
<211> LENGTH: 20
<212> TYPE: DNA
<213> ORGANISM: Artificial Sequence
<220> FEATURE:
<223> OTHER INFORMATION: Synthetic sequence

<400> SEQUENCE: 38
gcaggagagt caaaggtctg                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic sequence

<400> SEQUENCE: 39
gttgccatgg agattgttgc                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic sequence

<400> SEQUENCE: 40
cagctcagtg atgtcattgc                                                 20

<210> SEQ ID NO 41
<211> LENGTH: 21
<212> TYPE: DNA
<213> ORGANISM: Artificial Sequence
<220> FEATURE:
<223> OTHER INFORMATION: Synthetic sequence

<400> SEQUENCE: 41
ccttgacctc tgctaatgtg g                                               21

<210> SEQ ID NO 42
<211> LENGTH: 20
<212> TYPE: DNA
<213> ORGANISM: Artificial Sequence
<220> FEATURE:
<223> OTHER INFORMATION: Synthetic sequence

<400> SEQUENCE: 42
cacctgtcca acagctacag                                                 20

<210> SEQ ID NO 43
<211> LENGTH: 21
<212> TYPE: DNA
<213> ORGANISM: Artificial Sequence
<220> FEATURE:

<223> OTHER INFORMATION: Synthetic sequence

<400> SEQUENCE: 43
agaatgtatc ttcaggcctg c                                      21

<210> SEQ ID NO 44
<211> LENGTH: 20
<212> TYPE: DNA
<213> ORGANISM: Artificial Sequence
<220> FEATURE:
<223> OTHER INFORMATION: Synthetic sequence

<400> SEQUENCE: 44
aagtaatcac tctgggtggc                                        20

<210> SEQ ID NO 45
<211> LENGTH: 20
<212> TYPE: DNA
<213> ORGANISM: Artificial Sequence
<220> FEATURE:
<223> OTHER INFORMATION: Synthetic sequence

<400> SEQUENCE: 45
agctcacaga caaccttgtg                                        20

<210> SEQ ID NO 46
<211> LENGTH: 20
<212> TYPE: DNA
<213> ORGANISM: Artificial Sequence
<220> FEATURE:
<223> OTHER INFORMATION: Synthetic sequence

<400> SEQUENCE: 46
gcaatagaca cctacaggcg                                        20

<210> SEQ ID NO 47
<211> LENGTH: 20
<212> TYPE: DNA
<213> ORGANISM: Artificial Sequence
<220> FEATURE:
<223> OTHER INFORMATION: Synthetic sequence

<400> SEQUENCE: 47
gcacattatc aaaggccacg                                        20

<210> SEQ ID NO 48
<211> LENGTH: 20
<212> TYPE: DNA
<213> ORGANISM: Artificial Sequence
<220> FEATURE:
<223> OTHER INFORMATION: Synthetic sequence

<400> SEQUENCE: 48
caacgaccta aagcatgtgc                                        20

<210> SEQ ID NO 49
<211> LENGTH: 20
<212> TYPE: DNA
<213> ORGANISM: Artificial Sequence
<220> FEATURE:
<223> OTHER INFORMATION: Synthetic sequence

<400> SEQUENCE: 49
gacatacatg gctttggcag                                        20

```
<210> SEQ ID NO 50
<211> LENGTH: 22
<212> TYPE: DNA
<213> ORGANISM: Artificial Sequence
<220> FEATURE:
<223> OTHER INFORMATION: Synthetic sequence

<400> SEQUENCE: 50
gagatactgc cacttatgca cg                                              22

<210> SEQ ID NO 51
<211> LENGTH: 20
<212> TYPE: DNA
<213> ORGANISM: Artificial Sequence
<220> FEATURE:
<223> OTHER INFORMATION: Synthetic sequence

<400> SEQUENCE: 51
cgtgctaata gtctcagggc                                                 20

<210> SEQ ID NO 52
<211> LENGTH: 20
<212> TYPE: DNA
<213> ORGANISM: Artificial Sequence
<220> FEATURE:
<223> OTHER INFORMATION: Synthetic sequence

<400> SEQUENCE: 52
cgacgcttca ttgcttcatt                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence

<400> SEQUENCE: 53
cttgcgccaa acaattgtcc                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic sequence

<400> SEQUENCE: 54
gctgcagagt ttgcattcat                                                 20

<210> SEQ ID NO 55
<211> LENGTH: 21
<212> TYPE: DNA
<213> ORGANISM: Artificial Sequence
<220> FEATURE:
<223> OTHER INFORMATION: Synthetic sequence

<400> SEQUENCE: 55
catacacaca gaccgagagt c                                               21

<210> SEQ ID NO 56
<211> LENGTH: 20
<212> TYPE: DNA
<213> ORGANISM: Artificial Sequence
<220> FEATURE:
<223> OTHER INFORMATION: Synthetic sequence
```

```
<400> SEQUENCE: 56
ggatgtcagc cagcataagt                                            20

<210> SEQ ID NO 57
<211> LENGTH: 20
<212> TYPE: DNA
<213> ORGANISM: Artificial Sequence
<220> FEATURE:
<223> OTHER INFORMATION: Synthetic sequence

<400> SEQUENCE: 57
gcaagtgcca aacagttctc                                            20

<210> SEQ ID NO 58
<211> LENGTH: 21
<212> TYPE: DNA
<213> ORGANISM: Artificial Sequence
<220> FEATURE:
<223> OTHER INFORMATION: Synthetic sequence

<400> SEQUENCE: 58
gattccagca cacttgagtc t                                          21

<210> SEQ ID NO 59
<211> LENGTH: 20
<212> TYPE: DNA
<213> ORGANISM: Artificial Sequence
<220> FEATURE:
<223> OTHER INFORMATION: Synthetic sequence

<400> SEQUENCE: 59
ccgttgcagg tttaaatggc                                            20

<210> SEQ ID NO 60
<211> LENGTH: 20
<212> TYPE: DNA
<213> ORGANISM: Artificial Sequence
<220> FEATURE:
<223> OTHER INFORMATION: Synthetic sequence

<400> SEQUENCE: 60
caagagtgct ttatgggcct                                            20

<210> SEQ ID NO 61
<211> LENGTH: 21
<212> TYPE: DNA
<213> ORGANISM: Artificial Sequence
<220> FEATURE:
<223> OTHER INFORMATION: Synthetic sequence

<400> SEQUENCE: 61
gcactcaagg agatcagact g                                          21

<210> SEQ ID NO 62
<211> LENGTH: 21
<212> TYPE: DNA
<213> ORGANISM: Artificial Sequence
<220> FEATURE:
<223> OTHER INFORMATION: Synthetic sequence

<400> SEQUENCE: 62
ggctatcgaa ctacaaccac a                                          21

<210> SEQ ID NO 63
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 63
gtagctgtct gtggtgtgat c                                          21

<210> SEQ ID NO 64
<211> LENGTH: 22
<212> TYPE: DNA
<213> ORGANISM: Artificial Sequence
<220> FEATURE:
<223> OTHER INFORMATION: Synthetic sequence

<400> SEQUENCE: 64
caagaaactt cgagccttag ca                                         22

<210> SEQ ID NO 65
<211> LENGTH: 20
<212> TYPE: DNA
<213> ORGANISM: Artificial Sequence
<220> FEATURE:
<223> OTHER INFORMATION: Synthetic sequence

<400> SEQUENCE: 65
gtgaaccagt ccgagtgaaa                                            20

<210> SEQ ID NO 66
<211> LENGTH: 21
<212> TYPE: DNA
<213> ORGANISM: Artificial Sequence
<220> FEATURE:
<223> OTHER INFORMATION: Synthetic sequence

<400> SEQUENCE: 66
gcaaatgatg ttcagcacca c                                          21

<210> SEQ ID NO 67
<211> LENGTH: 20
<212> TYPE: DNA
<213> ORGANISM: Artificial Sequence
<220> FEATURE:
<223> OTHER INFORMATION: Synthetic sequence

<400> SEQUENCE: 67
ttcctccacc gaacgtgtct                                            20

<210> SEQ ID NO 68
<211> LENGTH: 20
<212> TYPE: DNA
<213> ORGANISM: Artificial Sequence
<220> FEATURE:
<223> OTHER INFORMATION: Synthetic sequence

<400> SEQUENCE: 68
gccctattgc aagccctctt                                            20

<210> SEQ ID NO 69
<211> LENGTH: 40
<212> TYPE: DNA
<213> ORGANISM: Artificial Sequence
<220> FEATURE:
<223> OTHER INFORMATION: Synthetic sequence

<400> SEQUENCE: 69
```
ttcctccacc gaacgtgtct agaccagcac aacttactcg          40

<210> SEQ ID NO 70
<211> LENGTH: 37
<212> TYPE: DNA
<213> ORGANISM: Artificial Sequence
<220> FEATURE:
<223> OTHER INFORMATION: Synthetic sequence

<400> SEQUENCE: 70
ttcctccacc gaacgtgtct ccaaatgcac ctgcctg          37

<210> SEQ ID NO 71
<211> LENGTH: 41
<212> TYPE: DNA
<213> ORGANISM: Artificial Sequence
<220> FEATURE:
<223> OTHER INFORMATION: Synthetic sequence

<400> SEQUENCE: 71
ttcctccacc gaacgtgtct agtttggaca aaggcaattc g          41

<210> SEQ ID NO 72
<211> LENGTH: 44
<212> TYPE: DNA
<213> ORGANISM: Artificial Sequence
<220> FEATURE:
<223> OTHER INFORMATION: Synthetic sequence

<400> SEQUENCE: 72
ttcctccacc gaacgtgtct tgagcttagc caatatcaag aagg          44

<210> SEQ ID NO 73
<211> LENGTH: 42
<212> TYPE: DNA
<213> ORGANISM: Artificial Sequence
<220> FEATURE:
<223> OTHER INFORMATION: Synthetic sequence

<400> SEQUENCE: 73
ttcctccacc gaacgtgtct acgtgaactt tccttggtac ac          42

<210> SEQ ID NO 74
<211> LENGTH: 44
<212> TYPE: DNA
<213> ORGANISM: Artificial Sequence
<220> FEATURE:
<223> OTHER INFORMATION: Synthetic sequence

<400> SEQUENCE: 74
ttcctccacc gaacgtgtct tgaagatgtt ctaatacctt gccg          44

<210> SEQ ID NO 75
<211> LENGTH: 38
<212> TYPE: DNA
<213> ORGANISM: Artificial Sequence
<220> FEATURE:
<223> OTHER INFORMATION: Synthetic sequence

<400> SEQUENCE: 75
ttcctccacc gaacgtgtct cagtgtggag actgaacg          38

<210> SEQ ID NO 76
<211> LENGTH: 43
<212> TYPE: DNA
<213> ORGANISM: Artificial Sequence

```
<220> FEATURE:
<223> OTHER INFORMATION: Synthetic sequence

<400> SEQUENCE: 76
ttcctccacc gaacgtgtct aggcagggta atgtcatgaa atg          43

<210> SEQ ID NO 77
<211> LENGTH: 37
<212> TYPE: DNA
<213> ORGANISM: Artificial Sequence
<220> FEATURE:
<223> OTHER INFORMATION: Synthetic sequence

<400> SEQUENCE: 77
ttcctccacc gaacgtgtct gattgtctgg agcgctg                 37

<210> SEQ ID NO 78
<211> LENGTH: 36
<212> TYPE: DNA
<213> ORGANISM: Artificial Sequence
<220> FEATURE:
<223> OTHER INFORMATION: Synthetic sequence

<400> SEQUENCE: 78
ttcctccacc gaacgtgtct agggagcaat aggccg                  36

<210> SEQ ID NO 79
<211> LENGTH: 37
<212> TYPE: DNA
<213> ORGANISM: Artificial Sequence
<220> FEATURE:
<223> OTHER INFORMATION: Synthetic sequence

<400> SEQUENCE: 79
ttcctccacc gaacgtgtct ctgcagggta caacacg                 37

<210> SEQ ID NO 80
<211> LENGTH: 38
<212> TYPE: DNA
<213> ORGANISM: Artificial Sequence
<220> FEATURE:
<223> OTHER INFORMATION: Synthetic sequence

<400> SEQUENCE: 80
ttcctccacc gaacgtgtct cgtatctggg aagacggc                38

<210> SEQ ID NO 81
<211> LENGTH: 40
<212> TYPE: DNA
<213> ORGANISM: Artificial Sequence
<220> FEATURE:
<223> OTHER INFORMATION: Synthetic sequence

<400> SEQUENCE: 81
ttcctccacc gaacgtgtct cctgtaatcc cttgcaatgc              40

<210> SEQ ID NO 82
<211> LENGTH: 38
<212> TYPE: DNA
<213> ORGANISM: Artificial Sequence
<220> FEATURE:
<223> OTHER INFORMATION: Synthetic sequence

<400> SEQUENCE: 82
ttcctccacc gaacgtgtct ggtctcagca cggttctg                38
```

<210> SEQ ID NO 83
<211> LENGTH: 37
<212> TYPE: DNA
<213> ORGANISM: Artificial Sequence
<220> FEATURE:
<223> OTHER INFORMATION: Synthetic sequence

<400> SEQUENCE: 83
ttcctccacc gaacgtgtct gcacctccct accacac                              37

<210> SEQ ID NO 84
<211> LENGTH: 41
<212> TYPE: DNA
<213> ORGANISM: Artificial Sequence
<220> FEATURE:
<223> OTHER INFORMATION: Synthetic sequence

<400> SEQUENCE: 84
ttcctccacc gaacgtgtct gcctctagct agagagaagt c                         41

<210> SEQ ID NO 85
<211> LENGTH: 39
<212> TYPE: DNA
<213> ORGANISM: Artificial Sequence
<220> FEATURE:
<223> OTHER INFORMATION: Synthetic sequence

<400> SEQUENCE: 85
ttcctccacc gaacgtgtct ctggcagtct agccgttac                            39

<210> SEQ ID NO 86
<211> LENGTH: 43
<212> TYPE: DNA
<213> ORGANISM: Artificial Sequence
<220> FEATURE:
<223> OTHER INFORMATION: Synthetic sequence

<400> SEQUENCE: 86
ttcctccacc gaacgtgtct tgtcttagaa tttggcaact ggc                       43

<210> SEQ ID NO 87
<211> LENGTH: 39
<212> TYPE: DNA
<213> ORGANISM: Artificial Sequence
<220> FEATURE:
<223> OTHER INFORMATION: Synthetic sequence

<400> SEQUENCE: 87
ttcctccacc gaacgtgtct gcaggaaagc ctactgaac                            39

<210> SEQ ID NO 88
<211> LENGTH: 39
<212> TYPE: DNA
<213> ORGANISM: Artificial Sequence
<220> FEATURE:
<223> OTHER INFORMATION: Synthetic sequence

<400> SEQUENCE: 88
ttcctccacc gaacgtgtct gggagccaga gaaatgtcc                            39

<210> SEQ ID NO 89
<211> LENGTH: 44
<212> TYPE: DNA
<213> ORGANISM: Artificial Sequence
<220> FEATURE:
<223> OTHER INFORMATION: Synthetic sequence

<400> SEQUENCE: 89
ttcctccacc gaacgtgtct tgtctccagt tccacttcat ttag                    44

<210> SEQ ID NO 90
<211> LENGTH: 39
<212> TYPE: DNA
<213> ORGANISM: Artificial Sequence
<220> FEATURE:
<223> OTHER INFORMATION: Synthetic sequence

<400> SEQUENCE: 90
ttcctccacc gaacgtgtct cccgttaatt gcctactcg                          39

<210> SEQ ID NO 91
<211> LENGTH: 38
<212> TYPE: DNA
<213> ORGANISM: Artificial Sequence
<220> FEATURE:
<223> OTHER INFORMATION: Synthetic sequence

<400> SEQUENCE: 91
ttcctccacc gaacgtgtct ctcggtccca ctggaaag                           38

<210> SEQ ID NO 92
<211> LENGTH: 41
<212> TYPE: DNA
<213> ORGANISM: Artificial Sequence
<220> FEATURE:
<223> OTHER INFORMATION: Synthetic sequence

<400> SEQUENCE: 92
ttcctccacc gaacgtgtct acacccatga ttcagttact g                       41

<210> SEQ ID NO 93
<211> LENGTH: 41
<212> TYPE: DNA
<213> ORGANISM: Artificial Sequence
<220> FEATURE:
<223> OTHER INFORMATION: Synthetic sequence

<400> SEQUENCE: 93
ttcctccacc gaacgtgtct gctagtatga acatcacagg c                       41

<210> SEQ ID NO 94
<211> LENGTH: 43
<212> TYPE: DNA
<213> ORGANISM: Artificial Sequence
<220> FEATURE:
<223> OTHER INFORMATION: Synthetic sequence

<400> SEQUENCE: 94
ttcctccacc gaacgtgtct acaaatgagt aagaagcgag tcg                     43

<210> SEQ ID NO 95
<211> LENGTH: 38
<212> TYPE: DNA
<213> ORGANISM: Artificial Sequence
<220> FEATURE:
<223> OTHER INFORMATION: Synthetic sequence

<400> SEQUENCE: 95
ttcctccacc gaacgtgtct gataagggtt gctctgcg                           38

<210> SEQ ID NO 96

<211> LENGTH: 37
<212> TYPE: DNA
<213> ORGANISM: Artificial Sequence
<220> FEATURE:
<223> OTHER INFORMATION: Synthetic sequence

<400> SEQUENCE: 96
ttcctccacc gaacgtgtct ccatgcacca gctaccc         37

<210> SEQ ID NO 97
<211> LENGTH: 40
<212> TYPE: DNA
<213> ORGANISM: Artificial Sequence
<220> FEATURE:
<223> OTHER INFORMATION: Synthetic sequence

<400> SEQUENCE: 97
ttcctccacc gaacgtgtct aactgtaccc tactcccagc         40

<210> SEQ ID NO 98
<211> LENGTH: 41
<212> TYPE: DNA
<213> ORGANISM: Artificial Sequence
<220> FEATURE:
<223> OTHER INFORMATION: Synthetic sequence

<400> SEQUENCE: 98
ttcctccacc gaacgtgtct aggaccaagg gaccagttta g         41

<210> SEQ ID NO 99
<211> LENGTH: 42
<212> TYPE: DNA
<213> ORGANISM: Artificial Sequence
<220> FEATURE:
<223> OTHER INFORMATION: Synthetic sequence

<400> SEQUENCE: 99
ttcctccacc gaacgtgtct agagttcctc caagaaattg cg         42

<210> SEQ ID NO 100
<211> LENGTH: 44
<212> TYPE: DNA
<213> ORGANISM: Artificial Sequence
<220> FEATURE:
<223> OTHER INFORMATION: Synthetic sequence

<400> SEQUENCE: 100
ttcctccacc gaacgtgtct acattataca gcatgctggc tatc         44

<210> SEQ ID NO 101
<211> LENGTH: 41
<212> TYPE: DNA
<213> ORGANISM: Artificial Sequence
<220> FEATURE:
<223> OTHER INFORMATION: Synthetic sequence

<400> SEQUENCE: 101
ttcctccacc gaacgtgtct gaggaagaaa gtgaggtttg c         41

<210> SEQ ID NO 102
<211> LENGTH: 44
<212> TYPE: DNA
<213> ORGANISM: Artificial Sequence
<220> FEATURE:
<223> OTHER INFORMATION: Synthetic sequence

<400> SEQUENCE: 102
ttcctccacc gaacgtgtct ctgaattatg tgcttaccaa gagc    44

<210> SEQ ID NO 103
<211> LENGTH: 44
<212> TYPE: DNA
<213> ORGANISM: Artificial Sequence
<220> FEATURE:
<223> OTHER INFORMATION: Synthetic sequence

<400> SEQUENCE: 103
ttcctccacc gaacgtgtct tgggttctga taaccttatc aagc    44

<210> SEQ ID NO 104
<211> LENGTH: 39
<212> TYPE: DNA
<213> ORGANISM: Artificial Sequence
<220> FEATURE:
<223> OTHER INFORMATION: Synthetic sequence

<400> SEQUENCE: 104
ttcctccacc gaacgtgtct ggttagtcaa acatgctgc    39

<210> SEQ ID NO 105
<211> LENGTH: 42
<212> TYPE: DNA
<213> ORGANISM: Artificial Sequence
<220> FEATURE:
<223> OTHER INFORMATION: Synthetic sequence

<400> SEQUENCE: 105
ttcctccacc gaacgtgtct gacactggca gaatcaaatc ac    42

<210> SEQ ID NO 106
<211> LENGTH: 44
<212> TYPE: DNA
<213> ORGANISM: Artificial Sequence
<220> FEATURE:
<223> OTHER INFORMATION: Synthetic sequence

<400> SEQUENCE: 106
ttcctccacc gaacgtgtct agagttacac ctttagctaa ccac    44

<210> SEQ ID NO 107
<211> LENGTH: 38
<212> TYPE: DNA
<213> ORGANISM: Artificial Sequence
<220> FEATURE:
<223> OTHER INFORMATION: Synthetic sequence

<400> SEQUENCE: 107
ttcctccacc gaacgtgtct ccaggagttc aagaagcg    38

<210> SEQ ID NO 108
<211> LENGTH: 41
<212> TYPE: DNA
<213> ORGANISM: Artificial Sequence
<220> FEATURE:
<223> OTHER INFORMATION: Synthetic sequence

<400> SEQUENCE: 108
ttcctccacc gaacgtgtct accactcctt tctcccatct c    41

<210> SEQ ID NO 109
<211> LENGTH: 44
<212> TYPE: DNA

```
<213> ORGANISM: Artificial Sequence
<220> FEATURE:
<223> OTHER INFORMATION: Synthetic sequence

<400> SEQUENCE: 109
ttcctccacc gaacgtgtct gtcttatggg acaatggttg atag         44

<210> SEQ ID NO 110
<211> LENGTH: 38
<212> TYPE: DNA
<213> ORGANISM: Artificial Sequence
<220> FEATURE:
<223> OTHER INFORMATION: Synthetic sequence

<400> SEQUENCE: 110
ttcctccacc gaacgtgtct ctaccctcaa ccctcgtc               38

<210> SEQ ID NO 111
<211> LENGTH: 38
<212> TYPE: DNA
<213> ORGANISM: Artificial Sequence
<220> FEATURE:
<223> OTHER INFORMATION: Synthetic sequence

<400> SEQUENCE: 111
ttcctccacc gaacgtgtct ccaagactga tcatgccg               38

<210> SEQ ID NO 112
<211> LENGTH: 40
<212> TYPE: DNA
<213> ORGANISM: Artificial Sequence
<220> FEATURE:
<223> OTHER INFORMATION: Synthetic sequence

<400> SEQUENCE: 112
gccctattgc aagccctctt agaccagcac aacttactta             40

<210> SEQ ID NO 113
<211> LENGTH: 37
<212> TYPE: DNA
<213> ORGANISM: Artificial Sequence
<220> FEATURE:
<223> OTHER INFORMATION: Synthetic sequence

<400> SEQUENCE: 113
gccctattgc aagccctctt ccaaattcac ctgccca                37

<210> SEQ ID NO 114
<211> LENGTH: 41
<212> TYPE: DNA
<213> ORGANISM: Artificial Sequence
<220> FEATURE:
<223> OTHER INFORMATION: Synthetic sequence

<400> SEQUENCE: 114
gccctattgc aagccctctt agtttggaca aaggcgattt a           41

<210> SEQ ID NO 115
<211> LENGTH: 44
<212> TYPE: DNA
<213> ORGANISM: Artificial Sequence
<220> FEATURE:
<223> OTHER INFORMATION: Synthetic sequence

<400> SEQUENCE: 115
gccctattgc aagccctctt tgagcttagc caatatcaac aaga        44
```

<210> SEQ ID NO 116
<211> LENGTH: 42
<212> TYPE: DNA
<213> ORGANISM: Artificial Sequence
<220> FEATURE:
<223> OTHER INFORMATION: Synthetic sequence

<400> SEQUENCE: 116
gccctattgc aagccctctt acgtgaactt tccttggtaa at                           42

<210> SEQ ID NO 117
<211> LENGTH: 44
<212> TYPE: DNA
<213> ORGANISM: Artificial Sequence
<220> FEATURE:
<223> OTHER INFORMATION: Synthetic sequence

<400> SEQUENCE: 117
gccctattgc aagccctctt tgaagatgtt ctaatacctt gcta                         44

<210> SEQ ID NO 118
<211> LENGTH: 38
<212> TYPE: DNA
<213> ORGANISM: Artificial Sequence
<220> FEATURE:
<223> OTHER INFORMATION: Synthetic sequence

<400> SEQUENCE: 118
gccctattgc aagccctctt cagtgtggag accgaaca                                38

<210> SEQ ID NO 119
<211> LENGTH: 43
<212> TYPE: DNA
<213> ORGANISM: Artificial Sequence
<220> FEATURE:
<223> OTHER INFORMATION: Synthetic sequence

<400> SEQUENCE: 119
gccctattgc aagccctctt aggcagggta atgtcatgaa gtt                          43

<210> SEQ ID NO 120
<211> LENGTH: 37
<212> TYPE: DNA
<213> ORGANISM: Artificial Sequence
<220> FEATURE:
<223> OTHER INFORMATION: Synthetic sequence

<400> SEQUENCE: 120
gccctattgc aagccctctt gattgtctgg agggctc                                 37

<210> SEQ ID NO 121
<211> LENGTH: 36
<212> TYPE: DNA
<213> ORGANISM: Artificial Sequence
<220> FEATURE:
<223> OTHER INFORMATION: Synthetic sequence

<400> SEQUENCE: 121
gccctattgc aagccctctt agggagcaat aggcta                                  36

<210> SEQ ID NO 122
<211> LENGTH: 37
<212> TYPE: DNA
<213> ORGANISM: Artificial Sequence
<220> FEATURE:

<223> OTHER INFORMATION: Synthetic sequence

<400> SEQUENCE: 122
gccctattgc aagccctctt ctgcagggta caagaca                               37

<210> SEQ ID NO 123
<211> LENGTH: 38
<212> TYPE: DNA
<213> ORGANISM: Artificial Sequence
<220> FEATURE:
<223> OTHER INFORMATION: Synthetic sequence

<400> SEQUENCE: 123
gccctattgc aagccctctt cgtatctggg aagatggg                              38

<210> SEQ ID NO 124
<211> LENGTH: 40
<212> TYPE: DNA
<213> ORGANISM: Artificial Sequence
<220> FEATURE:
<223> OTHER INFORMATION: Synthetic sequence

<400> SEQUENCE: 124
gccctattgc aagccctctt cctgtaatcc cttgcaataa                            40

<210> SEQ ID NO 125
<211> LENGTH: 38
<212> TYPE: DNA
<213> ORGANISM: Artificial Sequence
<220> FEATURE:
<223> OTHER INFORMATION: Synthetic sequence

<400> SEQUENCE: 125
gccctattgc aagccctctt ggtctcagca cggtcctt                              38

<210> SEQ ID NO 126
<211> LENGTH: 37
<212> TYPE: DNA
<213> ORGANISM: Artificial Sequence
<220> FEATURE:
<223> OTHER INFORMATION: Synthetic sequence

<400> SEQUENCE: 126
gccctattgc aagccctctt gcacctccct atcacat                               37

<210> SEQ ID NO 127
<211> LENGTH: 41
<212> TYPE: DNA
<213> ORGANISM: Artificial Sequence
<220> FEATURE:
<223> OTHER INFORMATION: Synthetic sequence

<400> SEQUENCE: 127
gccctattgc aagccctctt gcctctagct agagagaagc g                          41

<210> SEQ ID NO 128
<211> LENGTH: 39
<212> TYPE: DNA
<213> ORGANISM: Artificial Sequence
<220> FEATURE:
<223> OTHER INFORMATION: Synthetic sequence

<400> SEQUENCE: 128
gccctattgc aagccctctt ctggcagtct agccattat                             39

```
<210> SEQ ID NO 129
<211> LENGTH: 43
<212> TYPE: DNA
<213> ORGANISM: Artificial Sequence
<220> FEATURE:
<223> OTHER INFORMATION: Synthetic sequence

<400> SEQUENCE: 129
gccctattgc aagccctctt tgtcttagaa tttggcaact agt          43

<210> SEQ ID NO 130
<211> LENGTH: 39
<212> TYPE: DNA
<213> ORGANISM: Artificial Sequence
<220> FEATURE:
<223> OTHER INFORMATION: Synthetic sequence

<400> SEQUENCE: 130
gccctattgc aagccctctt gcaggaaagc ctattgaat              39

<210> SEQ ID NO 131
<211> LENGTH: 39
<212> TYPE: DNA
<213> ORGANISM: Artificial Sequence
<220> FEATURE:
<223> OTHER INFORMATION: Synthetic sequence

<400> SEQUENCE: 131
gccctattgc aagccctctt gggagccaga gaaatttct              39

<210> SEQ ID NO 132
<211> LENGTH: 44
<212> TYPE: DNA
<213> ORGANISM: Artificial Sequence
<220> FEATURE:
<223> OTHER INFORMATION: Synthetic sequence

<400> SEQUENCE: 132
gccctattgc aagccctctt tgtctccagt tccacttcat gtaa         44

<210> SEQ ID NO 133
<211> LENGTH: 39
<212> TYPE: DNA
<213> ORGANISM: Artificial Sequence
<220> FEATURE:
<223> OTHER INFORMATION: Synthetic sequence

<400> SEQUENCE: 133
gccctattgc aagccctctt cccgttaatt gcctattta              39

<210> SEQ ID NO 134
<211> LENGTH: 38
<212> TYPE: DNA
<213> ORGANISM: Artificial Sequence
<220> FEATURE:
<223> OTHER INFORMATION: Synthetic sequence

<400> SEQUENCE: 134
gccctattgc aagccctctt ctcggtccca ctgggaaa               38

<210> SEQ ID NO 135
<211> LENGTH: 41
<212> TYPE: DNA
<213> ORGANISM: Artificial Sequence
<220> FEATURE:
<223> OTHER INFORMATION: Synthetic sequence
```

<400> SEQUENCE: 135
gccctattgc aagccctctt acacccatga ttcagttacc a                    41

<210> SEQ ID NO 136
<211> LENGTH: 41
<212> TYPE: DNA
<213> ORGANISM: Artificial Sequence
<220> FEATURE:
<223> OTHER INFORMATION: Synthetic sequence

<400> SEQUENCE: 136
gccctattgc aagccctctt gctagtatga acatcacaag t                    41

<210> SEQ ID NO 137
<211> LENGTH: 43
<212> TYPE: DNA
<213> ORGANISM: Artificial Sequence
<220> FEATURE:
<223> OTHER INFORMATION: Synthetic sequence

<400> SEQUENCE: 137
gccctattgc aagccctctt acaaatgagt aagaagcgag tta                  43

<210> SEQ ID NO 138
<211> LENGTH: 38
<212> TYPE: DNA
<213> ORGANISM: Artificial Sequence
<220> FEATURE:
<223> OTHER INFORMATION: Synthetic sequence

<400> SEQUENCE: 138
gccctattgc aagccctctt gataagggtt gctctaca                        38

<210> SEQ ID NO 139
<211> LENGTH: 37
<212> TYPE: DNA
<213> ORGANISM: Artificial Sequence
<220> FEATURE:
<223> OTHER INFORMATION: Synthetic sequence

<400> SEQUENCE: 139
gccctattgc aagccctctt ccatgcacca gctacta                         37

<210> SEQ ID NO 140
<211> LENGTH: 40
<212> TYPE: DNA
<213> ORGANISM: Artificial Sequence
<220> FEATURE:
<223> OTHER INFORMATION: Synthetic sequence

<400> SEQUENCE: 140
gccctattgc aagccctctt aactgtaccc tactcccaat                      40

<210> SEQ ID NO 141
<211> LENGTH: 41
<212> TYPE: DNA
<213> ORGANISM: Artificial Sequence
<220> FEATURE:
<223> OTHER INFORMATION: Synthetic sequence

<400> SEQUENCE: 141
gccctattgc aagccctctt aggaccaagg gaccagttca c                    41

<210> SEQ ID NO 142
<211> LENGTH: 42

<212> TYPE: DNA
<213> ORGANISM: Artificial Sequence
<220> FEATURE:
<223> OTHER INFORMATION: Synthetic sequence

<400> SEQUENCE: 142
gccctattgc aagccctctt agagttcctc caagaaattg ta        42

<210> SEQ ID NO 143
<211> LENGTH: 44
<212> TYPE: DNA
<213> ORGANISM: Artificial Sequence
<220> FEATURE:
<223> OTHER INFORMATION: Synthetic sequence

<400> SEQUENCE: 143
gccctattgc aagccctctt acattataca gcatgctggt taga      44

<210> SEQ ID NO 144
<211> LENGTH: 41
<212> TYPE: DNA
<213> ORGANISM: Artificial Sequence
<220> FEATURE:
<223> OTHER INFORMATION: Synthetic sequence

<400> SEQUENCE: 144
gccctattgc aagccctctt gaggaagaaa gtgagatttg t         41

<210> SEQ ID NO 145
<211> LENGTH: 44
<212> TYPE: DNA
<213> ORGANISM: Artificial Sequence
<220> FEATURE:
<223> OTHER INFORMATION: Synthetic sequence

<400> SEQUENCE: 145
gccctattgc aagccctctt ctgaattatg tgcttaccag gagt      44

<210> SEQ ID NO 146
<211> LENGTH: 44
<212> TYPE: DNA
<213> ORGANISM: Artificial Sequence
<220> FEATURE:
<223> OTHER INFORMATION: Synthetic sequence

<400> SEQUENCE: 146
gccctattgc aagccctctt tgggttctga taaccttatc aact      44

<210> SEQ ID NO 147
<211> LENGTH: 39
<212> TYPE: DNA
<213> ORGANISM: Artificial Sequence
<220> FEATURE:
<223> OTHER INFORMATION: Synthetic sequence

<400> SEQUENCE: 147
gccctattgc aagccctctt ggttagtcaa acatgttgt            39

<210> SEQ ID NO 148
<211> LENGTH: 42
<212> TYPE: DNA
<213> ORGANISM: Artificial Sequence
<220> FEATURE:
<223> OTHER INFORMATION: Synthetic sequence

<400> SEQUENCE: 148
gccctattgc aagccctctt gacactggca gaatcaaacc aa                              42

<210> SEQ ID NO 149
<211> LENGTH: 44
<212> TYPE: DNA
<213> ORGANISM: Artificial Sequence
<220> FEATURE:
<223> OTHER INFORMATION: Synthetic sequence

<400> SEQUENCE: 149
gccctattgc aagccctctt agagttacac ctttagctaa ctag                            44

<210> SEQ ID NO 150
<211> LENGTH: 38
<212> TYPE: DNA
<213> ORGANISM: Artificial Sequence
<220> FEATURE:
<223> OTHER INFORMATION: Synthetic sequence

<400> SEQUENCE: 150
gccctattgc aagccctctt ccaggagttc aaggagca                                   38

<210> SEQ ID NO 151
<211> LENGTH: 41
<212> TYPE: DNA
<213> ORGANISM: Artificial Sequence
<220> FEATURE:
<223> OTHER INFORMATION: Synthetic sequence

<400> SEQUENCE: 151
gccctattgc aagccctctt accactcctt tctcccgtct t                               41

<210> SEQ ID NO 152
<211> LENGTH: 44
<212> TYPE: DNA
<213> ORGANISM: Artificial Sequence
<220> FEATURE:
<223> OTHER INFORMATION: Synthetic sequence

<400> SEQUENCE: 152
gccctattgc aagccctctt gtcttatggg acaatggtcg atat                            44

<210> SEQ ID NO 153
<211> LENGTH: 38
<212> TYPE: DNA
<213> ORGANISM: Artificial Sequence
<220> FEATURE:
<223> OTHER INFORMATION: Synthetic sequence

<400> SEQUENCE: 153
gccctattgc aagccctctt ctaccctcaa ccctcatt                                   38

<210> SEQ ID NO 154
<211> LENGTH: 38
<212> TYPE: DNA
<213> ORGANISM: Artificial Sequence
<220> FEATURE:
<223> OTHER INFORMATION: Synthetic sequence

<400> SEQUENCE: 154
gccctattgc aagccctctt ccaagactga tcatgcta                                   38

<210> SEQ ID NO 155
<211> LENGTH: 61
<212> TYPE: DNA
<213> ORGANISM: Artificial Sequence
<220> FEATURE:
<223> OTHER INFORMATION: Synthetic sequence

<400> SEQUENCE: 155
cacttgacaa agttctcacg cgccgaagtt ctccgaagga tgccctcatc ttcttccctg    60
c                                                                   61

<210> SEQ ID NO 156
<211> LENGTH: 61
<212> TYPE: DNA
<213> ORGANISM: Artificial Sequence
<220> FEATURE:
<223> OTHER INFORMATION: Synthetic sequence

<400> SEQUENCE: 156
cattagggat taacggcttg ggacagactg acggagcttc agccctcatc ttcttccctg    60
c                                                                   61

<210> SEQ ID NO 157
<211> LENGTH: 63
<212> TYPE: DNA
<213> ORGANISM: Artificial Sequence
<220> FEATURE:
<223> OTHER INFORMATION: Synthetic sequence

<400> SEQUENCE: 157
cacacgttaa gaagactttc tgctgactct gccgcacatg atcgccctca tcttcttccc    60
tgc                                                                 63

<210> SEQ ID NO 158
<211> LENGTH: 62
<212> TYPE: DNA
<213> ORGANISM: Artificial Sequence
<220> FEATURE:
<223> OTHER INFORMATION: Synthetic sequence

<400> SEQUENCE: 158
ctaagtgccc tccatgagaa aggatccgat agccctctgc aggccctcat cttcttccct    60
gc                                                                  62

<210> SEQ ID NO 159
<211> LENGTH: 60
<212> TYPE: DNA
<213> ORGANISM: Artificial Sequence
<220> FEATURE:
<223> OTHER INFORMATION: Synthetic sequence

<400> SEQUENCE: 159
gcacagattt cccacactct caacaggcct gctaaacacc gccctcatct tcttccctgc    60

<210> SEQ ID NO 160
<211> LENGTH: 61
<212> TYPE: DNA
<213> ORGANISM: Artificial Sequence
<220> FEATURE:
<223> OTHER INFORMATION: Synthetic sequence

<400> SEQUENCE: 160
cttacaggag gtctggcatc aggtcaacaa ccgagggact cgccctcatc ttcttccctg    60
c                                                                   61

<210> SEQ ID NO 161

```
<211> LENGTH: 59
<212> TYPE: DNA
<213> ORGANISM: Artificial Sequence
<220> FEATURE:
<223> OTHER INFORMATION: Synthetic sequence

<400> SEQUENCE: 161
ccacaatgag aaggcagagt tgtcattaat gctggcggcg ccctcatctt cttccctgc      59

<210> SEQ ID NO 162
<211> LENGTH: 60
<212> TYPE: DNA
<213> ORGANISM: Artificial Sequence
<220> FEATURE:
<223> OTHER INFORMATION: Synthetic sequence

<400> SEQUENCE: 162
gctgtggcat agctacactc cggtgacggt ttgcaacttt gccctcatct tcttccctgc     60

<210> SEQ ID NO 163
<211> LENGTH: 60
<212> TYPE: DNA
<213> ORGANISM: Artificial Sequence
<220> FEATURE:
<223> OTHER INFORMATION: Synthetic sequence

<400> SEQUENCE: 163
cagggtaatt tgtgggtctg gtccggcagt taagggtctc gccctcatct tcttccctgc     60

<210> SEQ ID NO 164
<211> LENGTH: 62
<212> TYPE: DNA
<213> ORGANISM: Artificial Sequence
<220> FEATURE:
<223> OTHER INFORMATION: Synthetic sequence

<400> SEQUENCE: 164
gggctatcca gaaagataag aatactcaca aacgactgcg cagccctcat cttcttccct     60
gc                                                                    62

<210> SEQ ID NO 165
<211> LENGTH: 63
<212> TYPE: DNA
<213> ORGANISM: Artificial Sequence
<220> FEATURE:
<223> OTHER INFORMATION: Synthetic sequence

<400> SEQUENCE: 165
cataactggt ggagtatttc actcgtatat ggccgactgg agggccctca tcttcttccc     60
tgc                                                                   63

<210> SEQ ID NO 166
<211> LENGTH: 64
<212> TYPE: DNA
<213> ORGANISM: Artificial Sequence
<220> FEATURE:
<223> OTHER INFORMATION: Synthetic sequence

<400> SEQUENCE: 166
cttcaaggaa gaaattcaac agggtagggt ttgcggcgat aagggccctc atcttcttcc     60
ctgc                                                                  64

<210> SEQ ID NO 167
<211> LENGTH: 62
```

```
<212> TYPE: DNA
<213> ORGANISM: Artificial Sequence
<220> FEATURE:
<223> OTHER INFORMATION: Synthetic sequence

<400> SEQUENCE: 167
catggattca acacagcaaa caccaagtca accacccgag acgccctcat cttcttccct    60
gc                                                                    62

<210> SEQ ID NO 168
<211> LENGTH: 62
<212> TYPE: DNA
<213> ORGANISM: Artificial Sequence
<220> FEATURE:
<223> OTHER INFORMATION: Synthetic sequence

<400> SEQUENCE: 168
ctctgacctc cttcactctt acacttccct ggccttcctt ctgccctcat cttcttccct    60
gc                                                                    62

<210> SEQ ID NO 169
<211> LENGTH: 62
<212> TYPE: DNA
<213> ORGANISM: Artificial Sequence
<220> FEATURE:
<223> OTHER INFORMATION: Synthetic sequence

<400> SEQUENCE: 169
gctttcattt gtgctaaacc tcgcttgggt cctctcctga acgccctcat cttcttccct    60
gc                                                                    62

<210> SEQ ID NO 170
<211> LENGTH: 58
<212> TYPE: DNA
<213> ORGANISM: Artificial Sequence
<220> FEATURE:
<223> OTHER INFORMATION: Synthetic sequence

<400> SEQUENCE: 170
catcccagat gccctcataa cgtccgaacc acaatgctgc cctcatcttc ttccctgc      58

<210> SEQ ID NO 171
<211> LENGTH: 62
<212> TYPE: DNA
<213> ORGANISM: Artificial Sequence
<220> FEATURE:
<223> OTHER INFORMATION: Synthetic sequence

<400> SEQUENCE: 171
gtagaaatcc caaggcaatc agctcctcgc atccaacagt cggccctcat cttcttccct    60
gc                                                                    62

<210> SEQ ID NO 172
<211> LENGTH: 63
<212> TYPE: DNA
<213> ORGANISM: Artificial Sequence
<220> FEATURE:
<223> OTHER INFORMATION: Synthetic sequence

<400> SEQUENCE: 172
gaacaactaa ctccacagaa cccccaccgt agcactcctt cttgccctca tcttcttccc    60
tgc                                                                   63
```

```
<210> SEQ ID NO 173
<211> LENGTH: 59
<212> TYPE: DNA
<213> ORGANISM: Artificial Sequence
<220> FEATURE:
<223> OTHER INFORMATION: Synthetic sequence

<400> SEQUENCE: 173
gtgcagagga caggaagaac ggagcgtcgg tagtgtaaag ccctcatctt cttccctgc    59

<210> SEQ ID NO 174
<211> LENGTH: 63
<212> TYPE: DNA
<213> ORGANISM: Artificial Sequence
<220> FEATURE:
<223> OTHER INFORMATION: Synthetic sequence

<400> SEQUENCE: 174
ggtgcttcaa gacatacacc ttaacaactc gacgaaccta ccggccctca tcttcttccc    60
tgc                                                                63

<210> SEQ ID NO 175
<211> LENGTH: 60
<212> TYPE: DNA
<213> ORGANISM: Artificial Sequence
<220> FEATURE:
<223> OTHER INFORMATION: Synthetic sequence

<400> SEQUENCE: 175
ggaacctctg tgaccttgga tggcccatcc ttatgtgctg gccctcatct tcttccctgc    60

<210> SEQ ID NO 176
<211> LENGTH: 59
<212> TYPE: DNA
<213> ORGANISM: Artificial Sequence
<220> FEATURE:
<223> OTHER INFORMATION: Synthetic sequence

<400> SEQUENCE: 176
cccagtggta ccttctgaag gtcgttattg ctcaagcccg ccctcatctt cttccctgc    59

<210> SEQ ID NO 177
<211> LENGTH: 63
<212> TYPE: DNA
<213> ORGANISM: Artificial Sequence
<220> FEATURE:
<223> OTHER INFORMATION: Synthetic sequence

<400> SEQUENCE: 177
cttctgttgc ttatttgggt aacttgattc tggccctccc atcgccctca tcttcttccc    60
tgc                                                                63

<210> SEQ ID NO 178
<211> LENGTH: 56
<212> TYPE: DNA
<213> ORGANISM: Artificial Sequence
<220> FEATURE:
<223> OTHER INFORMATION: Synthetic sequence

<400> SEQUENCE: 178
cccactggat gcctccctca cgccggctat ttaggtgccc tcatcttctt ccctgc    56

<210> SEQ ID NO 179
<211> LENGTH: 58
```

```
<212> TYPE: DNA
<213> ORGANISM: Artificial Sequence
<220> FEATURE:
<223> OTHER INFORMATION: Synthetic sequence

<400> SEQUENCE: 179
cggagagacg catctgaaag tctgggtagg tggaggacgc cctcatcttc ttccctgc      58

<210> SEQ ID NO 180
<211> LENGTH: 61
<212> TYPE: DNA
<213> ORGANISM: Artificial Sequence
<220> FEATURE:
<223> OTHER INFORMATION: Synthetic sequence

<400> SEQUENCE: 180
caggatttcc agcttacagg gcgactgagc cacatccaac tgccctcatc ttcttccctg    60
c                                                                    61

<210> SEQ ID NO 181
<211> LENGTH: 60
<212> TYPE: DNA
<213> ORGANISM: Artificial Sequence
<220> FEATURE:
<223> OTHER INFORMATION: Synthetic sequence

<400> SEQUENCE: 181
cttgcaagat gtgcctctta gagcctcagc cggaattgaa gccctcatct tcttccctgc    60

<210> SEQ ID NO 182
<211> LENGTH: 62
<212> TYPE: DNA
<213> ORGANISM: Artificial Sequence
<220> FEATURE:
<223> OTHER INFORMATION: Synthetic sequence

<400> SEQUENCE: 182
gggtggtttc tctaaacaca aattgccatt ctgcaccaat gcgccctcat cttcttccct    60
gc                                                                   62

<210> SEQ ID NO 183
<211> LENGTH: 62
<212> TYPE: DNA
<213> ORGANISM: Artificial Sequence
<220> FEATURE:
<223> OTHER INFORMATION: Synthetic sequence

<400> SEQUENCE: 183
gcagggtatt gagagaagga tctattggtg ttcgcggctg atgccctcat cttcttccct    60
gc                                                                   62

<210> SEQ ID NO 184
<211> LENGTH: 62
<212> TYPE: DNA
<213> ORGANISM: Artificial Sequence
<220> FEATURE:
<223> OTHER INFORMATION: Synthetic sequence

<400> SEQUENCE: 184
gtgcacattt cttgatgaag ggatgggcgt aacaggagga ctgccctcat cttcttccct    60
gc                                                                   62

<210> SEQ ID NO 185
```

```
<211> LENGTH: 62
<212> TYPE: DNA
<213> ORGANISM: Artificial Sequence
<220> FEATURE:
<223> OTHER INFORMATION: Synthetic sequence

<400> SEQUENCE: 185
gagcaatgcc tgtttcatga gaggaatggc ctacctgcat cagccctcat cttcttccct    60
gc                                                                   62

<210> SEQ ID NO 186
<211> LENGTH: 64
<212> TYPE: DNA
<213> ORGANISM: Artificial Sequence
<220> FEATURE:
<223> OTHER INFORMATION: Synthetic sequence

<400> SEQUENCE: 186
gttaacatta tacagcatgg tggccccgtt gttgtcatcg catcgccctc atcttcttcc    60
ctgc                                                                 64

<210> SEQ ID NO 187
<211> LENGTH: 59
<212> TYPE: DNA
<213> ORGANISM: Artificial Sequence
<220> FEATURE:
<223> OTHER INFORMATION: Synthetic sequence

<400> SEQUENCE: 187
gcagaacatg tcctgaagcg ttcgatgcgt cccatgagtg ccctcatctt cttccctgc     59

<210> SEQ ID NO 188
<211> LENGTH: 60
<212> TYPE: DNA
<213> ORGANISM: Artificial Sequence
<220> FEATURE:
<223> OTHER INFORMATION: Synthetic sequence

<400> SEQUENCE: 188
cagcttgttc ccaaacccat caacccgcgt agatgttcct gccctcatct tcttccctgc    60

<210> SEQ ID NO 189
<211> LENGTH: 61
<212> TYPE: DNA
<213> ORGANISM: Artificial Sequence
<220> FEATURE:
<223> OTHER INFORMATION: Synthetic sequence

<400> SEQUENCE: 189
caaagtgtgg aagttgcttc cgccagctca agagtgtagc cgccctcatc ttcttccctg    60
c                                                                    61

<210> SEQ ID NO 190
<211> LENGTH: 58
<212> TYPE: DNA
<213> ORGANISM: Artificial Sequence
<220> FEATURE:
<223> OTHER INFORMATION: Synthetic sequence

<400> SEQUENCE: 190
ggtcgacttt gtccatcctt cttgatcctg cgcgatgtgc cctcatcttc ttccctgc      58

<210> SEQ ID NO 191
<211> LENGTH: 59
```

```
<212> TYPE: DNA
<213> ORGANISM: Artificial Sequence
<220> FEATURE:
<223> OTHER INFORMATION: Synthetic sequence

<400> SEQUENCE: 191
ctctgttgcc tgtggactca tcgcaggcgt tccctatacg ccctcatctt cttccctgc      59

<210> SEQ ID NO 192
<211> LENGTH: 64
<212> TYPE: DNA
<213> ORGANISM: Artificial Sequence
<220> FEATURE:
<223> OTHER INFORMATION: Synthetic sequence

<400> SEQUENCE: 192
ctaactagaa ttagtctgcc tgcctattgg acctccgacc acgagccctc atcttcttcc      60
ctgc                                                                  64

<210> SEQ ID NO 193
<211> LENGTH: 59
<212> TYPE: DNA
<213> ORGANISM: Artificial Sequence
<220> FEATURE:
<223> OTHER INFORMATION: Synthetic sequence

<400> SEQUENCE: 193
gtgagccata atcgtgtcaa gccaccattt agatccgcgg ccctcatctt cttccctgc      59

<210> SEQ ID NO 194
<211> LENGTH: 63
<212> TYPE: DNA
<213> ORGANISM: Artificial Sequence
<220> FEATURE:
<223> OTHER INFORMATION: Synthetic sequence

<400> SEQUENCE: 194
gagaattaat gctccctctc ctggaccagt agaagtctgc ccggccctca tcttcttccc      60
tgc                                                                   63

<210> SEQ ID NO 195
<211> LENGTH: 59
<212> TYPE: DNA
<213> ORGANISM: Artificial Sequence
<220> FEATURE:
<223> OTHER INFORMATION: Synthetic sequence

<400> SEQUENCE: 195
gtggtctgct gttgaccaat ttcagaatgg ccgagctgtg ccctcatctt cttccctgc      59

<210> SEQ ID NO 196
<211> LENGTH: 60
<212> TYPE: DNA
<213> ORGANISM: Artificial Sequence
<220> FEATURE:
<223> OTHER INFORMATION: Synthetic sequence

<400> SEQUENCE: 196
ggttgcaact gctgatctat aggtgaccct cttgtacgcc gccctcatct tcttccctgc      60

<210> SEQ ID NO 197
<211> LENGTH: 58
<212> TYPE: DNA
<213> ORGANISM: Artificial Sequence
<220> FEATURE:
```

<223> OTHER INFORMATION: Synthetic sequence

<400> SEQUENCE: 197
ctttcccagt caaggcaggg cgcgtcctta tttccatcgc cctcatcttc ttccctgc    58

<210> SEQ ID NO 198
<211> LENGTH: 20
<212> TYPE: DNA
<213> ORGANISM: Artificial Sequence
<220> FEATURE:
<223> OTHER INFORMATION: Synthetic sequence

<400> SEQUENCE: 198
agaccagcac aacttactcg    20

<210> SEQ ID NO 199
<211> LENGTH: 17
<212> TYPE: DNA
<213> ORGANISM: Artificial Sequence
<220> FEATURE:
<223> OTHER INFORMATION: Synthetic sequence

<400> SEQUENCE: 199
ccaaatgcac ctgcctg    17

<210> SEQ ID NO 200
<211> LENGTH: 21
<212> TYPE: DNA
<213> ORGANISM: Artificial Sequence
<220> FEATURE:
<223> OTHER INFORMATION: Synthetic sequence

<400> SEQUENCE: 200
agtttggaca aaggcaattc g    21

<210> SEQ ID NO 201
<211> LENGTH: 24
<212> TYPE: DNA
<213> ORGANISM: Artificial Sequence
<220> FEATURE:
<223> OTHER INFORMATION: Synthetic sequence

<400> SEQUENCE: 201
tgagcttagc caatatcaag aagg    24

<210> SEQ ID NO 202
<211> LENGTH: 22
<212> TYPE: DNA
<213> ORGANISM: Artificial Sequence
<220> FEATURE:
<223> OTHER INFORMATION: Synthetic sequence

<400> SEQUENCE: 202
acgtgaactt tccttggtac ac    22

<210> SEQ ID NO 203
<211> LENGTH: 24
<212> TYPE: DNA
<213> ORGANISM: Artificial Sequence
<220> FEATURE:
<223> OTHER INFORMATION: Synthetic sequence

<400> SEQUENCE: 203
tgaagatgtt ctaatacctt gccg    24

```
<210> SEQ ID NO 204
<211> LENGTH: 18
<212> TYPE: DNA
<213> ORGANISM: Artificial Sequence
<220> FEATURE:
<223> OTHER INFORMATION: Synthetic sequence

<400> SEQUENCE: 204
cagtgtggag actgaacg                                                  18

<210> SEQ ID NO 205
<211> LENGTH: 23
<212> TYPE: DNA
<213> ORGANISM: Artificial Sequence
<220> FEATURE:
<223> OTHER INFORMATION: Synthetic sequence

<400> SEQUENCE: 205
aggcagggta atgtcatgaa atg                                            23

<210> SEQ ID NO 206
<211> LENGTH: 17
<212> TYPE: DNA
<213> ORGANISM: Artificial Sequence
<220> FEATURE:
<223> OTHER INFORMATION: Synthetic sequence

<400> SEQUENCE: 206
gattgtctgg agcgctg                                                   17

<210> SEQ ID NO 207
<211> LENGTH: 16
<212> TYPE: DNA
<213> ORGANISM: Artificial Sequence
<220> FEATURE:
<223> OTHER INFORMATION: Synthetic sequence

<400> SEQUENCE: 207
agggagcaat aggccg                                                    16

<210> SEQ ID NO 208
<211> LENGTH: 17
<212> TYPE: DNA
<213> ORGANISM: Artificial Sequence
<220> FEATURE:
<223> OTHER INFORMATION: Synthetic sequence

<400> SEQUENCE: 208
ctgcagggta caacacg                                                   17

<210> SEQ ID NO 209
<211> LENGTH: 18
<212> TYPE: DNA
<213> ORGANISM: Artificial Sequence
<220> FEATURE:
<223> OTHER INFORMATION: Synthetic sequence

<400> SEQUENCE: 209
cgtatctggg aagacggc                                                  18

<210> SEQ ID NO 210
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 210
cctgtaatcc cttgcaatgc                                               20

<210> SEQ ID NO 211
<211> LENGTH: 18
<212> TYPE: DNA
<213> ORGANISM: Artificial Sequence
<220> FEATURE:
<223> OTHER INFORMATION: Synthetic sequence

<400> SEQUENCE: 211
ggtctcagca cggttctg                                                 18

<210> SEQ ID NO 212
<211> LENGTH: 17
<212> TYPE: DNA
<213> ORGANISM: Artificial Sequence
<220> FEATURE:
<223> OTHER INFORMATION: Synthetic sequence

<400> SEQUENCE: 212
gcacctccct accacac                                                  17

<210> SEQ ID NO 213
<211> LENGTH: 21
<212> TYPE: DNA
<213> ORGANISM: Artificial Sequence
<220> FEATURE:
<223> OTHER INFORMATION: Synthetic sequence

<400> SEQUENCE: 213
gcctctagct agagagaagt c                                             21

<210> SEQ ID NO 214
<211> LENGTH: 19
<212> TYPE: DNA
<213> ORGANISM: Artificial Sequence
<220> FEATURE:
<223> OTHER INFORMATION: Synthetic sequence

<400> SEQUENCE: 214
ctggcagtct agccgttac                                                19

<210> SEQ ID NO 215
<211> LENGTH: 23
<212> TYPE: DNA
<213> ORGANISM: Artificial Sequence
<220> FEATURE:
<223> OTHER INFORMATION: Synthetic sequence

<400> SEQUENCE: 215
tgtcttagaa tttggcaact ggc                                           23

<210> SEQ ID NO 216
<211> LENGTH: 19
<212> TYPE: DNA
<213> ORGANISM: Artificial Sequence
<220> FEATURE:
<223> OTHER INFORMATION: Synthetic sequence

<400> SEQUENCE: 216
gcaggaaagc ctactgaac                                                19

<210> SEQ ID NO 217
<211> LENGTH: 19

```
<212> TYPE: DNA
<213> ORGANISM: Artificial Sequence
<220> FEATURE:
<223> OTHER INFORMATION: Synthetic sequence

<400> SEQUENCE: 217
gggagccaga gaaatgtcc                                                  19

<210> SEQ ID NO 218
<211> LENGTH: 24
<212> TYPE: DNA
<213> ORGANISM: Artificial Sequence
<220> FEATURE:
<223> OTHER INFORMATION: Synthetic sequence

<400> SEQUENCE: 218
tgtctccagt tccacttcat ttag                                            24

<210> SEQ ID NO 219
<211> LENGTH: 19
<212> TYPE: DNA
<213> ORGANISM: Artificial Sequence
<220> FEATURE:
<223> OTHER INFORMATION: Synthetic sequence

<400> SEQUENCE: 219
cccgttaatt gcctactcg                                                  19

<210> SEQ ID NO 220
<211> LENGTH: 18
<212> TYPE: DNA
<213> ORGANISM: Artificial Sequence
<220> FEATURE:
<223> OTHER INFORMATION: Synthetic sequence

<400> SEQUENCE: 220
ctcggtccca ctggaaag                                                   18

<210> SEQ ID NO 221
<211> LENGTH: 21
<212> TYPE: DNA
<213> ORGANISM: Artificial Sequence
<220> FEATURE:
<223> OTHER INFORMATION: Synthetic sequence

<400> SEQUENCE: 221
acacccatga ttcagttact g                                               21

<210> SEQ ID NO 222
<211> LENGTH: 21
<212> TYPE: DNA
<213> ORGANISM: Artificial Sequence
<220> FEATURE:
<223> OTHER INFORMATION: Synthetic sequence

<400> SEQUENCE: 222
gctagtatga acatcacagg c                                               21

<210> SEQ ID NO 223
<211> LENGTH: 23
<212> TYPE: DNA
<213> ORGANISM: Artificial Sequence
<220> FEATURE:
<223> OTHER INFORMATION: Synthetic sequence

<400> SEQUENCE: 223
```

```
acaaatgagt aagaagcgag tcg                                           23
```

<210> SEQ ID NO 224
<211> LENGTH: 18
<212> TYPE: DNA
<213> ORGANISM: Artificial Sequence
<220> FEATURE:
<223> OTHER INFORMATION: Synthetic sequence

<400> SEQUENCE: 224

```
gataagggtt gctctgcg                                                 18
```

<210> SEQ ID NO 225
<211> LENGTH: 17
<212> TYPE: DNA
<213> ORGANISM: Artificial Sequence
<220> FEATURE:
<223> OTHER INFORMATION: Synthetic sequence

<400> SEQUENCE: 225

```
ccatgcacca gctaccc                                                  17
```

<210> SEQ ID NO 226
<211> LENGTH: 20
<212> TYPE: DNA
<213> ORGANISM: Artificial Sequence
<220> FEATURE:
<223> OTHER INFORMATION: Synthetic sequence

<400> SEQUENCE: 226

```
aactgtaccc tactcccagc                                               20
```

<210> SEQ ID NO 227
<211> LENGTH: 21
<212> TYPE: DNA
<213> ORGANISM: Artificial Sequence
<220> FEATURE:
<223> OTHER INFORMATION: Synthetic sequence

<400> SEQUENCE: 227

```
aggaccaagg gaccagttta g                                             21
```

<210> SEQ ID NO 228
<211> LENGTH: 22
<212> TYPE: DNA
<213> ORGANISM: Artificial Sequence
<220> FEATURE:
<223> OTHER INFORMATION: Synthetic sequence

<400> SEQUENCE: 228

```
agagttcctc caagaaattg cg                                            22
```

<210> SEQ ID NO 229
<211> LENGTH: 24
<212> TYPE: DNA
<213> ORGANISM: Artificial Sequence
<220> FEATURE:
<223> OTHER INFORMATION: Synthetic sequence

<400> SEQUENCE: 229

```
acattataca gcatgctggc tatc                                          24
```

<210> SEQ ID NO 230
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 230
gaggaagaaa gtgaggtttg c                                              21

<210> SEQ ID NO 231
<211> LENGTH: 24
<212> TYPE: DNA
<213> ORGANISM: Artificial Sequence
<220> FEATURE:
<223> OTHER INFORMATION: Synthetic sequence

<400> SEQUENCE: 231
ctgaattatg tgcttaccaa gagc                                           24

<210> SEQ ID NO 232
<211> LENGTH: 24
<212> TYPE: DNA
<213> ORGANISM: Artificial Sequence
<220> FEATURE:
<223> OTHER INFORMATION: Synthetic sequence

<400> SEQUENCE: 232
tgggttctga taaccttatc aagc                                           24

<210> SEQ ID NO 233
<211> LENGTH: 19
<212> TYPE: DNA
<213> ORGANISM: Artificial Sequence
<220> FEATURE:
<223> OTHER INFORMATION: Synthetic sequence

<400> SEQUENCE: 233
ggttagtcaa acatgctgc                                                 19

<210> SEQ ID NO 234
<211> LENGTH: 22
<212> TYPE: DNA
<213> ORGANISM: Artificial Sequence
<220> FEATURE:
<223> OTHER INFORMATION: Synthetic sequence

<400> SEQUENCE: 234
gacactggca gaatcaaatc ac                                             22

<210> SEQ ID NO 235
<211> LENGTH: 24
<212> TYPE: DNA
<213> ORGANISM: Artificial Sequence
<220> FEATURE:
<223> OTHER INFORMATION: Synthetic sequence

<400> SEQUENCE: 235
agagttacac ctttagctaa ccac                                           24

<210> SEQ ID NO 236
<211> LENGTH: 18
<212> TYPE: DNA
<213> ORGANISM: Artificial Sequence
<220> FEATURE:
<223> OTHER INFORMATION: Synthetic sequence

<400> SEQUENCE: 236
ccaggagttc aagaagcg                                                  18
```

```
<210> SEQ ID NO 237
<211> LENGTH: 21
<212> TYPE: DNA
<213> ORGANISM: Artificial Sequence
<220> FEATURE:
<223> OTHER INFORMATION: Synthetic sequence

<400> SEQUENCE: 237
accactcctt tctcccatct c                                          21

<210> SEQ ID NO 238
<211> LENGTH: 24
<212> TYPE: DNA
<213> ORGANISM: Artificial Sequence
<220> FEATURE:
<223> OTHER INFORMATION: Synthetic sequence

<400> SEQUENCE: 238
gtcttatggg acaatggttg atag                                       24

<210> SEQ ID NO 239
<211> LENGTH: 18
<212> TYPE: DNA
<213> ORGANISM: Artificial Sequence
<220> FEATURE:
<223> OTHER INFORMATION: Synthetic sequence

<400> SEQUENCE: 239
ctaccctcaa ccctcgtc                                              18

<210> SEQ ID NO 240
<211> LENGTH: 18
<212> TYPE: DNA
<213> ORGANISM: Artificial Sequence
<220> FEATURE:
<223> OTHER INFORMATION: Synthetic sequence

<400> SEQUENCE: 240
ccaagactga tcatgccg                                              18

<210> SEQ ID NO 241
<211> LENGTH: 20
<212> TYPE: DNA
<213> ORGANISM: Artificial Sequence
<220> FEATURE:
<223> OTHER INFORMATION: Synthetic sequence

<400> SEQUENCE: 241
agaccagcac aacttactta                                            20

<210> SEQ ID NO 242
<211> LENGTH: 17
<212> TYPE: DNA
<213> ORGANISM: Artificial Sequence
<220> FEATURE:
<223> OTHER INFORMATION: Synthetic sequence

<400> SEQUENCE: 242
ccaaattcac ctgccca                                               17

<210> SEQ ID NO 243
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 243
agtttggaca aaggcgattt a                                              21

<210> SEQ ID NO 244
<211> LENGTH: 24
<212> TYPE: DNA
<213> ORGANISM: Artificial Sequence
<220> FEATURE:
<223> OTHER INFORMATION: Synthetic sequence

<400> SEQUENCE: 244
tgagcttagc caatatcaac aaga                                           24

<210> SEQ ID NO 245
<211> LENGTH: 22
<212> TYPE: DNA
<213> ORGANISM: Artificial Sequence
<220> FEATURE:
<223> OTHER INFORMATION: Synthetic sequence

<400> SEQUENCE: 245
acgtgaactt tccttggtaa at                                             22

<210> SEQ ID NO 246
<211> LENGTH: 24
<212> TYPE: DNA
<213> ORGANISM: Artificial Sequence
<220> FEATURE:
<223> OTHER INFORMATION: Synthetic sequence

<400> SEQUENCE: 246
tgaagatgtt ctaatacctt gcta                                           24

<210> SEQ ID NO 247
<211> LENGTH: 18
<212> TYPE: DNA
<213> ORGANISM: Artificial Sequence
<220> FEATURE:
<223> OTHER INFORMATION: Synthetic sequence

<400> SEQUENCE: 247
cagtgtggag accgaaca                                                  18

<210> SEQ ID NO 248
<211> LENGTH: 23
<212> TYPE: DNA
<213> ORGANISM: Artificial Sequence
<220> FEATURE:
<223> OTHER INFORMATION: Synthetic sequence

<400> SEQUENCE: 248
aggcagggta atgtcatgaa gtt                                            23

<210> SEQ ID NO 249
<211> LENGTH: 17
<212> TYPE: DNA
<213> ORGANISM: Artificial Sequence
<220> FEATURE:
<223> OTHER INFORMATION: Synthetic sequence

<400> SEQUENCE: 249
gattgtctgg agggctc                                                   17

<210> SEQ ID NO 250
```

```
<211> LENGTH: 16
<212> TYPE: DNA
<213> ORGANISM: Artificial Sequence
<220> FEATURE:
<223> OTHER INFORMATION: Synthetic sequence

<400> SEQUENCE: 250
agggagcaat aggcta                                                        16

<210> SEQ ID NO 251
<211> LENGTH: 17
<212> TYPE: DNA
<213> ORGANISM: Artificial Sequence
<220> FEATURE:
<223> OTHER INFORMATION: Synthetic sequence

<400> SEQUENCE: 251
ctgcagggta caagaca                                                       17

<210> SEQ ID NO 252
<211> LENGTH: 18
<212> TYPE: DNA
<213> ORGANISM: Artificial Sequence
<220> FEATURE:
<223> OTHER INFORMATION: Synthetic sequence

<400> SEQUENCE: 252
cgtatctggg aagatggg                                                      18

<210> SEQ ID NO 253
<211> LENGTH: 20
<212> TYPE: DNA
<213> ORGANISM: Artificial Sequence
<220> FEATURE:
<223> OTHER INFORMATION: Synthetic sequence

<400> SEQUENCE: 253
cctgtaatcc cttgcaataa                                                    20

<210> SEQ ID NO 254
<211> LENGTH: 18
<212> TYPE: DNA
<213> ORGANISM: Artificial Sequence
<220> FEATURE:
<223> OTHER INFORMATION: Synthetic sequence

<400> SEQUENCE: 254
ggtctcagca cggtcctt                                                      18

<210> SEQ ID NO 255
<211> LENGTH: 17
<212> TYPE: DNA
<213> ORGANISM: Artificial Sequence
<220> FEATURE:
<223> OTHER INFORMATION: Synthetic sequence

<400> SEQUENCE: 255
gcacctccct atcacat                                                       17

<210> SEQ ID NO 256
<211> LENGTH: 21
<212> TYPE: DNA
<213> ORGANISM: Artificial Sequence
<220> FEATURE:
<223> OTHER INFORMATION: Synthetic sequence

<400> SEQUENCE: 256
```
gcctctagct agagagaagc g                                      21

<210> SEQ ID NO 257
<211> LENGTH: 19
<212> TYPE: DNA
<213> ORGANISM: Artificial Sequence
<220> FEATURE:
<223> OTHER INFORMATION: Synthetic sequence

<400> SEQUENCE: 257
ctggcagtct agccattat                                         19

<210> SEQ ID NO 258
<211> LENGTH: 23
<212> TYPE: DNA
<213> ORGANISM: Artificial Sequence
<220> FEATURE:
<223> OTHER INFORMATION: Synthetic sequence

<400> SEQUENCE: 258
tgtcttagaa tttggcaact agt                                    23

<210> SEQ ID NO 259
<211> LENGTH: 19
<212> TYPE: DNA
<213> ORGANISM: Artificial Sequence
<220> FEATURE:
<223> OTHER INFORMATION: Synthetic sequence

<400> SEQUENCE: 259
gcaggaaagc ctattgaat                                         19

<210> SEQ ID NO 260
<211> LENGTH: 19
<212> TYPE: DNA
<213> ORGANISM: Artificial Sequence
<220> FEATURE:
<223> OTHER INFORMATION: Synthetic sequence

<400> SEQUENCE: 260
gggagccaga gaaatttct                                         19

<210> SEQ ID NO 261
<211> LENGTH: 24
<212> TYPE: DNA
<213> ORGANISM: Artificial Sequence
<220> FEATURE:
<223> OTHER INFORMATION: Synthetic sequence

<400> SEQUENCE: 261
tgtctccagt tccacttcat gtaa                                   24

<210> SEQ ID NO 262
<211> LENGTH: 19
<212> TYPE: DNA
<213> ORGANISM: Artificial Sequence
<220> FEATURE:
<223> OTHER INFORMATION: Synthetic sequence

<400> SEQUENCE: 262
cccgttaatt gcctattta                                         19

<210> SEQ ID NO 263
<211> LENGTH: 18
<212> TYPE: DNA

```
<213> ORGANISM: Artificial Sequence
<220> FEATURE:
<223> OTHER INFORMATION: Synthetic sequence

<400> SEQUENCE: 263
ctcggtccca ctgggaaa                                                     18

<210> SEQ ID NO 264
<211> LENGTH: 21
<212> TYPE: DNA
<213> ORGANISM: Artificial Sequence
<220> FEATURE:
<223> OTHER INFORMATION: Synthetic sequence

<400> SEQUENCE: 264
acacccatga ttcagttacc a                                                 21

<210> SEQ ID NO 265
<211> LENGTH: 21
<212> TYPE: DNA
<213> ORGANISM: Artificial Sequence
<220> FEATURE:
<223> OTHER INFORMATION: Synthetic sequence

<400> SEQUENCE: 265
gctagtatga acatcacaag t                                                 21

<210> SEQ ID NO 266
<211> LENGTH: 23
<212> TYPE: DNA
<213> ORGANISM: Artificial Sequence
<220> FEATURE:
<223> OTHER INFORMATION: Synthetic sequence

<400> SEQUENCE: 266
acaaatgagt aagaagcgag tta                                               23

<210> SEQ ID NO 267
<211> LENGTH: 18
<212> TYPE: DNA
<213> ORGANISM: Artificial Sequence
<220> FEATURE:
<223> OTHER INFORMATION: Synthetic sequence

<400> SEQUENCE: 267
gataagggtt gctctaca                                                     18

<210> SEQ ID NO 268
<211> LENGTH: 17
<212> TYPE: DNA
<213> ORGANISM: Artificial Sequence
<220> FEATURE:
<223> OTHER INFORMATION: Synthetic sequence

<400> SEQUENCE: 268
ccatgcacca gctacta                                                      17

<210> SEQ ID NO 269
<211> LENGTH: 20
<212> TYPE: DNA
<213> ORGANISM: Artificial Sequence
<220> FEATURE:
<223> OTHER INFORMATION: Synthetic sequence

<400> SEQUENCE: 269
aactgtaccc tactcccaat                                                   20
```

<210> SEQ ID NO 270
<211> LENGTH: 21
<212> TYPE: DNA
<213> ORGANISM: Artificial Sequence
<220> FEATURE:
<223> OTHER INFORMATION: Synthetic sequence

<400> SEQUENCE: 270
aggaccaagg gaccagttca c                                              21

<210> SEQ ID NO 271
<211> LENGTH: 22
<212> TYPE: DNA
<213> ORGANISM: Artificial Sequence
<220> FEATURE:
<223> OTHER INFORMATION: Synthetic sequence

<400> SEQUENCE: 271
agagttcctc caagaaattg ta                                             22

<210> SEQ ID NO 272
<211> LENGTH: 24
<212> TYPE: DNA
<213> ORGANISM: Artificial Sequence
<220> FEATURE:
<223> OTHER INFORMATION: Synthetic sequence

<400> SEQUENCE: 272
acattataca gcatgctggt taga                                           24

<210> SEQ ID NO 273
<211> LENGTH: 21
<212> TYPE: DNA
<213> ORGANISM: Artificial Sequence
<220> FEATURE:
<223> OTHER INFORMATION: Synthetic sequence

<400> SEQUENCE: 273
gaggaagaaa gtgagatttg t                                              21

<210> SEQ ID NO 274
<211> LENGTH: 24
<212> TYPE: DNA
<213> ORGANISM: Artificial Sequence
<220> FEATURE:
<223> OTHER INFORMATION: Synthetic sequence

<400> SEQUENCE: 274
ctgaattatg tgcttaccag gagt                                           24

<210> SEQ ID NO 275
<211> LENGTH: 24
<212> TYPE: DNA
<213> ORGANISM: Artificial Sequence
<220> FEATURE:
<223> OTHER INFORMATION: Synthetic sequence

<400> SEQUENCE: 275
tgggttctga taaccttatc aact                                           24

<210> SEQ ID NO 276
<211> LENGTH: 19
<212> TYPE: DNA
<213> ORGANISM: Artificial Sequence
<220> FEATURE:

<223> OTHER INFORMATION: Synthetic sequence

<400> SEQUENCE: 276
ggttagtcaa acatgttgt                                                    19

<210> SEQ ID NO 277
<211> LENGTH: 22
<212> TYPE: DNA
<213> ORGANISM: Artificial Sequence
<220> FEATURE:
<223> OTHER INFORMATION: Synthetic sequence

<400> SEQUENCE: 277
gacactggca gaatcaaacc aa                                                22

<210> SEQ ID NO 278
<211> LENGTH: 24
<212> TYPE: DNA
<213> ORGANISM: Artificial Sequence
<220> FEATURE:
<223> OTHER INFORMATION: Synthetic sequence

<400> SEQUENCE: 278
agagttacac ctttagctaa ctag                                              24

<210> SEQ ID NO 279
<211> LENGTH: 18
<212> TYPE: DNA
<213> ORGANISM: Artificial Sequence
<220> FEATURE:
<223> OTHER INFORMATION: Synthetic sequence

<400> SEQUENCE: 279
ccaggagttc aaggagca                                                     18

<210> SEQ ID NO 280
<211> LENGTH: 21
<212> TYPE: DNA
<213> ORGANISM: Artificial Sequence
<220> FEATURE:
<223> OTHER INFORMATION: Synthetic sequence

<400> SEQUENCE: 280
accactcctt tctcccgtct t                                                 21

<210> SEQ ID NO 281
<211> LENGTH: 24
<212> TYPE: DNA
<213> ORGANISM: Artificial Sequence
<220> FEATURE:
<223> OTHER INFORMATION: Synthetic sequence

<400> SEQUENCE: 281
gtcttatggg acaatggtcg atat                                              24

<210> SEQ ID NO 282
<211> LENGTH: 18
<212> TYPE: DNA
<213> ORGANISM: Artificial Sequence
<220> FEATURE:
<223> OTHER INFORMATION: Synthetic sequence

<400> SEQUENCE: 282
ctaccctcaa ccctcatt                                                     18

-continued

```
<210> SEQ ID NO 283
<211> LENGTH: 18
<212> TYPE: DNA
<213> ORGANISM: Artificial Sequence
<220> FEATURE:
<223> OTHER INFORMATION: Synthetic sequence

<400> SEQUENCE: 283
ccaagactga tcatgcta                                                       18

<210> SEQ ID NO 284
<211> LENGTH: 21
<212> TYPE: DNA
<213> ORGANISM: Artificial Sequence
<220> FEATURE:
<223> OTHER INFORMATION: Synthetic sequence

<400> SEQUENCE: 284
cacttgacaa agttctcacg c                                                   21

<210> SEQ ID NO 285
<211> LENGTH: 21
<212> TYPE: DNA
<213> ORGANISM: Artificial Sequence
<220> FEATURE:
<223> OTHER INFORMATION: Synthetic sequence

<400> SEQUENCE: 285
cattagggat taacggcttg g                                                   21

<210> SEQ ID NO 286
<211> LENGTH: 23
<212> TYPE: DNA
<213> ORGANISM: Artificial Sequence
<220> FEATURE:
<223> OTHER INFORMATION: Synthetic sequence

<400> SEQUENCE: 286
cacacgttaa gaagactttc tgc                                                 23

<210> SEQ ID NO 287
<211> LENGTH: 22
<212> TYPE: DNA
<213> ORGANISM: Artificial Sequence
<220> FEATURE:
<223> OTHER INFORMATION: Synthetic sequence

<400> SEQUENCE: 287
ctaagtgccc tccatgagaa ag                                                  22

<210> SEQ ID NO 288
<211> LENGTH: 20
<212> TYPE: DNA
<213> ORGANISM: Artificial Sequence
<220> FEATURE:
<223> OTHER INFORMATION: Synthetic sequence

<400> SEQUENCE: 288
gcacagattt cccacactct                                                     20

<210> SEQ ID NO 289
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 289
cttacaggag gtctggcatc a                                              21

<210> SEQ ID NO 290
<211> LENGTH: 19
<212> TYPE: DNA
<213> ORGANISM: Artificial Sequence
<220> FEATURE:
<223> OTHER INFORMATION: Synthetic sequence

<400> SEQUENCE: 290
ccacaatgag aaggcagag                                                 19

<210> SEQ ID NO 291
<211> LENGTH: 20
<212> TYPE: DNA
<213> ORGANISM: Artificial Sequence
<220> FEATURE:
<223> OTHER INFORMATION: Synthetic sequence

<400> SEQUENCE: 291
gctgtggcat agctacactc                                                20

<210> SEQ ID NO 292
<211> LENGTH: 20
<212> TYPE: DNA
<213> ORGANISM: Artificial Sequence
<220> FEATURE:
<223> OTHER INFORMATION: Synthetic sequence

<400> SEQUENCE: 292
cagggtaatt tgtgggtctg                                                20

<210> SEQ ID NO 293
<211> LENGTH: 22
<212> TYPE: DNA
<213> ORGANISM: Artificial Sequence
<220> FEATURE:
<223> OTHER INFORMATION: Synthetic sequence

<400> SEQUENCE: 293
gggctatcca gaaagataag aa                                             22

<210> SEQ ID NO 294
<211> LENGTH: 23
<212> TYPE: DNA
<213> ORGANISM: Artificial Sequence
<220> FEATURE:
<223> OTHER INFORMATION: Synthetic sequence

<400> SEQUENCE: 294
cataactggt ggagtatttc act                                            23

<210> SEQ ID NO 295
<211> LENGTH: 24
<212> TYPE: DNA
<213> ORGANISM: Artificial Sequence
<220> FEATURE:
<223> OTHER INFORMATION: Synthetic sequence

<400> SEQUENCE: 295
cttcaaggaa gaaattcaac aggg                                           24

<210> SEQ ID NO 296
<211> LENGTH: 22
```

```
<212> TYPE: DNA
<213> ORGANISM: Artificial Sequence
<220> FEATURE:
<223> OTHER INFORMATION: Synthetic sequence

<400> SEQUENCE: 296
catggattca acacagcaaa ca                                              22

<210> SEQ ID NO 297
<211> LENGTH: 22
<212> TYPE: DNA
<213> ORGANISM: Artificial Sequence
<220> FEATURE:
<223> OTHER INFORMATION: Synthetic sequence

<400> SEQUENCE: 297
ctctgacctc cttcactctt ac                                              22

<210> SEQ ID NO 298
<211> LENGTH: 22
<212> TYPE: DNA
<213> ORGANISM: Artificial Sequence
<220> FEATURE:
<223> OTHER INFORMATION: Synthetic sequence

<400> SEQUENCE: 298
gctttcattt gtgctaaacc tc                                              22

<210> SEQ ID NO 299
<211> LENGTH: 18
<212> TYPE: DNA
<213> ORGANISM: Artificial Sequence
<220> FEATURE:
<223> OTHER INFORMATION: Synthetic sequence

<400> SEQUENCE: 299
catcccagat gccctcat                                                   18

<210> SEQ ID NO 300
<211> LENGTH: 22
<212> TYPE: DNA
<213> ORGANISM: Artificial Sequence
<220> FEATURE:
<223> OTHER INFORMATION: Synthetic sequence

<400> SEQUENCE: 300
gtagaaatcc caaggcaatc ag                                              22

<210> SEQ ID NO 301
<211> LENGTH: 23
<212> TYPE: DNA
<213> ORGANISM: Artificial Sequence
<220> FEATURE:
<223> OTHER INFORMATION: Synthetic sequence

<400> SEQUENCE: 301
gaacaactaa ctccacagaa ccc                                             23

<210> SEQ ID NO 302
<211> LENGTH: 19
<212> TYPE: DNA
<213> ORGANISM: Artificial Sequence
<220> FEATURE:
<223> OTHER INFORMATION: Synthetic sequence

<400> SEQUENCE: 302
```
gtgcagagga caggaagaa                                                19

<210> SEQ ID NO 303
<211> LENGTH: 23
<212> TYPE: DNA
<213> ORGANISM: Artificial Sequence
<220> FEATURE:
<223> OTHER INFORMATION: Synthetic sequence

<400> SEQUENCE: 303
ggtgcttcaa gacatacacc tta                                           23

<210> SEQ ID NO 304
<211> LENGTH: 20
<212> TYPE: DNA
<213> ORGANISM: Artificial Sequence
<220> FEATURE:
<223> OTHER INFORMATION: Synthetic sequence

<400> SEQUENCE: 304
ggaacctctg tgaccttgga                                               20

<210> SEQ ID NO 305
<211> LENGTH: 19
<212> TYPE: DNA
<213> ORGANISM: Artificial Sequence
<220> FEATURE:
<223> OTHER INFORMATION: Synthetic sequence

<400> SEQUENCE: 305
cccagtggta ccttctgaa                                                19

<210> SEQ ID NO 306
<211> LENGTH: 23
<212> TYPE: DNA
<213> ORGANISM: Artificial Sequence
<220> FEATURE:
<223> OTHER INFORMATION: Synthetic sequence

<400> SEQUENCE: 306
cttctgttgc ttatttgggt aac                                           23

<210> SEQ ID NO 307
<211> LENGTH: 16
<212> TYPE: DNA
<213> ORGANISM: Artificial Sequence
<220> FEATURE:
<223> OTHER INFORMATION: Synthetic sequence

<400> SEQUENCE: 307
cccactggat gcctcc                                                   16

<210> SEQ ID NO 308
<211> LENGTH: 18
<212> TYPE: DNA
<213> ORGANISM: Artificial Sequence
<220> FEATURE:
<223> OTHER INFORMATION: Synthetic sequence

<400> SEQUENCE: 308
cggagagacg catctgaa                                                 18

<210> SEQ ID NO 309
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 309
caggatttcc agcttacagg g                                              21

<210> SEQ ID NO 310
<211> LENGTH: 20
<212> TYPE: DNA
<213> ORGANISM: Artificial Sequence
<220> FEATURE:
<223> OTHER INFORMATION: Synthetic sequence

<400> SEQUENCE: 310
cttgcaagat gtgcctctta                                                20

<210> SEQ ID NO 311
<211> LENGTH: 22
<212> TYPE: DNA
<213> ORGANISM: Artificial Sequence
<220> FEATURE:
<223> OTHER INFORMATION: Synthetic sequence

<400> SEQUENCE: 311
gggtggtttc tctaaacaca aa                                             22

<210> SEQ ID NO 312
<211> LENGTH: 22
<212> TYPE: DNA
<213> ORGANISM: Artificial Sequence
<220> FEATURE:
<223> OTHER INFORMATION: Synthetic sequence

<400> SEQUENCE: 312
gcagggtatt gagagaagga tc                                             22

<210> SEQ ID NO 313
<211> LENGTH: 22
<212> TYPE: DNA
<213> ORGANISM: Artificial Sequence
<220> FEATURE:
<223> OTHER INFORMATION: Synthetic sequence

<400> SEQUENCE: 313
gtgcacattt cttgatgaag gg                                             22

<210> SEQ ID NO 314
<211> LENGTH: 22
<212> TYPE: DNA
<213> ORGANISM: Artificial Sequence
<220> FEATURE:
<223> OTHER INFORMATION: Synthetic sequence

<400> SEQUENCE: 314
gagcaatgcc tgtttcatga ga                                             22

<210> SEQ ID NO 315
<211> LENGTH: 24
<212> TYPE: DNA
<213> ORGANISM: Artificial Sequence
<220> FEATURE:
<223> OTHER INFORMATION: Synthetic sequence

<400> SEQUENCE: 315
gttaacatta tacagcatgg tggc                                           24
```

```
<210> SEQ ID NO 316
<211> LENGTH: 19
<212> TYPE: DNA
<213> ORGANISM: Artificial Sequence
<220> FEATURE:
<223> OTHER INFORMATION: Synthetic sequence

<400> SEQUENCE: 316
gcagaacatg tcctgaagc                                                       19

<210> SEQ ID NO 317
<211> LENGTH: 20
<212> TYPE: DNA
<213> ORGANISM: Artificial Sequence
<220> FEATURE:
<223> OTHER INFORMATION: Synthetic sequence

<400> SEQUENCE: 317
cagcttgttc ccaaacccat                                                      20

<210> SEQ ID NO 318
<211> LENGTH: 21
<212> TYPE: DNA
<213> ORGANISM: Artificial Sequence
<220> FEATURE:
<223> OTHER INFORMATION: Synthetic sequence

<400> SEQUENCE: 318
caaagtgtgg aagttgcttc c                                                    21

<210> SEQ ID NO 319
<211> LENGTH: 18
<212> TYPE: DNA
<213> ORGANISM: Artificial Sequence
<220> FEATURE:
<223> OTHER INFORMATION: Synthetic sequence

<400> SEQUENCE: 319
ggtcgacttt gtccatcc                                                        18

<210> SEQ ID NO 320
<211> LENGTH: 19
<212> TYPE: DNA
<213> ORGANISM: Artificial Sequence
<220> FEATURE:
<223> OTHER INFORMATION: Synthetic sequence

<400> SEQUENCE: 320
ctctgttgcc tgtggactc                                                       19

<210> SEQ ID NO 321
<211> LENGTH: 24
<212> TYPE: DNA
<213> ORGANISM: Artificial Sequence
<220> FEATURE:
<223> OTHER INFORMATION: Synthetic sequence

<400> SEQUENCE: 321
ctaactagaa ttagtctgcc tgcc                                                 24

<210> SEQ ID NO 322
<211> LENGTH: 19
<212> TYPE: DNA
<213> ORGANISM: Artificial Sequence
<220> FEATURE:
<223> OTHER INFORMATION: Synthetic sequence
```

```
<400> SEQUENCE: 322
gtgagccata atcgtgtca                                                    19

<210> SEQ ID NO 323
<211> LENGTH: 23
<212> TYPE: DNA
<213> ORGANISM: Artificial Sequence
<220> FEATURE:
<223> OTHER INFORMATION: Synthetic sequence

<400> SEQUENCE: 323
gagaattaat gctccctctc ctg                                               23

<210> SEQ ID NO 324
<211> LENGTH: 19
<212> TYPE: DNA
<213> ORGANISM: Artificial Sequence
<220> FEATURE:
<223> OTHER INFORMATION: Synthetic sequence

<400> SEQUENCE: 324
gtggtctgct gttgaccaa                                                    19

<210> SEQ ID NO 325
<211> LENGTH: 20
<212> TYPE: DNA
<213> ORGANISM: Artificial Sequence
<220> FEATURE:
<223> OTHER INFORMATION: Synthetic sequence

<400> SEQUENCE: 325
ggttgcaact gctgatctat                                                   20

<210> SEQ ID NO 326
<211> LENGTH: 18
<212> TYPE: DNA
<213> ORGANISM: Artificial Sequence
<220> FEATURE:
<223> OTHER INFORMATION: Synthetic sequence

<400> SEQUENCE: 326
ctttcccagt caaggcag                                                     18

<210> SEQ ID NO 327
<211> LENGTH: 20
<212> TYPE: DNA
<213> ORGANISM: Artificial Sequence
<220> FEATURE:
<223> OTHER INFORMATION: Synthetic sequence

<400> SEQUENCE: 327
gccgaagttc tccgaaggat                                                   20

<210> SEQ ID NO 328
<211> LENGTH: 20
<212> TYPE: DNA
<213> ORGANISM: Artificial Sequence
<220> FEATURE:
<223> OTHER INFORMATION: Synthetic sequence

<400> SEQUENCE: 328
gacagactga cggagcttca                                                   20

<210> SEQ ID NO 329
```

```
<211> LENGTH: 20
<212> TYPE: DNA
<213> ORGANISM: Artificial Sequence
<220> FEATURE:
<223> OTHER INFORMATION: Synthetic sequence

<400> SEQUENCE: 329
tgactctgcc gcacatgatc                                               20

<210> SEQ ID NO 330
<211> LENGTH: 20
<212> TYPE: DNA
<213> ORGANISM: Artificial Sequence
<220> FEATURE:
<223> OTHER INFORMATION: Synthetic sequence

<400> SEQUENCE: 330
gatccgatag ccctctgcag                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic sequence

<400> SEQUENCE: 331
caacaggcct gctaaacacc                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic sequence

<400> SEQUENCE: 332
ggtcaacaac cgagggactc                                               20

<210> SEQ ID NO 333
<211> LENGTH: 20
<212> TYPE: DNA
<213> ORGANISM: Artificial Sequence
<220> FEATURE:
<223> OTHER INFORMATION: Synthetic sequence

<400> SEQUENCE: 333
ttgtcattaa tgctggcggc                                               20

<210> SEQ ID NO 334
<211> LENGTH: 20
<212> TYPE: DNA
<213> ORGANISM: Artificial Sequence
<220> FEATURE:
<223> OTHER INFORMATION: Synthetic sequence

<400> SEQUENCE: 334
cggtgacggt ttgcaacttt                                               20

<210> SEQ ID NO 335
<211> LENGTH: 20
<212> TYPE: DNA
<213> ORGANISM: Artificial Sequence
<220> FEATURE:
<223> OTHER INFORMATION: Synthetic sequence

<400> SEQUENCE: 335
```
gtccggcagt taagggtctc                                                   20

<210> SEQ ID NO 336
<211> LENGTH: 20
<212> TYPE: DNA
<213> ORGANISM: Artificial Sequence
<220> FEATURE:
<223> OTHER INFORMATION: Synthetic sequence

<400> SEQUENCE: 336
tactcacaaa cgactgcgca                                                   20

<210> SEQ ID NO 337
<211> LENGTH: 20
<212> TYPE: DNA
<213> ORGANISM: Artificial Sequence
<220> FEATURE:
<223> OTHER INFORMATION: Synthetic sequence

<400> SEQUENCE: 337
cgtatatggc cgactggagg                                                   20

<210> SEQ ID NO 338
<211> LENGTH: 20
<212> TYPE: DNA
<213> ORGANISM: Artificial Sequence
<220> FEATURE:
<223> OTHER INFORMATION: Synthetic sequence

<400> SEQUENCE: 338
tagggtttgc ggcgataagg                                                   20

<210> SEQ ID NO 339
<211> LENGTH: 20
<212> TYPE: DNA
<213> ORGANISM: Artificial Sequence
<220> FEATURE:
<223> OTHER INFORMATION: Synthetic sequence

<400> SEQUENCE: 339
ccaagtcaac cacccgagac                                                   20

<210> SEQ ID NO 340
<211> LENGTH: 20
<212> TYPE: DNA
<213> ORGANISM: Artificial Sequence
<220> FEATURE:
<223> OTHER INFORMATION: Synthetic sequence

<400> SEQUENCE: 340
acttccctgg ccttccttct                                                   20

<210> SEQ ID NO 341
<211> LENGTH: 20
<212> TYPE: DNA
<213> ORGANISM: Artificial Sequence
<220> FEATURE:
<223> OTHER INFORMATION: Synthetic sequence

<400> SEQUENCE: 341
gcttgggtcc tctcctgaac                                                   20

<210> SEQ ID NO 342
<211> LENGTH: 20
<212> TYPE: DNA

```
<213> ORGANISM: Artificial Sequence
<220> FEATURE:
<223> OTHER INFORMATION: Synthetic sequence

<400> SEQUENCE: 342
aacgtccgaa ccacaatgct                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic sequence

<400> SEQUENCE: 343
ctcctcgcat ccaacagtcg                                              20

<210> SEQ ID NO 344
<211> LENGTH: 20
<212> TYPE: DNA
<213> ORGANISM: Artificial Sequence
<220> FEATURE:
<223> OTHER INFORMATION: Synthetic sequence

<400> SEQUENCE: 344
ccaccgtagc actccttctt                                              20

<210> SEQ ID NO 345
<211> LENGTH: 20
<212> TYPE: DNA
<213> ORGANISM: Artificial Sequence
<220> FEATURE:
<223> OTHER INFORMATION: Synthetic sequence

<400> SEQUENCE: 345
cggagcgtcg gtagtgtaaa                                              20

<210> SEQ ID NO 346
<211> LENGTH: 20
<212> TYPE: DNA
<213> ORGANISM: Artificial Sequence
<220> FEATURE:
<223> OTHER INFORMATION: Synthetic sequence

<400> SEQUENCE: 346
acaactcgac gaacctaccg                                              20

<210> SEQ ID NO 347
<211> LENGTH: 20
<212> TYPE: DNA
<213> ORGANISM: Artificial Sequence
<220> FEATURE:
<223> OTHER INFORMATION: Synthetic sequence

<400> SEQUENCE: 347
tggcccatcc ttatgtgctg                                              20

<210> SEQ ID NO 348
<211> LENGTH: 20
<212> TYPE: DNA
<213> ORGANISM: Artificial Sequence
<220> FEATURE:
<223> OTHER INFORMATION: Synthetic sequence

<400> SEQUENCE: 348
ggtcgttatt gctcaagccc                                              20
```

```
<210> SEQ ID NO 349
<211> LENGTH: 20
<212> TYPE: DNA
<213> ORGANISM: Artificial Sequence
<220> FEATURE:
<223> OTHER INFORMATION: Synthetic sequence

<400> SEQUENCE: 349
ttgattctgg ccctcccatc                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic sequence

<400> SEQUENCE: 350
ctcacgccgg ctatttaggt                                              20

<210> SEQ ID NO 351
<211> LENGTH: 20
<212> TYPE: DNA
<213> ORGANISM: Artificial Sequence
<220> FEATURE:
<223> OTHER INFORMATION: Synthetic sequence

<400> SEQUENCE: 351
agtctgggta ggtggaggac                                              20

<210> SEQ ID NO 352
<211> LENGTH: 20
<212> TYPE: DNA
<213> ORGANISM: Artificial Sequence
<220> FEATURE:
<223> OTHER INFORMATION: Synthetic sequence

<400> SEQUENCE: 352
cgactgagcc acatccaact                                              20

<210> SEQ ID NO 353
<211> LENGTH: 20
<212> TYPE: DNA
<213> ORGANISM: Artificial Sequence
<220> FEATURE:
<223> OTHER INFORMATION: Synthetic sequence

<400> SEQUENCE: 353
gagcctcagc cggaattgaa                                              20

<210> SEQ ID NO 354
<211> LENGTH: 20
<212> TYPE: DNA
<213> ORGANISM: Artificial Sequence
<220> FEATURE:
<223> OTHER INFORMATION: Synthetic sequence

<400> SEQUENCE: 354
ttgccattct gcaccaatgc                                              20

<210> SEQ ID NO 355
<211> LENGTH: 20
<212> TYPE: DNA
<213> ORGANISM: Artificial Sequence
<220> FEATURE:
```

<223> OTHER INFORMATION: Synthetic sequence

<400> SEQUENCE: 355
tattggtgtt cgcggctgat                                            20

<210> SEQ ID NO 356
<211> LENGTH: 20
<212> TYPE: DNA
<213> ORGANISM: Artificial Sequence
<220> FEATURE:
<223> OTHER INFORMATION: Synthetic sequence

<400> SEQUENCE: 356
atgggcgtaa caggaggact                                            20

<210> SEQ ID NO 357
<211> LENGTH: 20
<212> TYPE: DNA
<213> ORGANISM: Artificial Sequence
<220> FEATURE:
<223> OTHER INFORMATION: Synthetic sequence

<400> SEQUENCE: 357
ggaatggcct acctgcatca                                            20

<210> SEQ ID NO 358
<211> LENGTH: 20
<212> TYPE: DNA
<213> ORGANISM: Artificial Sequence
<220> FEATURE:
<223> OTHER INFORMATION: Synthetic sequence

<400> SEQUENCE: 358
cccgttgttg tcatcgcatc                                            20

<210> SEQ ID NO 359
<211> LENGTH: 20
<212> TYPE: DNA
<213> ORGANISM: Artificial Sequence
<220> FEATURE:
<223> OTHER INFORMATION: Synthetic sequence

<400> SEQUENCE: 359
gttcgatgcg tcccatgagt                                            20

<210> SEQ ID NO 360
<211> LENGTH: 20
<212> TYPE: DNA
<213> ORGANISM: Artificial Sequence
<220> FEATURE:
<223> OTHER INFORMATION: Synthetic sequence

<400> SEQUENCE: 360
caacccgcgt agatgttcct                                            20

<210> SEQ ID NO 361
<211> LENGTH: 20
<212> TYPE: DNA
<213> ORGANISM: Artificial Sequence
<220> FEATURE:
<223> OTHER INFORMATION: Synthetic sequence

<400> SEQUENCE: 361
gccagctcaa gagtgtagcc                                            20

<210> SEQ ID NO 362
<211> LENGTH: 20
<212> TYPE: DNA
<213> ORGANISM: Artificial Sequence
<220> FEATURE:
<223> OTHER INFORMATION: Synthetic sequence

<400> SEQUENCE: 362
ttcttgatcc tgcgcgatgt                                          20

<210> SEQ ID NO 363
<211> LENGTH: 20
<212> TYPE: DNA
<213> ORGANISM: Artificial Sequence
<220> FEATURE:
<223> OTHER INFORMATION: Synthetic sequence

<400> SEQUENCE: 363
atcgcaggcg ttccctatac                                          20

<210> SEQ ID NO 364
<211> LENGTH: 20
<212> TYPE: DNA
<213> ORGANISM: Artificial Sequence
<220> FEATURE:
<223> OTHER INFORMATION: Synthetic sequence

<400> SEQUENCE: 364
tattggacct ccgaccacga                                          20

<210> SEQ ID NO 365
<211> LENGTH: 20
<212> TYPE: DNA
<213> ORGANISM: Artificial Sequence
<220> FEATURE:
<223> OTHER INFORMATION: Synthetic sequence

<400> SEQUENCE: 365
agccaccatt tagatccgcg                                          20

<210> SEQ ID NO 366
<211> LENGTH: 20
<212> TYPE: DNA
<213> ORGANISM: Artificial Sequence
<220> FEATURE:
<223> OTHER INFORMATION: Synthetic sequence

<400> SEQUENCE: 366
gaccagtaga agtctgcccg                                          20

<210> SEQ ID NO 367
<211> LENGTH: 20
<212> TYPE: DNA
<213> ORGANISM: Artificial Sequence
<220> FEATURE:
<223> OTHER INFORMATION: Synthetic sequence

<400> SEQUENCE: 367
tttcagaatg gccgagctgt                                          20

<210> SEQ ID NO 368
<211> LENGTH: 20
<212> TYPE: DNA
<213> ORGANISM: Artificial Sequence
<220> FEATURE:
<223> OTHER INFORMATION: Synthetic sequence

```
<400> SEQUENCE: 368
aggtgacctt cttgtacgcc                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic sequence

<400> SEQUENCE: 369
ggcgcgtcct tatttccatc                                              20
```

ASSAYS FOR SINGLE MOLECULE DETECTION AND USE THEREOF

BACKGROUND OF THE INVENTION

Sequence Listing Submission Via EFS-Web

A computer readable text file, entitled "SequenceListing.txt" created on or about Aug. 8, 2017, with a file size of about 72 kb contains the sequence listing for this application and is hereby incorporated by reference in its entirety.

The invention relates to methods of detecting a genetic variation in a genetic sample from a subject. Detecting a genetic variation is important in many aspects of human biology.

SUMMARY

The invention relates to methods of detecting a genetic variation in a genetic sample from a subject. The invention further relates to methods of detecting a genetic variation in a genetic sample from a subject using labeled probes and counting the number of labels in the probes.

BRIEF DESCRIPTION OF THE DRAWINGS

FIGS. 21-46 depict exemplary probe sets described herein.

DETAILED DESCRIPTION OF THE INVENTION

Figure 1:
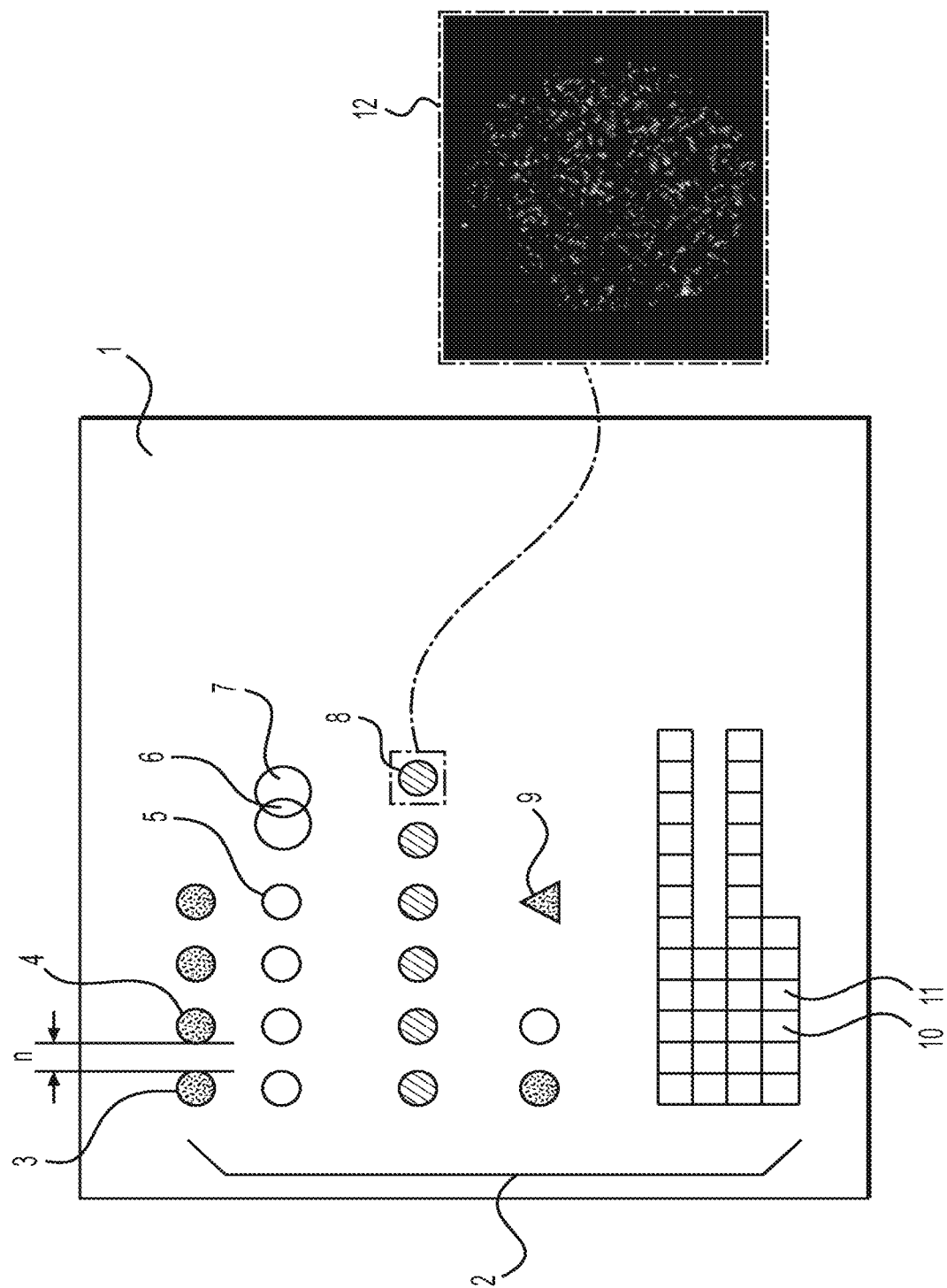
FIG. 1 depicts exemplary array members comprising binding partners, tags, affinity tags, tagging probes, probe sets, and/or litigated probe sets described herein on a substrate.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found, for example, in Kimmel and Oliver, DNA Microarrays (2006) Elsevier; Campbell, DNA Microarray, Synthesis and Synthetic DNA (2012) Nova Science; Bowtell and Sambrook, DNA Microarrays: Molecular Cloning Manual (2003) Cold Spring Harbor Laboratory Press. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

The invention relates to methods of detecting a genetic variation in a genetic sample from a subject. The genetic variation herein may include, but is not limited to, one or more substitution, inversion, insertion, deletion, or mutation in nucleotide sequences (e.g., DNA and RNA) and proteins (e.g., peptide and protein), one or more rare allele, polymorphism, single nucleotide polymorphism (SNP), large-scale genetic polymorphism, such as inversions and translocations, differences in the abundance and/or copy number (e.g., copy number variants, CNVs) of one or more nucleotide molecules (e.g., DNA), trisomy, monosomy, and genomic rearrangements. In some embodiments, the genetic variation may be related to metastasis, presence, absence, and/or risk of a disease, such as cancer, pharmacokinetic variability, drug toxicity, adverse events, recurrence, and/or presence, absence, or risk of organ transplant rejection in the subject. For example, copy number changes in the HER2 gene affect whether a breast cancer patient will respond to Herceptin treatment or not. Similarly, detecting an increase in copy number of chromosome 21 (or 18, or 13, or sex chromosomes) in blood from a pregnant woman may be used to as a non-invasive diagnostic for Down's Syndrome in an unborn child. An additional example is the detection of alleles from a transplanted organ that are not present in the recipient genome—monitoring the frequency, or copy number, of these alleles may identify signs of potential organ rejection. Various methods may be used to detect such changes (e.g., rtPCR, sequencing and microarrays). One of the methods is to count individual, labeled molecules to either detect the presence of a mutation (e.g., EGFR mutation in cancer) or an excess of a specific genomic sequence or region (e.g., Chromosome 21 in Down's Syndrome). Counting single molecules may be done in a number of ways, with a common readout being to deposit the molecules on a surface and image.

Moreover, the genetic variation may be de novo genetic mutations, such as single- or multi-base mutations, translocations, subchromosomal amplifications and deletions, and aneuploidy. In some embodiments, the genetic variation may mean an alternative nucleotide sequence at a genetic locus that may be present in a population of individuals and that includes nucleotide substitutions, insertions, and deletions with respect to other members of the population. In additional embodiments, the genetic variation may be aneuploidy. In yet additional embodiments, the genetic variation may be trisomy 13, trisomy 18, trisomy 21, aneuploidy of X (e.g., trisomy XXX and trisomy XXY), or aneuploidy of Y (e.g., trisomy XYY). In further embodiments, the genetic variation may be in region 22q11.2, 1q21.1, 9q34, 1p36, 4p, 5p, 7q11.23, 11q24.1, 17p, 11p15, 18q, or 22q13. In further embodiments, the genetic variation may be a microdeletion or microamplification.

In some embodiments, detecting, discovering, determining, measuring, evaluating, counting, and assessing the genetic variation are used interchangeably and include quantitative and/or qualitative determinations, including, for example, identifying the genetic variation, determining presence and/or absence of the genetic variation, and quantifying the genetic variation. In further embodiments, the methods of the present disclosure may detect multiple genetic variations. The term "and/or" used herein is defined to indicate any combination of the components. Moreover, the singular forms "a," "an," and "the" may further include plural referents unless the context clearly dictates otherwise. Thus, for example, reference to "a nucleotide region" refers to one, more than one, or mixtures of such regions, and reference to "an assay" may include reference to equivalent steps and methods known to those skilled in the art, and so forth.

"Sample" means a quantity of material from a biological, environmental, medical, or patient source in which detection, measurement, or labeling of target nucleic acids, peptides, and/or proteins is sought. On the one hand it is meant to include a specimen or culture (e.g., microbiological cultures). On the other hand, it is meant to include both biological and environmental samples. A sample may include a specimen of synthetic origin. Environmental samples include environmental material, such as surface matter, soil, water and industrial samples, as well as samples obtained from food and dairy processing instruments, apparatus, equipment, utensils, disposable and non-disposable items. "Genetic sample" may be any liquid or solid sample with heritable and/or non-heritable biological information coded in the nucleotide sequences of nucleic acids. The sample may be obtained from a source, including, but not limited to, whole blood, serum, plasma, urine, saliva, sweat, fecal matter, tears, intestinal fluid, mucous membrane samples, lung tissue, tumors, transplanted organs, fetus, and/or other sources. Genetic samples may be from an animal, including human, fluid, solid (e.g., stool) or tissue. Genetic samples may include materials taken from a patient including, but not limited to cultures, blood, saliva, cerebral spinal fluid, pleural fluid, milk, lymph, sputum, semen, needle aspirates, and the like. Moreover, the genetic sample may be a fetal genetic material from a maternal blood sample. The fetal genetic material may be isolated and separated from the maternal blood sample. The genetic sample may be a mixture of fetal and maternal genetic material. In addition, the genetic sample may include aberrant genetic sequences arising from tumor formation or metastasis, and/or donor DNA signatures present in a transplant recipient. In additional embodiments, when the genetic sample is plasma, the method may comprise isolating the plasma from a blood sample of the subject. In further embodiments, when genetic sample is serum, the method may comprise isolating the serum from a blood sample of the subject. In yet additional embodiments, when the genetic sample is a cell free DNA (cfDNA) sample, the method further comprises isolating the cell free DNA sample from a sample obtained from the source described herein. The cell free DNA sample herein means a population of DNA molecules circulating freely in the bloodstream, outside of any cell or organelle. In the case of a pregnancy, cell free DNA from the mother carries a mixture of both maternal DNA as well as fetal DNA. These examples are not to be construed as limiting the sample types applicable to the present invention.

In some embodiments, the method of the present disclosure may comprise selecting and/or isolating genetic locus or loci of interest, and quantifying the amount of each locus present (for example for determining copy number) and/or the relative amounts of different locus variants (for example two alleles of a given DNA sequence). Region, region of interest, locus, or locus of interest in reference to a genome or target polynucleotide used herein means a contiguous sub-region or segment of the genome or target polynucleotide. As used herein, region, regions or interest, locus, locus, or locus of interest in a nucleotide molecule may refer to the position of a nucleotide, a gene or a portion of a gene in a genome, including mitochondrial DNA or other non-chromosomal DNA, or it may refer to any contiguous portion of genomic sequence whether or not it is within, or associated with, a gene. A region, region of interest, locus, locus, or locus of interest in a nucleotide molecule may be from a single nucleotide to a segment of a few hundred or a few thousand nucleotides in length or more. In some embodiments, a region or locus of interest may have a reference sequence associated with it. "Reference sequence" used herein denotes a sequence to which a locus of interest in a nucleic acid is being compared. In certain embodiments, a reference sequence is considered a "wild type" sequence for a locus of interest. A nucleic acid that contains a locus of interest having a sequence that varies from a reference sequence for the locus of interest is sometimes referred to as "polymorphic" or "mutant" or "genetic variation." A nucleic acid that contains a locus of interest having a sequence that does not vary from a reference sequence for the locus of interest is sometimes referred to as "non-polymorphic" or "wild type" or "non-genetic variation." In certain embodiments, a locus of interest may have more than one distinct reference sequence associated with it (e.g., where a locus of interest is known to have a polymorphism that is to be considered a normal or wild type). In some embodiments, the method of the present disclosure may also comprise electing and/or isolating peptide or peptides of interest, and qualifying the amount of each peptide present and/or relative amounts of different peptides.

In additional embodiments, the region of interest described herein may include "consensus genetic variant sequence" which refers to the nucleic acid or protein sequence, the nucleic or amino acids of which are known to occur with high frequency in a population of individuals who carry the gene which codes for a protein not functioning normally, or in which the nucleic acid itself does not function normally. Moreover, the region of interest described herein may include "consensus normal gene sequence" which refers to a nucleic acid sequence, the nucleic acid of which are known to occur at their respective positions with high frequency in a population of individuals who carry the gene which codes for a protein not functioning normally, or which itself does not function normally. In further embodiments, the control region that is not the region of interest or the reference sequence described herein may include "consensus normal sequence" which refers to the nucleic acid or protein sequence, the nucleic or amino acids of which are known to occur with high frequency in a population of individuals who carry the gene which codes for a normally functioning protein, or in which the nucleic acid itself has normal function.

The methods described herein may produce highly accurate measurements of genetic variation. One type of variation described herein includes the relative abundance of two or more distinct genomic loci. In this case, the loci may be small (e.g., as small as about 300, 250, 200, 150, 100, or 50 nucleotides or less), moderate in size (e.g., from 1,000, 10,000, 100,000 or one million nucleotides), and as large as a portion of a chromosome arm or the entire chromosome or sets of chromosomes. The results of this method may determine the abundance of one locus to another. The precision and accuracy of the methods of the present disclosure may enable the detection of very small changes in copy number (as low as about 25, 10, 5, 4, 3, 2, 1, 0.5, 0.1, 0.05, 0.02 or 0.01% or less), which enables identification of a very dilute signature of genetic variation. For Example, a signature of fetal aneuploidy may be found in a maternal blood sample where the fetal genetic aberration is diluted by the maternal blood, and an observable copy number of change of about 2% is indicative of fetal trisomy.

As used herein, the term "about" means modifying, for example, lengths of nucleotide sequences, degrees of errors, dimensions, the quantity of an ingredient in a composition, concentrations, volumes, process temperature, process time, yields, flow rates, pressures, and like values, and ranges thereof, refers to variation in the numerical quantity that may occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 50, 25, 10, 9, 8, 7, 6, 5, 4, 3, 2, 1 percent or less of the stated reference value.

In some embodiments, the subject may be a pregnant subject, human, a subject with a high risk of a genetic disease (e.g., cancer), all of the various families of domestic animals, as well as feral or wild animals. In some embodiments, the genetic variation may be a genetic variation in the fetus of the pregnant subject (e.g., copy number variants and aneuploidy in the fetus). In some embodiments, the subject is a pregnant subject, and the genetic variation is a variation in the fetus of the pregnant subject in a region selected from the group consisting of 22q11.2, 1q21.1, 9q34, 1p36, 4p, 5p, 7q11.23, 11q24.1, 17p, 11p15, 18q, and 22q13, (e.g., a mutation and/or copy number change in any of regions 22q11.2, 1q21.1, 9q34, 1p36, 4p, 5p, 7q11.23, 11q24.1, 17p, 11p15, 18q, and 22q13). Fetus described herein means an unborn offspring of a human or other animal. In some embodiments, the fetus may be the offspring more than 1, 2, 3, 4, 5, 6, 7, 8, 9, 10, 11, 12, 13, 14, 15, 16, 17, 18, 19, 20 weeks after conception. In additional embodiments, the fetus may be an offspring conceived by implants, in vitro fertilization, multiple pregnancies, or twinning. In additional embodiments, the fetus may be part of a pair of twins (identical or non-identical), or a trio of triplets (identical or non-identical)

The inventions according to some embodiments encompass at least two major components: an assay for the selective identification of genomic loci, and a technology for quantifying these loci with high accuracy. The assay may include methods of selectively labeling and/or isolating one or more nucleic acid sequences, in such a manner that the labeling step itself is sufficient to yield molecules (defined as "probe products," "ligated probe set," "conjugated probe set," "ligated probes," "conjugated probes," or "labeled molecules" in this invention) containing all necessary information for identification of a particular sequence in the context of a particular assay. For example, the assay may comprise contacting, binding, and/or hybridizing probes to a sample, ligating and/or conjugating the probes, optionally amplifying the ligated/conjugated probes, and immobilizing the probes to a substrate. In some embodiments, the assays and methods described herein may be performed on a single input sample in parallel as a multiplex assay as described herein The probe product, ligated probe set, conjugated probe set, ligated probes, conjugated probes, and labeled molecules may be single, contiguous molecule resulting from the performance of enzymatic action on a probe set, such as an assay. In a probe product or a labeled molecule, one or more individual probes from a probe set may be covalently modified such that they form a singular distinct molecular species as compared to either probes or probe sets. As a result, probe products or a labeled molecule may be chemically distinct and may therefore be identified, counted, isolated, or further manipulated apart from probes or probe sets.

For example, probe products may contain one or more identification labels, and one or more affinity tags for isolation and/or immobilization. In some embodiments, no additional modifications of probe products (e.g., DNA sequence determination) need to be performed. In some embodiments, no additional interrogations of the DNA sequence are required. The probe products containing the labels may be directly counted, typically after an immobilization step onto a solid substrate. For example, organic fluorophore labels are used to label probe products, and the probe products are directly counted by immobilizing the probe products to a glass substrate and subsequent imaging via a fluorescent microscope and a digital camera. In other embodiments, the label may be selectively quenched or removed depending on whether the labeled molecule has interacted with its complementary genomic locus. In additional embodiments, two labels on opposite portions of the probe product may work in concert to deliver a fluorescence resonance energy transfer (FRET) signal depending on whether the labeled molecule has interacted with its complementary genomic locus. For a given genomic locus, labeling probes containing the labels be designed for any sequence region within that locus. A set of multiple labeling probes with same or different labels may also be designed for a single genomic locus. In this case, a probe may selectively isolate and label a different region within a particular locus, or overlapping regions within a locus. In some embodiments, the probe products containing affinity tags are immobilized onto the substrate via the affinity tags. For example, affinity tags are used to immobilize probe products onto the substrate, and the probe products containing the affinity tags are directly counted. For a given genomic locus, tagging probes containing the affinity tags be designed for any sequence region within that locus. A set of multiple tagging probes with same or different affinity tags may also be designed for a single genomic locus. In this case, a probe may selectively isolate and tag a different region within a particular locus, or overlapping regions within a locus.

In one aspect, the methods of the present disclosure may comprise contacting probe sets described herein with the genetic sample described herein. In some embodiments, the methods of the present disclosure may comprise contacting multiple probe sets, such as first and second probe sets, to the genetic sample. In additional embodiments, each of the probe sets comprises a labeling probe and a tagging probe. For example, the first probe set comprises a first labeling probe and a first tagging probe, and the second probe set comprises a second labeling probe and a second tagging probe.

Contacting the probe sets to the genetic sample may be performed simultaneously or after hybridizing, ligating, amplifying and/or immobilizing the probes. Moreover, contacting the probe sets to the genetic sample may be performed simultaneously or before hybridizing, ligating, amplifying, and/or immobilizing the probes.

For a given genomic locus or region of a nucleotide molecule in the genetic sample, a single nucleic acid sequence within that locus, or multiple nucleic acid sequences within that locus may be interrogated and/or quantified via the creation of probe products. The interrogated sequences within a genomic locus may be distinct and/or overlapping, and may or may not contain genetic polymorphisms. A probe product is formed by the design of one or more oligonucleotides called a "probe set." For example, the probe product may be formed by ligating the probe set by ligating the probes in the probe set. A probe set comprises at least one probe that hybridize, conjugate, bind, or immobilize to a target molecule, including nucleic acids (e.g., DNA and RNA), peptides, and proteins. In some embodiments, a probe may comprise an isolated, purified, naturally-occurring, non-naturally occurring, and/or artificial material, for example, including oligonucleotides of any length (e.g., 5, 10, 20, 30, 40, 50, 100, or 150 nucleotides or less), in which at least a portion(s) (e.g., 50, 60, 70, 80, 85, 90, 91, 92, 93, 94, 95, 96, 97, 98, 99, or 100%) of the oligonucleotide sequences is complementary to a sequence motif and/or hybridization domain present in one or more target molecules, such that the probe is configured to hybridize (or interact in a similar manner) in part or in total to one or more target molecules or nucleic acid region of interest. The part of the target molecule or the nucleic acid region of interest to which a probe hybridizes is called the probe's "hybridization domain," which may be in part or in total of the target molecule or the nucleic acid region of interest as described herein.

A probe may be single-stranded or double-stranded. In some embodiments, the probe may be prepared from in a purified restriction digest or produced synthetically, recombinantly or by PCR amplification. In additional embodiments, the probe may comprise a material that binds to a particular peptide sequence. A probe set described herein may comprise a set of one or more probes designed to correspond to a single genomic location or a peptide in a protein sequence.

"Nucleotide" used herein means either a deoxyribonucleotide or a ribonucleotide or any nucleotide analogue (e.g., DNA and RNA). Nucleotide analogues include nucleotides having modifications in the chemical structure of the base, sugar and/or phosphate, including, but not limited to, 5'-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, $NH_2$, NHR, $NR_2$, or CN. shRNAs also may comprise non-natural elements such as non-natural nucleotides, e.g., ionosin and xanthine, non-natural sugars, e.g., 2'-methoxy ribose, or non-natural phosphodiester linkages, e.g., methylphosphonates, phosphorothioates and peptides. In one embodiment, the shRNA further comprises an element or a modification that renders the shRNA resistant to nuclease digestion. "Polynucleotide" or "oligonucleotide" is used interchangeably and each means a linear polymer of nucleotide monomers. Monomers making up polynucleotides and oligonucleotides are capable of specifically binding to a natural and/or artificial polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogues thereof, e.g., naturally occurring or non-naturally occurring analogues. Non-naturally occurring analogues may include PNAs, LNAs, phosphorothioate internucleosidic linkages, nucleotides containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogues of internucleosidic linkages, sugar moieties, or nucleotides at any or some positions. Polynucleotides typically range in size from a few monomeric units when they are referred to as "oligonucleotides" to several thousand monomeric units. Whenever a polynucleotide or oligonucleotide is represented by a sequence of letters (upper or lower case), such as "ATGCCTG," it will be understood that the nucleotides are in 5'→3' order from left to right. Usually polynucleotides comprise the four natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogues, e.g., including modified nucleotides, sugars, or internucleosidic linkages. It is clear to those skilled in the art that where an enzyme has specific oligonucleotide or polynucleotide substrate requirements for activity, e.g., single stranded DNA, RNA, RNA/DNA duplex, or the like, then selection of appropriate composition for the oligonucleotide or polynucleotide substrates is well within the knowledge of one of ordinary skill.

In another aspect, the methods of the present disclosure may comprise hybridizing at least parts of the first and second probe sets to first and second nucleic acid regions of interest in nucleotide molecules of the genetic sample, respectively. The hybridization of the probes to the nucleic acid of interest may be performed simultaneously or after contacting the probes to the genetic sample, ligating, amplifying and/or immobilizing the probes. Moreover, the hybridization of the probes to the nucleic acid of interest may be performed simultaneously or before ligating, amplifying, and/or immobilizing the probes. A part or full part of the probe may hybridize to a part or full part of the region of interest in single or double stranded nucleotide molecules, protein, or antibody in a sample. The region of interest hybridized to the probe may be from 1 to 50 nucleotides, 50 to 1000 nucleotides, 100 to 500 nucleotides, 5, 10, 50, 100, 200 nucleotides or less, or 2, 5, 10, 50, 100, 200, 500, 1000 nucleotides or more. Probes may be designed or configured to hybridize perfectly with a target region or molecule, or they may be designed such that a single-base mismatch (e.g., at a single nucleotide polymorphism, or SNP site), or a small number of such mismatches, fails to yield a hybrid of probe and target molecule.

In additional embodiments, the first labeling probe and/or the first tagging probe are hybridized to the first nucleic acid region of interest, and the second labeling probe and/or the second tagging probes are hybridized to the second nucleic acid region of interest. In additional embodiments, multiple or all probes and/or other components (e.g., labelling probes, tagging probes, and gap probes) of a probe set that are hybridized to a nucleic acid region of interest are adjacent to each other. When two of the probes and/or components hybridized to the nucleic acid region of interest are "adjacent" or "immediately adjacent," there is no nucleotide between the hybridization domains of the two probes in the nucleic acid region of interest. In this embodiment, the different probes within a probe set may be covalently ligated together to form a larger oligonucleotide molecule. In another embodiment, a probe set may be designed to hybridize to a non-contiguous, but proximal, portion of the nucleic acid region of interest, such that there is a "gap" of one or more nucleotides on the nucleic acid region of interest, in between hybridized probes from a probe set, that is not occupied by a probe. In this embodiment, a DNA polymerase or another enzyme may be used to synthesize a new polynucleotide sequence, in some cases covalently joining two probes from a single probe set. Within a probe set, any probe may bear one or more labels, or affinity tags used for either locus identification or isolation. In one aspect, the first and second labeling probes are hybridized to the first and second nucleic acid regions of interest in nucleotide molecules of the genetic sample, respectively; the first and second tagging probes are hybridized to the first and second nucleic acid regions of interest in nucleotide molecules of the genetic sample, respectively; the first labeling probe is hybridized to a region adjacent to where the first tagging probe is hybridized; and the second labeling probe is hybridized to a region adjacent to where the second tagging probe is hybridized.

The hybridization occurs in such a manner that the probes within a probe set may be modified to form a new, larger molecular entity (e.g., a probe product). The probes herein may hybridize to the nucleic acid regions of interest under stringent conditions. As used herein the term "stringency" is used in reference to the conditions of temperature, ionic strength, and the presence of other compounds such as organic solvents, under which nucleic acid hybridizations are conducted. "Stringency" typically occurs in a range from about $T_m$° C. to about 20° C. to 25° C. below $T_m$. A stringent hybridization may be used to isolate and detect identical polynucleotide sequences or to isolate and detect similar or related polynucleotide sequences. Under "stringent conditions" the nucleotide sequence, in its entirety or portions thereof, will hybridize to its exact complement and closely related sequences. Low stringency conditions comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400), 5 g BSA) and 100 µg/ml denatured salmon sperm DNA followed by washing in a solution comprising 2.0+SSPE, 0.1% SDS at room temperature when a probe of about 100 to about 1000 nucleotides in length is employed. It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5+SSPE, 1% SDS, 5×Denhardt's reagent and 100 µg/ml denatured salmon sperm DNA followed by washing in a solution comprising 0.1+SSPE and 0.1% SDS at 68° C. when a probe of about 100 to about 1000 nucleotides in length is employed.

In some embodiments, the probe product may be formed only if the probes within a probe set are correctly hybridized. Therefore, the probe products may be formed with high stringency and high accuracy. Again, the probe products may contain sufficient information for identifying the genomic sequence for which the probe product was designed to interrogate. Therefore, generation and direct quantification of a particular probe product (in this case, by molecular counting) may reflect the abundance of a particular genetic sequence in the originating sample.

In additional embodiments, the nucleic acid regions of interest, to which the probes are configured to hybridize to, are located in different chromosomes. For example, the first nucleic acid region of interest is located in chromosome 21, and the second nucleic acid region of interest is not located in chromosome 21 (e.g., located in chromosome 18).

In another aspect, the methods of the present disclosure may comprise ligating the first labeling probe and the first tagging probe, and ligating the second labeling probe and the second tagging probe. The ligation of the probes may be performed simultaneously or after contacting the probes to the genetic sample, amplifying and/or immobilizing the probes. Moreover, the ligation of the probes may be performed simultaneously or before contacting the probes to the genetic sample, amplifying, and/or immobilizing the probes. The ligation herein means the process of joining two probes (e.g., joining two nucleotide molecules) together. For example, ligation herein may involve the formation of a 3',5'-phosphodiester bond that links two nucleotides, and a joining agent that is an agent capable of causing ligation may be an enzyme or a chemical.

In another aspect, the methods of the present disclosure may comprise amplifying the ligated probes and/or ligated probe sets. The amplification of the ligated probes may be performed simultaneously or after contacting the probes to the genetic sample, ligating, hybridizing and/or immobilizing the probes. Moreover, the amplification of the ligated probes may be performed simultaneously or before immobilizing the probes. Amplification herein is defined as the production of additional copies of the probe and/or probe product and may be carried out using polymerase chain reaction technologies well known in the art. As used herein, the term "polymerase chain reaction" ("PCR") refers to a method for increasing the concentration of a segment of a target sequence (e.g., in a mixture of genomic DNA) without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (e.g., hybridization with a labeled probe). In addition to genomic DNA, any oligonucleotide sequence may be amplified with the appropriate set of primer molecules. In particular, the amplified segments created by the PCR process itself are, themselves, efficient templates for subsequent PCR amplifications. An amplification may be a "real-time" amplification if a detection chemistry is available that permits a reaction product to be measured as the amplification reaction progresses, e.g., "real-time PCR," or "real-time NASBA" as described in Leone et al, Nucleic Acids Research, 26: 2150-2155 (1998).

Primers are usually single-stranded for maximum efficiency in amplification, but may alternatively be double-stranded. If double-stranded, the primer is usually first treated to separate its strands before being used to prepare extension products. This denaturation step is typically influenced by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded nucleotides linked at its 3' end complementary to the template in the process of DNA synthesis.

A "primer pair" as used herein refers to a forward primer and a corresponding reverse primer, having nucleic acid sequences suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer may be designed as a "forward primer" (which initiates nucleic acid synthesis from a 5'-end of the target nucleic acid) or as a "reverse primer" (which initiates nucleic acid synthesis from a 5'-end of the extension product produced from synthesis initiated from the forward primer). Likewise, the second primer may be designed as a forward primer or a reverse primer.

In some embodiments, the nucleic acid region of interest in the nucleotide molecule herein may be amplified by the amplification methods described herein. The nucleic acids in a sample may or may not be amplified prior to analysis, using a universal amplification method (e.g., whole genome amplification and whole genome PCR). The amplification of the nucleic acid region of interest may be performed simultaneously or after contacting the probes to the genetic sample, ligating, amplifying and/or immobilizing the probes. Moreover, the amplification of the ligated probes may be performed simultaneously or before contacting the probes to the genetic sample, ligating the probes, immobilizing the probes, and/or counting the labels.

In additional embodiments, the method excludes amplification of the nucleotide molecules of the genetic sample after the hybridization or the ligation. In further embodiments, the method excludes amplification of the nucleotide molecules of the genetic sample after the hybridization and the ligation.

In another aspect, the methods of the present disclosure may comprise immobilizing the tagging probes to a predetermined location on a substrate. The immobilization of the probe to a substrate may be performed simultaneously or after contacting the probes to the genetic sample, hybridizing the probes to the nucleic acid region of interest, ligating and/or amplifying the probes. Moreover, the immobilization of the probe to a substrate may be performed simultaneously or before contacting the probes to the genetic sample, hybridizing the probes to the nucleic acid region of interest, ligating, amplifying and/or counting the probes. Immobilization herein means directly or indirectly binding the tagging probes to the pre-determined location on the substrate by a physical or chemical bond. In some embodiments, the substrate herein may comprise a binding partner that is configured to contact and bind to a part or full tag in the tagging probe described herein and immobilize the tag and thus the tagging probe comprising the tag. The tag of the tagging probe may comprise a corresponding binding partner of the binding partner on the substrate as described herein.

Immobilization may be performed by hybridizing a part or full tagging probe to a part or full binding partner on the substrate. For example, the immobilizing step comprises hybridizing at least a part of the tag or tagging nucleotide sequence to a corresponding nucleotide molecule immobilized on the substrate. Here, the corresponding nucleotide molecule is a binding partner of the tag or tagging nucleotide sequence that is configured to hybridize partially or fully to the tag or tagging nucleotide sequence. In some embodiments, the oligonucleotide or polynucleotide binding partners may be single stranded and may be covalently attached to the substrate, for example, by 5'-end or a 3'-end. Immobilization may also be performed by the following exemplary binding partners and binding means: Biotin-oligonucleotide complexed with Avidin, Strepatavidin or Neutravidin; SH-oligonucleotide covalently linked via a disulphide bond to a SH-surface; Amine-oligonucleotide covalently linked to an activated carboxylate or an aldehyde group; Phenylboronic acid (PBA)-oligonucleotide complexed with salicylhydroxamic acid (SHA); Acrydite-oligonucleotide reacted with thiol or silane surface or co-polyemerized with acrylamide monomer to form polyacrylamide, or by other methods known in the art. For some applications where it is preferable to have a charged surface, surface layers may be composed of a polyelectrolyte multilayer (PEM) structure as shown in U.S. Patent Application Publication No. 2002/025529. In some embodiments, the immobilization may be performed by well-known procedures, for example, comprising contacting the probes with the support having binding partners attached for a certain period of time, and after the probes are depleted for the extension, the support with the immobilized extension products is optionally rinsed using a suitable liquid. In additional embodiments, immobilizing probe products onto a substrate may allow for rigorous washing for removing components from the biological sample and the assay, thus reducing background noise and improving accuracy.

"Solid support," "support," "substrate," and "solid phase support" are used interchangeably and refer to a material or group of materials having a rigid or semi-rigid surface or surfaces. In some embodiments, at least one surface of the substrate will be substantially flat, although in some embodiments it may be desirable to physically separate synthesis regions for different compounds with, for example, wells, raised regions, pins, etched trenches, or the like. In additional embodiments, the substrate may comprise at least one planar solid phase support (e.g., a glass microscope slide). According to other embodiments, the substrate(s) will take the form of beads, resins, gels, microspheres, or other geometric configurations. In one aspect, the substrate according to some embodiments of the present disclosure excludes beads, resins, gels, and/or microspheres.

In some embodiments, as shown in FIG. 1, the binding partners, the tags, the affinity tags, labels, the probes (e.g., tagging probes and labeling probes), and/or the probe sets described herein may be immobilized on a substrate (1) as an array (2). The array herein has multiple members (3-10) that may or may not have an overlap (6) between the members. Each member may have at least an area with no overlap with another member (3-5 and 7-10). In additional embodiments, each member may have different shapes (e.g., circular spots (3-8), triangles (9), and squares (10)) and dimensions. A member of an array may have an area about from 1 to $10^7$ micron$^2$, from 100 to $10^7$ micron$^2$, from $10^3$ to $10^8$ micron$^2$, from $10^4$ to $10^7$ micron$^2$; from $10^5$ to $10^7$ micron$^2$; about 0.0001, 0.001, 0.01, 0.1, 1, 10, 100, $10^3$, $10^4$, $10^5$, $10^6$, $10^7$, $10^8$ or more micron$^2$; and/or about 0.001, 0.01, 0.1, 1, 10, 100, $10^3$, $10^4$, $10^5$, $10^6$, $10^7$, $10^8$ or less micron$^2$. An image of an exemplary member (8) according to some embodiments of the present invention is shown as item 12. Moreover, two or more members comprising the binding partners, the tags, the affinity tags, labels, the probes (e.g., tagging probes and labeling probes), and/or the probe sets of the same type may have the same shape and dimension. Specifically, the members of an array comprising the binding partners, tags, affinity tags, labels, tagging probes and/or probe sets configured or used to detect the same genetic variation or a control according to the methods described herein may have the same shapes and dimensions. Further, each and every member of the arrays on the substrate may have the same shapes and dimensions. In other embodiments, the members of an array comprising the binding partners, tags, affinity tags, labels, probes and/or probe sets configured or used to detect different genetic variations and/or controls according to the methods described herein may have the same shapes and dimensions. In addition, each member of the array may comprise different binding partners, the tags, the affinity tags, labels, the probes, and/or the probe sets.

In some embodiments, two members of the array may be separated by (i) a distance, in which there may be no or only very few binding partners, the tags, the affinity tags, labels, the probes (e.g., tagging probes and labeling probes), and/or the probe sets immobilized, and/or (ii) any separator distinguishing one member from the other (e.g., heightened substrate, any material preventing binding of the binding partners, the tags, the affinity tags, the probes (e.g., tagging probes), and/or the probe sets to the substrate, and any non-probe material between the members). In additional embodiments, the members of the array may be distinguished from each other at least by their locations alone. The members of the array may be separated by a distance about from 0 to $10^4$ microns, from 0 to $10^3$ microns, from $10^2$ to $10^4$ microns, or from $10^2$ to $10^3$ microns; about 0, 0.001, 0.1, 1, 2, 3, 4, 5, 10, 50, 100, $10^3$, $10^4$, $10^5$, $10^6$, $10^7$, or $10^8$ microns or more; and/or about 0, 0.001, 0.1, 1, 2, 3, 4, 5, 10, 50, 100, $10^3$, $10^4$, $10^5$, $10^6$, $10^7$, or $10^8$ microns or less. Here, the distance by which two members of the array are separated may be determined by the shortest distance between the edges of the members. For example, in FIG. 1, the distance by which two members, items 3 and 4, of an array (2) are separated is the distance indicated by item n. Moreover, for example, the shortest distance by which the members of the array (2) on a substrate (1) are separated is 0, as the distance by which two members, items 10 and 11, of the array are separated. In other embodiments, two members of the array may not be separated and may be overlapped (6). In such embodiments, each member may have at least an area with no overlap with another member (7).

In further embodiments, an array and the members of the array of the binding partners, the tags, the affinity tags, labels, the probes, and/or the probe sets described herein may be located on predetermined locations on the substrate, and the shapes and dimensions of each member of the array and the distance between the members may be predetermined prior to the immobilization. The predetermined location herein means a location that is determined or identified prior to the immobilization. For example, the shape and dimension of each member of an array is determined or identified prior to the immobilization.

In additional embodiments, the substrate may comprise an array of binding partners, each member of the array comprising the binding partners, such as oligonucleotides or polynucleotides, that are immobilized (e.g., by a chemical bond that would be not broken during the hybridization of probes to the binding partners of the substrate described herein) to a spatially defined region or location; that is, the regions or locations are spatially discrete or separated by a defined region or location on the substrate. In further embodiments, the substrate may comprise an array, each member of which comprises binding partners binding to a spatially defined region or location. Each of the spatially defined locations configured to comprise the binding partners may additionally be "addressable" in that its location and the identity of its immobilized binding partners are known or predetermined, for example, prior to its use, analysis, or attaching to their binding partners in tagging probes and/or probe sets. The term "addressable" with respect to the probe sets immobilized to the substrate means that the nucleotide sequence or other physical and/or chemical characteristics of an end-attached part (e.g., a binding partner of the binding partner of the substrate, tag, affinity tag, and tagging probe) of a probe set described herein may be determined from its address, i.e., a one-to-one correspondence between the sequence or other property of the end-attached part of the probe set and a spatial location on, or characteristic of, the substrate to which the probe set is immobilized. For example, an address of an end-attached part of a probe set is a spatial location, e.g., the planar coordinates of a particular region immobilizing copies of the end-attached part of the probe set. However, end-attached parts of probe sets may be addressed in other ways too, e.g., by color, frequency of micro-transponder, or the like, e.g., Chandler et al, PCT publication WO 97/14028, which is herein incorporated by reference in their entirety for all purposes. In further embodiments, the methods described herein exclude "random microarray," which refers to a microarray whose spatially discrete regions of binding partners (e.g., oligonucleotides or polynucleotides) of the substrate and/or the end-attached parts of probe sets are not spatially addressed. That is, the identity of the attached binding partners, tag, affinity tag, tagging probe, and/or probe sets is not discernable, at least initially, from its location. In one aspect, the methods described herein exclude random microarrays that are planar arrays of microbeads.

An array of nucleic acid according to some embodiments of the present disclosure may be produced by any method well known in the art, including but not limited to those described in U.S. Patent Application Publication No. 2013/0172216, which is incorporated by reference in its entirety for all purpose; Schena, Microarrays: A Practical Approach (IRL Press, Oxford, 2000). For example, a DNA capture array may be used. The DNA capture array is a solid substrate (e.g., a glass slide) with localized oligonucleotides covalently attached to the surface. These oligonucleotides may have one or more types on the surface, and may further be segregated geographically across the substrate. Under hybridization conditions, DNA capture arrays will preferentially bind complementary targets compared to other non-specific moieties, thereby acting to both localize targets to the surface and separate them from un-desired species.

In some embodiments, the first and second labeling probes and/or the amplified labeling probes thereof ligated to the immobilized tagging probes comprise first and second labels, respectively.

The labeling probe herein means a probe that comprises or is configured to bind to a label. The labeling probe itself may comprise a label or may be modified to comprise or bind to a label. The amplified probe herein is defined to be the additional copies of an initial probe produced after amplification of the initial probe as described herein. Accordingly, the amplified probes may have a sequence that is the nucleotide sequences of the initial probes and/or complementary sequence of the nucleotide sequences of the initial probes. The amplified probes may contain a sequence that is partial or complete match to the nucleotide sequences of the initial probes. The terms "complementary" or "complementarity" are used in reference to a sequence of nucleotides related by the base-pairing rules. For example, the sequence "5'-CAGT-3'," is complementary to the sequence "5'-ACTG-3'." Complementarity may be "partial" or "total." "Partial" complementarity is where one or more nucleic acid nucleotides in a probe is not matched according to the base pairing rules while others are matched. "Total" or "complete" complementarity between nucleic acids is where each and every nucleic acid base in the probe is matched with another base under the base pairing rules.

Immobilized probe herein is defined to be a probe that is directly or indirectly binding to the substrate by a physical or chemical bond. In some embodiments, a labeling probe may be immobilized to a substrate indirectly via ligation to a tagging probe immobilized to the substrate described herein.

A label herein means an organic, naturally occurring, synthetic, artificial, or non-naturally occurring molecule, dye, or moiety having a property or characteristic that is capable of detection and, optionally, of quantitation. A label may be directly detectable (e.g., radioisotopes, fluorophores, chemiluminophores, enzymes, colloidal particles, fluorescent substances, Quantum dots or other nanoparticles, nanostructures, metal compounds, organometallic labels, and peptide aptamers); or a label may be indirectly detectable using specific binding partners. Examples of the fluorescent substances include fluorescent dyes such as fluorescein, phosphor, rhodamine, polymethine dye derivatives, and the like. Examples of a commercially available fluorescent substance include fluorescent dyes, such as BODYPY FL (trademark, produced by Molecular Probes, Inc.), FluoreP-rime (product name, produced by Amersham Pharmacia Biotech, Inc.), Fluoredite (product name, produced by Millipore Corporation), FAM (produced by ABI Inc.), Cy 3 and Cy 5 (produced by Amersham pharmacia), TAMRA (produced by Molecular Probes, Inc.), Pacific Blue, TAMRA, Alexa 488, Alexa 594, Alexa 647, Atto 488, Atto 590, Atto 647N and the like. "Quantum dot" (QD) means a nano-scale semiconductor crystalline structure, usually made from cadmium selenide, and absorbs light and then re-emits it a couple of nanoseconds later in a specific color. QDs with a variety of conjugated or reactive surfaces, e.g., amino, carboxyl, streptavidin, protein A, biotin, and immunoglobulins, are also encompassed in the present disclosure.

In additional embodiments, the first and second labels are different so that the labels may be distinguished from each other. In further embodiments, the first and second labels are different in their physical, optical, and/or chemical properties.

In some embodiments, the immobilized labels are optically resolvable. The term "optically resolvable label" or "optically individually resolvable label" herein means a group of labels that may be distinguished from each other by their photonic emission, or other optical properties, for example, after immobilization as described herein. In additional embodiments, even though the labels may have the same optical and/or spectral emission properties, the immobilized labels may be distinguished from each other spatially. In some embodiments, the labels of the same type, which is defined to be labels having the same optical properties, are immobilized on the substrate, for example as a member of an array described herein, at a density and/or spacing such that the individual probe products are resolvable as shown in item 12 of FIG. 1. In this disclosure, the "same labels" are defined to be labels having identical chemical and physical compositions. The "different labels" herein mean labels having different chemical and/or physical compositions, including "labels of different types" having different optical properties. The "different labels of the same type" herein means labels having different chemical and/or physical compositions, but the same optical properties.

Item 12 of FIG. 1 depicts an image of an exemplary member of an array comprising immobilized labels. In these embodiments, the labels are spatially addressable as the location of a molecule specifies its identity (and in spatial combinatorial synthesis, the identity is a consequence of location). In additional embodiments, one member of the array on the substrate may have one or multiple labeled probes immobilized to the member. When multiple labeled probes are immobilized to one member of the array, the labels of the same type in the labeled probes immobilized to the one member of an array on the substrate may be distinguished from each other spatially as shown in item 12 of FIG. 1. In some embodiments, the immobilized labels of the same type are separated by a distance about from 1 to 1000 nm, from 5 to 100 nm, or from 10 to 100 nm; about 100, 150, 200, 250, 300, 350, or 400 nm or more; and/or about 50, 100, 150, 200, 250, 300, 350, or 400 nm or less in all dimensions. The density of the probe products and their labels on the substrates may be up to many millions (and up to one billion or more) probe products to be counted per substrate. The ability to count large numbers of probe products containing the labels allows for accurate quantification of nucleic acid sequences.

In some embodiments, the immobilized first and second tagging probes and/or the amplified tagging probes thereof comprise first and second tags, respectively. The tagging probe herein means a probe that is configured to directly or indirectly bind to the substrate. The tagging probe itself may bind to the substrate or may be modified to bind to the substrate. A tag or affinity tag herein means a motif for specific isolation, enrichment or immobilization of probe products. Examples of the tag or affinity tag include a binding partner described herein, unique DNA sequences allowing for sequence-specific capture including natural genomic and/or artificial non-genomic sequence, biotin-streptavidin, His-tags, FLAG octapeptide, click chemistry (e.g., pairs of functional groups that rapidly and selectively react with each other under mild, aqueous conditions), and antibodies (e.g., azide-cycline). For example, the immobilizing step comprises hybridizing at least a part of the tag, affinity tag, or tagging nucleotide sequence to a corresponding nucleotide molecule immobilized on the substrate. The tag or affinity tag is configured to bind to entities including, but not limited to a bead, a magnetic bead, a microscope slide, a coverslip, a microarray or a molecule. In some embodiments, the immobilizing step is performed by immobilizing the tags to the predetermined location of the substrate.

In another aspect, the numbers of different labels immobilized on the substrate and thus the numbers of different immobilized probe products comprising the labels are counted. For example, the probe products from each genetic locus are grouped together, and the labels in the immobilized probe products are counted. In some embodiments, multiple sequences within a genomic locus may be interrogated via the creation of multiple probe product types. For this example, different probe products for the same genomic locus may be combined (possibly via immobilization to a common location of a substrate, e.g., as a member of an array described herein), and the labels in these probe products may be directly counted. Different probe products for the same genomic locus may be also separated (possibly via immobilization to different locations of a substrate, e.g., as different members of an array described herein), and the labels in these probe products may be directly counted. In additional embodiments, the substrate may have one or more specific affinity tag in each location on a substrate, e.g., as a member of an array on the substrate. Therefore, another method for quantifying nucleic acid sequences occurs via immobilization of probe products for a single genomic locus (this may be one probe product type, or may be a set of more than one probe product for a particular genomic locus) to the same location of a substrate (e.g., as the same member of an array described herein) as probe products corresponding to a second genomic locus, which may or may not serve as a reference or control locus. In this case, the probe products from the first genomic locus will be distinguishable from the probe products from the second genomic locus, based on the presence of different labels used in generating the probe products.

In one example, for detecting trisomy 21 (aneuploidy) of a fetus through examination of a maternal blood sample, a set of probe products corresponding to chromosome 21 would be generated, for example with a red fluorophore label, and counted. A second set of probe products would also be generated from a reference, or control locus, for example chromosome 18, and counted. This second set of probe products may be generated, for example, with a green fluorophore label.

In some embodiments, these probe products may be prepared such that they are grouped together by locus (in this case chromosome 21 or chromosome 18) and counted separately on a substrate. That is, the probe products corresponding to chromosome 21 may be isolated and counted separately, and the probe products corresponding to chromosome 18 may be isolated and counted separately. In additional embodiments, these probe products may be also prepared in such a way that they are grouped together in the same location of a substrate (e.g., as the same member of an array described herein. In this case, on the same region of a substrate, the probe products bearing a red fluorophore will correspond to chromosome 21, and the probe products with a green fluorophore will correspond to chromosome 18. For example, since all of these probe products are individually resolvable and may therefore be counted very accurately, an increased frequency of chromosome 21 probe products relative to chromosome 18 probe products (even as small as 0.01, 0.1, one or more percent or less) will signify the presence of trisomy 21 in a fetus. In this case, the probe products for chromosome 18 may serve as a control.

In another aspect, the methods of the present disclosure may comprise counting the labels of the probe sets immobilized to the substrate. In some embodiments, the methods may comprise counting (i) a first number of the first label immobilized to the substrate, and (ii) a second number of the second label immobilized to the substrate. The counting step may be performed after immobilizing the ligated probe set to a substrate, and the substrate with immobilized ligated probe sets may be stored in a condition to prevent degradation of the ligated probe sets (e.g., at room temperature or a temperature below the room temperature) before the counting step is performed.

In order to accurately quantify the relative abundance of different genomic sequences, for example, for quantification of DNA copy number or for quantification of allele frequency, a large number of probe products may be counted. For example, a label may be detected and counted based on measuring, for example, physicochemical, electromagnetic, electrical, optoelectronic or electrochemical properties, or characteristics of the immobilized label.

In some embodiments, the label may be detected by scanning probe microscopy (SPM), scanning tunneling microscopy (STM) and atomic force microscopy (AFM), electron microscopy, optical interrogation/detection techniques including, but not limited to, near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques may also be used in a spectroscopic mode. The actual detection is by charge coupled device (CCD) cameras and intensified CCDs, photodiodes and/or photomultiplier tubes. In some embodiments, the counting step comprises an optical analysis, detecting an optical property of a label. In additional embodiments, the optical analysis comprises an image analysis as described herein.

In another aspect, the counting step comprises reading the substrate in first and second imaging channels that correspond to the first and second labels, respectively, and producing one or more images of the substrate, wherein the first and second labeling probes are resolvable in the one or more images. In some embodiments, the counting step comprises spatial filtering for image segmentation. In additional embodiments, the counting step comprises watershedding analysis, or a hybrid method for image segmentation.

The methods described herein may also look at the frequency of different alleles at the same genetic locus (e.g., two alleles of a given single nucleotide polymorphisms). The accuracy of these methods may detect very small changes in frequency (e.g., as low as about 10, 5, 4, 3, 2, 1, 0.5, 0.1 or 0.01% or less). As an example, in the case of organ transplantation, a blood sample will contain a very dilute genetic signature from the donated organ. This signature may be the presence of an allele that is not in the recipient of the donated organ's genome. The methods described herein may detect very small deviations in allele frequency (e.g., as low as about 10, 5, 4, 3, 2, 1, 0.5, 0.1 or 0.01% or less) and may identify the presence of donor DNA in a host sample (e.g., blood sample). An unhealthy transplanted organ may result in elevated levels of donor DNA in the host blood—a rise of only a few percent (e.g., as low as about 10, 5, 4, 3, 2, 1, 0.5, 0.1 or 0.01% or less). The methods described herein may be sensitive enough to identify changes in allele frequency with the necessary sensitivity, and therefore may accurately determine the presence and changing amounts of donor DNA in host blood.

In another aspect, the methods of the present disclosure may comprise comparing the first and second numbers to determine the genetic variation in the genetic sample. In some embodiments, the comparing step comprises obtaining an estimate of a relative number of the nucleotide molecules having the first and second nucleic acid regions of interest.

In another aspect, the methods of the present disclosure may comprise labeling the first and second labeling probes with the first and second labels, respectively, prior to the contacting step (e.g., during manufacturing the probes). Labeling the probe may be performed simultaneously or after contacting the probes to the genetic sample, hybridizing, ligating, amplifying and/or immobilizing the probes. Moreover, labeling the probe may be performed simultaneously or before contacting the probes to the genetic sample, hybridizing, ligating, amplifying, and/or immobilizing the probes. Labeling a probe may comprise adding, immobilizing, or binding a label to the probe by a physical or chemical bond. Labels may be placed anywhere within the sequence of a probe, including at the 5' or 3'-end.

In another aspect, the methods of the present disclosure may comprise tagging the first and second tagging probes with first and second tags, respectively, prior to the contacting step. (e.g., during the manufacturing the probes). Tagging the probe may be performed simultaneously or after contacting the probes to the genetic sample, hybridizing, ligating, amplifying and/or labeling the probes. Moreover, tagging the probe may be performed simultaneously or before contacting the probes to the genetic sample, hybridizing, ligating, amplifying, immobilizing and/or labeling the probes. Tagging a probe may comprise adding, immobilizing, or binding a tag to the probe by a physical or chemical bond. Tags may be placed anywhere within the sequence of a probe, including at the 5' or 3'-end.

In another aspect, the probe sets herein may be designed to have tags according to the predetermined locations to which the tags are to be immobilized. In some embodiments, the tags in all probe sets configured to detect a genetic variation are the same and are configured to be immobilized to same locations on the substrate directly or indirectly. In additional embodiments, the first and second tags are the same, and each of the rest of the tags is different from the first or second tag. In further embodiments, each or a group of members of the array of multiple predetermined locations on a substrate may have a unique tag to be immobilized.

In another aspect, the probe sets according to some embodiments may be amplified, and labeled probe sets may be produced during the process of amplification. In another aspect, each of the labeling probes may comprise a forward or reverse priming sequence, and each of the tagging probes may comprise a corresponding reverse or forward priming sequence and a tagging nucleotide sequence as a tag. The forward and reverse priming sequences are the sequences that are configured to hybridize to the corresponding forward and reverse primers, respectively. In some embodiments, the amplifying step comprises amplifying (i) the ligated first labeling and tagging probes with first forward and reverse primers hybridizing to the forward and reverse priming sequences, respectively, wherein the first forward or reverse primer hybridizing to the first labeling probe comprises the first label, and (ii) the ligated second labeling and tagging probes with second forward and reverse primers hybridizing to the forward and reverse priming sequences, respectively, wherein the second forward or reverse primer hybridizing to the second labeling probe comprises the second label. In additional embodiments, the amplified tagging nucleotide sequences of the tagging probes are immobilized to a pre-determined location on a substrate, wherein the amplified tagging nucleotide sequences of the first and second tagging probes are the first and second tags. In some embodiments, the first and second tags are the same and/or are configured to bind to the same location on the substrate. In another embodiment, the first and second tags are different and/or are configured to bind to different locations on the substrate. In further embodiments, when the probes are amplified, the method comprises counting numbers of the labels in the amplified probes and/or probe sets immobilized on the substrate. For example, the first number is the number of the first label in the amplified first probe set immobilized to the substrate, and the second number is the number of the second label in the amplified second probe set immobilized to the substrate.

In another aspect, the probe sets according to some embodiments may be amplified, and labeled probe sets may be produced using labeled reverse primers without using a forward primer. In another aspect, each of the labeling probes may comprise a reverse priming sequence, and each of the tagging probes may comprise a tagging nucleotide sequence as a tag. In some embodiments, the amplifying step may comprise amplifying (i) the ligated first labeling and tagging probes with a first reverse primer hybridizing to a first reverse priming sequence of the first labeling probe, wherein the first reverse primer comprises the first label, and (ii) the ligated second labeling and tagging probes with a second reverse primer hybridizing to a second reverse priming sequence of the second labeling probe, wherein the second reverse primer comprises the second label. In additional embodiments, the amplified tagging nucleotide sequences of the tagging probes are immobilized to a pre-determined location on a substrate, wherein the amplified tagging nucleotide sequences of the first and second tagging probes are the first and second tags. In further embodiments, the first number is the number of the first label in the amplified first probe set immobilized to the substrate, and the second number is the number of the second label in the amplified second probe set immobilized to the substrate.

In another aspect, the ligated probe sets according to some embodiments may be produced using a ligase chain reaction. In another aspect, the method described herein comprises contacting third and fourth probe sets to the genetic sample, wherein the third probe set comprises a third labeling probe and a third tagging probe, and the fourth probe set comprises a fourth labeling probe and a fourth tagging probe. The method may further comprise hybridizing the first and second probe sets to first and second sense nucleic acid strands of interest in single stranded nucleotide molecules from the double stranded nucleotide molecules of the genetic sample, respectively; and hybridizing the third and fourth probe sets to anti-sense nucleic acid strands of the first and second sense nucleic acid strands of interest, respectively. The method may further comprise producing ligated first, second, third, and fourth probe sets at least by ligating (i) the first labeling probe and the first tagging probe, (ii) the second labeling probe and the second tagging probe, (iii) the third labeling probe and the third tagging probe, and (iv) the fourth labeling probe and the fourth tagging probe. The method may further comprise performing a ligase chain reaction known in the art to amplify the ligated probe and/or ligated probe sets. In some embodiments, the ligase chain reaction may comprise hybridizing non-ligated first, second, third and fourth probe sets to the ligated third, fourth, first, and second probe sets, respectively, and ligating at least (i) the first labeling probe and the first tagging probe, (ii) the second labeling probe and the second tagging probe, (iii) the third labeling probe and the third tagging probe, and (iv) the fourth labeling probe and the fourth tagging probe of the non-ligated probe sets. The method may further comprise immobilizing the tagging probes to the pre-determined location on a substrate, wherein the first, second, third and fourth labeling probes ligated to the immobilized first, second, third and fourth tagging probes, respectively, comprise first, second, third and fourth labels, respectively; the immobilized labels are optically resolvable; the immobilized first, second, third and fourth tagging probes comprise first, second, third and fourth tags, respectively, and the immobilizing step is performed by immobilizing the tags to the predetermined location. The method may further comprise counting (i) the first sum of the first and third labels immobilized to the substrate, and (ii) the second sum of the second and fourth labels immobilized to the substrate, and comparing the first and second sums to determine the genetic variation in the genetic sample. In yet additional embodiments, the method further comprises labeling the first, second, third and fourth labeling probes with the first, second, third and fourth labels, respectively, prior to the contacting step. In yet further embodiments, the first and third labels are the same, and the second and fourth labels are the same.

In another aspect, the method described herein comprises contacting third and fourth probe sets to the genetic sample, wherein the third probe set comprises a third labeling probe and a third tagging probe, and the fourth probe set comprises a fourth labeling probe and a fourth tagging probe, the first and third labeling probes comprises a first reverse priming sequence, the second and fourth labeling probes comprises a second reverse priming sequence, and each of the tagging probes comprises a tagging nucleotide sequence as a tag. The method may further comprise hybridizing the first and second probe sets to first and second sense nucleic acid strands of interest, respectively, in single stranded nucleotide molecules from double stranded nucleotide molecules of the genetic sample; and hybridizing at least parts of the third and fourth probe sets to anti-sense nucleic acid strands of the first and second sense nucleic acid strands of interest, respectively; producing ligated first, second, third, and fourth probe sets by ligating (i) the first labeling probe and the first tagging probe, (ii) the second labeling probe and the second tagging probe, (iii) the third labeling probe and the third tagging probe, and (iv) the fourth labeling probe and the fourth tagging probe. The method may further comprise performing a ligase chain reaction. In some embodiments, the ligase chain reaction comprises hybridizing at least parts of the non-ligated first, second, third and fourth probe sets to the ligated third, fourth, first, and second probe sets, respectively, and ligating (i) the first labeling probe and the first tagging probe, (ii) the second labeling probe and the second tagging probe, (iii) the third labeling probe and the third tagging probe, and (iv) the fourth labeling probe and the fourth tagging probe of the non-ligated probe set. The method may further comprise amplifying (i) the ligated first and third probe sets with a first reverse primer hybridizing to the first reverse priming sequence, wherein the first reverse primer comprises the first label, and (ii) the ligated second and fourth probe sets with a second reverse primer hybridizing to the second reverse priming sequence, wherein the second reverse primer comprises the second label, the amplified tagging nucleotide sequences of the tagging probes are immobilized to a pre-determined location on a substrate, wherein the amplified tagging nucleotide sequences of the first, second, third and fourth tagging probes are first, second, third and fourth tags, the first number is the number of the first label in the amplified first and third probe sets immobilized to the substrate, and the second number is the number of the second label in the amplified second and fourth probe sets immobilized to the substrate.

In another aspect, the ligated first and second labeling probes are at the 3'-end of the first and second ligated probe set and comprise first and second reverse priming sequences hybridizing to the first and second reverse primers, respectively. In some embodiments, the first and second reverse primers comprise the first and second labels. In additional embodiments, the ligated first and second tagging probes are at the 5'-end of the first and second ligated probe set. In further embodiments, the ligated first and second tagging probes are at the 5'-end of the first and second ligated probe set and comprise first and second corresponding forward priming sequences hybridizing to the first and second forward primers, respectively.

In another aspect, the method herein comprises digesting double stranded molecules in the sample to produce single stranded molecules. In some embodiments, the amplifying step comprises contacting an exonuclease to the amplified probe and/or probe set, and digesting the amplified probe and/or probe set from the 5'-end of one strand of the double stranded amplified probe and/or probe set. For example, the amplifying step comprises contacting an exonuclease to the amplified probe in a probe set, and digesting the amplified probe set from the 5'-end of one strand of the double stranded amplified probe set. In additional embodiments, the one strand of the amplified probe and probe set contacting the exonuclease does not have any label at the 5'-end. The contacting of the exonuclease to the unlabeled double stranded probes may digest the unlabeled strand from the 5'-end producing single stranded probes. In another aspect, the 5'-end of the amplified probe set comprising the label at the 5'-end may be protected from exonuclease digestion.

In another aspect, the method may detect from 1 to 100, from 1 to 50, from 2 to 40, or from 5 to 10 genetic variations; 2, 3, 4, 5, 6, 7, 8, 9, 10 or more genetic variations; and 100, 50, 30, 20, 10 or less genetic variations. In some embodiments, the method described herein may detect x number of genetic variations using at least (x+1) number of different probe sets. In these embodiments, a number of labels from one type of probe sets may be compared with one or more numbers of labels from the rest of the different types of probe sets. In some embodiments, the method described herein may detect genetic variation in a continuous manner across the entire genome at various resolutions, for example, at 300,000 base resolution such that 100 distributed variations across all chromosomes are separately interrogated and quantified. In additional embodiments, the base resolution is in the range of one or ten to 100 thousand nucleotides up to one million, ten million, or 100 million or more nucleotides.

In another aspect, the method according to some embodiments may detect at least two genetic variations. In some embodiments, the method described herein may further comprise contacting a fifth probe set to the genetic sample, wherein the fifth probe set comprises a fifth labeling probe and a fifth tagging probe. The method may further comprise hybridizing at least a part of the fifth probe set to the third nucleic acid region of interest in nucleotide molecules of the genetic sample, wherein the third nucleic acid region of interest is different from the first and second nucleic acid regions of interest. The method may further comprise ligating the fifth probe set at least by ligating the fifth labeling probe and the fifth tagging probe. The method may further comprise amplifying the ligated probe sets. The method may further comprise immobilizing each of the tagging probe to a pre-determined location on a substrate, wherein the fifth labeling probe and/or the amplified labeling probe thereof ligated to the immobilized tagging probe comprise a fifth label, the fifth label is different from the first and second labels, the immobilized labels are optically resolvable, the immobilized fifth tagging probe and/or the amplified tagging probe thereof comprise a fifth tag, and the immobilizing step is performed by immobilizing the tags to the predetermined location. The method may comprise counting a third number of the fifth label immobilized to the substrate, and comparing the third number to the first and/or second number(s) to determine the second genetic variation in the genetic sample. In some embodiments, the subject may be a pregnant subject, the first genetic variation is trisomy 21 in the fetus of the pregnant subject, and the second genetic variation is selected from the group consisting of trisomy 13, trisomy 18, aneuploidy of X, and aneuploidy of Y in the fetus of the pregnant subject.

In another aspect, the method according to some embodiments may detect at least three genetic variations. In some embodiments, the method described herein further comprises contacting a sixth probe set to the genetic sample, wherein the sixth probe set comprises a sixth labeling probe and a sixth tagging probe. The method may further comprise hybridizing at least a part of the sixth probe set to the fourth nucleic acid region of interest in nucleotide molecules of the genetic sample, wherein the fourth nucleic acid region of interest is different from the first, second, and third nucleic acid regions of interest. The method may further comprise ligating the sixth probe set at least by ligating the sixth labeling probe and the sixth tagging probe. The method may further comprise amplifying the ligated probe sets. The method may further comprise immobilizing each of the tagging probes to a pre-determined location on a substrate, wherein the sixth labeling probe and/or the amplified labeling probe thereof ligated to the immobilized tagging probe comprise a sixth label, the sixth label is different from the first and second labels, the immobilized labels are optically resolvable, the immobilized sixth tagging probe and/or the amplified tagging probe thereof comprise a sixth tag, and the immobilizing step is performed by immobilizing the tags to the predetermined location. The method may further comprise counting a fourth number of the sixth label immobilized to the substrate, and comparing the fourth number to the first, second and/or third number to determine the third genetic variation in the genetic sample.

In another aspect, the method may according to some embodiments detect at least four genetic variations. In some embodiments, the method described herein further comprises contacting a seventh probe set to the genetic sample, wherein the seventh probe set comprises a seventh labeling probe and a seventh tagging probe. The method may further comprise hybridizing at least a part of the seventh probe set to the fifth nucleic acid region of interest in nucleotide molecules of the genetic sample, wherein the fifth nucleic acid region of interest is different from the first, second, third and fourth nucleic acid regions of interest. The method may further comprise ligating the seventh probe set at least by ligating the seventh labeling probe and the seventh tagging probe. The method may further comprise optionally amplifying the ligated probe sets. The method may further comprise immobilizing each of the tagging probes to a pre-determined location on a substrate, wherein the seventh labeling probe and/or the amplified labeling probe thereof ligated to the immobilized tagging probe comprise a seventh label, the seventh label is different from the first and second labels, the immobilized labels are optically resolvable, the immobilized seventh tagging probe and/or the amplified tagging probe thereof comprise a seventh tag, and the immobilizing step is performed by immobilizing the tags to the predetermined location. The method may further comprise counting a fifth number of the seventh label immobilized to the substrate, and comparing the fifth number to the first, second, third and/or fourth number(s) to determine the fourth genetic variation in the genetic sample.

In another aspect, the method according to some embodiments may detect at least five genetic variations. In some embodiments, the method described herein further comprises contacting an eighth probe set to the genetic sample, wherein the eighth probe set comprises a eighth labeling probe and a eighth tagging probe. The method may further comprise hybridizing at least a part of the eighth probe set to the sixth nucleic acid region of interest in nucleotide molecules of the genetic sample, wherein the sixth nucleic acid region of interest is different from the first, second, third, fourth, and fifth nucleic acid regions of interest. The method may further comprise ligating the eighth probe set at least by ligating the eighth labeling probe and the eighth tagging probe. The method may further comprise amplifying the ligated probe sets. The method may further comprise immobilizing each of the tagging probes to a pre-determined location on a substrate, wherein the eighth labeling probe and/or the amplified labeling probe thereof ligated to the immobilized tagging probe comprise a eighth label, the eighth label is different from the first and second labels, the immobilized labels are optically resolvable, the immobilized eighth tagging probe and/or the amplified tagging probe thereof comprise a eighth tag, and the immobilizing step is performed by immobilizing the tags to the predetermined location. The method may further comprise counting a sixth number of the eighth label immobilized to the substrate, and comparing the sixth number to the first, second, third, fourth and/or fifth number(s) to determine the fifth genetic variation in the genetic sample. In some embodiments, the subject is a pregnant subject, and the first, second, third, fourth, and fifth genetic variations are trisomy 13, trisomy 18, trisomy 21, aneuploidy X, and aneuploidy Y in the fetus of the pregnant subject.

In another aspect, the subject is a pregnant subject, the genetic variation is trisomy 21 in the fetus of the pregnant subject, the first nucleic acid region of interest is located in chromosome 21, and the second nucleic acid region of interest is not located in the chromosome 21.

In another aspect, the subject is a pregnant subject, the genetic variation is trisomy 21 in the fetus of the pregnant subject, the first nucleic acid region of interest is located in chromosome 21, and the second nucleic acid region of interest is located in chromosome 18.

In one aspect, the probe set herein may comprise two, three, four, five or more labeling probes, and/or two, three, four, five or more labels. In some embodiments, the method described herein may further comprise the first and second probe sets further comprise third and fourth labeling probes, respectively; the immobilized first probe set and/or amplified first probe set further comprise a ninth label in the third labeling probe and/or amplified product thereof; and the immobilized second probe set and/or amplified second probe set further comprise a tenth label in the fourth labeling probe and/or amplified product thereof. In these embodiments, if the ninth and tenth labels are different from the first and second labels, this method may be used to confirm the number counted for the first and second labels. If the ninth and tenth labels are the same from the first and second labels, respectively, this method may be used to improve the accuracy of detection labels immobilized to each of the nucleic acid regions of interest. For example, using multiple labels would be brighter than using one label, and therefore multiple labels may be more easily detected than one label.

In additional embodiments, (i) the immobilized first probe set and/or amplified first probe set further comprise an eleventh label in the labeling probe, and (ii) the immobilized second probe set and/or amplified second probe set further comprises a twelfth label that is different from the eleventh label in the labeling probe. In further embodiments, wherein the first, second, eleventh and twelfth labels are different from one another, and the counting step further comprises counting numbers of the eleventh and twelfth labels immobilized on the substrate.

In another aspect, the method described herein may be performed with a control sample. In some embodiments, the method may further comprise repeating the steps with a control sample different from the genetic sample from the subject. The method may further comprise counting control numbers of the labels immobilized to the substrate, and comparing the control numbers to the first, second, third, fourth, fifth and/or sixth number to confirm the genetic variation in the genetic sample.

In another aspect, the subject may be a pregnant subject, and the genetic variation is a genetic variation in the fetus of the pregnant subject. In such embodiments, the method may use a Single Nucleotide Polymorphism (SNP) site to determine whether the proportion (e.g., concentration, and number percentage based on the number of nucleotide molecules in the sample) of fetal material (e.g., the fetal fraction) is sufficient so that the genetic variation of the fetus may be detected from a sample from the pregnant subject with a reasonable statistical significance. In additional embodiments, the method may further comprise contacting maternal and paternal probe sets to the genetic sample, wherein the maternal probe set comprises a maternal labeling probe and a maternal tagging probe, and the paternal probe set comprises a paternal labeling probe and a paternal tagging probe. The method may further comprise hybridizing at least a part of each of the maternal and paternal probe sets to a nucleic acid region of interest in nucleotide molecules of the genetic sample, the nucleic acid region of interest comprising a predetermined SNP site, wherein the at least a part of the maternal probe set hybridizes to a first allele at the SNP site, the at least a part of the paternal probe set hybridizes to a second allele at the SNP site, and the first and second alleles are different from each other. The method may further comprise ligating the material and paternal probe sets at least by ligating (i) the maternal labeling and tagging probes, and (ii) the paternal labeling and tagging probes. The method may further comprise amplifying the ligated probes. The method may further comprise immobilizing the tagging probes to a pre-determined location on a substrate, wherein the maternal and paternal labeling probes and/or the amplified labeling probes thereof ligated to the immobilized tagging probes comprise maternal and paternal labels, respectively; the maternal and paternal labels are different, and the immobilized labels are optically resolvable. The method may further comprise counting the numbers of the maternal and paternal labels, and determining whether a proportion of a fetal material in the genetic sample is sufficient to detect the genetic variation in the fetus based on the numbers of the maternal and paternal labels. The method may further comprise determining the proportion of the fetal material in the genetic sample.

In some embodiments, when the subject is a pregnant subject, and the genetic variation is a genetic variation in the fetus of the pregnant subject, the method may further comprise contacting allele A and allele B probe sets that are allele-specific to the genetic sample, wherein the allele A probe set comprises an allele A labeling probe and an allele A tagging probe, and the allele B probe set comprises an allele B labeling probe and an allele B tagging probe. The method may further comprise hybridizing at least a part of each of the allele A and allele B probe sets to a nucleic acid region of interest in nucleotide molecules of the genetic sample, the nucleic acid region of interest comprising a predetermined single nucleotide polymorphism (SNP) site for which a maternal allelic profile (i.e., genotype) differs from a fetal allelic profile at the SNP site (For example, maternal allelic composition may be AA and fetal allelic composition may be AB, or BB. In another example, maternal allelic composition may be AB and fetal allelic composition may be AA, or BB.), wherein the at least a part of the allele A probe set hybridizes to a first allele at the SNP site, the at least a part of the allele B probe set hybridizes to a second allele at the SNP site, and the first and second alleles are different from each other. The method may further comprise ligating the allele A and allele B probe sets at least by ligating (i) the allele A labeling and tagging probes, and (ii) the allele B labeling and tagging probes. The method may further comprise amplifying the ligated probe sets. The method may further comprise immobilizing the tagging probes to a pre-determined location on a substrate, wherein the allele A and allele B labeling probes and/or the amplified labeling probes thereof ligated to the immobilized tagging probes comprise allele A and allele B labels, respectively, the allele A and allele B labels are different, and the immobilized labels are optically resolvable. The method may further comprise counting the numbers of the allele A and allele B labels, and determining whether a proportion of a fetal material in the genetic sample is sufficient to detect the genetic variation in the fetus based on the numbers of the allele A and allele B labels. The method may further comprise determining the proportion of the fetal material in the genetic sample.

In some embodiments, when the subject is a pregnant subject, the genetic variation is a genetic variation in the fetus of the pregnant subject, and the genetic sample comprises a Y chromosome, the method may further comprise contacting maternal and paternal probe sets to the genetic sample, wherein the maternal probe set comprises a maternal labeling probe and a maternal tagging probe, and the paternal probe set comprises a paternal labeling probe and a paternal tagging probe. The method may further comprise hybridizing at least parts of the maternal and paternal probe sets to maternal and paternal nucleic acid regions of interest in nucleotide molecules of the genetic sample, respectively, wherein the paternal nucleic acid region of interest is located in the Y chromosome, and the maternal nucleic acid region of interest is not located in the Y chromosome. The method may further comprise ligating the maternal and paternal probe sets at least by ligating (i) the maternal labeling and tagging probes, and (ii) the paternal labeling and tagging probes. The method may further comprise amplifying the ligated probes. The method may further comprise nucleic acid region of interest comprising a predetermined single nucleotide polymorphism (SNP) site containing more than one SNP, for example two or three SNPs. Further, the SNP site may contain SNPs with high linkage disequilibrium such that labeling and tagging probes are configured to take advantage of the improved energetics of multiple SNP matches or mismatches versus only one. The method may further comprise immobilizing the tagging probes to a pre-determined location on a substrate, wherein the maternal and paternal labeling probes and/or the amplified labeling probes thereof ligated to the immobilized tagging probes comprise maternal and paternal labels, respectively, the maternal and paternal labels are different, and the immobilized labels are optically resolvable. The method may further comprise counting the numbers of the maternal and paternal labels, and determining whether a proportion of a fetal material in the genetic sample is sufficient to detect the genetic variation in the fetus based on the numbers of the maternal and paternal labels. The method may further comprise determining the proportion of the fetal material in the genetic sample.

In additional embodiments, other genetic variations (e.g., single base deletion, microsatellite, and small insertions) may be used in place of the genetic variation at the SNP site described herein.

In one aspect, the probe set described herein may comprise three or more probes, including at least one probe between the labeling and tagging probes. In some embodiments, the first and second probe sets further comprises first and second gap probes, respectively; the first gap probe hybridizes to a region between the regions where the first labeling probe and the first tagging probe hybridize; the second gap probe hybridizes to a region between the regions where the second labeling probe and the second tagging probe hybridize. The method may further comprise the ligating step comprises ligating at least (i) the first labeling probe, the first tagging probe, and the first gap probe, and (ii) the second labeling probe, the second tagging probe, and the second gap probe. In additional embodiments, the gap probe may comprise a label. For example, the first and second gap probes and/or amplified products thereof are labeled with labels (e.g., thirteenth and fourteenth labels, respectively), and each of the labels may be different from the rest of the labels (e.g., the first and second labels). The labels in the gap probes (e.g., thirteenth and fourteenth labels) may be the same or different from each other. In another aspect, the first and second labeling probes are hybridized to the first and second nucleic acid regions of interest in nucleotide molecules of the genetic sample, respectively; the first and second tagging probes are hybridized to the first and second nucleic acid regions of interest in nucleotide molecules of the genetic sample, respectively; the first and second gap probes are hybridized to the first and second nucleic acid regions of interest in nucleotide molecules of the genetic sample, respectively. In some embodiments, there are from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 or more; or 1, 2, 3, 4, 5, 6, 7, 8, 9, 10, 15, 25, 35, 45, 55, 110, 160, or 300 or less between the regions where the first labeling probe and tagging probes are hybridized; and there are from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 nucleotides or more; or 1, 2, 3, 4, 5, 6, 7, 8, 9, 10, 15, 25, 35, 45, 55, 110, 160, or 300 nucleotides or less between the regions where the second labeling probe and tagging probes are hybridized. In additional embodiments, the gap probe between a labeling probe and a tagging probe may have a length from 0 to 100 nucleotides, 1 to 100 nucleotides, 2 to 50 nucleotides; 3 to 30 nucleotides, 0, 1, 2, 3, 4, 5, 6, 7, 8, 9, 10, 20, 30, 40, 50, 100, 150, or 200 or more; or 1, 2, 3, 4, 5, 6, 7, 8, 9, 10, 15, 25, 35, 45, 55, 110, 160, or 300 or less.

In another aspect, the probe set described herein may comprise a spacer ligated and/or conjugated to the labeling probe and the tagging probe. The spacer may or may not comprise oligonucleotides. The spacer may comprise an isolated, purified, naturally-occurring, or non-naturally occurring material, including oligonucleotide of any length (e.g., 5, 10, 20, 30, 40, 50, 100, or 150 nucleotides or less). In some embodiments, the probe may be in a purified restriction digest or produced synthetically, recombinantly or by PCR amplification. For example, the first labeling and tagging probes are conjugated by a first spacer, the second labeling and tagging probes are conjugated by a second spacer, and the first and second spacers are not hybridized to the nucleotide molecules of the genetic sample. In some embodiments, the method further comprises digesting the hybridized genetic sample with an enzyme, and breaking a bond in the first and second spacers after the digestion.

In another aspect, the method described herein excludes identifying a sequence in the nucleotide molecules of the genetic sample, and/or sequencing of the nucleic acid region (s) of interest and/or the probes. In some embodiments, the method excluding sequencing of the probes includes excluding sequencing a barcode and/or affinity tag in a tagging probe. In additional embodiments, the immobilized probe sets to detect different genetic variations, nucleotide regions of interest, and/or peptides of interest need not be detected or scanned separately because sequencing is not required in the methods described herein. In additional embodiments, the numbers of different labels immobilized to the substrate were counted simultaneously (e.g., by a single scanning and/or imaging), and thus the numbers of different labels were not separately counted. In another aspect, the method described herein excludes bulk array readout or analog quantification. The bulk array readout herein means a single measurement that measures the cumulative, combined signal from multiple labels of a single type, optionally combined with a second measurement of the cumulative, combined signal from numerous labels of a second type, without resolving a signal from each label. A result is drawn from the combination of the one or more such measurements in which the individual labels are not resolved. In another aspect, the method described herein may include a single measurement that measures the same labels, different labels of the same type, and/or labels of the same type in which the individual labels are resolved. The method described herein may exclude analog quantification and may employ digital quantification, in which only the number of labels is determined (ascertained through measurements of individual label intensity and shape), and not the cumulative or combined optical intensity of the labels.

In another aspect, the probe set described herein may comprise a binder. A binder is the same material as the tag or affinity tag describe herein. In some embodiments, the method further comprises immobilizing the binder to a solid phase after the ligating steps. The method may further comprise isolating the ligated probe sets from non-ligated probes. In additional embodiments, the binder comprises biotin, and the solid phase comprises a magnetic bead.

In another aspect, the counting step described herein may further comprise calibrating, verifying, and/or confirming the counted numbers. Calibrating herein means checking and/or adjusting the accuracy of the counted number. Verifying and confirming herein mean determining whether the counted number is accurate or not, and/or how much the error is, if exists.

Figure 2:
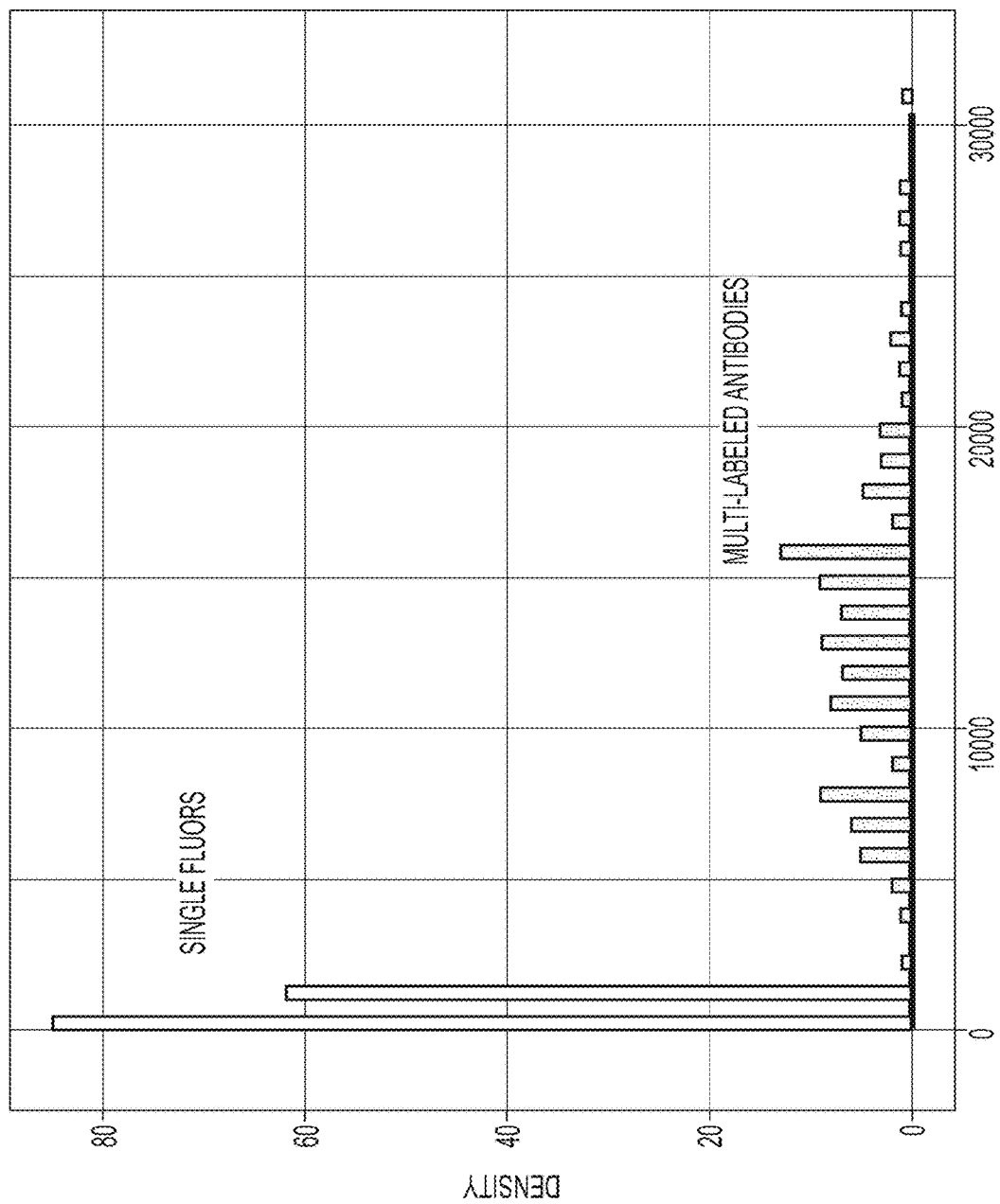
FIG. 2 depicts a normalized histogram of signal intensity measured from both single label samples and multi-label antibodies.

In another aspect, intensity and/or single-to-noise is used as a method of identifying single labels. When dye molecules or other optical labels are in close proximity, they are often impossible to discriminate with fluorescence-based imaging due to the intrinsic limit of the diffraction of light. That is, two labels that are close together will be indistinguishable with no visible gap between them. One exemplary method for determining the number of labels at a given location is to examine the relative signal and/or signal-to-noise compared to locations known to have a single fluor. Two or more labels will usually emit a brighter signal (and one that can more clearly be differentiated from the background) than will a single fluor. FIG. 2 shows the normalized histogram of signal intensity measured from both single label samples and multi-label antibodies (both Alexa 546; verified through bleach profiles). The two populations were clearly separable, and multiple labels may be clearly distinguished from single labels.

In some embodiments, the counting step may comprise measuring optical signals from the immobilized labels, and calibrating the counted numbers by distinguishing an optical signal from a single label from the rest of the optical signals from background and/or multiple labels. In some embodiments, the distinguishing comprises calculating a relative signal and/or single-to-noise intensity of the optical signal compared to an intensity of an optical signal from a single label. The distinguishing may further comprise determining whether the optical signal is from a single label. In additional embodiments, the optical signal is from a single label if the relative signal and/or single-to-noise intensity of an optical signal differs from an intensity of an optical signal from a single label by a predetermined amount or less. In further embodiments, the predetermined amount is from 0% to 100%, from 0% to 150%, 10% to 200%, 0, 1, 2, 3, 4, 5, 10, 20, 30, or 40% or more, and/or 300, 200, 100, 50, 30, 10, or 5% or less of the intensity of the optical signal from a single label.

In another aspect, different labels may have different blinking and bleaching properties. They may also have different excitation properties. In order to compare the number of dye molecules for two different labels, it is necessary to ensure that the two dyes are behaving in a similar manner and have similar emission characteristics. For example, if one dye is much dimmer than another, the number of molecules may be under-counted in this channel. Several factors may be titrated to give the optimal equivalence between the dyes. For example, the counting step and/or calibrating step may comprise optimizing (i) powers of light sources to excite the labels, (ii) types of the light sources, (ii) exposure times for the labels, and/or (iv) filter sets for the labels to match the optical signals from the labels, and measuring optical signals from the labels. These factors may be varied singly or in combination. Further, the metric being optimized may vary. For example, it may be overall intensity, signal-to-noise, least background, lowest variance in intensity or any other characteristic.

Figure 3:
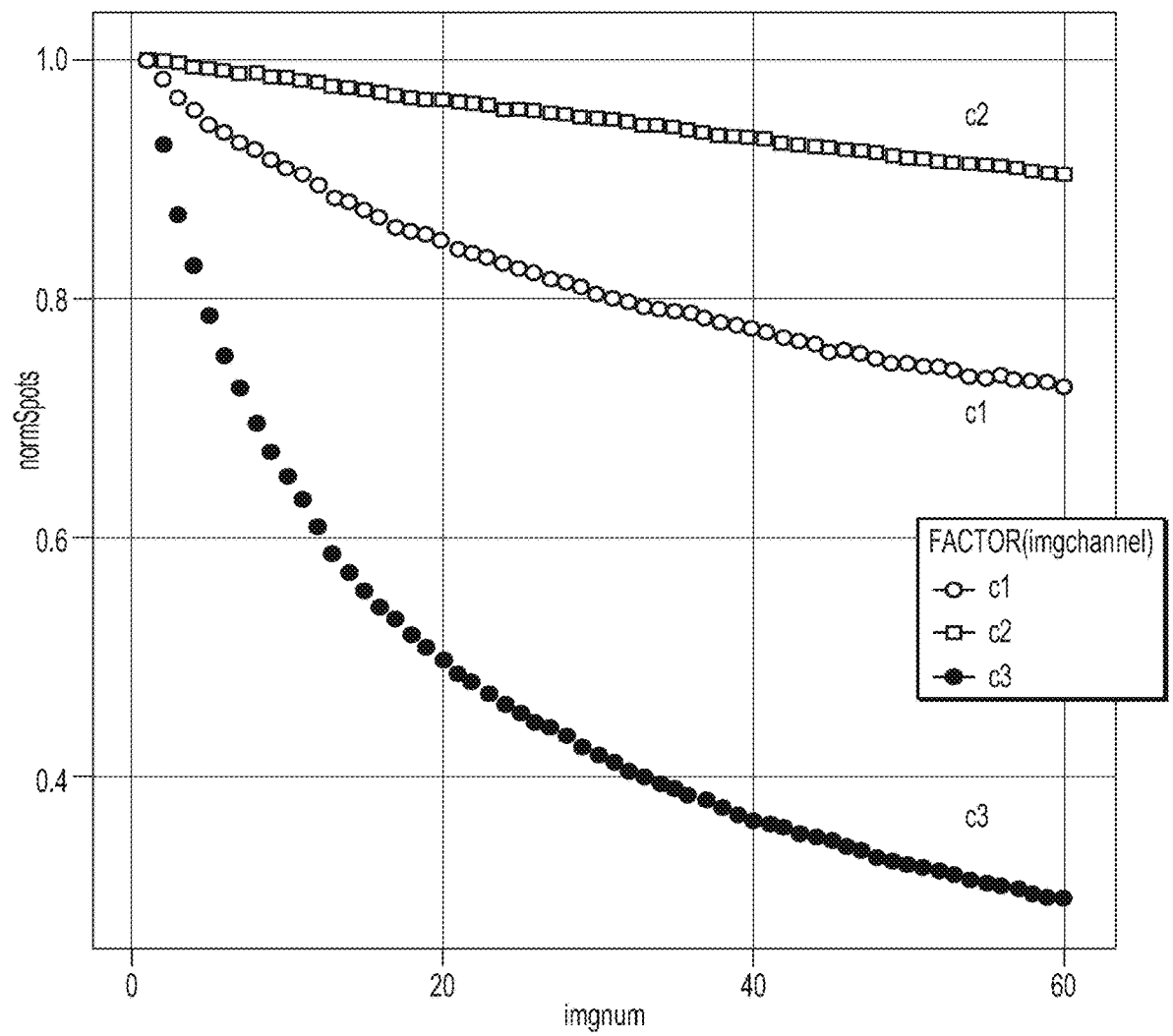
FIG. 3 depicts average bleaching profiles from various labels.
Figure 4:
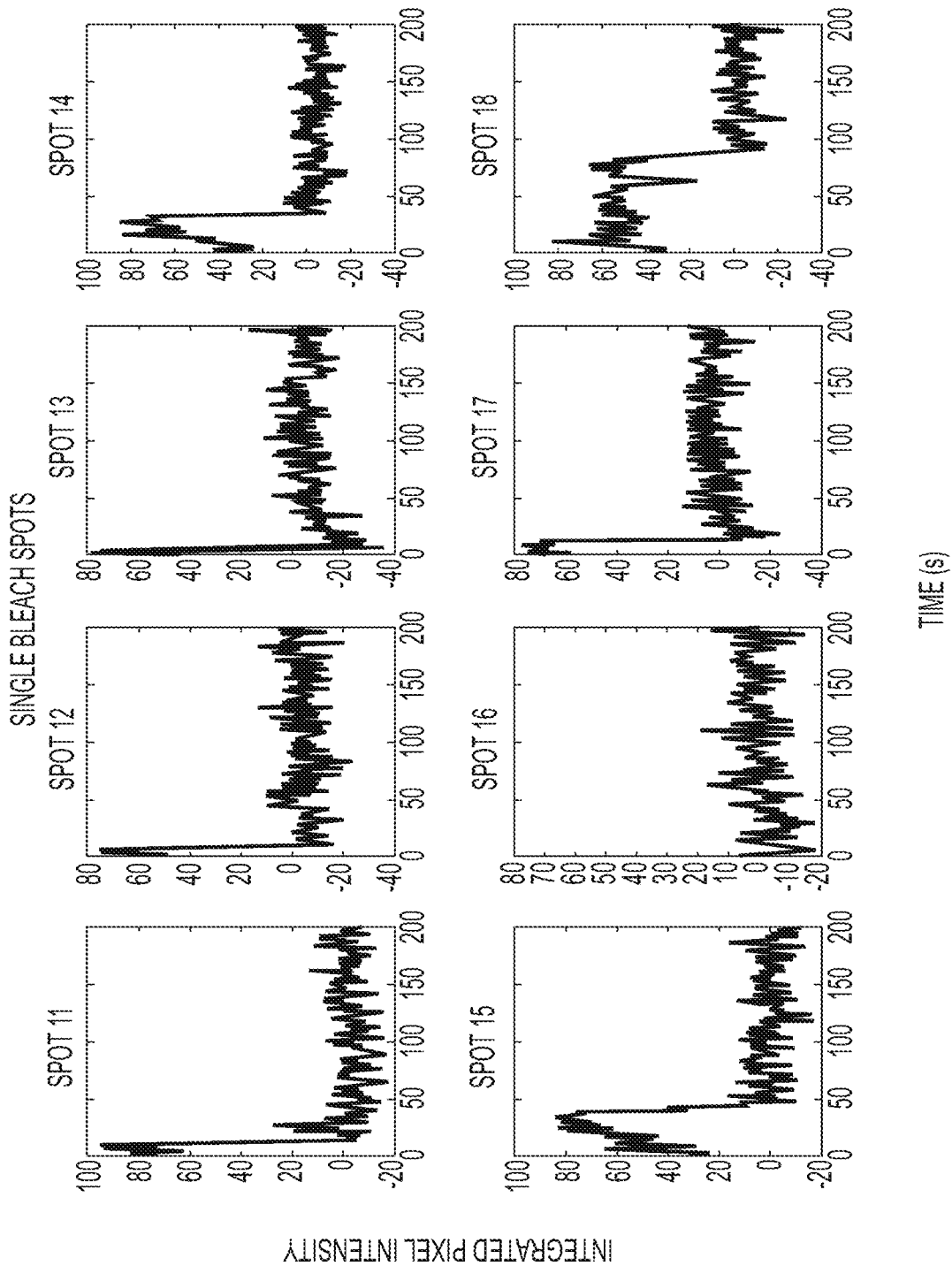
FIGS. 4-13 show the integrated label intensity graphs over time for various Alexa 488 labels.
Figure 5:
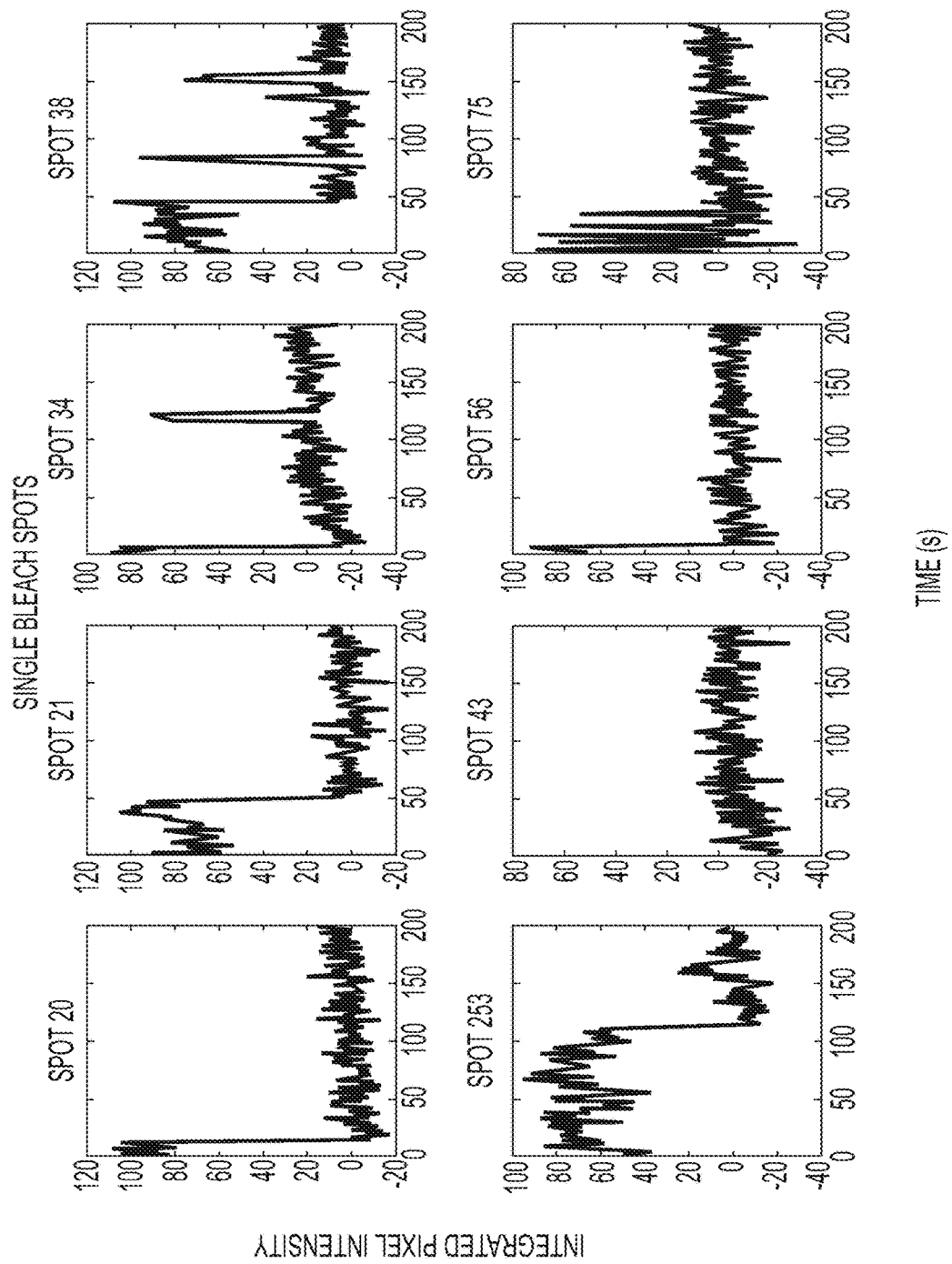
Figure 6:
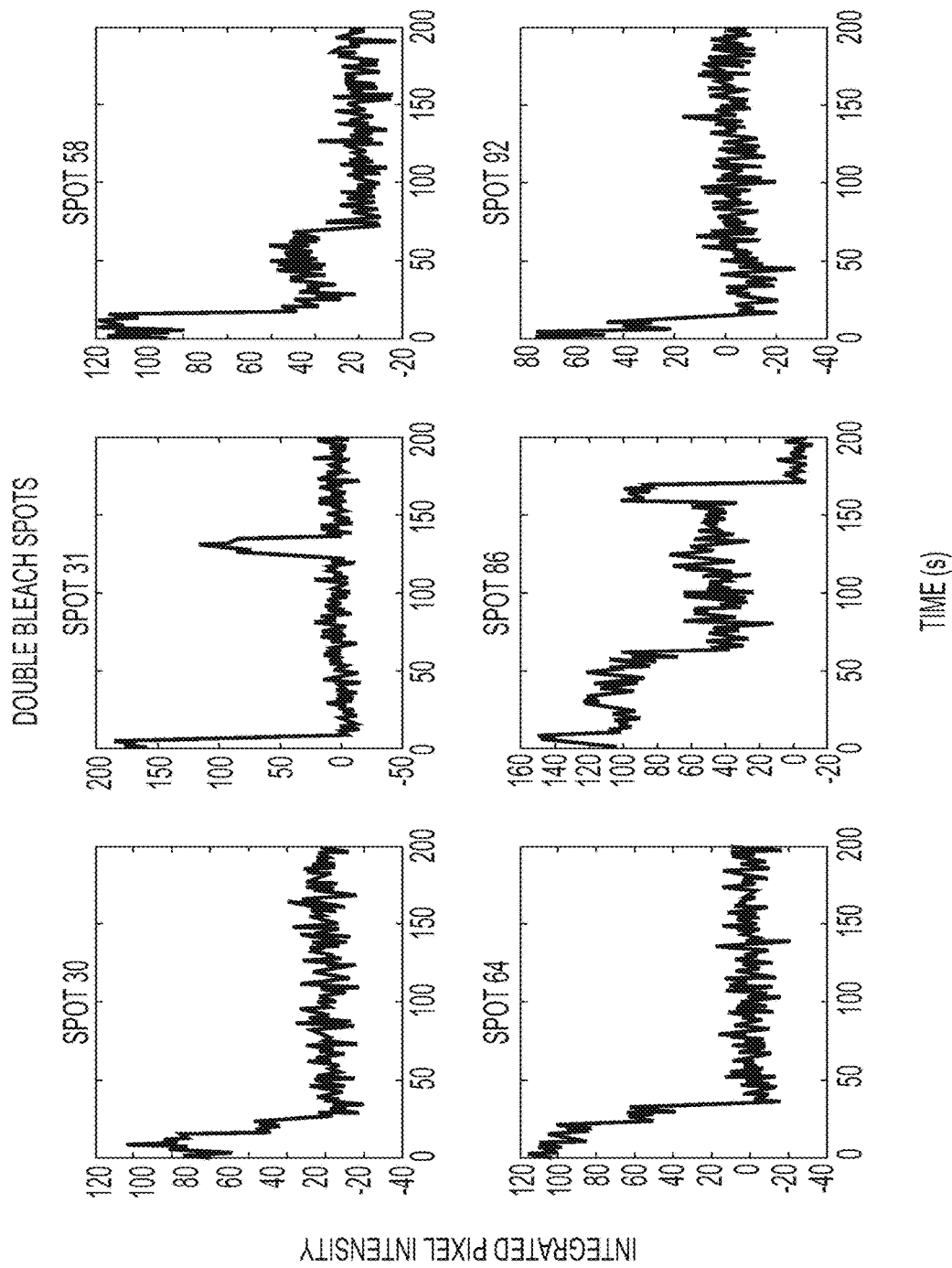
Figure 7:
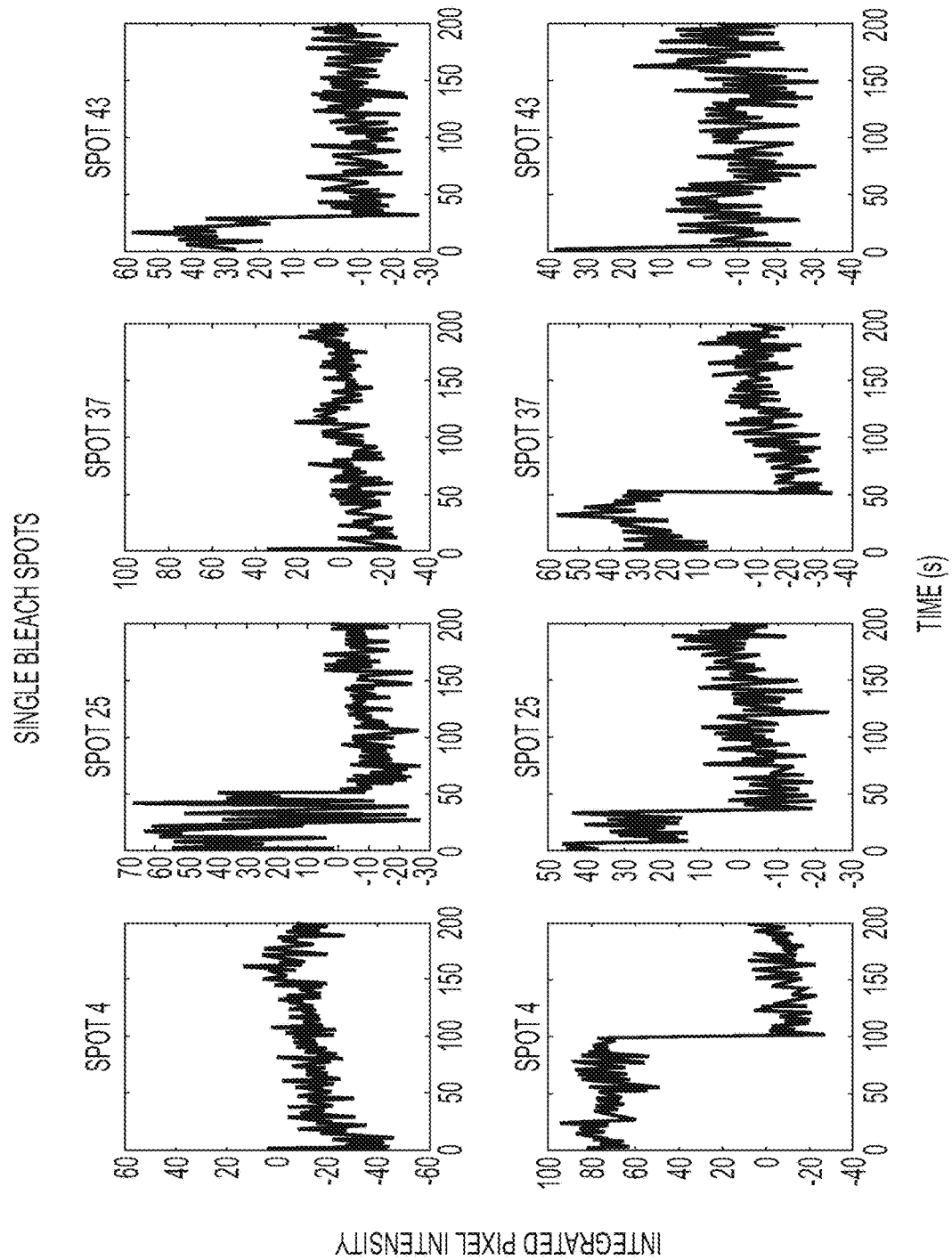
Figure 8:
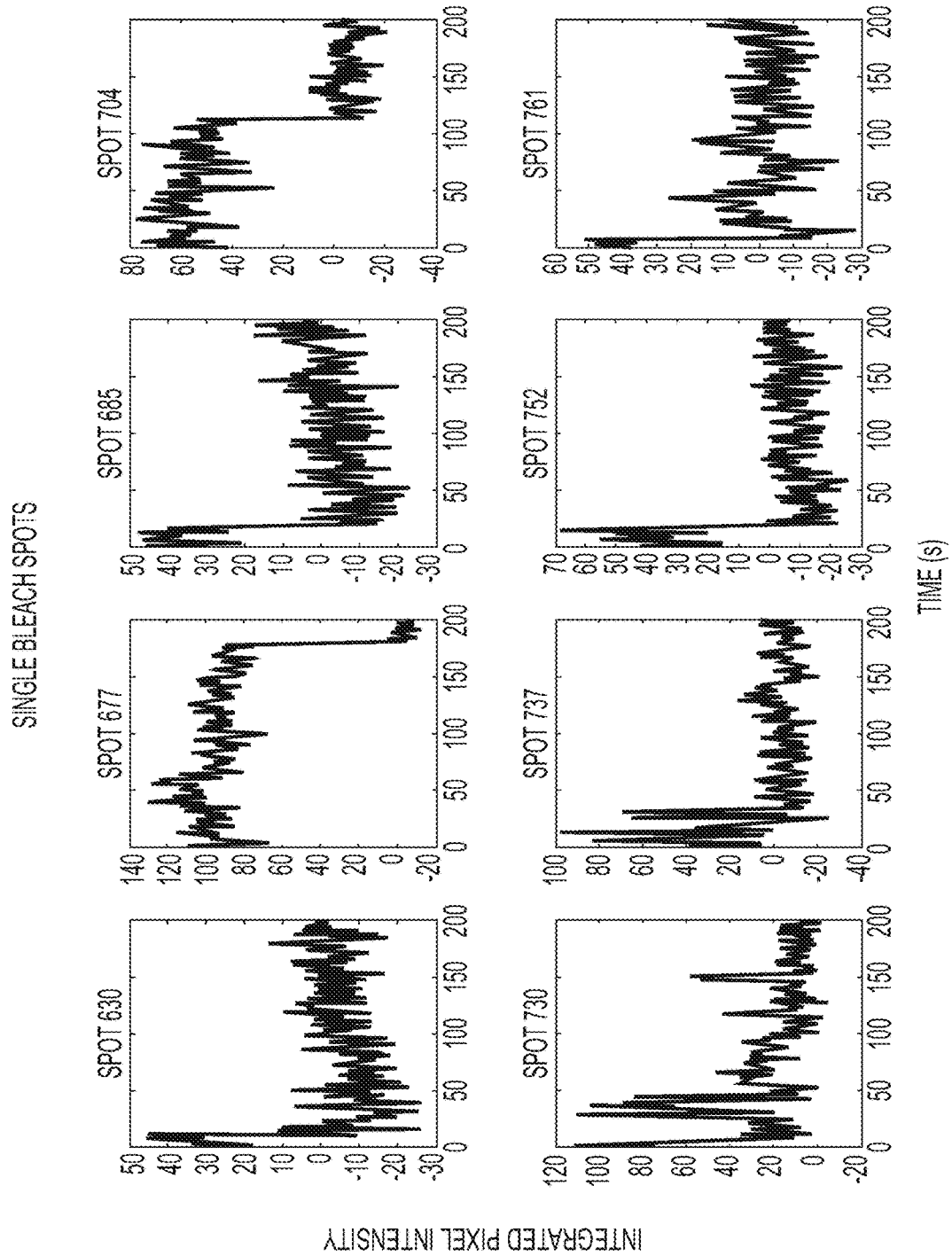
Figure 9:
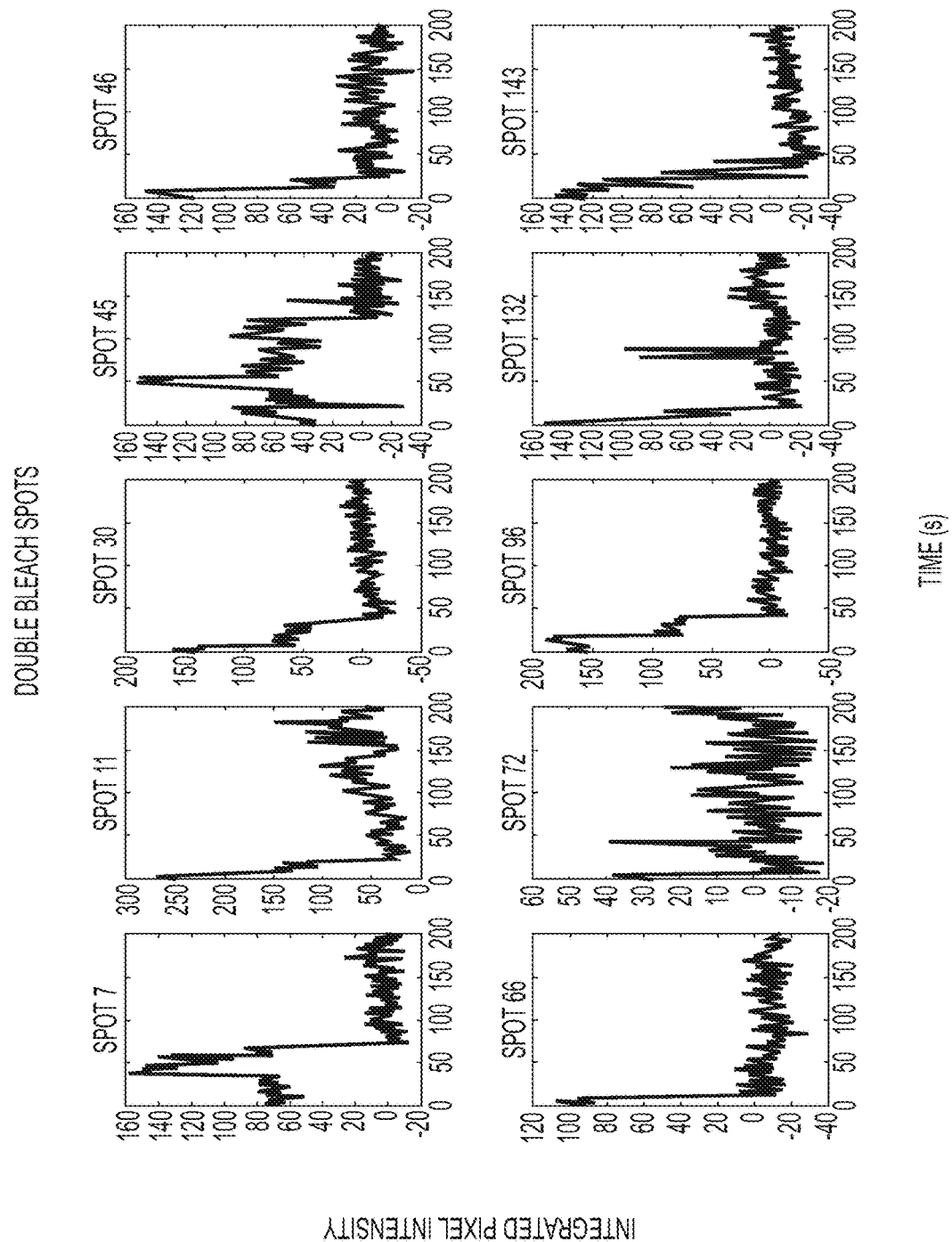
Figure 10:
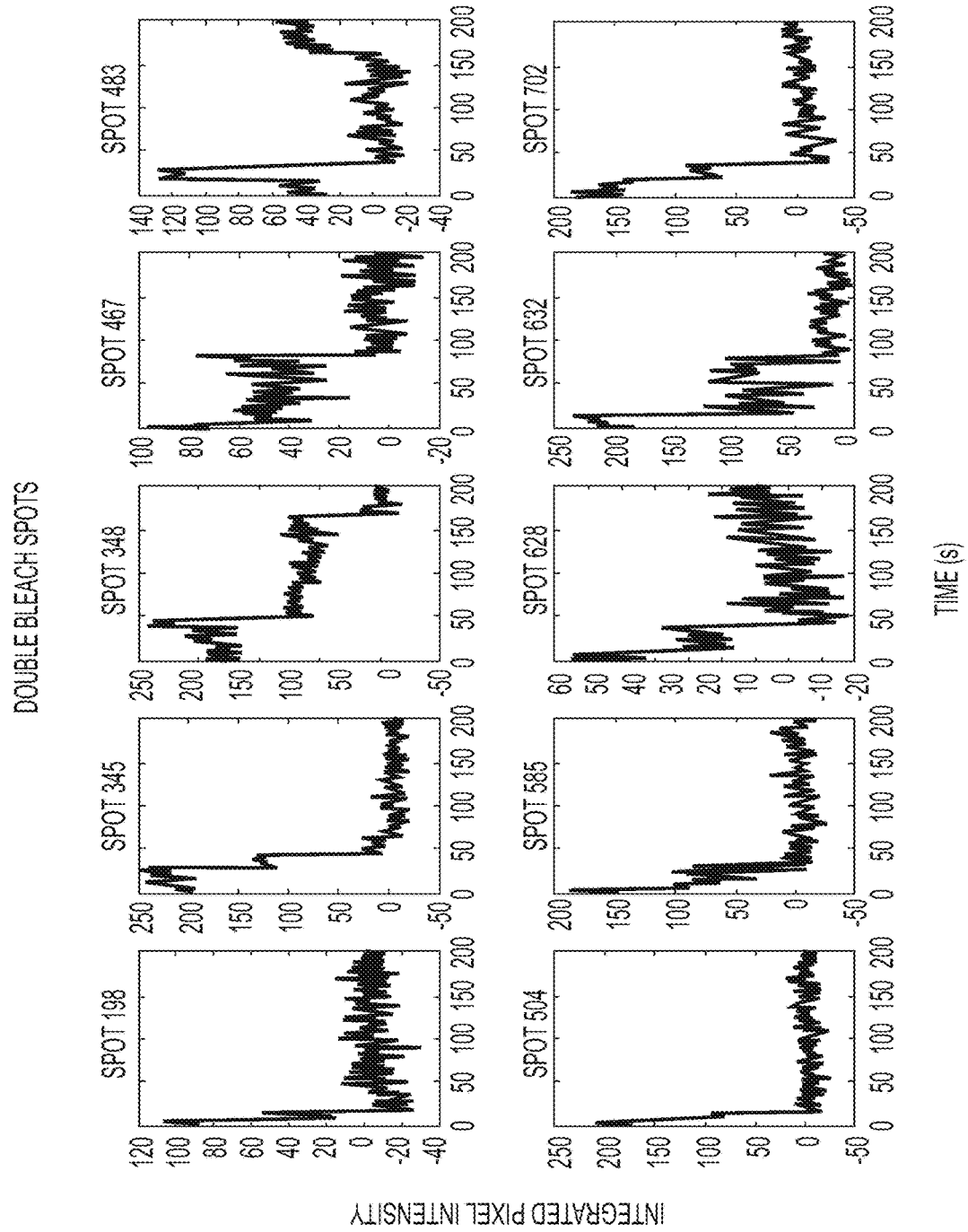
Figure 11:
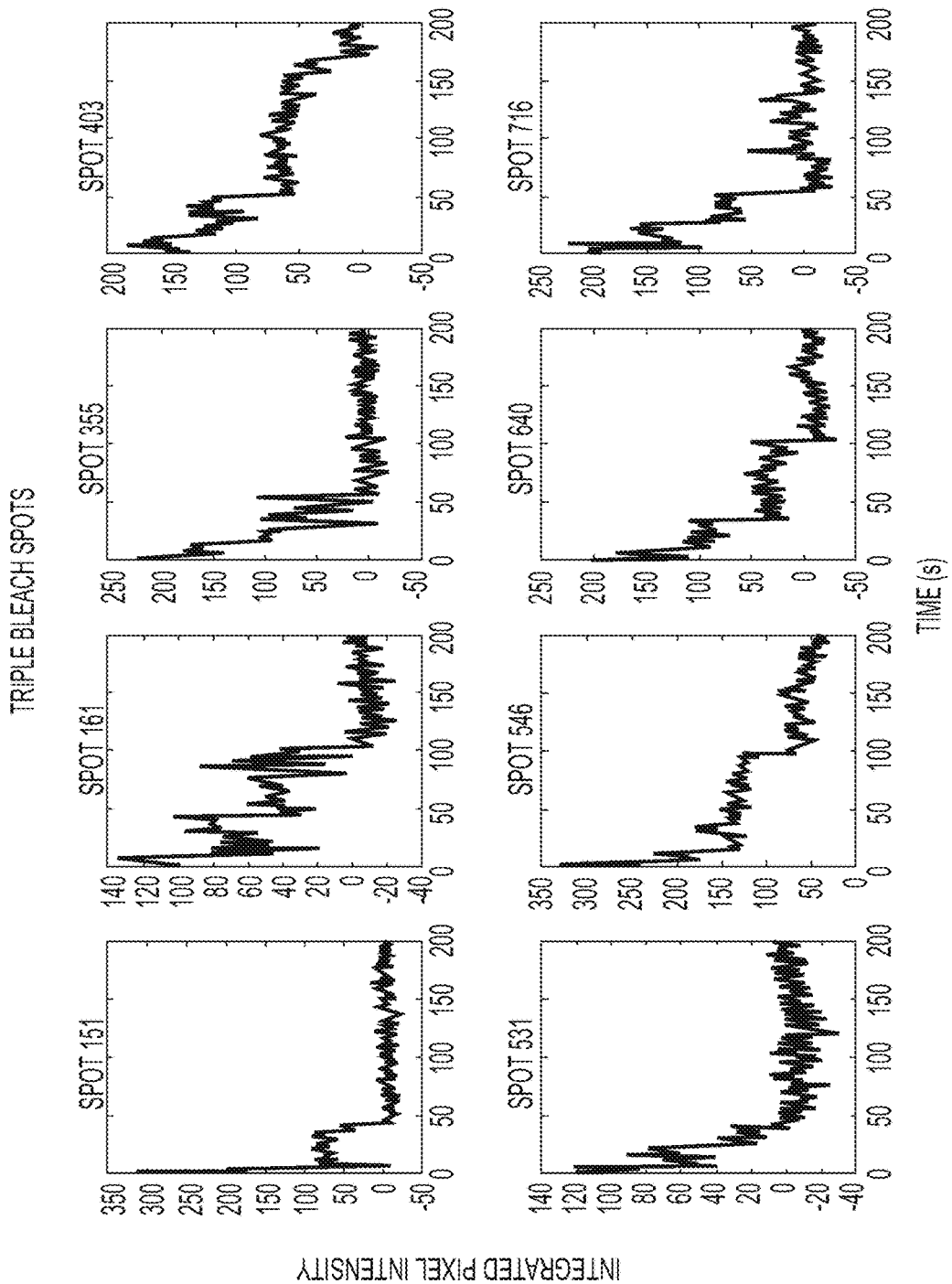
Figure 12:
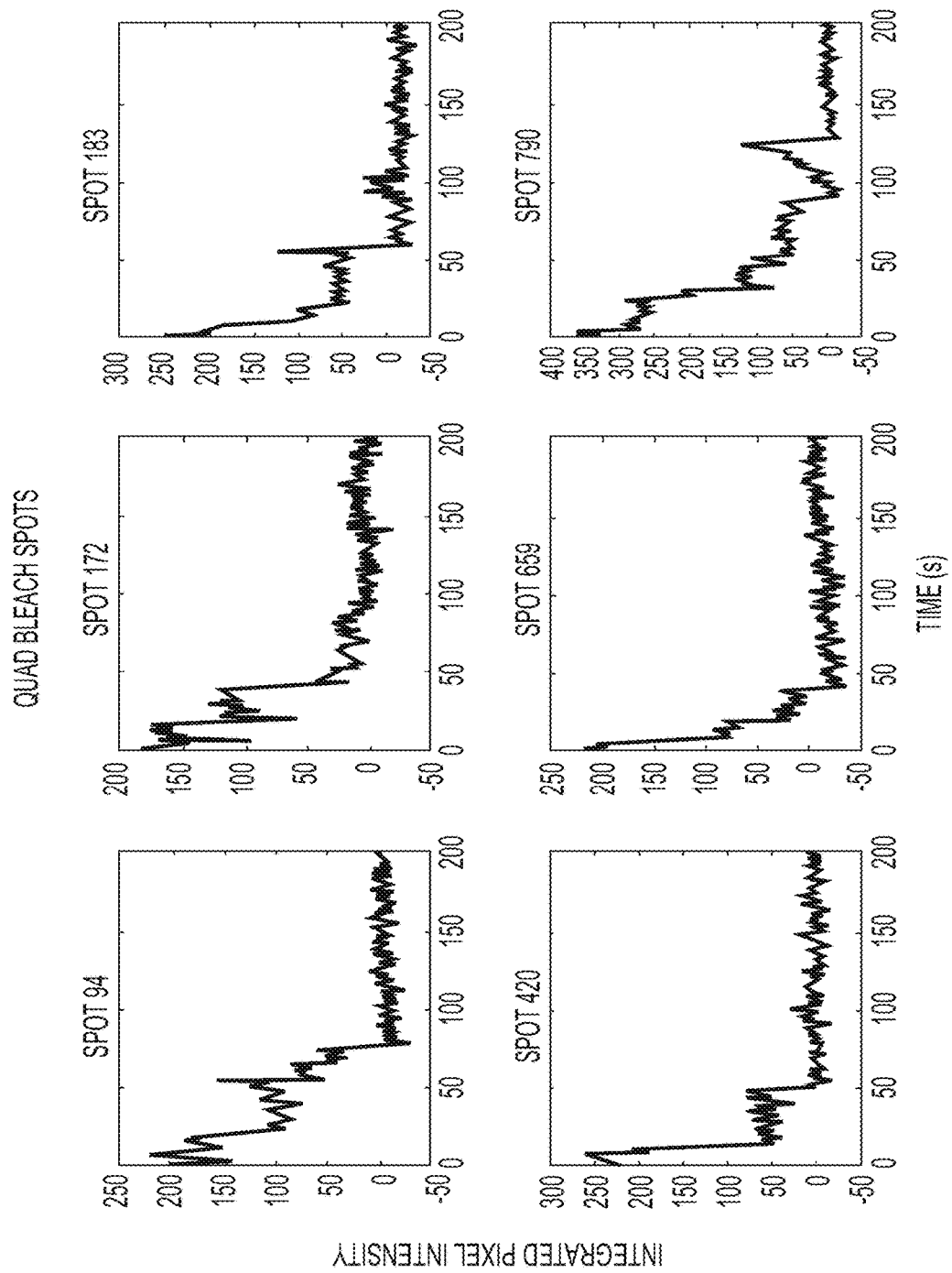
Figure 13:
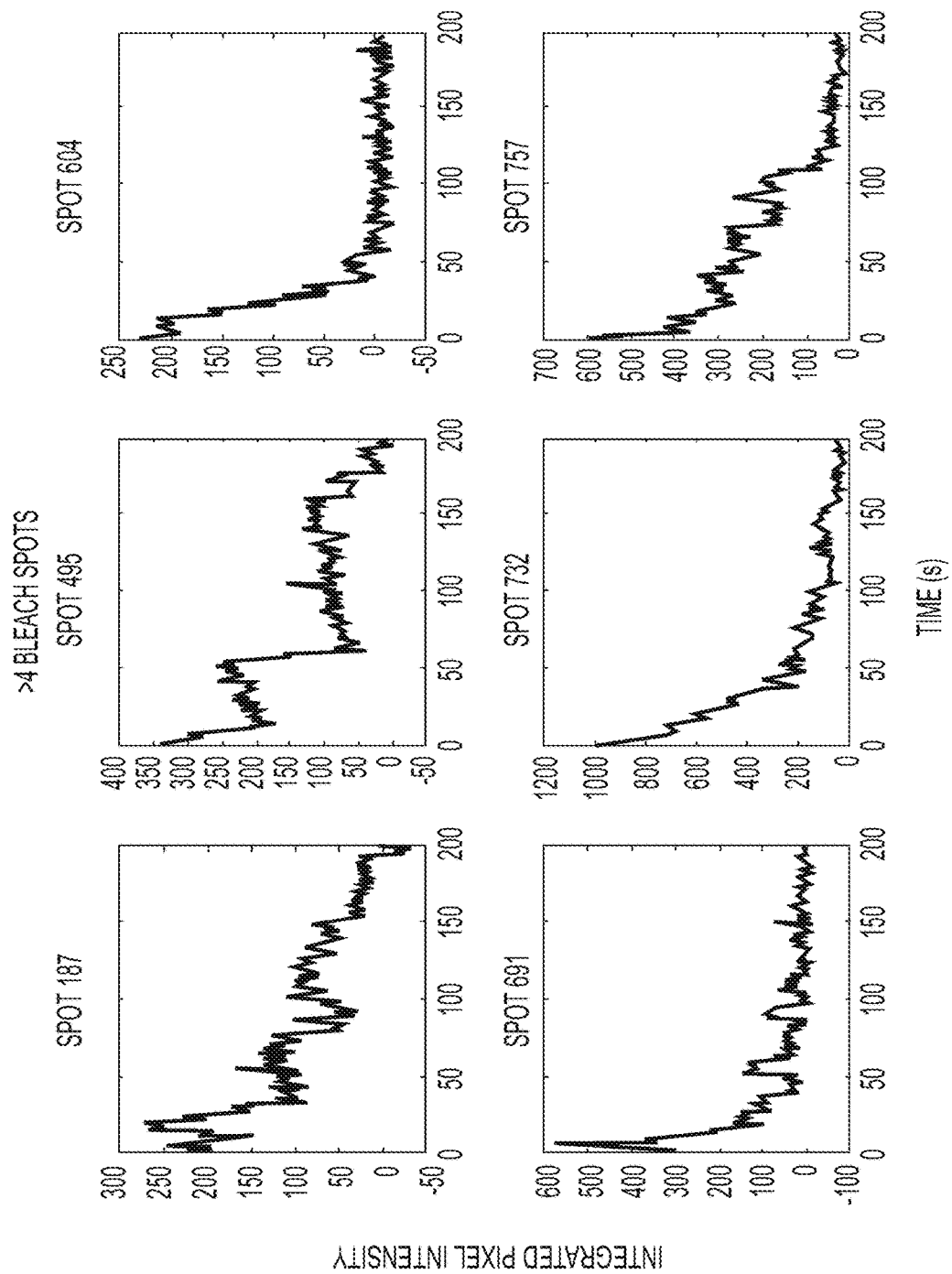

Bleaching profiles are label specific and may be used to add information for distinguishing label types. FIG. 3 shows average bleaching profiles from various labels. The plot shows the normalized counts per label type as a function of successive images that were collected over a 60 second interval. Item c1 is Cy3 fluor, item c2 is Atto647 fluor, and item c3 is Alexa488 fluor.

In another aspect, blinking behavior may be used as a method of identifying single labels. Many dye molecules are known to temporarily go into a dark state (e.g., Burnette et al., Proc. Natl. Acad. Sci. USA (2011) 108: 21081-21086). This produces a blinking effect, where a label will go through one or more steps of bright-dark-bright. The length and number of these dark periods may vary. The current invention uses this blinking behavior to discriminate one label from two or more labels that may appear similar in diffraction limited imaging. If there are multiple labels present, it is unlikely the signal will completely disappear during the blinking. More likely is that the intensity will fall as one of the labels goes dark, but the others do not. The probability of all the labels blinking simultaneously (and so looking like a single fluor) may be calculated based on the specific blinking characteristics of a dye.

In some embodiments, the optical signals from the labels are measured for at least two time points, and an optical signal is from a single label if the intensity of the optical signal is reduced by a single step function. In some embodiments, the two time points may be separated by from 0.1 to 30 minutes, from 1 second to 20 minutes, from 10 seconds to 10 minutes; 0.01, 0.1, 1, 2, 3, 4, 5, 10, 20, 30, 40, 50, 60 seconds or more; and/or 1, 2, 3, 4, 5, 10, 20, 30, 40, 50, 60 seconds or less. In additional embodiments, an intensity of the optical signal from a single label has a single step decrease over time, and an intensity of the optical signal from two or more labels has multiple step decreases over time. In further embodiments, the optical signals from the labels are measured for at least two time points and are normalized to bleaching profiles of the labels. In another aspect, the method described herein and/or the counting step may further comprises measuring an optical signal from a control label for at least two time points, and comparing the optical signal from the control label with the optical signals from the labels to determine an increase or decrease of the optical signal from the labels.

In another aspect, the counting step further comprises confirming the counting by using a control molecule. A control molecule may be used to determine the change in frequency of a molecule type. Often, the experimental goal is to determine the abundance of two or more types of molecules either in the absolute or in relation to one another. Consider the example of two molecules labeled with two different dyes. If the null hypothesis is that they are at equal frequency, they may be enumerated on a single-molecule array and the ratio of the counts compared to the null hypothesis. The "single-molecule array" herein is defined as an array configured to detect a single molecule, including, for example, the arrays described in U.S. Patent Application Publication No. 2013/0172216. If the ratio varies from 1:1, this implies they two molecules are at different frequencies. However, it may not be clear a priori whether one has increased abundance or the other has decreased abundance. If a third dye is used as a control molecule that should also be at equal frequency, this should have a 1:1 ratio with both the other dyes. Consider the example of two molecules labeled with dyes A and B, the goal being to see if the molecule labeled with dye B is at increased or decreased frequency compared to the molecule labeled with dye A. A third molecule labeled with dye C is included in the experiment in a way that it should be at the same abundance as the other two molecules. If the ratio of molecules labeled A and B respectively is 1:2, then either the first molecule has decreased frequency or the second has increased frequency. If the ratio of the molecules labeled A and C is 1:1 and the ratio of molecules labeled B and C is 1:2, then it is likely that the molecule labeled with dye B has increased with frequency with respect to the molecule labeled with dye A. An example of this would be in determining DNA copy number changes in a diploid genome. It is important to know if one sequence is amplified or the other deleted and using a control molecule allows for this determination. Note the control may be another region of the genome or an artificial control sequence.

In some embodiments, the results of the method described herein (e.g., counted numbers of labels) may be confirmed by using different labels but the same tags used in the initial method. Such confirming may be performed simultaneously with the initial method or after performing the initial method. In additional embodiments, the confirming described herein comprises contacting first and second control probe sets to the genetic sample, wherein the first control probe set comprises a first control labeling probe and the first tagging probe, which is the same tag of the first probe set described herein, and the second control probe set comprises a second control labeling probe and the second tagging probe, which is the same tag of the second probe set described herein. The confirmation may further comprise hybridizing at least a part of the first and second control probe sets to the first and second nucleic acid regions of interest in nucleotide molecules of the genetic sample, respectively. The confirmation may further comprise ligating the first control probe set at least by ligating the first control labeling probe and the first tagging probe. The confirmation may further comprise ligating the second control probe set at least by ligating the second control labeling probe and the second tagging probe. The confirmation may further comprise amplifying the ligated probe sets. The confirmation may further comprise immobilizing each of the tagging probes to a pre-determined location on a substrate, wherein the first and second control labeling probes and/or the amplified labeling probes thereof ligated to the immobilized tagging probes comprise first and second control labels, respectively, the first and second control labels are different, and the immobilized labels are optically resolvable. The confirmation may further comprise measuring the optical signals from the control labels immobilized to the substrate. The confirmation may further comprise comparing the optical signals from the immobilized first and second control labels to the optical signals from the immobilized first and second labels to determine whether an error based on the labels exists. The "error based on a label" used herein means any error caused by the label that may not have occurred if a different label is used in the method. In some embodiments, the first label and the second control label are the same, and the second label and the first control label are the same.

Bleaching may be used as a method of identifying single labels. A key element of the readout is that individual labels be "resolvable," i.e., distinct. This is trivial at low densities on a surface when the likelihood of labels in close proximity is very low. For higher densities, assuming the labels are at random locations (i.e., Poissonian), the chances of close neighbors increases to the point where significant numbers of labels have neighbors whose fluorescent emission partially (or fully) overlaps with their own emission. At this point, the labels are no longer "resolvable," and in a transition regime exists between single-label detection (i.e., digital detection) and classic multi-label array-type detection (e.g., analogue detection) where the average signal from many molecules is measured. Put differently, a digital counting regime of individual molecules is switched to an analog regime of average-fluorescent-intensity from many molecules.

One solution to increase the loading range while maintaining individual resolvability is to take advantage of fluorophore bleaching. Extended exposure to light may cause labels to bleach, that is, lose their property of fluorescence. That is, over time, a label may be extinguished. This usually occurs as a step function, with the label appearing to "switch off." The current invention may use this bleaching behavior to discriminate one label from two or more labels that may appear similar in diffraction limited imaging. For multiple labels, extinction would be expected to occur via a series of step-wise decreases in the signal intensity. For example, FIGS. 4-13 show the integrated label intensity vs. time (showing bleaching events as changes in intensity) graphs that were obtained for various Alexa 488 labels. Single versus multiple label species may be easily differentiated (e.g. depending on whether the intensity of the optical signal is reduced by single versus multiple step(s) as shown in the graphs).

In another aspect, the method herein may comprise calibrating and/or confirming the counted numbers by label swapping or dye swapping. In some embodiments where probe product 1 and 2 are labeled with labels 1 and 2, respectively, various modes of error may mimic the differential frequency of the probe products. For example, if a ratio of 1:2 is observed between label 1 and label 2, this may be due to genuine differences in frequency (probe product 2 is twice as common as probe product 1), differences in hybridization efficiency (the probe products are at equal abundance, but probe product 2 hybridizes more efficiently than probe product 1) or differences in the properties of the labels (for example, if the labels are fluorescent dyes, label 1 may bleach faster, blink more frequently, give lower signal or lower signal-to-noise than label 2). If the same experiment is repeated with the labels switched, the ratio should be reversed, if it is a genuine observation of different frequencies of the molecules, with label 1 now twice as common as label 2. However, if it is due to differential hybridization efficiency the ratio will be ≤2:1. If the 1:2 ratio was due to the properties of the labels, the ratio will switch to 2:1 of label 1 to label 2 if they are actually at equal frequency. This approach can be extended to any number of labeled probe sets.

In some embodiments, the first nucleic acid region of interest is located in a first chromosome, and the second nucleic acid region of interest is located in a second chromosome, different from the first chromosome. The counting step may further comprise confirming the counting, wherein the confirming step comprises contacting first and second control probe sets to the genetic sample, wherein the first control probe set comprises a first control labeling probe and a first control tagging probe, and the second control probe set comprises a second control labeling probe and the second control tagging probe. The confirming step may further comprise hybridizing at least a part of the first and second control probe sets to first and second control regions located in the first and second chromosomes, respectively, wherein the first and second control regions are different from the first and second nucleic acid regions of interest. The confirming step may further comprise ligating the first and second control probe sets at least by ligating (i) the first control labeling and tagging probes, and (ii) the second control labeling and tagging probes. The confirming step may further comprise amplifying the ligated probe sets. The confirming step may further comprise immobilizing (i) the first probe set and the second control probe set to a first pre-determined location, and (ii) the second probe set and the first control probe set to a second pre-determined location. In some embodiments, the first and second control labeling probes and/or the amplified labeling probes thereof ligated to the immobilized tagging probes comprise a first and second control labels, respectively, the first label and the second control label are different, the second label and the first control labels are different, the immobilized labels are optically resolvable, the immobilized first and second control tagging probes and/or the amplified tagging probes thereof comprise first and second control tags, respectively, and the immobilizing step is performed by immobilizing the tags to the predetermined locations. The confirming step may further comprise measuring the optical signals from the control labels immobilized to the substrate. The confirming step may further comprise comparing the optical signals from the immobilized control labels to the optical signals from the immobilized first and second labels to determine whether an error based on the nucleic acid region of interest exists. In further embodiments, the first tag and the second control tag are the same, and the second tag and the first control tag are the same.

In another aspect, the counting step of the method described herein may further comprise calibrating and/or confirming the counted numbers by (i) repeating some or all the steps of the methods (e.g., steps including the contacting, binding, hybridizing, ligating, amplifying, and/or immobilizing) described herein with a different probe set(s) configured to bind and/or hybridize to the same nucleotide and/or peptide region(s) of interest or a different region(s) in the same chromosome of interest, and (ii) averaging the counted numbers of labels in the probe sets bound and/or hybridized to the same a nucleotide and/or peptide region of interest or to the same chromosome of interest. In some embodiments, the averaging step may be performed before the comparing step so that the averaged counted numbers of labels in a group of different probe sets that bind and/or hybridize to the same nucleotide and/or peptide region of interest are compared, instead of the counted numbers of the labels in the individual probe sets. In another aspect, the method described herein may further comprise calibrating and/or confirming the detection of the genetic variation by (i) repeating some or all the steps of the methods (e.g., steps including the contacting, binding, hybridizing, ligating, amplifying, immobilizing, and/or counting) described herein with different probe sets configured to bind and/or hybridize to control regions that does not have any known genetic variation, and (ii) averaging the counted numbers of labels in the probe sets bound and/or hybridized to the control regions. In some embodiments, the averaged numbers of the labels in the probe sets that bind and/or hybridize to control regions are compared to the numbers of the labels in the probe sets that bind and/or hybridized to the regions of interest described herein to confirm the genetic variation in the genetic sample. In another aspect, the steps of the calibrating and/or confirming may be repeated simultaneously with the initial steps, or after performing the initial steps.

Figure 14:
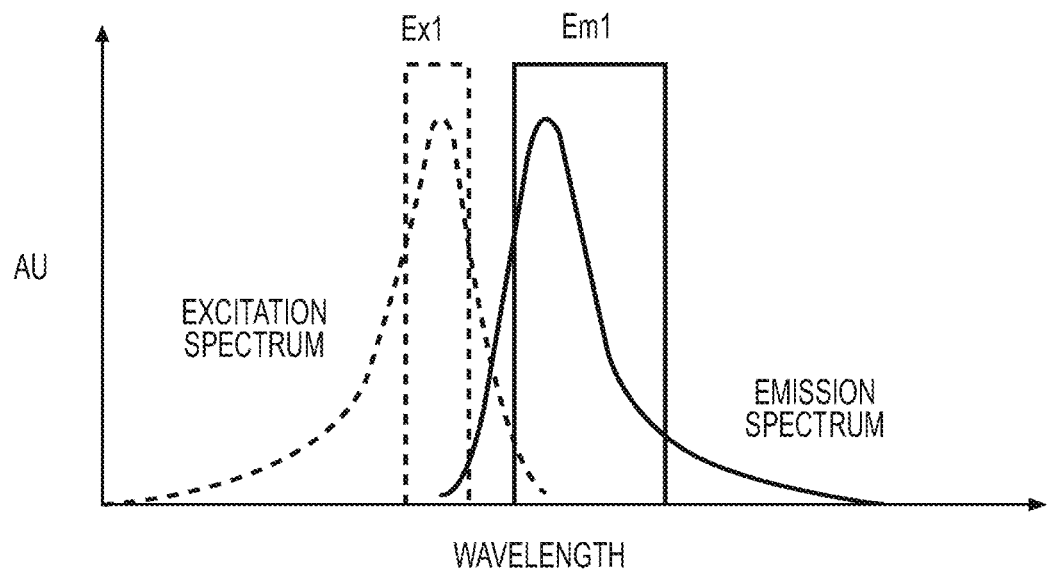
FIG. 14 depicts excitation spectrum and emission spectrum through a standard operation when excitation of a fluorophore is achieved by illuminating with a narrow spectral band aligned with the absorption maxima of that species.
Figure 15:
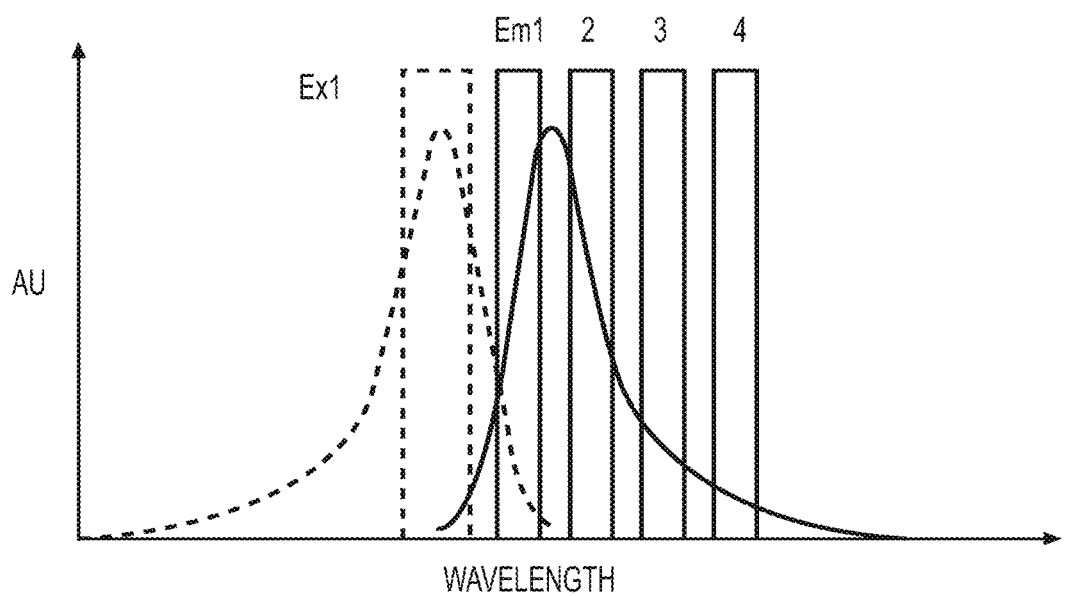
FIG. 15 depicts excitation spectrum and emission spectrum through interrogation with various excitation colors and collected emission bands different from (or in addition to) the case for the standard operation.
Figure 16:
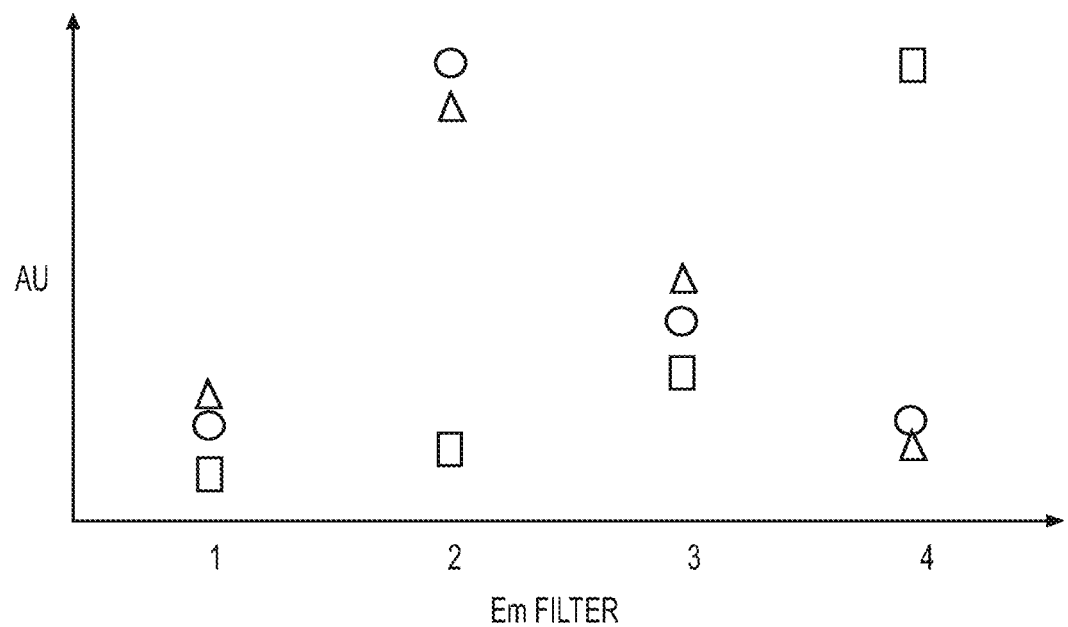
FIG. 16 shows results when the light from these various imaging configurations, e.g., various emission filters, is collected and compared to calibration values for the fluorophores of interest.
Figure 17:
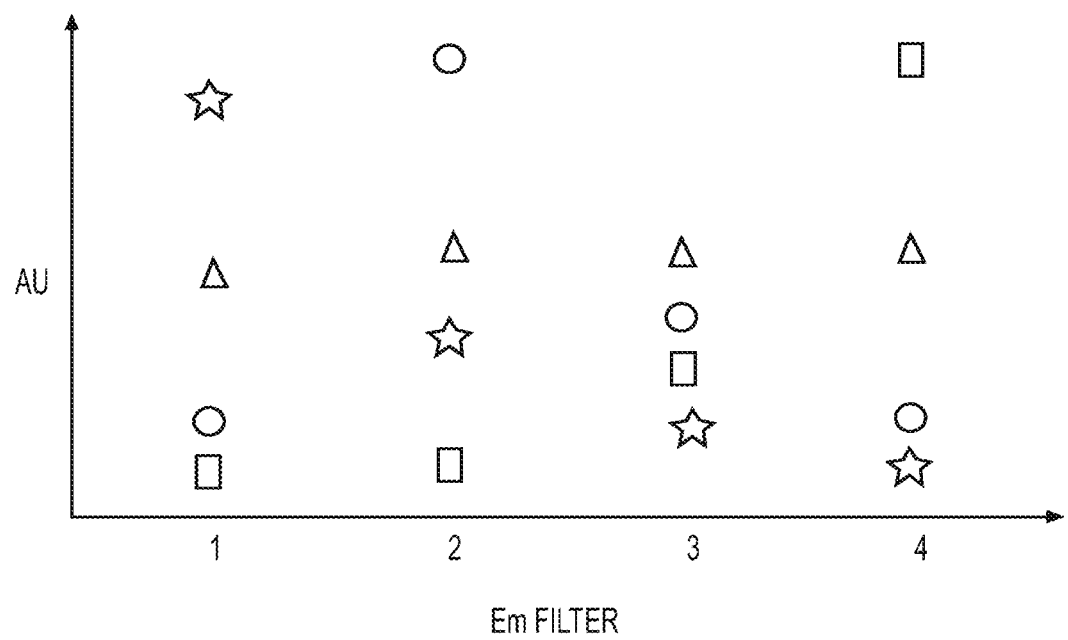
FIG. 17 shows results collected with various references, including those with a flat emission profile (Contaminant 1; triangles), or a blue-weighted profile (Contaminant 2; stars).

In another aspect, labels (e.g., fluorescent dyes) from one or more populations may be measured and/or identified based on their underlying spectral characteristics. Most fluorescent imaging systems include the option of collecting images in multiple spectral channels, controlled by the combination of light source and spectral excitation/emission/dichroic filters. This enables the same fluorescent species on a given sample to be interrogated with multiple different input light color bands as well as capturing desired output light color bands. Under normal operation, excitation of a fluorophore is achieved by illuminating with a narrow spectral band aligned with the absorption maxima of that species (e.g., with a broadband LED or arclamp and excitation filter to spectrally shape the output, or a spectrally homogenous laser), and the majority of the emission from the fluorophore is collected with a matched emission filter and a long-pass dichroic to differentiate excitation and emission (FIG. 14). In alternate operations, the unique identity of a fluorescent moiety may be confirmed through interrogation with various excitation colors and collected emission bands different from (or in addition to) the case for standard operation (FIG. 15). The light from these various imaging configurations, e.g., various emission filters, is collected and compared to calibration values for the fluorophores of interest (FIG. 16). In the example case, the experimental measurement (dots) matches the expected calibration/reference data for that fluorophore (triangles) but does not agree well with an alternate hypothesis (squares). Given test and calibration data for one or more channels, a goodness-of-fit or chi-squared may be calculated for each hypothesis calibration spectrum, and the best fit selected, in an automated and robust fashion. Various references may be of interest, including fluorophores used in the system, as well as common fluorescent contaminants, e.g., those with a flat emission profile (Contaminant 1; triangle), or a blue-weighted profile (Contaminant 2; stars) (FIG. 17).

Figure 18:
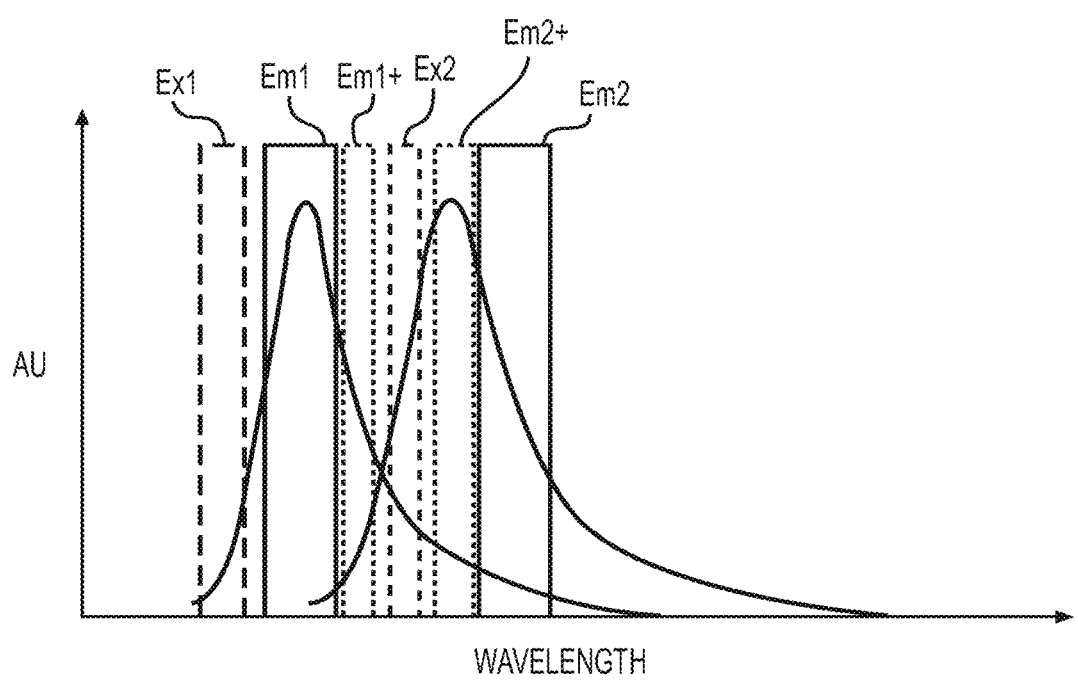
FIG. 18 depicts significantly-different excitation bands of two fluorophores.

The design constraints for filter selection may be different from standard designs for which the goal is simply to maximize collected light in a single channel while avoiding significant contributions from other channels. In our invention the goal is spectral selectivity rather than solely light collection. For example, consider two fluorophores with significantly-different excitation bands, shown in FIG. 18 (note, only the excitation regions are shown and no excitation spectra). A standard design would maximize the capture of Fluor 1 emission (with Em1 filter, solid line) and minimize catching the leading edge from Fluor 2, and Fluor 2 would be optimally captured by Em2 (which is slightly red-shifted to avoid significant collection of Fluor 1 light). In our design, verifying the presence of Fluor 2 with the Em1 filter is desired leading to widening of the band to be captured ("Em1+", fine dashed line). This creates additional information to verify the identity of Fluor 2. Similarly, Em2 may be widened or shifted towards Fluor 1 to capture more of that fluor's light (Em2+, fine dashed line). This increase in spectral information must also be balanced with the total available light from a given fluorophore to maintain detectability. Put differently, the contribution from a given fluorophore in a given channel is only significant if the corresponding signal is above the background noise, and therefore informative, unless a negative control is intended. In this way, the spectral signature of a fluorescent entity may be used for robust identification and capturing more light may be a second priority if species-unique features may be more effectively quantitated.

Given probe products may be labeled with more than one type of fluorophore such that the spectral signature is more complex. For example, probe products may always carry a universal fluor, e.g., Alexa647, and a locus-specific fluorophore, e.g., Alexa 555 for Locus 1 and Alexa 594 for locus 2. Since contaminants will rarely carry yield the signature of two fluors, this may further increase the confidence of contamination rejection. Implementation would involve imaging in three or more channels in this example such that the presence or absence of each fluor may be ascertained, by the aforementioned goodness-of-fit method comparing test to reference, yielding calls of locus 1, locus 2 or not a locus product. Adding extra fluors aids fluor identification since more light is available for collection, but at the expense of yield of properly formed assay products and total imaging time (extra channels may be required). Other spectral modifiers may also be used to increase spectral information and uniqueness, including FRET pairs that shift the color when in close proximity or other moieties.

In another aspect, as described herein, the method of the present disclosure may be used to detect a genetic variation in peptide or proteins. In such as case, the methods may comprise contacting first and second probe sets to the genetic sample, wherein the first probe set comprises a first labeling probe and a first tagging probe, and the second probe set comprises a second labeling probe and a second tagging probe. The methods may further comprise binding the probe sets to peptide regions of interest by a physical or chemical bond, in place of the hybridizing step described herein in the case of detecting the genetic variation in nucleic acid molecules. Specifically, the methods may further comprise binding at least parts of the first and second probe sets to first and second peptide regions of interest in a peptide of protein of the genetic sample, respectively. For example, the binding may be performed by having a binder in at least one probe in the probe set that specifically binds to the peptide region of interest.

In some embodiments, the methods to detect a genetic variation in peptide or proteins may further comprise conjugating the first probe set by a chemical bond at least by conjugating the first labeling probe and the first tagging probe, and conjugating the second probe set at least by conjugating the second labeling probe and the second tagging probe, in place of the ligating step described herein in the case of detecting the genetic variation in nucleic acid molecules. The method may further comprise immobilization the tagging probes to a pre-determined location on a substrate as described herein. In additional embodiments, the first and second labeling probes conjugated to the immobilized tagging probes comprise first and second labels, respectively; the first and second labels are different; the immobilized labels are optically resolvable; the immobilized first and second tagging probes and/or the amplified tagging probes thereof comprise first and second tags, respectively; and the immobilizing step is performed by immobilizing the tags to the predetermined location. The methods may further comprise, as described herein, counting (i) a first number of the first label immobilized to the substrate, and (ii) a second number of the second label immobilized to the substrate; and comparing the first and second numbers to determine the genetic variation in the genetic sample.

Figure 19:
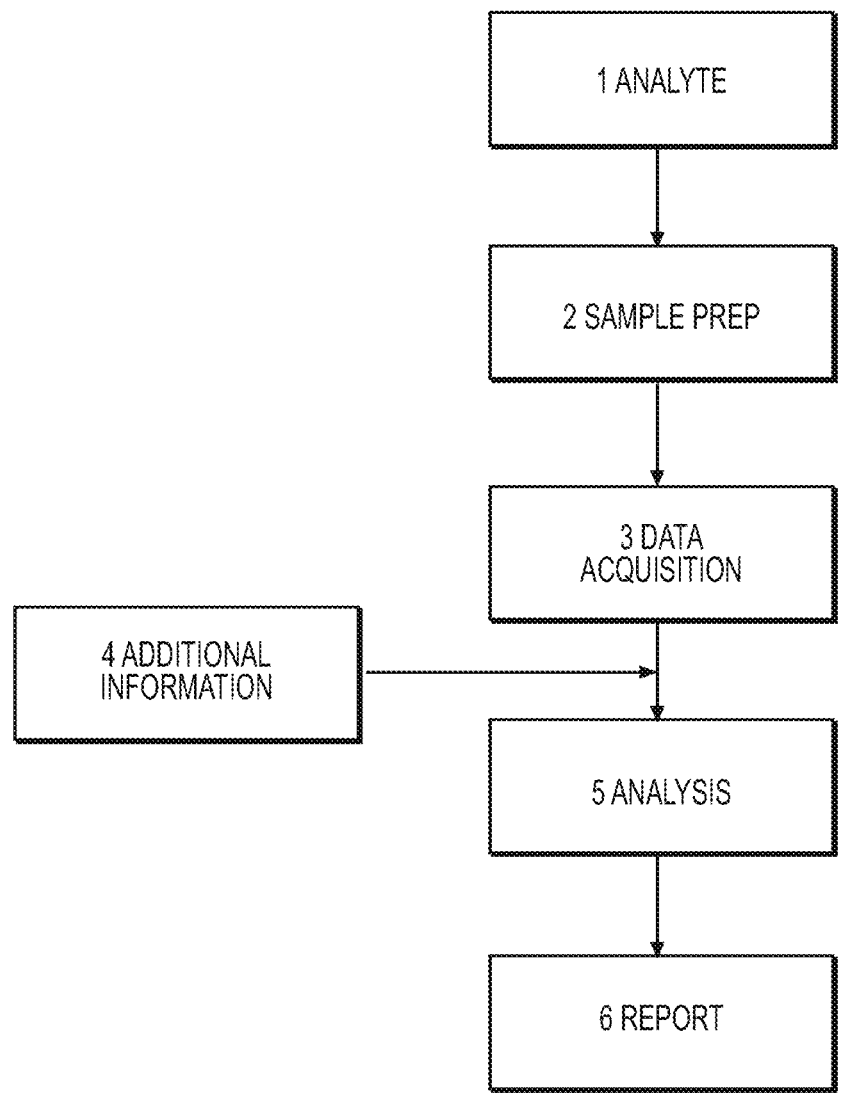
FIG. 19 depicts an exemplary system flow chart.
Figure 20:
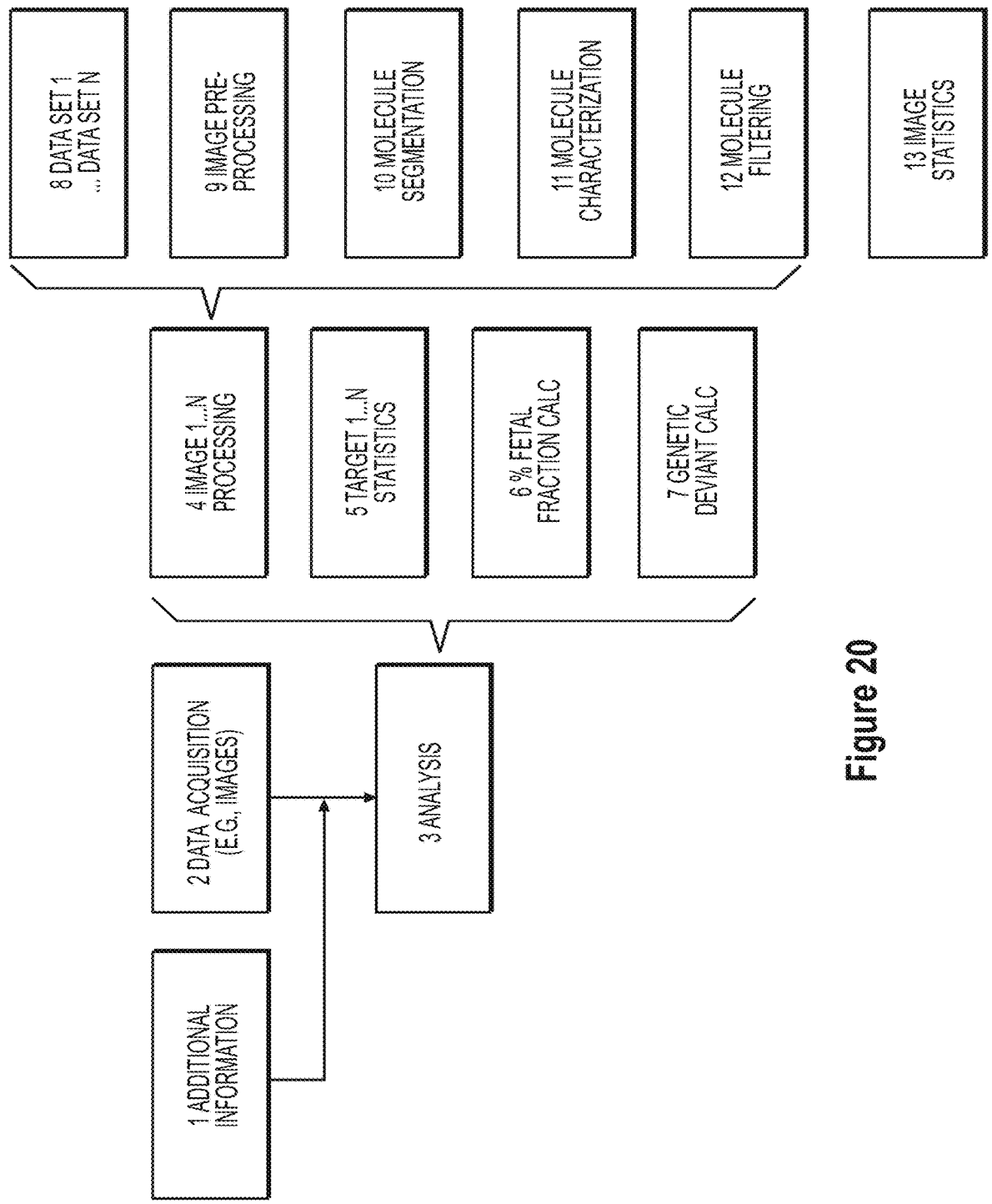
FIG. 20 depicts an exemplary system flow chart including various methods for analyzing data.

A system to detect a genetic variation according to the methods described herein includes various elements. Some elements include transforming a raw biological sample into a useful analyte. This analyte is then detected, generating data that are then processed into a report. Various modules that may be included in the system are shown in FIG. 19. More details of various methods for analyzing data, including e.g., image processing, are shown in FIG. 20. Analysis may be performed on a computer, and involve both a network connected to the device generating the data and a data server for storage of data and report. Optionally, additional information beyond the analyte data may be incorporated into the final report, e.g., maternal age or prior known risks. In some embodiments, the test system includes a series of modules, some of which are optional or may be repeated depending on the results of earlier modules. The test may comprise: (1) receiving a requisition, e.g., from an ordering clinician or physician, (2) receiving a patient sample, (3) performing an assay including quality controls on that sample resulting in a assay-product on an appropriate imaging substrate (e.g., contacting, binding, and/or hybridizing probes to a sample, ligating the probes, optionally amplifying the ligated probes, and immobilizing the probes to a substrate as described herein), (4) imaging the substrate in one or more spectral channels, (5) analyzing image data, (6) performing statistical calculations (e.g., comparing the first and second numbers to determine the genetic variation in the genetic sample), (7) creating and approving the clinical report, and (8) returning the report to the ordering clinician or physician. The test system may comprise a module configured to receive a requisition, e.g., from an ordering clinician or physician, a module configured to receive a patient sample, (3) a module configured to perform an assay including quality controls on that sample resulting in a assay-product on an appropriate imaging substrate, (4) a module configured to image the substrate in one or more spectral channels, (5) a module configured to analyze the image data, (6) a module configured to perform statistical calculations, (7) a module configured to create and confirm the clinical report, and and/or (8) a module configured to return the report to the ordering clinician or physician.

In one aspect, the assays and methods described herein may be performed on a single input sample simultaneously. For example, the method may comprise verifying the presence of fetal genomic molecules at or above a minimum threshold as described herein, followed by a step of estimating the target copy number state if and only if that minimum threshold is met. Therefore, one may separately run an allele-specific assay on the input sample for performing fetal fraction calculation, and a genomic target assay for computing the copy number state. In other embodiments, both assays and methods described herein may be carried out in parallel on the same sample at the same time in the same fluidic volume. Further quality control assays may also be carried out in parallel with the same universal assay processing steps. Since tags, affinity tags, and/or tagging probes in the probe products, ligated probe set, or labeled molecule to be immobilized to the substrate may be uniquely designed for every assay and every assay product, all of the parallel assay products may be localized, imaged and quantitated at different physical locations on the imaging substrate. In another aspect, the same assay or method (or some of their steps) described herein using the same probes and/or detecting the same genetic variation or control may be performed on multiple samples simultaneously either in the same or different modules (e.g., testing tube) described herein. In another aspect, assays and methods (or some of their steps) described herein using different probes and/or detecting different genetic variations or controls may be performed on single or multiple sample(s) simultaneously either in the same or different modules (e.g., testing tube).

In another aspect, image analysis may include image preprocessing, image segmentation to identify the labels, characterization of the label quality, filtering the population of detected labels based on quality, and performing statistical calculations depending on the nature of the image data. In some instances, such as when an allele-specific assay is performed and imaged, the fetal fraction may be computed. In others, such as the genomic target assay and imaging, the relative copy number state between two target genomic regions is computed. Analysis of the image data may occur in real-time on the same computer that is controlling the image acquisition, or on a networked computer, such that results from the analysis may be incorporated into the test workflow decision tree in near real-time.

In another aspect, steps (4) and (5) of the test above may be repeated multiple times for different portions of the imaging substrate such that the results dictate next steps. For example, the tests and methods described herein comprise confirming the presence and precise level of a fetal sample in a genetic sample obtained from a subject before testing for the relative copy number state of genomic targets. As described herein, an allele sensitive assay may be used to quantify the levels of fetal DNA relative to maternal DNA. The resulting probe products may be pulled down to a fetal fraction region 1 on the substrate, and imaged. In some embodiments, if and only if the calculated fetal fraction is above the minimum system requirement, the test may proceed and yield a valid result. In this way, testing of samples that fail to confirm at least the minimum input fetal fraction may be terminated before additional imaging and analysis takes place. Conversely, if the fetal fraction is above the minimum threshold, further imaging (step 4 of the test) of the genomic targets (e.g., chromosome 21, 18 or 13) may proceed followed by additional analysis (step 5 of the test). Other criteria may also be used and tested.

In another aspect, not every SNP probed in the allele-specific assay may result in useful information. For example, the maternal genomic material may have heterozygous alleles for a given SNP (e.g., allele pair AB), and the fetal material may also be heterozygous at that site (e.g., AB), hence the fetal material is indistinguishable and calculation of the fetal fraction fails. Another SNP site for the same input sample, however, may again show the maternal material to be heterozygous (e.g., AB) while the fetal material is homozygous (e.g., AA). In this example, the allele-specific assay may yield slightly more A counts than B counts due to the presence of the fetal DNA, from which the fetal fraction may be calculated. Since the SNP profile (i.e., genotype) cannot be known a priori for a given sample, multiple or numerous SNP sites should be designed such that nearly every possible sample will yield an informative SNP site. Each SNP site may be localized to a different physical location on the imaging substrate, for example by using a different tag for each SNP. However, for a given test, the fetal fraction may only be calculated successfully once. Therefore, a single or multiple locations on the substrate used to interrogate SNPs may be imaged and analyzed (e.g., in groups of one, two, three, four, five, ten, twenty, fifty or less and/or one, two, three, four, five, ten, twenty, fifty or more) until an informative SNP is detected. By alternating imaging and analysis, one may bypass imaging all possible SNP spots and significantly reduce average test duration while maintaining accuracy and robustness.

In another aspect, determining the fetal fraction of a sample may aide other aspects of the system beyond terminating tests for which the portion of fetal fraction in a sample is inadequate. For example, if the fetal fraction is high (e.g., 20%) then for a given statistical power, the number of counts required per genetic target (e.g., chr21) will be lower; if the fetal fraction is low (e.g., 1%) then for the same statistical power, a very high number of counts is required per genomic target to reach the same statistical significance. Therefore, following (4-1) imaging of the fetal fraction region 1, (5-1) analysis of those data resulting in a required counting throughput per genomic target, (4-2) imaging of genomic target region 2 commences at the required throughput, followed by (5-2) analysis of those image data and the test result for genomic variation of the input targets.

In another aspect, steps (4) and (5) of the test above may be repeated further for quality control purposes, including assessment of background levels of fluors on the imaging substrate, contaminating moieties, positive controls, or other causes of copy number variation beyond the immediate test (e.g., cancer in the mother or fetus, fetal chimeraism, twinning). Because image analysis may be real-time, and does not require completion of the entire imaging run before generating results (unlike DNA sequencing methods), intermediate results may dictate next steps from a decision tree, and tailor the test for ideal performance on an individual sample. Quality control may also encompass verification that the sample is of acceptable quality and present, the imaging substrate is properly configured, that the assay product is present and/or at the correct concentration or density, that there is acceptable levels of contamination, that the imaging instrument is functional and that analysis is yielding proper results, all feeding in to a final test report for review by the clinical team.

In another aspect, the test above comprises one or more of the following steps: (1) receiving a requisition (from, for example, an ordering clinician or physician), (2) receiving a patient sample, (3) performing an assay (including a allele-specific portion, genomic target portion and quality controls) on that sample resulting in a assay-product-containing imaging substrate, (4-1) imaging the allele-specific region of the substrate in one or more spectral channels, (5-1) analyzing allele-specific image data to compute the fetal fraction, (pending sufficient fetal fraction) (4-2) imaging the genomic target region of the substrate in one or more spectral channels, (5-2) analyzing genomic target region image data to compute the copy number state of the genomic targets, (4-3) imaging the quality control region of the substrate in one or more spectral channels, (5-3) analyzing quality control image data to compute validate and verify the test, (6) performing statistical calculations, (7) creating and approving the clinical report, and (8) sending the report back to the ordering clinician or physician.

In the following description, various exemplary embodiments are set forth in view of the Figures.

Figures 21, 22:
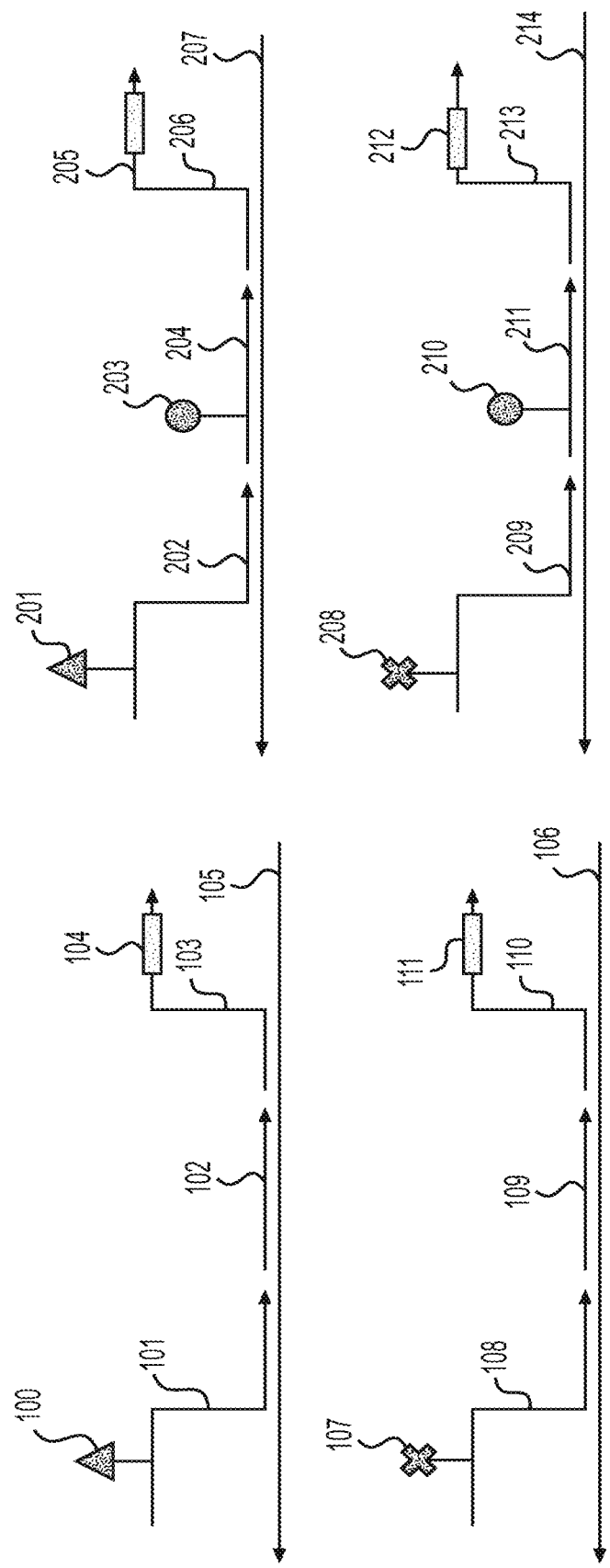

FIG. 21 is an implementation of an assay for quantifying genomic copy number at two genomic loci. In this embodiment of the assay, 105 and 106 are target molecules. 105 contains sequence corresponding to the first genomic locus "Locus 1" interrogated for copy number (example, chromosome 21), and 106 contains sequence corresponding the second genomic locus "Locus 2" interrogated for copy number (example, chromosome 18). FIG. 21 contains an example of one probe set per genomic locus, but in some embodiments of this assay, multiple probe sets will be designed to interrogate multiple regions within a genomic locus. For example, more than 10, or more than 100, or more than 500 probe sets may be designed that correspond to chromosome 21. FIG. 21 illustrates only a single probe set for each genomic locus, but importantly the scope of this invention allows for multiple probe sets for each genomic locus. FIG. 21 also illustrates a single hybridization event between a target molecule and a probe set. In practice, there will be multiple target molecules present in an assay sample. Many target molecules will contain the necessary sequences for hybridization to a probe set, and formation of a probe product. Different target molecules may hybridize to probe sets, as certain target molecules will bear genetic polymorphisms. In addition, target molecules that arise from genomic DNA may have a random assortment of molecule sizes, as well various beginning and ending sequences. In essence, there are multiple target molecules that may hybridize to a given probe set. In a single assay, multiple copies of a given probe set are added. Therefore, in a single assay up to thousands, or hundreds of thousands, or millions of specific probe products may be formed.

FIG. 21 depicts two probe sets, one probe set for Locus 1 and one probe set for Locus 2, although as aforementioned, multiple probes sets may be designed for each genomic locus. A first probe sets contains member probes 101, 102, 103. Item 101 contains label (100) type "A." Item 103 contains an affinity tag (104) which may be used for isolation and identification of the probe product. 102 may contain no modifications, such as a label or barcode. A second probe set with member probes 108, 109, 110 carries respective features as in the first probe set. However, 108 contains a label (107) of type "B," distinguishable from type "A." Item 110 contains an affinity tag (111) which may be identical to or unique from 104. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

One or more probe sets are added to target molecules in a single vessel and exposed to sequence-specific hybridization conditions.

For each probe set, the three probes (e.g., 101, 102, 103) are hybridized (or attached via a similar probe-target interaction) to the target molecule (105) such there are no gaps in between the probes on the target molecule. That is, the probes from the probe set are adjacent to one another and ligation competent.

Ligase is added to the hybridized probes and exposed to standard ligase conditions. The ligated probes form a probe product. All (or a majority of) probe products from Locus 1 have label type "A." All probe products from Locus 2 have label type "B." Quantification of the probe products corresponding to the genomic loci 1 & 2 occurs using labels "A" and "B."

In some embodiments, the probe products are immobilized onto a substrate using their affinity tags. For example, if the affinity tag is a DNA sequence, the probe products may be hybridized to regions of a DNA capture array at appropriate density for subsequent imaging.

Figure 48:
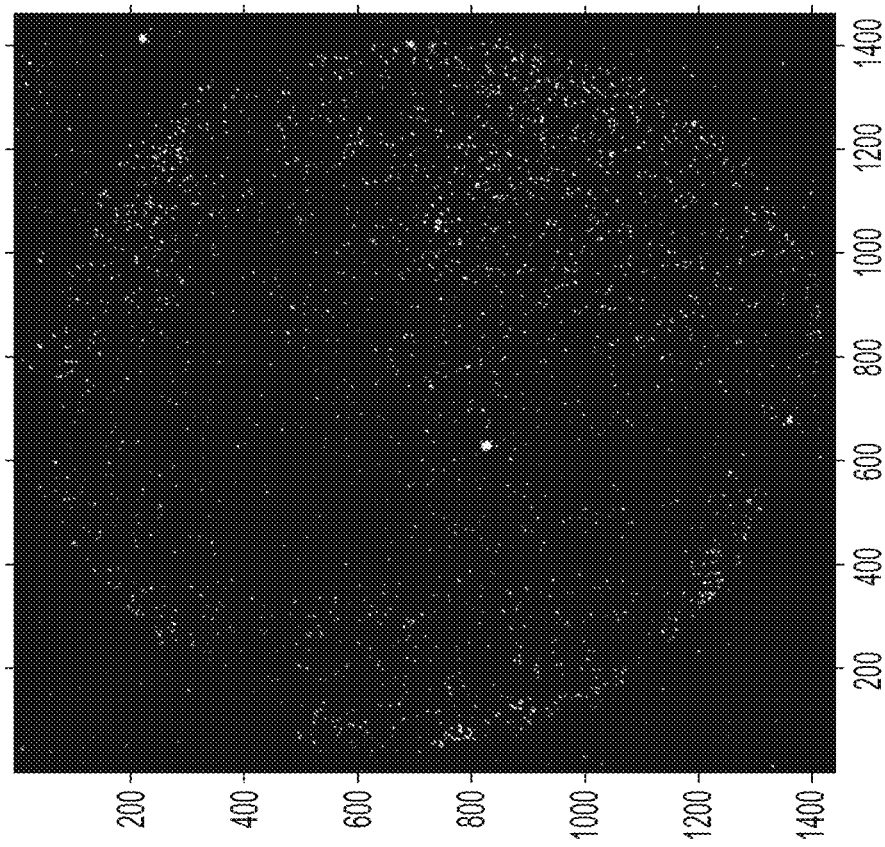
FIGS. 47 and 48 show the resulting fluorescence patterns when products contain unique affinity tag sequences and the underlying substrate contains complements to each of the unique affinity tags within the same location (e.g., as the same member) on a substrate.
Figure 47:
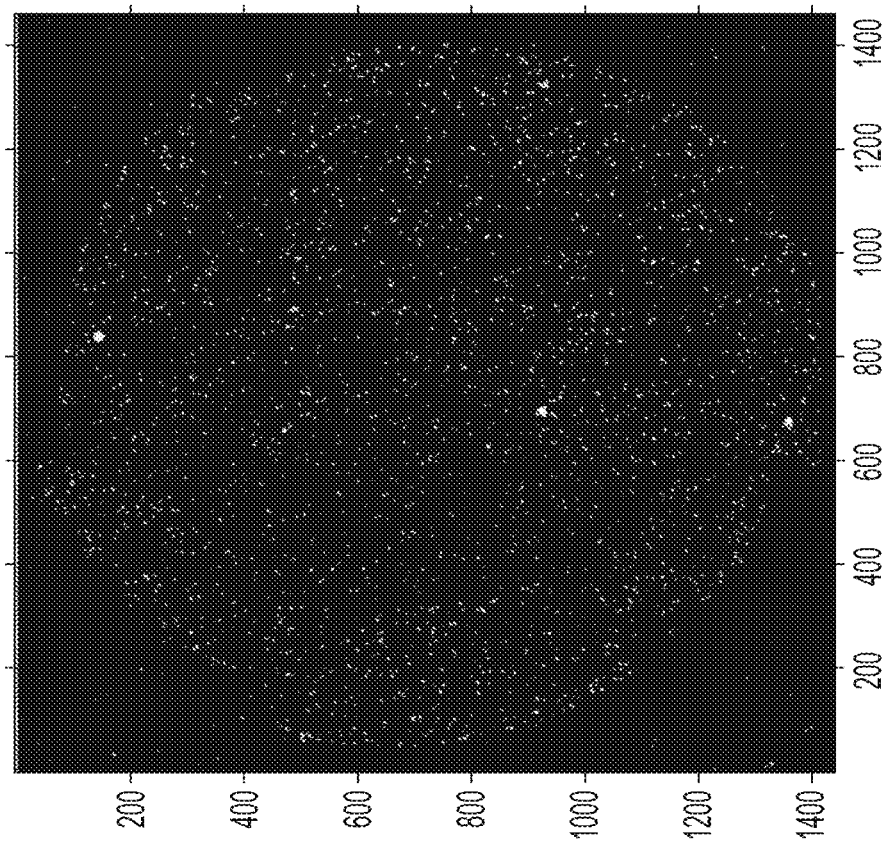

In some embodiments, affinity tags 104 and 111 contain unique and orthogonal sequences that allow surface-based positioning to one or more locations, which may be shared between hybridization products or not. FIGS. 47 and 48 show the resulting fluorescence patterns when products contain unique affinity tag sequences and the underlying substrate contains complements to each of the unique affinity tags within the same region (e.g., as the same member of an array) on a substrate. The images are of the same region of a substrate, but FIG. 47 shows Cy3 labels (covalently bound to chromosome 18 product), and FIG. 48 shows Alexa Fluor 647 labels (covalently bound to chromosome 21 product). Similar patterns may be generated for other assay embodiments that follow.

Figure 50:
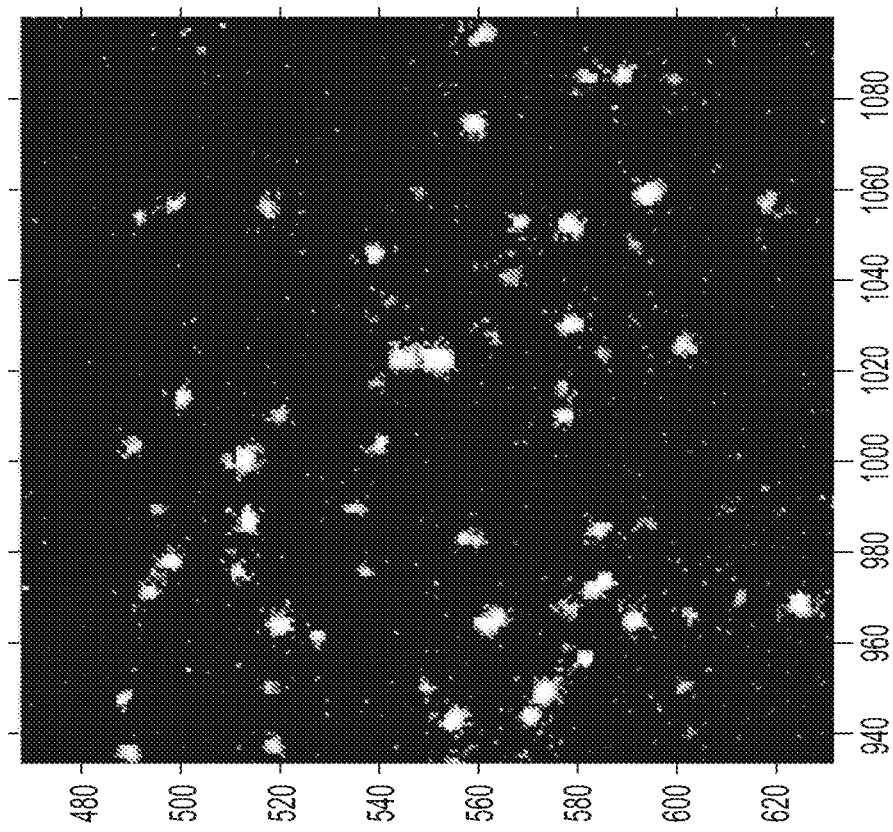
FIGS. 50 and 52 show zoomed-in locations of FIGS. 49 and 51, respectively.
Figure 49:
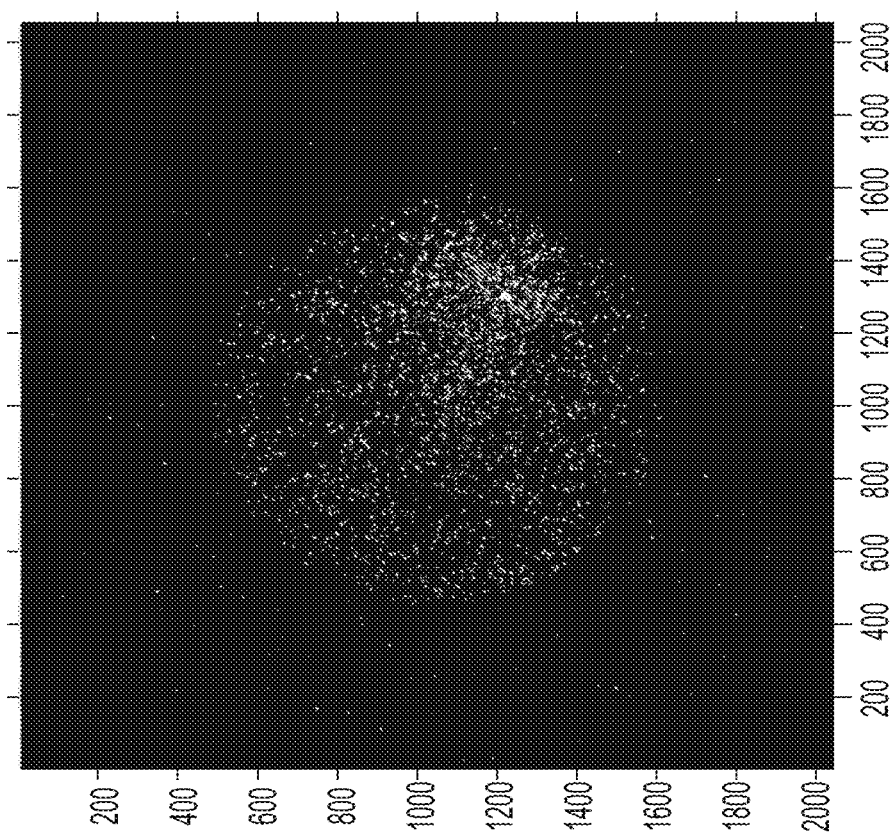
FIGS. 49 and 51 show the resulting fluorescence patterns when different products contain identical affinity tag sequences and the underlying substrate contains the complement to the affinity tag.
Figures 51, 52:
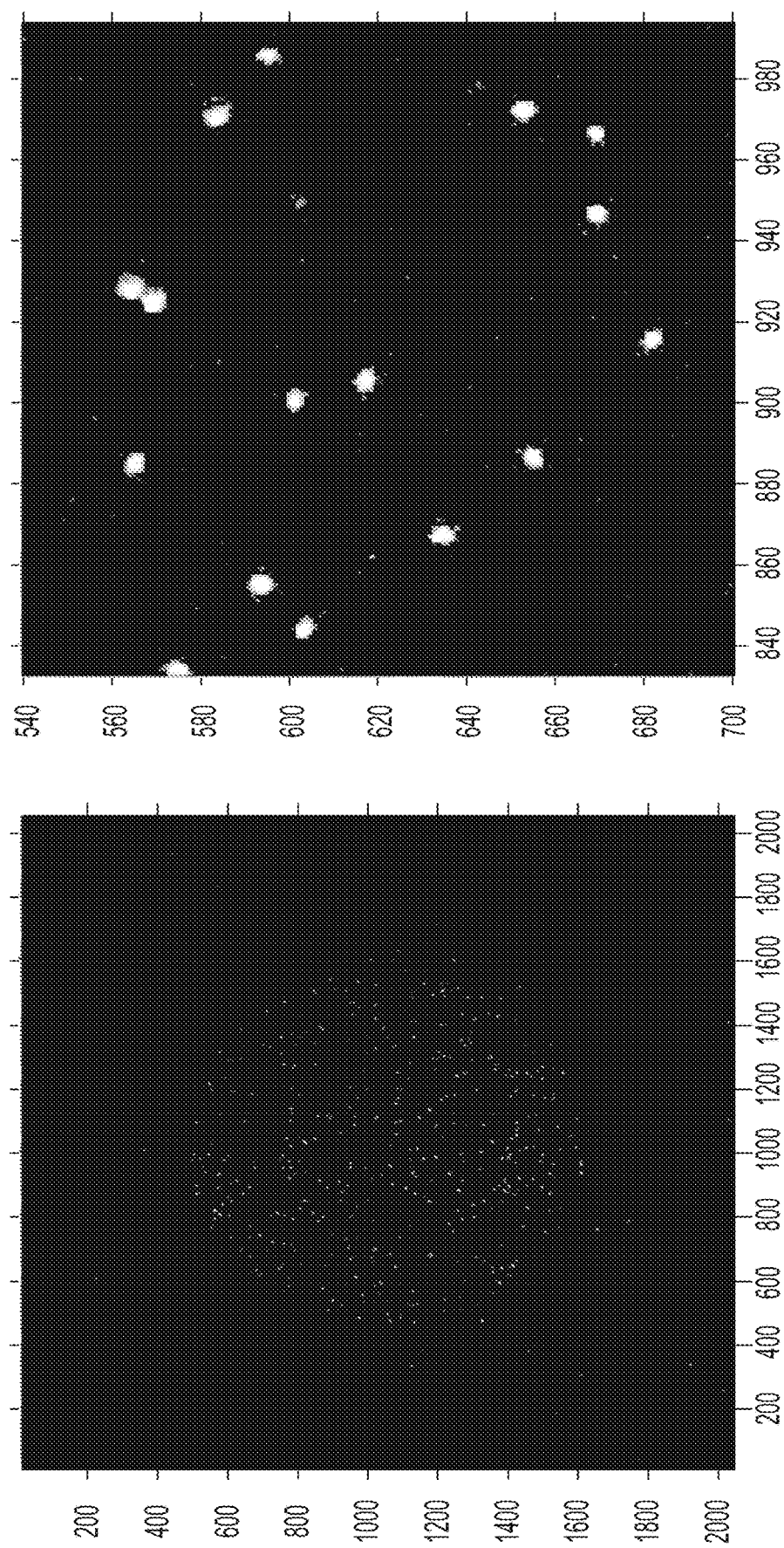

In another embodiment, affinity tags 104 and 111 contain identical sequences that allow surface-based positioning to the same region (e.g., as the same member of an array) on a substrate. That is, different products compete for the same binding sites. FIGS. 49 and 51 show the resulting fluorescence patterns when different products contain identical affinity tag sequences and the underlying substrate contains the complement to the affinity tag. The images are of the same location on a substrate, but FIG. 49 shows Cy3 labels (covalently bound to chromosome 18 product) and FIG. 51 shows Alexa Fluor 647 labels (covalently bound to chromosome 21 product). FIGS. 50 and 52 show zoomed-in regions of FIGS. 49 and 51, respectively, clearly demonstrating single-molecule resolution and individually-distinguishable labels. Similar patterns may be generated for other assay embodiments that follow.

Figure 54:
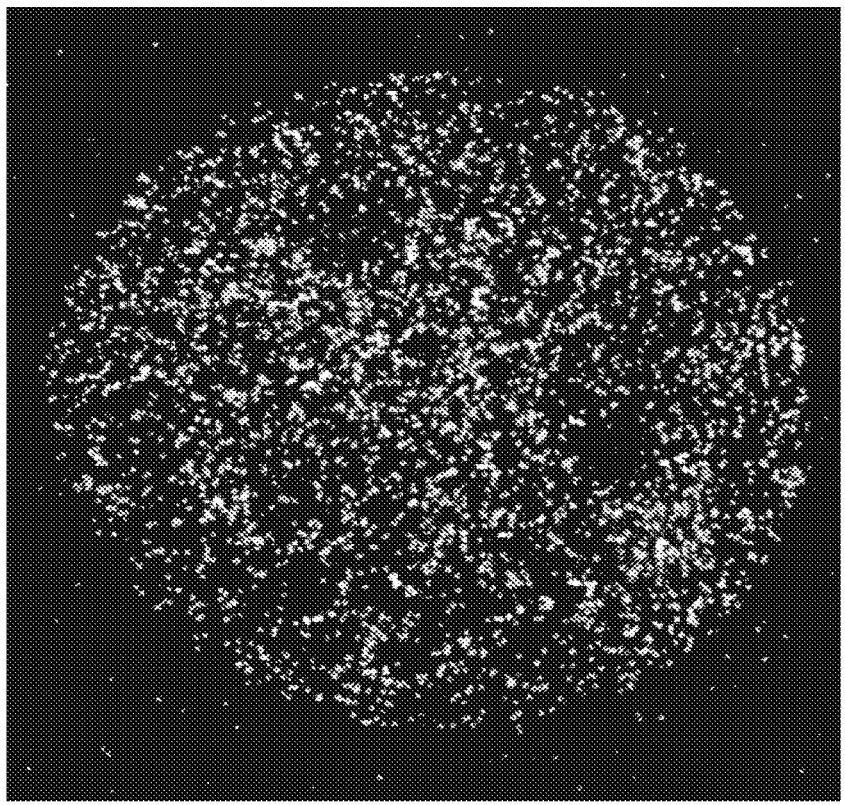
FIGS. 53 and 54 show the resulting fluorescence patterns when products contain unique affinity tag sequences and the underlying substrate has one location (e.g., as one member) containing the complement to one affinity tag complement, and another separate location (e.g., as another member) containing the complement to the other affinity tag.
Figure 53:
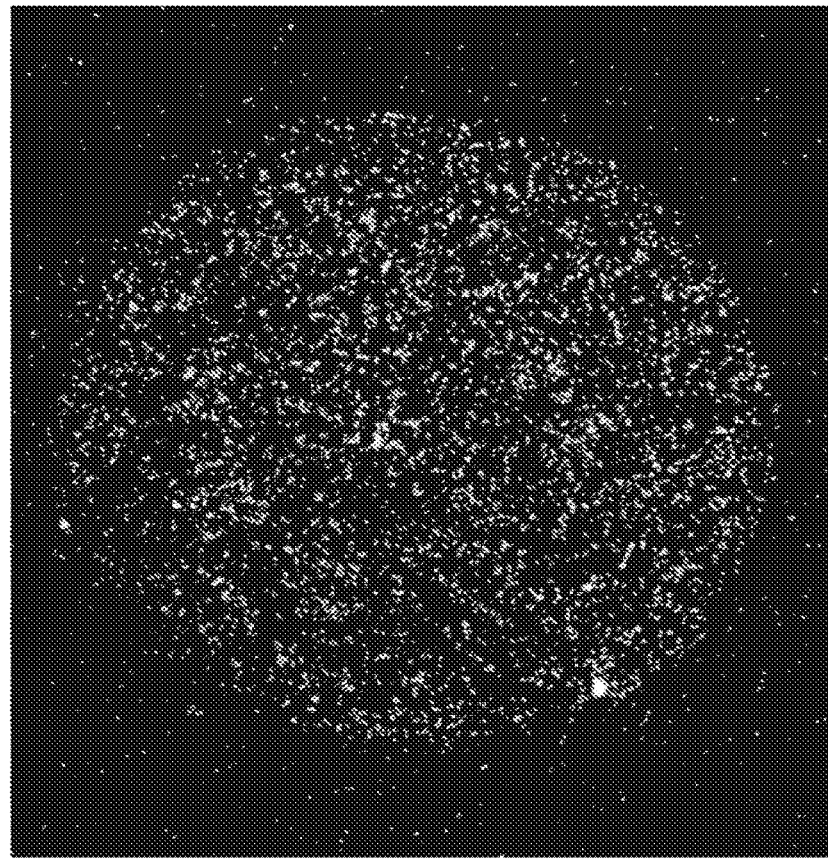

In another embodiment, affinity tags 104 and 111 contain unique and orthogonal sequences that allow surface-based positioning to more than one location on a substrate. FIGS. 53 and 54 show the resulting fluorescence patterns when products contain unique affinity tag sequences and the underlying substrate has one region containing the complement to one affinity tag complement, and another separate region containing the complement to the other affinity tag. The images are of two separate regions of a substrate, with each region containing a single affinity tag complement as previously described. FIG. 53 shows Cy3 labels (covalently bound to chromosome 21 product), and FIG. 54 shows Alexa Fluor 647 labels (covalently bound to chromosome 18 product). Similar patterns may be generated for other assay embodiments that follow.

One feature of this invention according to some embodiments is that specificity is achieved through the combination of multiple adjacent probes that must be successfully ligated together in order for the probe product to be successfully formed, captured and detected. If a probe product is not successfully formed for any reason, then it cannot be isolated, or enriched for using an affinity tag and detected. For example, if probe 101 is not successfully ligated to probe 102, then the resulting product cannot be detected. Similarly, if probe 103 is not successfully ligated to probe 102, then the resulting product cannot be isolated or enriched using an affinity tag.

Requiring all probes from the probe set to successfully hybridize to the target molecule and successfully ligate together provides high specificity and greatly reduces issues of cross-hybridization and therefore false positive signals.

In this assay, specificity is achieved through sequence-specific hybridization and ligation. In a preferred embodiment, the specificity of forming probe products occurs in the reaction vessel, prior to isolating or enriching for probe products, for example immobilization onto a surface or other solid substrate. This side-steps the challenge of standard surface based hybridization (e.g., genomic microarray) in which specificity must be entirely achieved through hybridization only with long (>40 bp) oligonucleotide sequences (e.g., Agilent and Affymetrix arrays).

The use of affinity tags allows the probe products to be immobilized on a substrate and therefore excess unbound probes to be washed away using standard methods or removed using standard methods. Therefore all or most of the labels on the surface are a part of a specifically formed probe product that is immobilized to the surface.

One feature of this invention according to some embodiments is that the surface capture does not affect the accuracy. That is, it does not introduce any bias. In one example, if the same affinity tag is used for probe sets from different genomic loci, with probe sets targeting each locus having a different label. Probe products from both genomic loci may be immobilized to the same location on the substrate using the same affinity tag. That is probe products from Locus 1 and Locus 2 will be captured with the same efficiency, so not introducing any locus specific bias.

In some embodiments, some or all of the unbound probes and/or target molecules are removed prior to surface capture using standard methods. This decreases interference between unbound probes and/or target molecules and the probe products during surface capture.

One feature of this invention according to some embodiments is that multiple affinity tag types may be placed in the same region of the substrate (for example, the same array spot or member of the array). This has many advantages, including placement of control or calibration markers. FIGS. 22-46 describe additional exemplary embodiments of this invention. These Figures do not represent all possible embodiments, and all other variations of this assay are included as a part of this invention. Additionally, all features of the embodiment described in FIG. 21 are applicable to all additional other embodiments of the assay described in this application.

FIG. 22 depicts a modification of the general procedure described in FIG. 21. FIG. 22 depicts two probe sets, one probe set for Locus 1 and one probe set for Locus 2, although as aforementioned, multiple probes sets may be designed for each genomic locus. 207 and 214 are target molecules corresponding to Locus 1 and Locus 2, respectively. A first probe sets contains member probes 202, 204, 206. 202 contains a label (201) of type "A." 206 contains an affinity tag (205) which may be used for isolation and identification of the probe product. A second probe set with member probes 209, 211, 231 carries respective features as in the first probe set. However, 209 contains a label (208) of type "B," distinguishable from type "A." 213 contains an affinity tag (212) which may be identical to or unique from 205. Many probe sets may be designed such that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique or a mixture of identical and unique, and the affinity tags for the many probe sets for Locus 2 may be identical or unique or a mixture of identical and unique. In this embodiment, the probes 204 and 211 may contain one or more labels (203, 210) of type "C." Therefore, probe products will contain a combination of labels. For Locus 1, probe products will contains labels of type "A" and type "C," whereas probe products from Locus 2 will contain labels of type "B" and type "C."

Figures 23, 24:
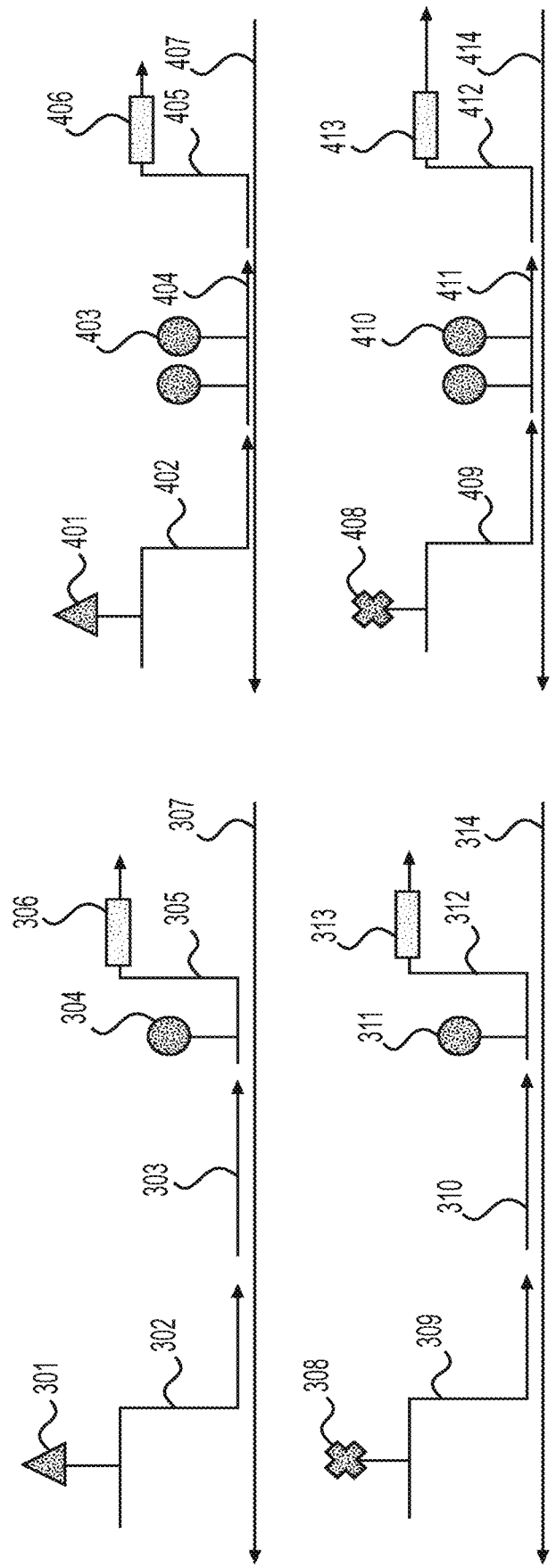

FIG. 23 depicts a modification of the general procedure described in FIG. 21. FIG. 23 depicts two probe sets, one probe set for Locus 1 and one probe set for Locus 2, although as aforementioned, multiple probes sets may be designed for each genomic locus. 307 and 314 are target molecules corresponding to Locus 1 and Locus 2, respectively. A first probe set contains member probes 302, 303, 305. 302 contains a label (301) of type "A." 305 contains an affinity tag (306) which may be used for isolation and identification of the probe product. A second probe set with member probes 309, 310, 312 carries respective features as in the first probe set. However, 309 contains a label (308) of type "B," distinguishable from type "A." 312 contains an affinity tag (313) which may be identical to or unique from 306. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 305 and 312 contain one or more labels (304, 311) of type "C." Therefore, probe products will contain a combination of labels. For Locus 1, probe products will contains labels of type "A" and type "C," whereas probe products from Locus 2 will contain labels of type "B" and type "C."

FIG. 24 depicts a modification of the general procedure described in FIG. 21. FIG. 24 depicts two probe sets, one probe set for Locus 1 and one probe set for Locus 2, although as aforementioned, multiple probes sets may be designed for each genomic locus. 407 and 414 are target molecules corresponding to Locus 1 and Locus 2, respectively.

A first probe sets contains member probes 402, 405. 402 contains a label (401) of type "A." 405 contains an affinity tag (406) which may be used for isolation and identification of the probe product.

A second probe set with member probes 409, 412 carries respective features as in the first probe set. However, 409 contains a label (408) of type "B," distinguishable from type "A." 412 contains an affinity tag (413) which may be identical to or unique from 406. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, probes 402 and 405 hybridize to sequences corresponding to Locus 1, but there is a "gap" on the target molecule consisting of one or more nucleotides between hybridized probes 402 and 405. In this embodiment, a DNA polymerase or other enzyme may be used to synthesize a new polynucleotide species (404) that covalently joins 402 and 405. That is, the probe product formed in this example is a single contiguous nucleic acid molecule with a sequence corresponding to Locus 1, and bearing the labels and/or affinity tags above. Additionally, 404 may contain one or more labels of type "C," possibly as a result of incorporation of a one of more nucleotides bearing a label of type "C." This example also conveys to the probe product formed for Locus 2, containing probes 409 and 412. Therefore, probe products will contain a combination of labels. For Locus 1, probe products will contains labels of type "A" and type "C," whereas probe products from Locus 2 will contain labels of type "B" and type "C."

Figure 25:
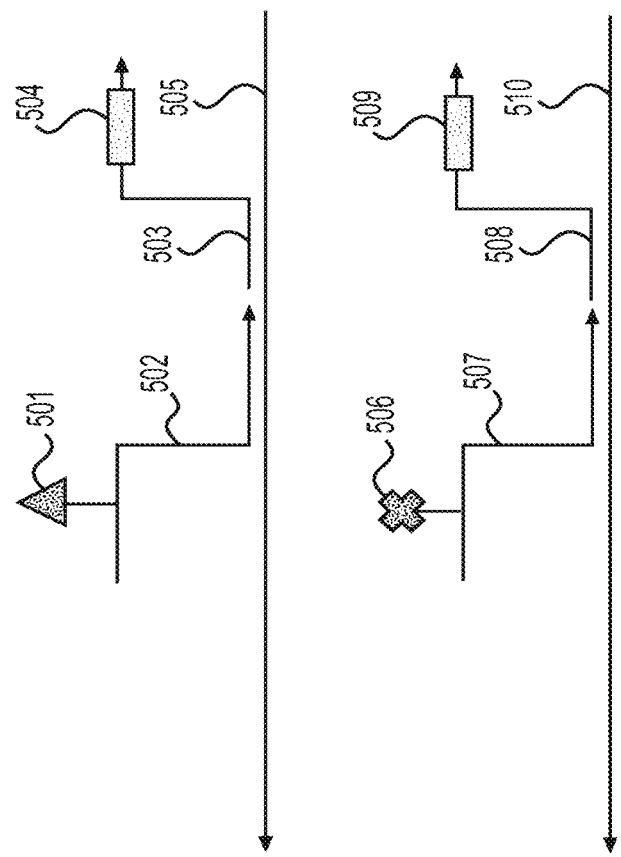

FIG. 25 depicts a modification of the general procedure described in FIG. 21. FIG. 25 depicts two probe sets, one probe set for Locus 1 and one probe set for Locus 2, although as aforementioned, multiple probes sets may be designed for each genomic locus. 505 and 510 are target molecules corresponding to Locus 1 and Locus 2, respectively. A first probe sets contains member probes 502, 503. 502 contains a label (501) of type "A." 503 contains an affinity tag (504) which may be used for isolation and identification of the probe product. A second probe set with member probes 507, 508 carries respective features as in the first probe set. However, 507 contains a label (506) of type "B," distinguishable from type "A." 508 contains an affinity tag (509) which may be identical to or unique from 504. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

Figure 26:
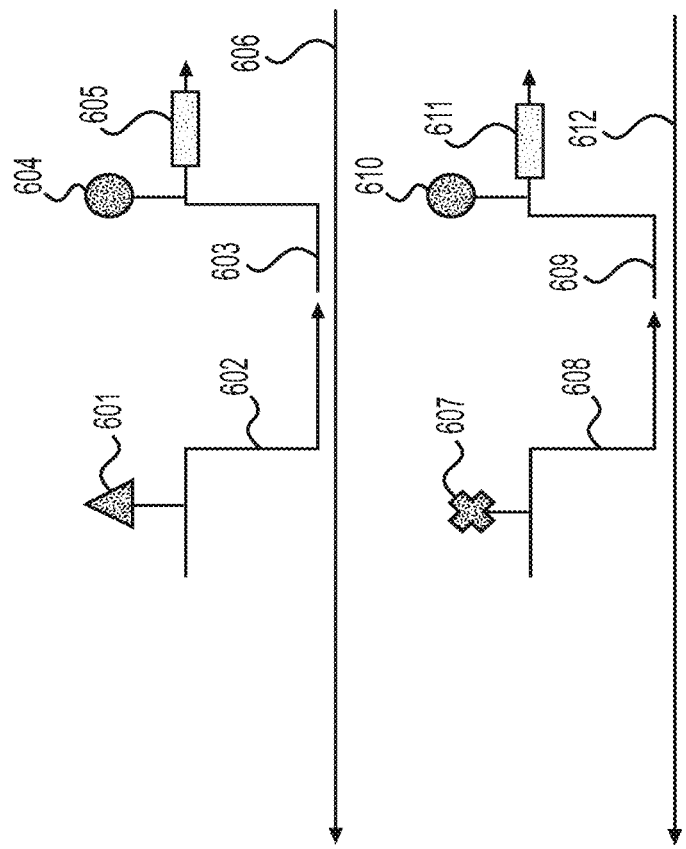

FIG. 26 depicts a modification of the general procedure described in FIG. 21. FIG. 26 depicts two probe sets, one probe set for Locus 1 and one probe set for Locus 2, although as aforementioned, multiple probes sets may be designed for each genomic locus. 606 and 612 are target molecules corresponding to Locus 1 and Locus 2, respectively. A first probe sets contains member probes 602, 603. 602 contains a label (601) of type "A." 603 contains an affinity tag (605) which may be used for isolation and identification of the probe product. A second probe set with member probes 608, 609 carries respective features as in the first probe set. However, 608 contains a label (607) of type "B," distinguishable from type "A." 609 contains an affinity tag (611) which may be identical to or unique from 605. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, the probes 603 and 609 contain one or more labels (604, 610) of type "C." Therefore, probe products will contain a combination of labels. For Locus 1, probe products will contains labels of type "A" and type "C," whereas probe products from Locus 2 will contain labels of type "B" and type "C."

Figures 27, 28:
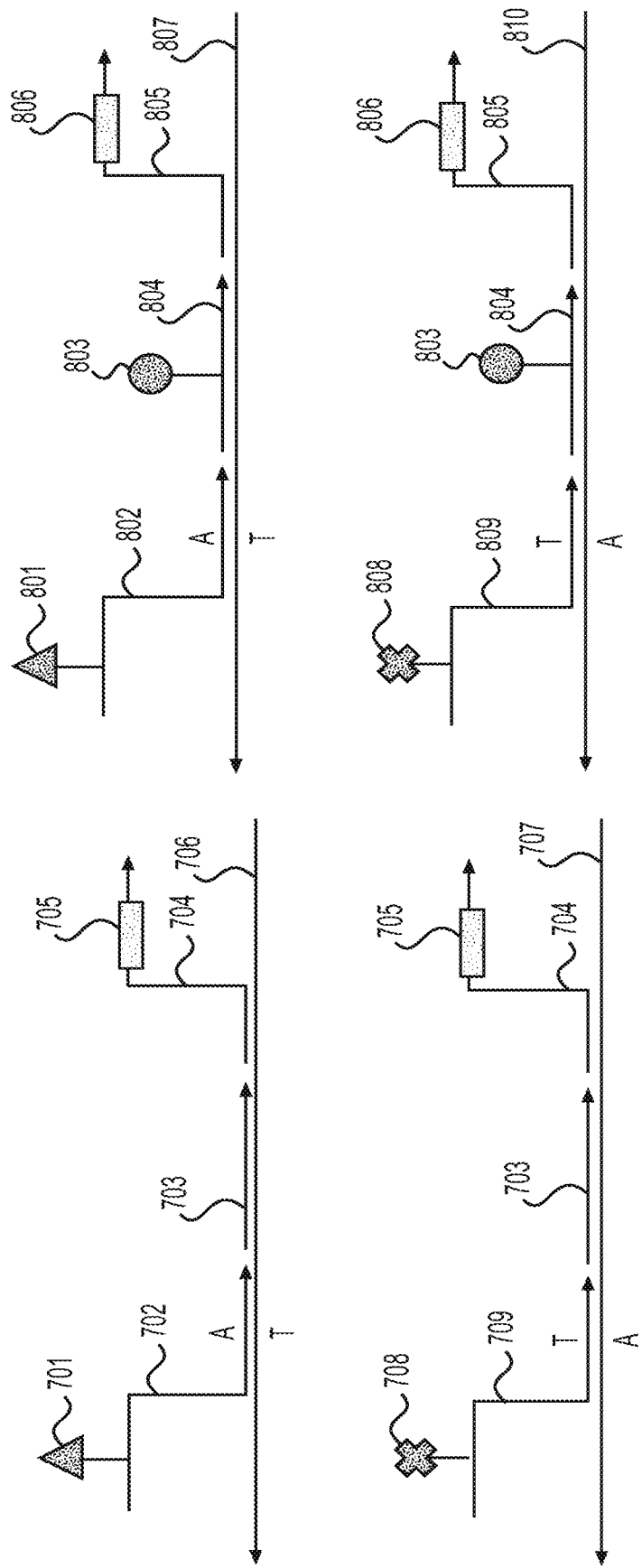

FIG. 27 depicts a modification of the general procedure described in FIG. 21. FIG. 27 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 27 depicts two probe sets—one probe set for Allele 1 and one probe set for Allele 2. 706 and 707 are target molecules corresponding to Allele 1 and Allele 2, respectively. A first probe set contains member probes 702, 703, 704. 702 contains a label (701) of type "A." 704 contains an affinity tag (705) which may be used for isolation and identification of the probe product. A second probe set with member probes 709, 703, 704 carries respective features as in the first probe set. In this embodiment, 703 and 704 are identical for both probe sets. However, 709 contains a label (708) of type "B," distinguishable from type "A." In this embodiment, 702 and 709 contain sequences that are nearly identical, and differ by only one nucleotide in the sequence. Therefore, hybridization sequences of these two probes, which are configured to hybridize to the regions for Allele 1 and Allele 2, contains complementary regions for Allele 1 (702), and Allele 2 (709). Further, the length of each hybridization domain on 702 and 709, as well as experimental hybridization conditions are designed such that probe 702 will only hybridize to Allele 1 and probe 709 will only hybridize to Allele 2. The purpose of this assay type is to accurately quantify the frequency of Allele 1 and Allele 2 in a sample.

FIG. 28 depicts a modification of the general procedure described in FIG. 21. FIG. 28 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 28 depicts two probe sets—one probe set for Allele 1 and one probe set for Allele 2. 807 and 810 are target molecules corresponding to Allele 1 and Allele 2, respectively. A first probe set contains member probes 802, 804, 805. 802 contains a label (801) of type "A." 805 contains an affinity tag (806) which may be used for isolation and identification of the probe product. A second probe set with member probes 809, 804, 805 carries respective features as in the first probe set. In this embodiment, 804 and 805 are identical for both probe sets. However, 809 contains a label (808) of type "B," distinguishable from type "A." In this embodiment, 802 and 809 contain sequences that are nearly identical, and differ by only one nucleotide in the sequence. Therefore, hybridization sequences of these two probes contain complementary regions for Allele 1 (802), and Allele 2 (809). Further, the length of each hybridization domain on 802 and 809, as well as experimental hybridization conditions are designed such that probe 802 will only hybridize to Allele 1 and probe 809 will only hybridize to Allele 2. The purpose of this assay type is to be able to accurately quantify the frequency of Allele 1 and Allele 2 in a sample. In this embodiment, the probe 804 contains one or more labels (803) of type "C." Therefore, probe products will contain a combination of labels. For Allele 1, probe products will contain labels of type "A" and type "C," whereas probe products from Allele 2 will contain labels of type "B" and type "C."

Figure 29:
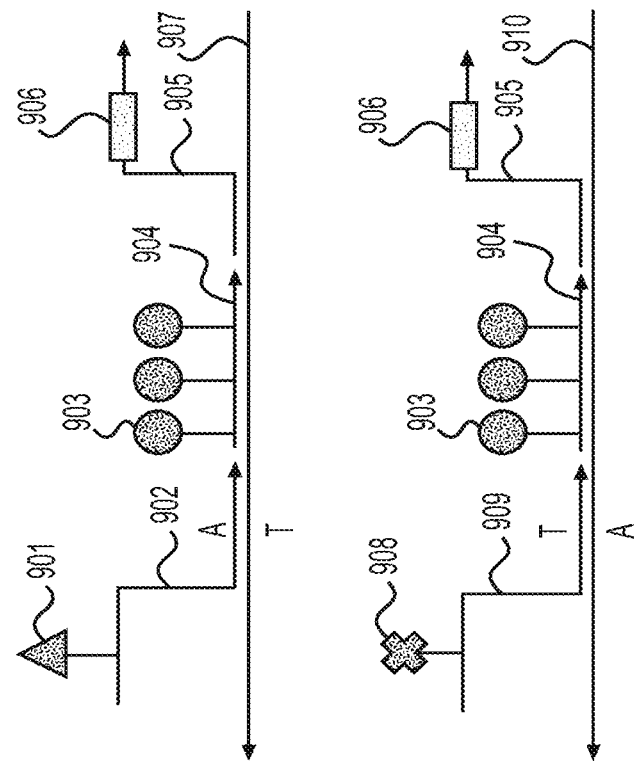

FIG. 29 depicts a modification of the general procedure described in FIG. 21. FIG. 29 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 29 depicts two probe sets, one probe set for Allele 1 and one probe set for Allele 2.

907 and 910 are target molecules corresponding to Allele 1 and Allele 2, respectively. A first probe set contains member probes 902, 905. 902 contains a label (901) of type "A." Item 905 contains an affinity tag (906) which may be used for isolation and identification of the probe product. A second probe set with member probes 909, 905 carries respective features as in the first probe set. In this embodiment, 905 is identical for both probe sets. However, 909 contains a label (908) of type "B," distinguishable from type "A." In this embodiment, 902 and 909 contain sequences that are nearly identical, and differ by only one nucleotide in the sequence. Therefore, hybridization sequences of these two probes contain complementary regions for Allele 1 (902), and Allele 2 (909). Further, the length of each hybridization domain on 902 and 909, as well as experimental hybridization conditions are designed such that probe 902 will only hybridize to Allele 1 and probe 909 will only hybridize to Allele 2. The purpose of this assay type is to be able to accurately quantify the frequency of Allele 1 and Allele 2 in a sample.

In this embodiment, probes 902 and 905 hybridize to sequences corresponding to Allele 1, such that there is a "gap" on the target molecule consisting of one or more nucleotides between hybridized probes 902 and 905. In this embodiment, a DNA polymerase or other enzyme may be used to synthesize a new polynucleotide species (904) that covalently joins 902 and 905. That is, the probe product formed in this example is a single contiguous nucleic acid molecule with a sequence corresponding to Allele 1, and bearing the labels and/or affinity tags above. Additionally, 904 may contain one or more labels of type "C," possibly as a result of incorporation of a nucleotide bearing a label of type "C." This example also conveys to the probe product formed for Allele 2, containing probes 909 and 905.

Figure 30:
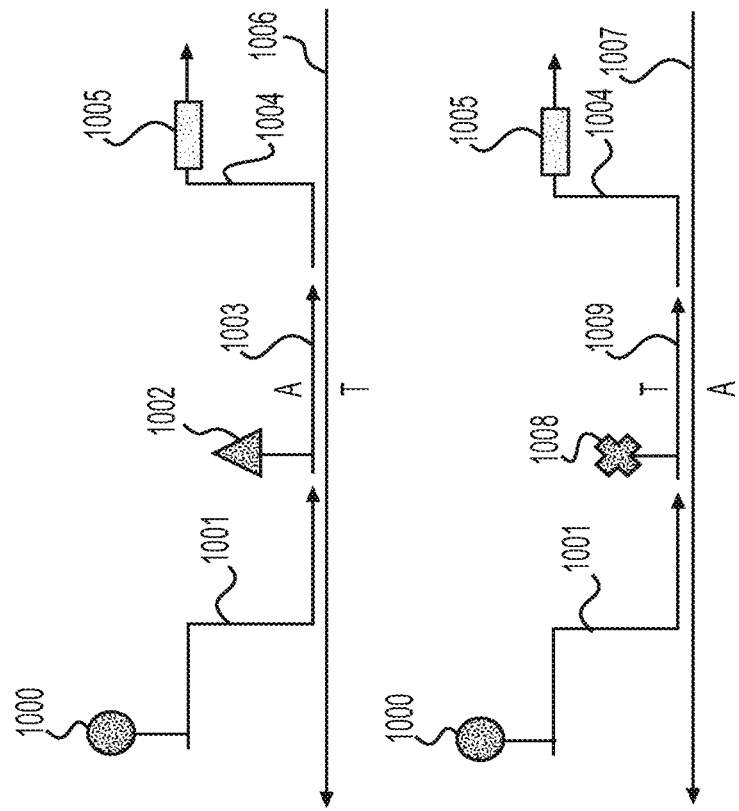

FIG. 30 depicts a modification of the general procedure described in FIG. 21. FIG. 30 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 30 depicts two probe sets, one probe set for Allele 1 and one probe set for Allele 2.

1006 and 1007 are target molecules corresponding to Allele 1 and Allele 2, respectively. A first probe set contains member probes 1001, 1003, 1004. 1003 contains a label (1002) of type "A." 1004 contains an affinity tag (1005) which may be used for isolation and identification of the probe product.

A second probe set with member probes 1001, 1009, 1004 carries respective features as in the first probe set. In this embodiment, 1001 is identical for both probe sets and 1004 is identical for both probe sets. However, 1009 contains a label (1008) of type "B," distinguishable from type "A."

In this embodiment, 1003 and 1009 contain sequences that are nearly identical, and differ by only one nucleotide in the sequence. Therefore, hybridization sequences of these two probes contains complementary regions for Allele 1 (1003), and Allele 2 (1009), respectively. Further, the length of each hybridization domain on 1003 and 1009, as well as experimental hybridization conditions are designed such that probe 1003 will only hybridize to Allele 1 and probe 1009 will only hybridize to Allele 2. The purpose of this assay type is to be able to accurately quantify the frequency of Allele 1 and Allele 2 in a sample. In this embodiment, the probe 1001 contains one or more labels (1000) of type "C." Therefore, probe products will contain a combination of labels. For Allele 1, probe products will contains labels of type "A" and type "C," whereas probe products from Allele 2 will contain labels of type "B" and type "C."

Figure 31:
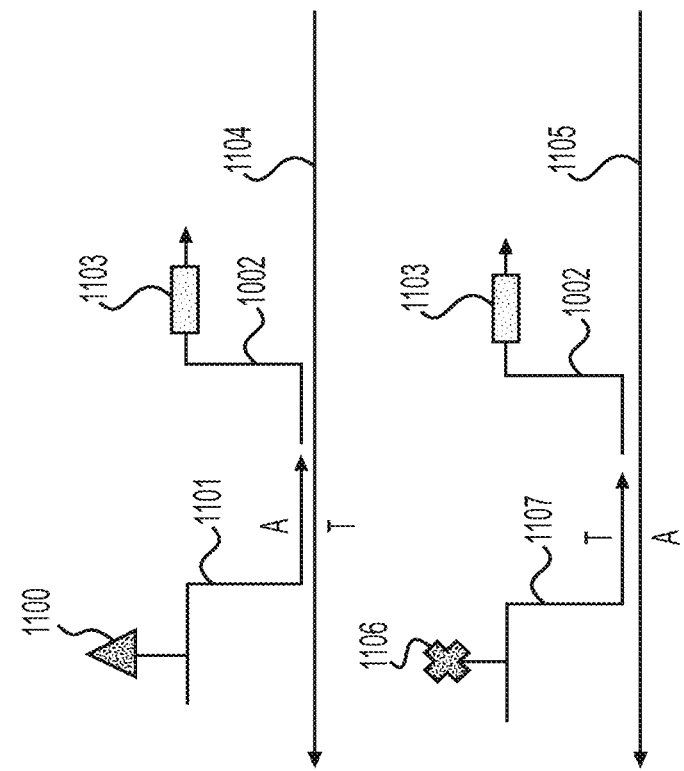

FIG. 31 depicts a modification of the general procedure described in FIG. 21. FIG. 31 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 31 depicts two probe sets—one probe set for Allele 1 and one probe set for Allele 2. 1104 and 1105 are target molecules corresponding to Allele 1 and Allele 2, respectively. A first probe set contains member probes 1101, 1102. 1101 contains a label (1100) of type "A." 1102 contains an affinity tag (1103) which may be used for isolation and identification of the probe product. A second probe set with member probes 1107, 1102 carries respective features as in the first probe set. In this embodiment, 1102 is identical for both probe sets. However, 1107 contains a label (1106) of type "B," distinguishable from type "A." In this embodiment, 1101 and 1107 contain sequences that are nearly identical, and differ by only one nucleotide in the sequence. Therefore, hybridization sequences of these two probes contains complementary regions for Allele 1 (1101), and Allele 2 (1107). Further, the length of each hybridization domain on 1101 and 1107, as well as experimental hybridization conditions are designed such that probe 1101 will only hybridize to Allele 1 and probe 1107 will only hybridize to Allele 2. The purpose of this assay type is to be able to accurately quantify the frequency of Allele 1 and Allele 2 in a sample.

Figure 32:
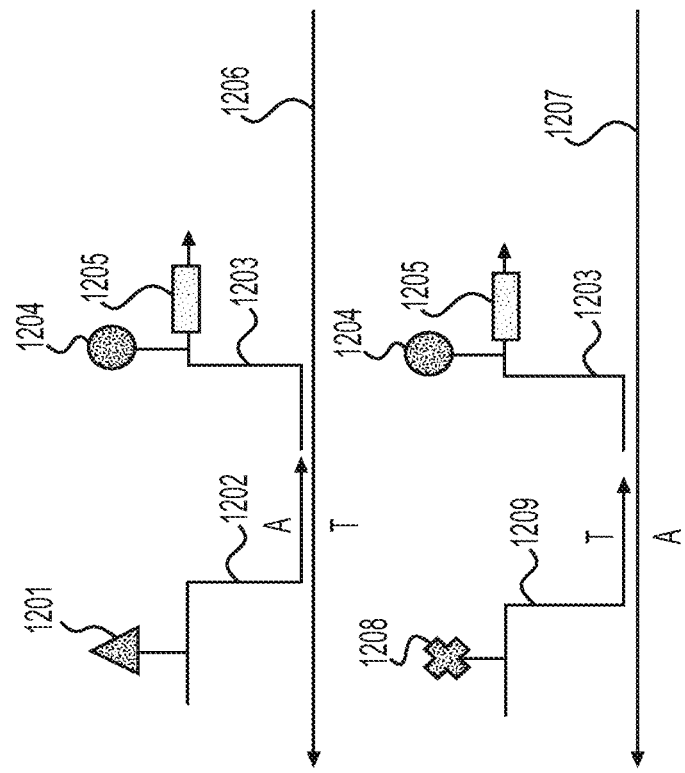

FIG. 32 depicts a modification of the general procedure described in FIG. 21. FIG. 32 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 32 depicts two probe sets—one probe set for Allele 1 and one probe set for Allele 2. 1206 and 1207 are target molecules corresponding to Allele 1 and Allele 2, respectively. A first probe set contains member probes 1202, 1203. 1202 contains a label (1201) of type "A." 1203 contains an affinity tag (1205) which may be used for isolation and identification of the probe product. A second probe set with member probes 1209, 1203 carries respective features as in the first probe set. In this embodiment, 1203 is identical for both probe sets. However, 1209 contains a label (1208) of type "B," distinguishable from type "A." In this embodiment, 1202 and 1209 contain sequences that are nearly identical, and differ by only one nucleotide in the sequence. Therefore, hybridization sequences of these two probes contains complementary regions for Allele 1 (1202), and Allele 2 (1209). Further, the length of each hybridization domain on 1202 and 1209, as well as experimental hybridization conditions are designed such that probe 1202 will only hybridize to Allele 1 and probe 1209 will only hybridize to Allele 2. The purpose of this assay type is to be able to accurately quantify the frequency of Allele 1 and Allele 2 in a sample. In this embodiment, the probe 1203 contains one or more labels (1204) of type "C." Therefore, probe product will contain a combination of labels. For Allele 1, probe products will contains labels of type "A" and type "C," whereas probe products from Allele 2 will contain labels of type "B" and type "C."

FIG. 33 depicts a modification of the general procedure described in FIG. 21. FIG. 33 depicts two probe sets, one probe set for Locus 1 and one probe set for Locus 2, although as aforementioned, multiple probes sets may be designed for each genomic locus. 1304 and 1305 are target molecules corresponding to Locus 1 and Locus 2, respectively. A first probe sets contains member probes 1301, 1302. 1301 contains a label (1300) of type "A." 1301 contains an affinity tag (1303) which may be used for isolation and identification of the probe product. A second probe set with member probes 1307, 1308 carries respective features as in the first probe set. However, 1307 contains a label (1306) of type "B," distinguishable from type "A." 1307 contains an affinity tag (1309) which may be identical to or unique from 1303. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1301 and 1307 have similar structures. For example, on probe 1301 there are two distinct hybridization domains, such that probe 1302 may be ligated to each end of 1301, forming a probe product consisting of a contiguous, topologically closed molecule of DNA (e.g., a circular molecule). The non-hybridizing sequence on probe 1301 may contain additional features, possibly restriction enzyme sites, or primer binding sites for universal amplification.

One feature of this embodiment is that all probe products are contiguous circular molecules. In this manner, probe products may be isolated from all other nucleic acids via enzymatic degradation of all linear nucleic acid molecules, for example, using an exonuclease.

FIG. 34 depicts a modification of the general procedure described in FIG. 21. FIG. 34 depicts two probe sets, one probe set for Locus 1 and one probe set for Locus 2, although as aforementioned, multiple probes sets may be designed for each genomic locus. 1405 and 1406 are target molecules corresponding to Locus 1 and Locus 2, respectively. A first probe sets contains member probes 1401, 1403. 1401 contains a label (1400) of type "A." 1401 contains an affinity tag (1404) which may be used for isolation and identification of the probe product. A second probe set with member probes 1408, 1410 carries respective features as in the first probe set. However, 1408 contains a label (1407) of type "B," distinguishable from type "A." 1408 contains an affinity tag (1411) which may be identical to or unique from 1404. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1401 and 1408 have similar structures. For example, on probe 1401 there are two distinct hybridization domains, such that probe 1403 may be ligated to each end of 1401, forming a probe product consisting of a contiguous, topologically closed molecule of DNA (e.g., a circular molecule). The non-hybridizing sequence on probe 1401 may contain additional features, possibly restriction enzyme sites, or primer binding sites for universal amplification.

One feature of this embodiment is that all probe products are contiguous circular molecules. In this manner, probe products may be isolated from all other nucleic acids via enzymatic degradation of all linear nucleic acid molecules, for example, using an exonuclease. In this embodiment, the probes 1403 and 1410 contain one or more labels (1402, 1409) of type "C." Therefore, probe products will contain a combination of labels. For Locus 1, probe products will contains labels of type "A" and type "C," whereas probe products from Locus 2 will contain labels of type "B" and type "C".

FIG. 35 depicts a modification of the general procedure described in FIG. 21. FIG. 35 depicts two probe sets, one probe set for Locus 1 and one probe set for Locus 2, although as aforementioned, multiple probes sets may be designed for each genomic locus. 1505 and 1506 are target molecules corresponding to Locus 1 and Locus 2, respectively. A first probe sets contains member probe 1501. 1501 contains a label (1500) of type "A." 1501 contains an affinity tag (1504) which may be used for isolation and identification of the probe product. A second probe set with member probe 1508 carries respective features as in the first probe set. However, 1508 contains a label (1507) of type "B," distinguishable from type "A." 1508 contains an affinity tag (1511) which may be identical to or unique from 1504. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique. In this embodiment, the probes 1501 and 1508 have similar structures.

For example, on probe 1501 there are two distinct hybridization domains, such that when hybridized against a target molecule, there is a gap between the two hybridization domains. In this embodiment, a DNA polymerase or other enzyme may be used to synthesize a new polynucleotide species (1503) that covalently fills the gap between the hybridization domains of 1501. That is, the probe product formed in this example is a single, contiguous, topologically closed molecule of DNA (e.g., a circular molecule) with a sequence corresponding to Locus 1, and bearing the labels and/or affinity tags above. Additionally, 1503 may contain one or more labels of type "C," possibly as a result of incorporation of a nucleotide bearing a label of type "C." This example also conveys to the probe product formed for Locus 2, containing probe 1508. The non-hybridizing sequence on probe 1501 and probe 1508 may contain additional features, possibly restriction enzyme sites. One feature of this embodiment is that all probe products are contiguous circular molecules. In this manner, probe products may be isolated from all other nucleic acids via enzymatic degradation of all linear nucleic acid molecules, for example, using an exonuclease. Probe products will contain a combination of labels. For Locus 1, probe products will contains labels of type "A" and type "C," whereas probe products from Locus 2 will contain labels of type "B" and type "C."

FIG. 36 depicts a modification of the general procedure described in FIG. 21. FIG. 36 depicts two probe sets, one probe set for Locus 1 and one probe set for Locus 2, although as aforementioned, multiple probes sets may be designed for each genomic locus. 1605 and 1606 are target molecules corresponding to Locus 1 and Locus 2, respectively.

A first probe sets contains member probe 1602. 1602 contains a label (1600) of type "A." 1602 contains an affinity tag (1601) which may be used for isolation and identification of the probe product.

A second probe set with member probe 1609 carries respective features as in the first probe set. However, 1609 contains a label (1608) of type "B," distinguishable from type "A." 1609 contains an affinity tag (1607) which may be identical to or unique from 1601. Many probe sets may designed that target "Locus 1," containing unique probe sequences but the same label type "A." Similarly, many probe sets may be designed that target "Locus 2," containing unique probe sequences but the same label type "B." In this embodiment, the affinity tags for the many probe sets for Locus 1 may be identical or unique, and the affinity tags for the many probe sets for Locus 2 may be identical or unique.

In this embodiment, probes 1602 and 1609 hybridize to sequences corresponding to Locus 1 or Locus 2 respectively, and a DNA polymerase or other enzyme may be used to synthesize a new polynucleotide sequence, for example 1603 in the case of Locus 1 or 1611 in the case of Locus 2. In this embodiment, 1603 and 1611 may contain one or more labels (1604) of type "C," possibly as a result of incorporation of one of more nucleotides bearing a label of type "C." This example also conveys to the probe product formed for Locus 2. Therefore, probe products will contain a combination of labels. For Locus 1, probe products will contains labels of type "A" and type "C," whereas probe products from Locus 2 will contain labels of type "B" and type "C." This embodiment results in probe products with high specificity for sequences in Locus 1 or Locus 2 respectively.

Figure 37:
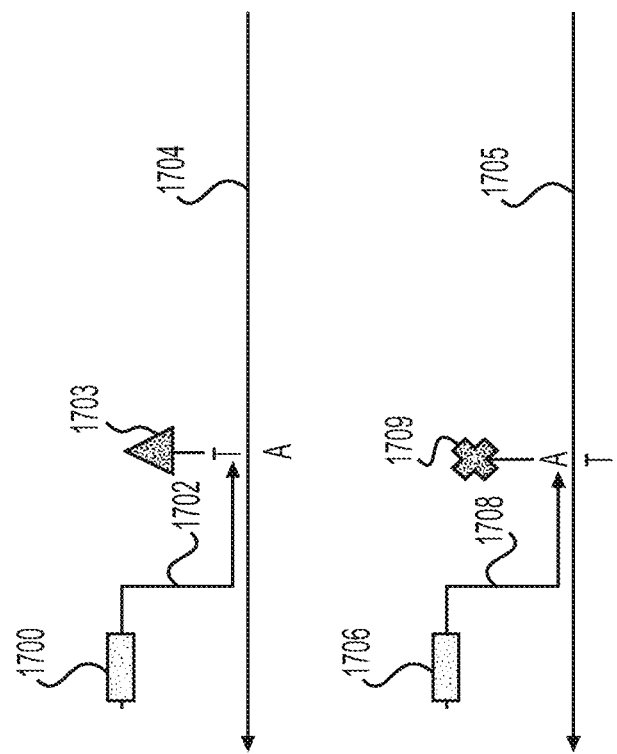

FIG. 37 depicts a modification of the general procedure described in FIG. 21. FIG. 37 depicts two probe sets, one probe set for Locus 1 and one probe set for Locus 2, although as aforementioned, multiple probes sets may be designed for each genomic locus. 1704 and 1705 are target molecules corresponding to Locus 1 and Locus 2, respectively.

A first probe sets contains member probe 1702. 1702 contains an affinity tag (1700) which may be used for isolation and identification of the probe product.

A second probe set with member probe 1708 carries respective features as in the first probe set. 1708 contains an affinity tag (1706) which may be identical to or unique from 1700. Many probe sets may designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1702 and 1708 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than for Locus 2. In this example, the first adjacent nucleotide next to the hybridization domain of 1702 is an "A," whereas the first adjacent nucleotide next to the hybridization domain of 1708 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, for example, the nucleotides may be dideoxy chain terminators. That is, only one new nucleotide shall be added to each probe sequence. In this example, the nucleotide added to probe 1702 will contain one or more labels (1703) of type "A." The nucleotide added to probe 1708 will contain one or more labels (1709) of type "B," such that the probe products for Locus 1 may be distinguished from the probe products from Locus 2.

Figure 38:
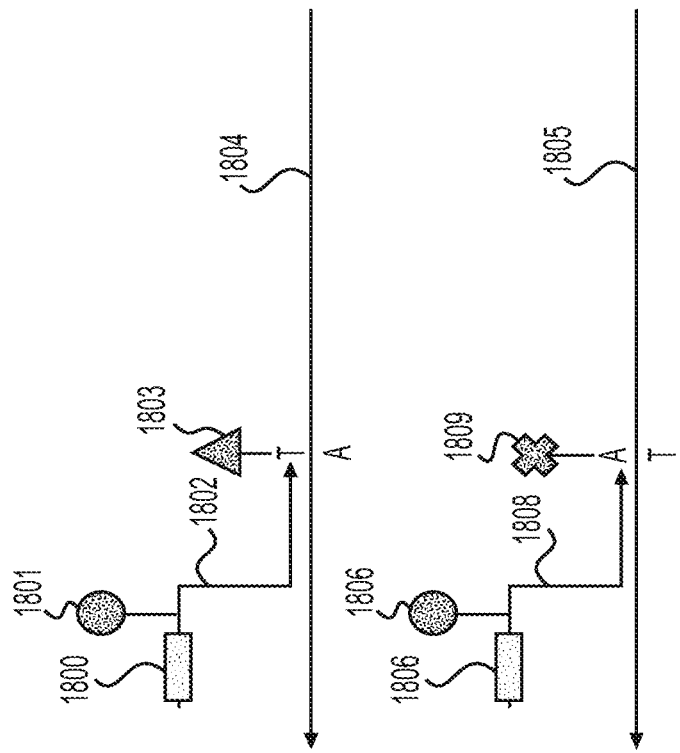

FIG. 38 depicts a modification of the general procedure described in FIG. 21. FIG. 38 depicts two probe sets, one probe set for Locus 1 and one probe set for Locus 2, although as aforementioned, multiple probes sets may be designed for each genomic locus. 1804 and 1805 are target molecules corresponding to Locus 1 and Locus 2, respectively.

A first probe sets contains member probe 1802. 1802 contains an affinity tag (1800) which may be used for isolation and identification of the probe product.

A second probe set with member probe 1808 carries respective features as in the first probe set. 1808 contains an affinity tag (1806) which may be identical to or unique from 1800. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1802 and 1808 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than for Locus 2. In this example, the first adjacent nucleotide next to the hybridization domain of 1802 is an "A," whereas the first adjacent nucleotide next to the hybridization domain of 1808 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 1802 will contain one or more labels (1803) of type "A." The nucleotide added to probe 1808 will contain one or more labels (1809) of type "B," such that the probe products for Locus 1 may be distinguished from the probe products from Locus 2.

In this embodiment, the probes 1802 and 1808 contain one or more labels (1801, 1806) of type "C." Therefore, probe products will contain a combination of labels. For Locus 1, probe products will contains labels of type "A" and type "C," whereas probe products from Locus 2 will contain labels of type "B" and type "C."

Figure 39:
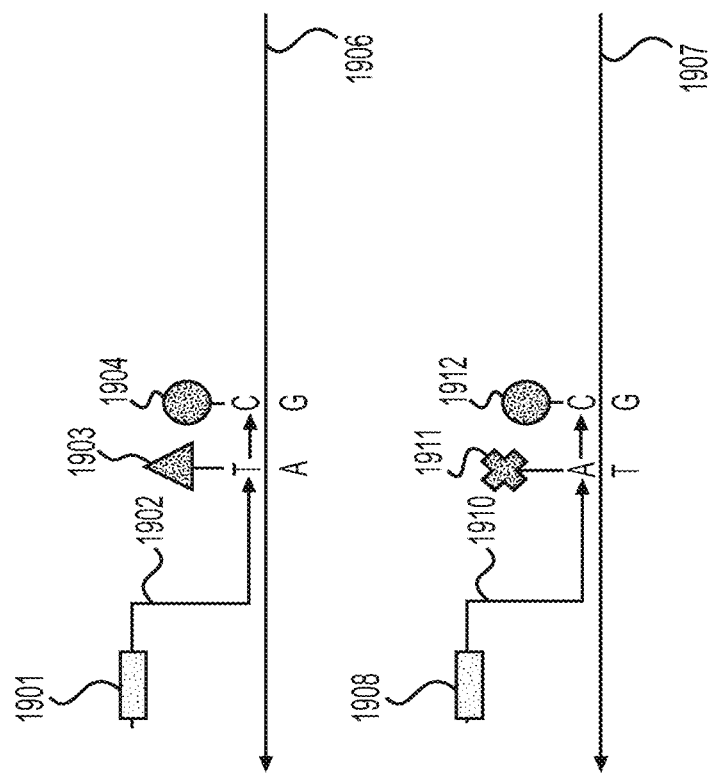

FIG. 39 depicts a modification of the general procedure described in FIG. 21. FIG. 39 depicts two probe sets, one probe set for Locus 1 and one probe set for Locus 2, although as aforementioned, multiple probes sets may be designed for each genomic locus. 1906 and 1907 are target molecules corresponding to Locus 1 and Locus 2, respectively.

A first probe set contains member probe 1902. 1902 contains an affinity tag (1901) which may be used for isolation and identification of the probe product.

A second probe set with member probe 1910 carries respective features as in the first probe set. 1910 contains an affinity tag (1908) which may be identical to or unique from 1901. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 1902 and 1910 hybridize to sequences corresponding to Locus 1 and Locus 2 respectively. The designs of each probe for Locus 1 and Locus 2 are such that the first adjacent nucleotide next to the hybridization domains contains a different nucleotide for Locus 1 than Locus 2. In this example, the first adjacent nucleotide next to the hybridization domain of 1902 is an "A," whereas the first adjacent nucleotide next to the hybridization domain of 1910 is a "T." In this embodiment, all probes for Locus 1 shall be designed such that the first nucleotide immediately adjacent to the hybridization domain shall consist of different nucleotide(s) than the first nucleotide immediately adjacent to the hybridization domain of the probes for Locus 2. That is, by design, probe sets from Locus 1 and Locus 2 may be distinguished from one another nucleotide on the identity of the first nucleotide immediately adjacent to the hybridization domain. A different nucleotide, not one used to distinguish probes from Locus 1 or Locus 2 shall serve as a chain terminator. In this particular example, an "A" nucleotide on a target molecule is used do distinguish probes for Locus 1 and a "T" nucleotide is used to distinguish probes for Locus 2. In this example, a "C" nucleotide may serve as a chain terminator. In this case, a "C" nucleotide will be added to the assay not is not capable of chain elongation (for example, a dideoxy C). One additional constraint is that the probe sequences are designed such that there are no instances of an identifying nucleotide for Locus 2 present on 1906 in between the distinguishing nucleotide for Locus 1 and the chain terminating nucleotide. In this example, there will be no "T" nucleotides present on 1906 after the hybridization domain of 1902 and before the G, which will pair with the chain terminator C.

In this embodiment, DNA polymerase or a similar enzyme will be used to synthesize new nucleotide sequences, and the nucleotide added at the distinguishing nucleotide location for Locus 1 will contain one or more labels (1903) of type "A." The nucleotide added at the distinguishing nucleotide location for Locus 2 will contain 1 or more labels (1911) of type "B," such that the probe products for Locus 1 may be distinguished from the probe products from Locus 2. In this embodiment, the nucleotide added at the chain terminating position will contain one or more labels (1912) of type "C." Therefore, probe products will contain a combination of labels. For Locus 1, probe products will contains labels of type "A" and type "C," whereas probe products from Locus 2 will contain labels of type "B" and type "C."

In another embodiment, the chain terminator may contain no label. In this embodiment, a fourth nucleotide may be added to the assay that contains one or more labels of type "C." This fourth nucleotide does not pair with the identifying nucleotide for Allele 1 (in this example, A), does not pair with the identifying nucleotide for Allele 2 (in this example, T), does not pair with the chain terminating nucleotide (in this example G). In this example, the fourth nucleotide that would bear one or more labels of type "C" is G, and will pair with C locations on 1906 and 1907. Therefore, probe products will contain a combination of labels. For Locus 1, probe products will contains labels of type "A" and type "C," whereas probe products from Locus 2 will contain labels of type "B" and type "C."

Figure 40:
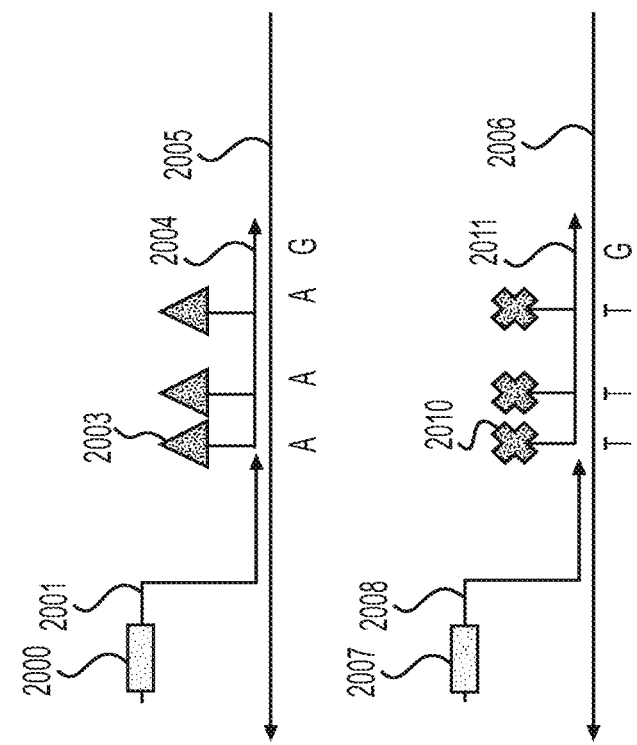

FIG. 40 depicts a modification of the general procedure described in FIG. 21. FIG. 40 depicts two probe sets, one probe set for Locus 1 and one probe set for Locus 2, although as aforementioned, multiple probes sets may be designed for each genomic locus. 2005 and 2006 are target molecules corresponding to Locus 1 and Locus 2, respectively.

A first probe sets contains member probe 2001. 2001 contains an affinity tag (2000) which may be used for isolation and identification of the probe product.

A second probe set with member probe 2008 carries respective features as in the first probe set. 2008 contains an affinity tag (2007) which may be identical to or unique from 2000. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 2001 and 2008 hybridize to sequences corresponding to Locus 1 and Locus 2 respectively. The designs of each probe for Locus 1 and Locus 2 are such that there are one or more instances of a distinguishing nucleotide (in this example, "A" is a distinguishing nucleotide for Locus 1 and "T" is a distinguishing nucleotide for Locus 2) followed by a chain terminating nucleotide (in this example "G") adjacent to the hybridization domain of the probes. Importantly there will be no instances of the distinguishing nucleotide for Locus 2 (in this example, "T") present in between the hybridization domain of 2001 on

2005 and the chain terminating nucleotide on 2005. Similarly, there will be no instance of the distinguishing nucleotide for Locus 1 (in this example, "A") present in between the hybridization domain of 2008 on 2006 and the chain terminating nucleotide on 2006.

In this embodiment, DNA polymerase or a similar enzyme will be used to synthesize new nucleotide sequences (2004, 2011) until the addition of a chain terminating nucleotide, one possible example would be a dideoxy C. In this embodiment, the nucleotides added at the distinguishing nucleotide locations for Locus 1 will contain one or more labels (2003) of type "A." The nucleotides added at the distinguishing nucleotide locations for Locus 2 will contain 1 or more labels (2010) of type "B," such that the probe products for Locus 1 may be clearly distinguished from the probe products from Locus 2.

FIG. 41 depicts a modification of the general procedure described in FIG. 21. FIG. 41 depicts two probe sets, one probe set for Locus 1 and one probe set for Locus 2, although as aforementioned, multiple probes sets may be designed for each genomic locus. 2105 and 2106 are target molecules corresponding to Locus 1 and Locus 2, respectively.

A first probe sets contains member probe 2102. 2102 contains an affinity tag (2100) which may be used for isolation and identification of the probe product.

A second probe set with member probe 2109 carries respective features as in the first probe set. 2109 contains an affinity tag (2107) which may be identical to or unique from 2100. Many probe sets may be designed that target "Locus 1," containing unique probe sequences. Similarly, many probe sets may be designed that target "Locus 2," containing unique probe sequences. In this embodiment, the affinity tags for the many probe sets for Locus 1 may be identical or unique, and the affinity tags for the many probe sets for Locus 2 may be identical or unique.

In this embodiment, probes 2102 and 2109 hybridize to sequences corresponding to Locus 1 and Locus 2 respectively. The designs of each probe for Locus 1 and Locus 2 are such that there are one or more instances of a distinguishing nucleotide (in this example, "A" is a distinguishing nucleotide for Locus 1 and "T" is a distinguishing nucleotide for Locus 2) followed by a chain terminating nucleotide (in this example "G") adjacent to the hybridization domain of the probes. Importantly there will be no instances of the distinguishing nucleotide for Locus 2 (in this example, "T") present in between the hybridization domain of 2102 on 2105 and the chain terminating nucleotide on 2105. Similarly, there will be no instance of the distinguishing nucleotide for Locus 1 (in this example, "A") present in between the hybridization domain of 2109 on 2106 and the chain terminating nucleotide on 2106.

In this embodiment, DNA polymerase or a similar enzyme will be used to synthesize new nucleotide sequences (2104, 2110) until the addition of a chain terminating nucleotide, one possible example would be a dideoxy C. In this embodiment, the nucleotides added at the distinguishing nucleotide locations for Locus 1 will contain one or more labels (2103) of type "A." The nucleotides added at the distinguishing nucleotide locations for Locus 2 will contain 1 or more labels (2110) of type "B," such that the probe products for Locus 1 may be clearly distinguished from the probe products from Locus 2.

In this embodiment, the probes 2102 and 2109 contain one or more labels (2101, 2108) of type "C." Therefore, probe products will contain a combination of labels. For Locus 1, probe products will contains labels of type "A" and type "C," whereas probe products from Locus 2 will contain labels of type "B" and type "C."

FIG. 42 depicts a modification of the general procedure described in FIG. 21. FIG. 42 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 42 depicts two probe sets—one probe set for Allele 1 and one probe set for Allele 2. 2203 and 2204 are target molecules corresponding to Allele 1 and Allele 2, respectively.

A first probe sets contains member probe 2201. 2201 contains an affinity tag (2200) which may be used for isolation and identification of the probe product. In this embodiment, the probe sets used for identification of the two different alleles are the same. That is, the probe set for Allele 2 consists of member probe 2201. In this embodiment, probe 2201 hybridizes to a sequence corresponding to Allele 1 and Allele 2 respectively in FIG. 42. The design of probe 2201 is such that the first adjacent nucleotide next to the hybridization domain contains a different nucleotide for Allele 1 than Allele 2. In other words, the first nucleotide adjacent to the hybridization domain may be a single nucleotide polymorphism, or SNP. In this example, the first adjacent nucleotide on 2203 next to the hybridization domain of 2201 is an "A," whereas the first adjacent nucleotide on 2204 next to the hybridization domain of 2201 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 2201 for Allele 1 will contain one or more labels (2202) of type "A." The nucleotide added to probe 2201 for Allele 2 will contain one or more labels (2205) of type "B," such that the probe products for Allele 1 may be clearly distinguished from the probe products from Allele 2. That is, the probe product for Allele 1 consists of probe 2201 plus one additional nucleotide bearing one or more labels of type "A," and the probe products for Allele 2 consists of probe 2201 plus one additional nucleotide bearing one or more labels of type "B."

Figure 43:
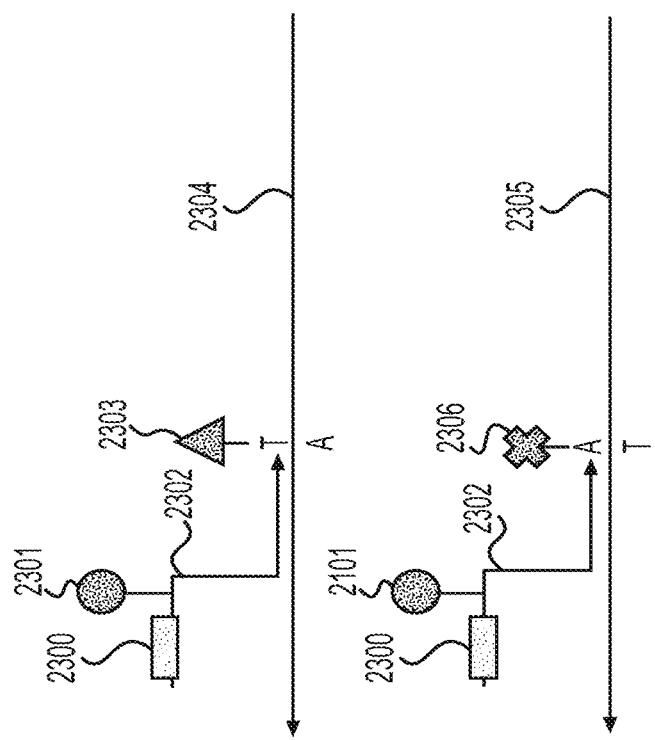

FIG. 43 depicts a modification of the general procedure described in FIG. 21. FIG. 43 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 43 depicts two probe sets—one probe set for Allele 1 and one probe set for Allele 2. 2304 and 2305 are target molecules corresponding to Allele 1 and Allele 2, respectively.

A first probe sets contains member probe 2302. 2302 contains an affinity tag (2300) which may be used for isolation and identification of the probe product. In this embodiment, the probe sets used for identification of the two different alleles are the same. That is, the probe set for Allele 2 consists of member probe 2302. In this embodiment, probe 2302 hybridizes to a sequence corresponding to Allele 1 and Allele 2 respectively in FIG. 43. The design of probe 2302 is such that the first adjacent nucleotide next to the hybridization domains contains a different nucleotide for Allele 1 than Allele 2. In other words, the first nucleotide adjacent to the hybridization domain may be a single nucleotide polymorphism, or SNP. In this example, the first adjacent nucleotide on 2304 next to the hybridization domain of 2302 is an "A," whereas the first adjacent nucleotide on 2305 next to the hybridization domain of 2302 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide substrates for the DNA polymerase are competent for a single addition, perhaps because the nucleotides added to the reaction mixture are dideoxy nucleotides. That is, only one new nucleotide shall be added to each probe sequence. In this example, the nucleotide added to probe 2302 for Allele 1 will contain one or more labels (2303) of type "A." The nucleotide added to probe 2302 for Allele 2 will contain one or more labels (2306) of type "B," such that the probe products for Allele 1 may be clearly distinguished from the probe products from Allele 2. That is, the probe product for Allele 1 consists of probe 2302 plus one additional nucleotide bearing one or more labels of type "A," and the probe products for Allele 2 consists of probe 2302 plus one additional nucleotide bearing one or more labels of type "B."

In this embodiment, the probes 2302 contain one or more labels (2301) of type "C." Therefore, probe products will contain a combination of labels. For Allele 1, probe products will contains labels of type "A" and type "C," whereas probe products from Allele 2 will contain labels of type "B" and type "C."

Figure 44:
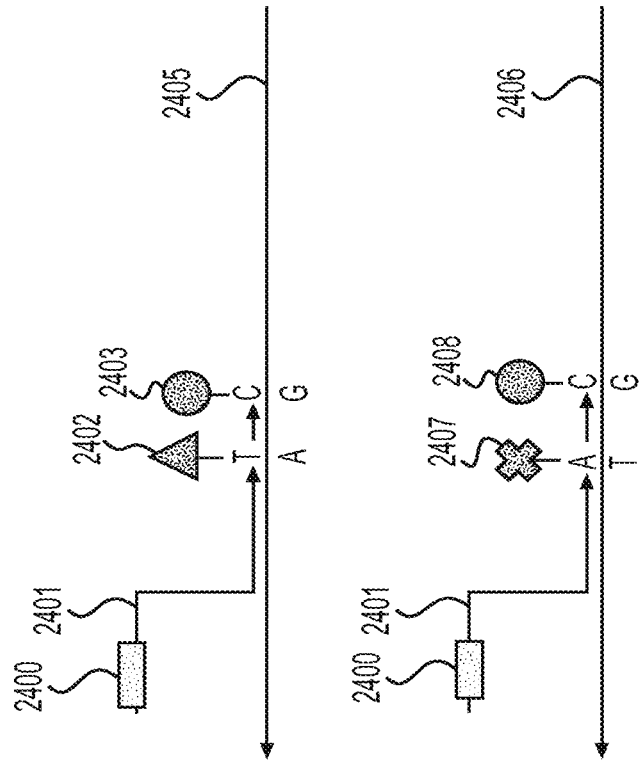

FIG. 44 depicts a modification of the general procedure described in FIG. 21. FIG. 44 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 44 depicts two probe sets—one probe set for Allele 1 and one probe set for Allele 2. 2405 and 2406 are target molecules corresponding to Allele 1 and Allele 2, respectively.

A first probe sets contains member probe 2401. 2401 contains an affinity tag (2400) which may be used for isolation and identification of the probe product. In this embodiment, the probe sets used for identification of two different alleles are the same. That is, the probe set for Allele 2 consists of member probe 2401. In this embodiment, probe 2401 hybridizes to a sequence corresponding to Allele 1 and Allele 2 respectively in FIG. 44. The design of probe for 2401 is such that the first adjacent nucleotide next to the hybridization domains contains a different nucleotide for Allele 1 than Allele 2. In other words, the first nucleotide adjacent to the hybridization domain may be a single nucleotide polymorphism, or SNP. In this example, the first adjacent nucleotide on 2405 next to the hybridization domain of 2401 is an "A," whereas the first adjacent nucleotide on 2406 next to the hybridization domain of 2401 is a "T." That is, probe products from Allele 1 and Allele 2 may be distinguished from one another based on the identity of the first nucleotide immediately adjacent to the hybridization domain.

In this embodiment, a DNA polymerase or other enzyme will be used to add at least one additional nucleotide to each of the probe sequences. In this example, the nucleotide added to probe 2401 for Allele 1 will contain one or more labels (2402) of type "A." The nucleotide added to probe 2401 for Allele 2 will contain one or more labels (2407) of type "B," such that the probe products for Locus 1 may be clearly distinguished from the probe products from Locus 2. That is, the probe product for Allele 1 contains probe 2401 plus an additional nucleotide bearing one or more labels of type "A," and the probe product for Allele 2 contains probe 2401 plus an additional nucleotide bearing one or more labels of type "B." A different nucleotide, not one used to distinguish Allele 1 from Allele 2 shall serve as a chain terminator. In this particular example, an "A" nucleotide on a target molecule is used to identify Allele 1 and a "T" nucleotide is used to identify Allele 2. In this example, a "C" nucleotide may serve as a chain terminator. In this case, a "C" nucleotide will be added to the assay that is not is not capable of chain elongation (for example, a dideoxy C). One additional constraint is that the probe sequences are designed such that there are no instances of an identifying nucleotide for Allele 2 is present on 2405 in between the distinguishing nucleotide for Allele 1 an the chain terminating nucleotide. In this example, there will be no "T" nucleotides present on 2405 after the hybridization domain of 2401 and before a G, which will pair with the chain terminator C.

In this embodiment, DNA polymerase or a similar enzyme will be used to synthesize new nucleotide sequences, and the nucleotide added at the distinguishing nucleotide location for Allele 1 will contain one or more labels (2402) of type "A." The nucleotide added at the distinguishing nucleotide location for Allele 2 will contain 1 or more labels (2407) of type "B," such that the probe products for Allele 1 may be clearly distinguished from the probe products from Allele 2. In this embodiment, the nucleotide added at the chain terminating position will contain one or more labels (2403) of type "C." Therefore, probe products will contain a combination of labels. For Allele 1, probe products will contains labels of type "A" and type "C," whereas probe products from Allele 2 will contain labels of type "B" and type "C."

FIG. 45 depicts a modification of the general procedure described in FIG. 21. FIG. 45 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 45 depicts two probe sets—one probe set for Allele 1 and one probe set for Allele 2. 2505 and 2506 are target molecules corresponding to Allele 1 and Allele 2, respectively.

A first probe sets contains member probe 2501. 2501 contains an affinity tag (2500) which may be used for isolation and identification of the probe product. In this embodiment, the probe sets used for identification of two different alleles are the same. That is, the probe set for Allele 2 consists of member probe 2501. In this embodiment, probe 2501 hybridizes to a sequence corresponding to Allele 1 and Allele 2 respectively in FIG. 45. The design of probe for 2501 is such that the first adjacent nucleotide next to the hybridization domains contains a different nucleotide for Allele 1 than Allele 2. In other words, the first nucleotide adjacent to the hybridization domain may be a single nucleotide polymorphism, or SNP. In this example, the first adjacent nucleotide on 2505 next to the hybridization domain of 2501 is an "A," whereas the first adjacent nucleotide on 2506 next to the hybridization domain of 2501 is a "T." That is, probe products from Allele 1 and Allele 2 may be distinguished from one another based on the identity of the first base immediately adjacent to the hybridization domain.

In this embodiment, a DNA polymerase or other enzyme will be used to add at least one additional nucleotide to each of the probe sequences. In this example, the nucleotide added to probe 2501 for Allele 1 will contain one or more labels (2502) of type "A." The nucleotide added to probe 2501 for Allele 2 will contain one or more labels (2507) of type "B," such that the probe products for Locus 1 may be clearly distinguished from the probe products from Locus 2. That is, the probe product for Allele 1 contains probe 2501 plus an additional nucleotide bearing one or more labels of type "A," and the probe product for Allele 2 contains probe 2501 plus an additional nucleotide bearing one or more labels of type "B." A different nucleotide, not one used to distinguish Allele 1 from Allele 2 shall serve as a chain terminator. In this particular example, an "A" nucleotide on a target molecule is used to identify Allele 1 and a "T" nucleotide is used to identify Allele 2 . In this example, a "C" nucleotide may serve as a chain terminator. In this case, a "C" nucleotide will be added to the assay that is not is not capable of chain elongation (for example, a dideoxy C). One additional constraint is that the probe sequences are designed such that no instances of an identifying nucleotide for Allele 2 are present on 2505 in between the distinguishing nucleotide for Allele 1 and the chain terminating nucleotide. In this example, there will be no "T" nucleotides present on 2505 after the hybridization domain of 2501 and before a G, which will pair with the chain terminator C.

In this embodiment, DNA polymerase or a similar enzyme will be used to synthesize new nucleotide sequences, and the nucleotide added at the distinguishing nucleotide location for Allele 1 will contain one or more labels (2502) of type "A." The nucleotide added at the distinguishing nucleotide location for Allele 2 will contain 1 or more labels (2507) of type "B," such that the probe products for Allele 1 may be clearly distinguished from the probe products from Allele 2. In this embodiment, a fourth nucleotide may be added to the assay that contains one or more labels (2508, 2503) of type "C." This fourth nucleotide does not pair with the identifying nucleotide for Allele 1 (in this example, A), does not pair with the identifying nucleotide for Allele 2 (in this example, T), does not pair with the chain terminating nucleotide (in this example G). In this example, the fourth nucleotide that would bear one or more labels of type "C" is G, and will pair with C locations on 2505 and 2506. Therefore, probe products will contain a combination of labels. For Allele 1, probe products will contains labels of type "A" and type "C," whereas probe products from Allele 2 will contain labels of type "B" and type "C."

FIG. 46 depicts a modification of the general procedure described in FIG. 21. FIG. 46 depicts two probe sets for identifying various alleles of the same genomic locus. For example, for distinguishing maternal and fetal alleles, in the case of cell free DNA isolated from a pregnant woman, or for distinguishing host and donor alleles, in the case of cell free DNA from a recipient of an organ transplant. FIG. 46 depicts two probe sets—one probe set for Allele 1 and one probe set for Allele 2. 2605 and 2606 are target molecules corresponding to Allele 1 and Allele 2, respectively. A first probe set contains member probe 2602. 2602 contains a label (2601) of type "A." 2602 contains an affinity tag (2600) which may be used for isolation and identification of the probe product.

A second probe set with member probe 2609 carries respective features as in the first probe set. However, 2609 contains a label (2608) of type "B," distinguishable from type "A." 2609 contains an affinity tag (2607) which may be identical to or unique from 2600.

In this embodiment, 2602 and 2609 contain sequences that are nearly identical, and differ by only one nucleotide in the sequence. Therefore, hybridization sequences of these two probes are complementary to Allele 1 (2605), or Allele 2 (2606). Further, the length of each hybridization domain on 2602 and 2609, as well as experimental hybridization conditions are designed such that probe 2602 will only hybridize to Allele 1 and probe 2609 will only hybridize to Allele 2. The purpose of this assay type is to be able to accurately quantify the frequency of Allele 1 and Allele 2 in a sample.

In this embodiment, DNA polymerase or other enzyme may be used to synthesize a new polynucleotide sequence, for example 2604 in the case of Allele 1 or 2611 in the case of Allele 2. In this embodiment, 2604 and 2611 may contain one or more labels (2603, 2610) of type "C," possibly as a result of incorporation of a one of more nucleotides bearing a label of type "C." Therefore, probe products will contain a combination of labels. For Allele 1, probe products will contains labels of type "A" and type "C," whereas probe products from Allele 2 will contain labels of type "B" and type "C." This embodiment results in probe products with high specificity for sequences in Allele 1 or Allele 2 respectively.

Figure 55:
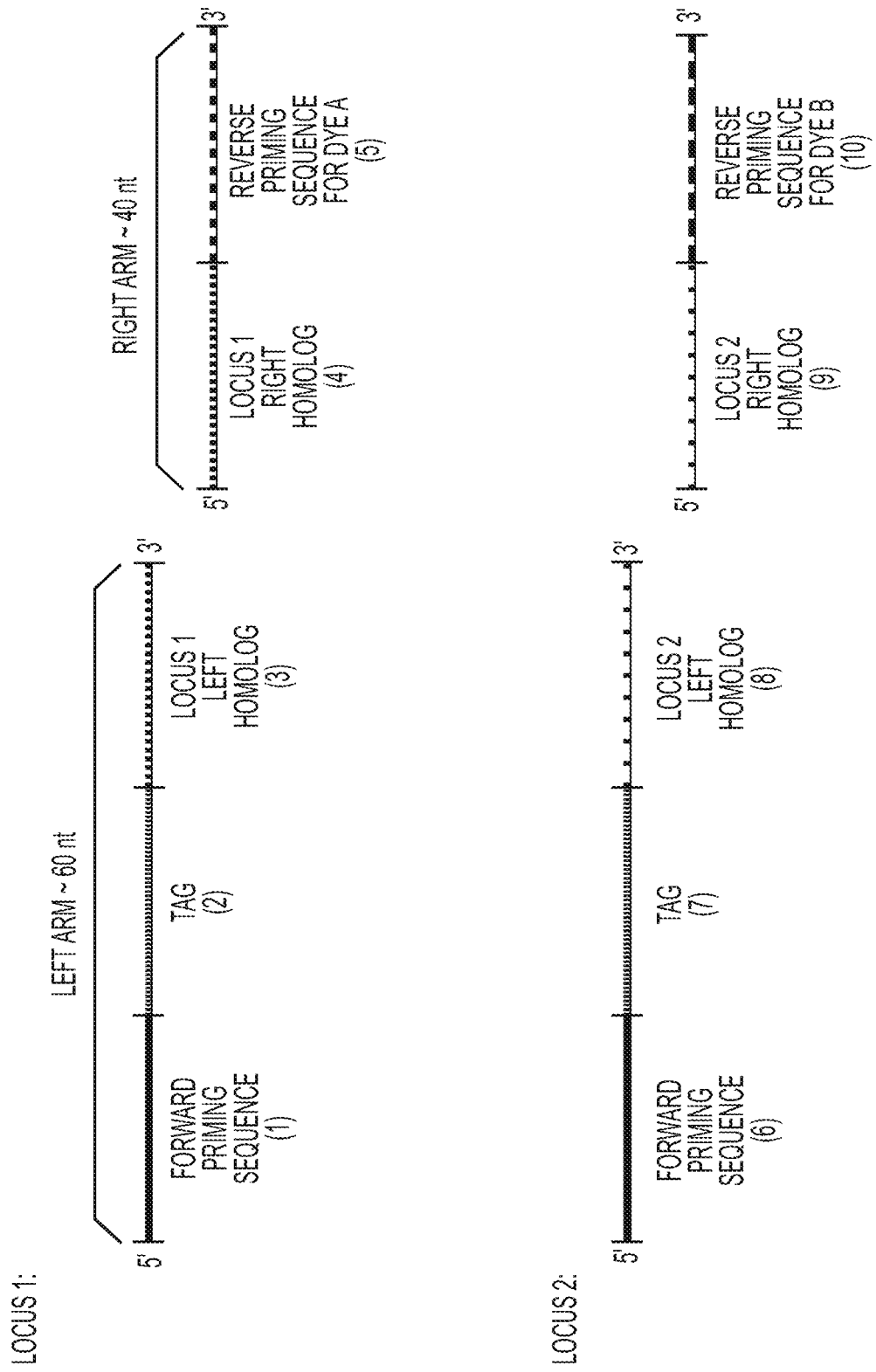
FIG. 55 depicts two probe sets; one probe set for Locus 1 and one probe set for Locus 2—although as aforementioned, multiple probes sets may be designed for each genomic locus.

FIGS. 55, 56, 57, 58A, 58B, and 58C illustrate a modification of the general procedure described with respect to FIGS. 21-46. FIG. 55 depicts two probe sets; one probe set for Locus 1 and one probe set for Locus 2—although as aforementioned, multiple probes sets may be designed for each genomic locus. The left arm of the Locus 1 probe set consists of a forward priming sequence, an affinity tag sequence and a homolog to Locus 1 sequence. The right arm of the Locus 1 probe set consists of a homolog to Locus 1 sequence and a reverse priming sequence for labeling the Locus 1 probe set with label A. The left arm of the Locus 2 probe set consists of a forward priming sequence, an affinity tag sequence and a homolog to Locus 2 sequence. The right arm of the Locus 2 probe set consists of a homolog to Locus 2 sequence and a reverse priming sequence for labeling the Locus 2 probe set with label B. The forward priming sequence and the affinity tag sequence are identical for the probe sets for both Locus 1 and Locus 2. The homologous sequences are specific to a single genomic locus. Locus homologous sequences for each probe set are immediately adjacent to one another such that when they hybridize to their target loci, they immediately abut one another and thus may be ligated to form one continuous molecule. The reverse priming sequence is specific to the label (e.g., label A or label B) to be used in labeling probe products for a particular locus for a particular affinity tag sequence.

Figure 56:
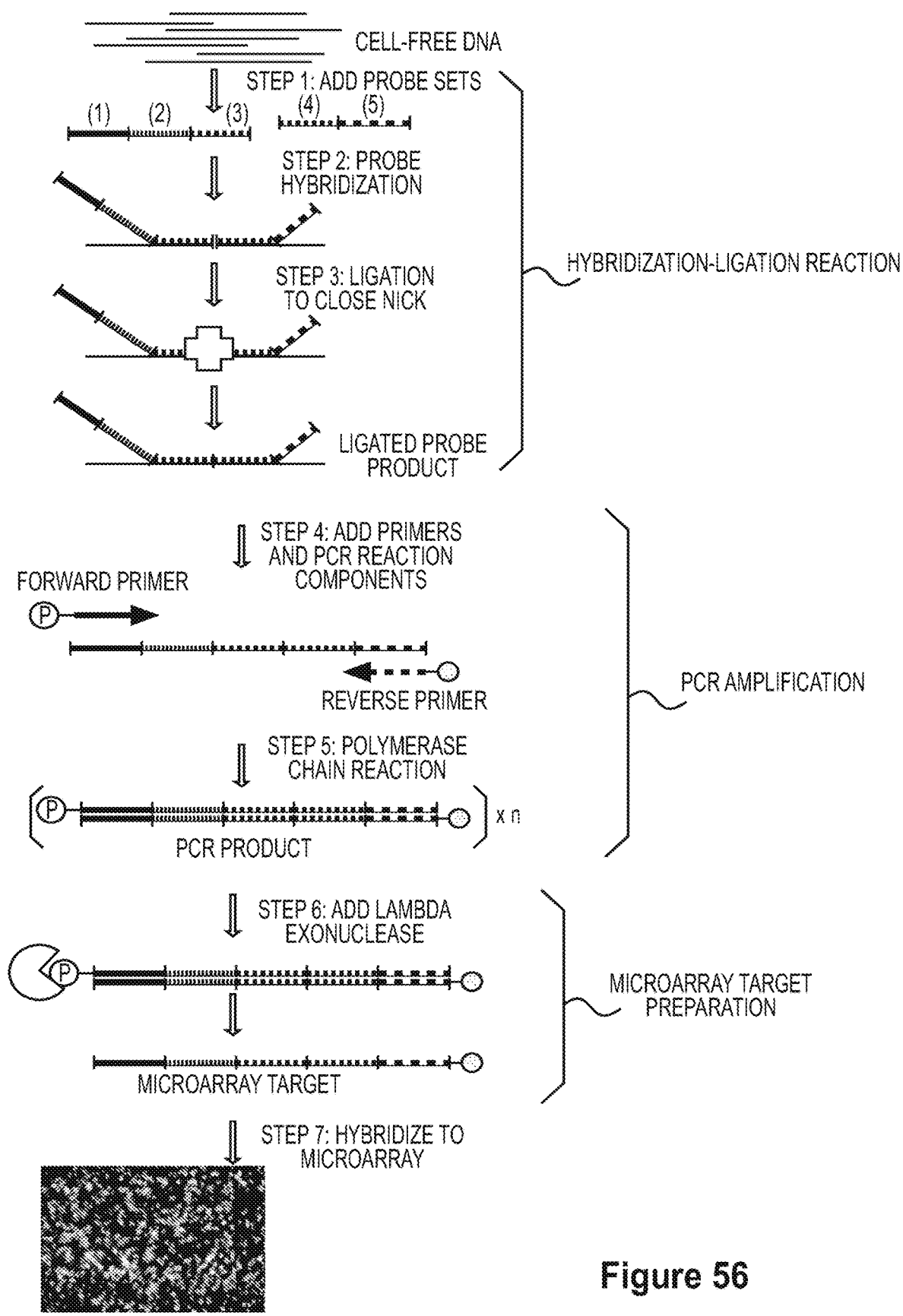
FIG. 56 depicts the procedural workflow that would be applied to the collection of probe sets.

FIG. 56 depicts the procedural workflow that would be applied to the collection of probe sets, such as those probe sets illustrated in FIG. 55. This depiction is based on one probe set for one genomic locus (e.g., the probe set for Locus 1 shown in FIG. 55). In Step 1, the collection of probe sets is mixed with purified cell-free DNA. In Step 2, the locus specific sequences in each probe set hybridize to their corresponding homologous sequences in the cell-free DNA sample. In Step 3, a ligase enzyme is added to catalyze the formation of a phosphodiester bond between the 3' base on the left arm homolog and the 5' arm of the right homolog, closing the nick between the two arms and thus forming one continuous molecule which is the probe product. In Step 4, modified primers and PCR reaction components (Taq polymerase, dNTPs, and reaction buffer) are added to amplify the ligated probe product. The Forward Primer is modified in that it has a 5' phosphate group that makes it a preferred template for the Lambda exonuclease used in Step 6 and the Reverse Primer is modified in that it contains the label (blue circle) that is specific to probe products for a particular locus for a particular affinity tag. In Step 5, the probe product is PCR amplified to yield a double-stranded PCR product in which the forward strand contains a 5' phosphate group and the reverse strand contains a 5' label. In Step 6, Lambda exonuclease is added to digest the forward strand in a 5' to 3' direction—the 5' phosphate group on the forward strand makes it a preferred template for Lambda exonuclease digestion. The resulting material is single-stranded (reverse strand only) with a 5' label. This represents the labeled target material for hybridization to a microarray or monolayer.

Figure 57:
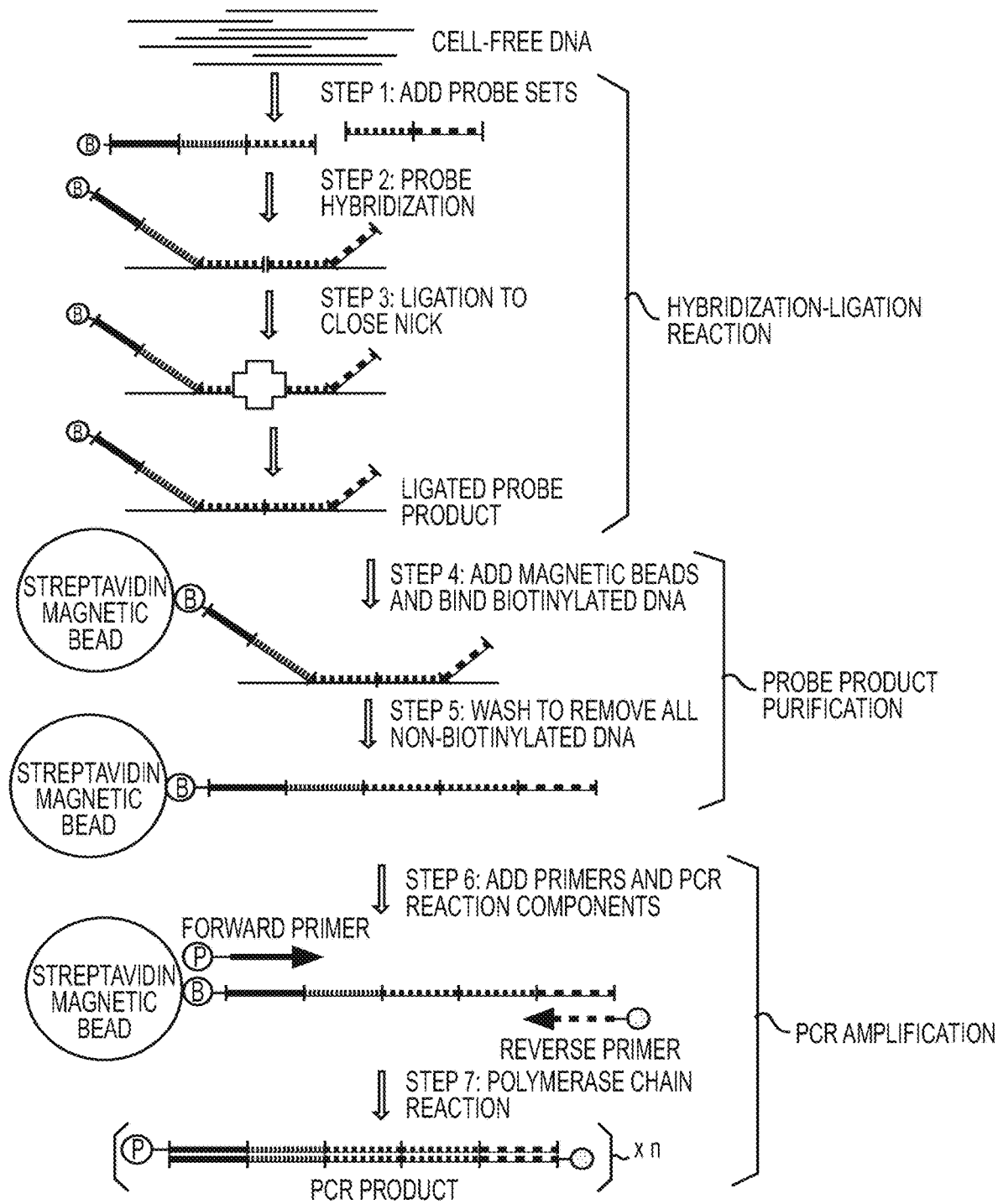
FIG. 57 depicts a modified version of the procedural workflow illustrated in FIG. 56.
Figure 57:
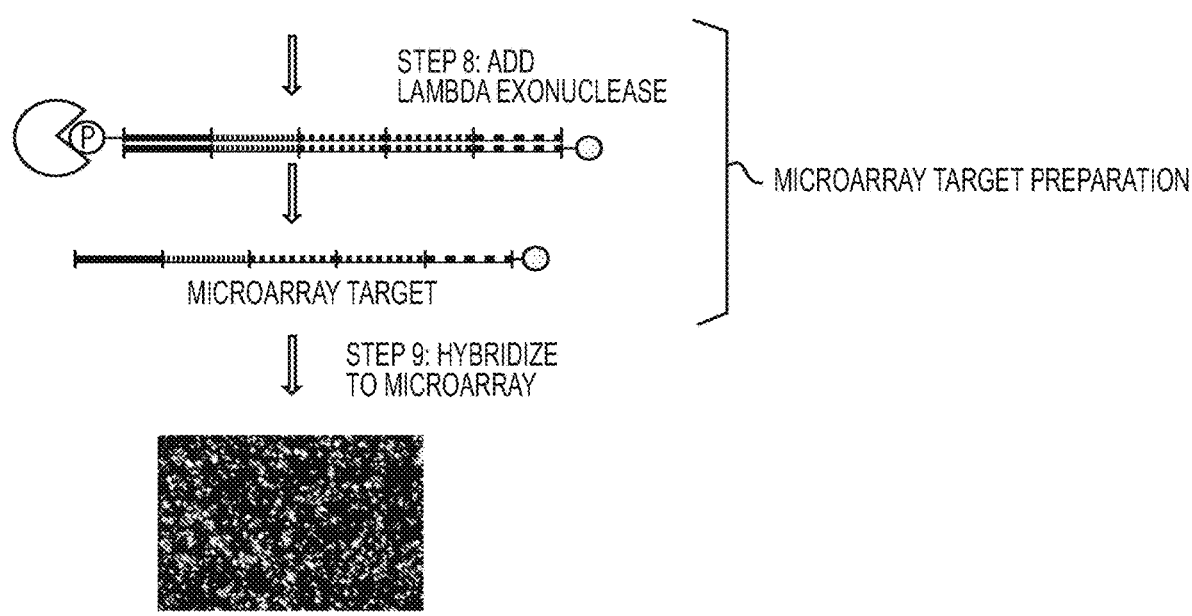

FIG. 57 depicts a modified version of the procedural workflow illustrated in FIG. 56. In this embodiment the left arm of each probe set contains a terminal biotin molecule as indicated by a "B" in Steps 1 to 6 of the Figure. This biotinylation enables the purification of the collection of probe products after completion of the hybridization-ligation reaction and prior to the PCR amplification. The workflow for this embodiment is identical to that described in FIG. 57 for Steps 1 to 3. In Step 4, streptavidin-coated magnetic beads are added to the hybridization-ligation reaction. The biotin molecule contained in the probe products will bind the products to the streptavidin. In Step 5, the magnetic beads are washed to remove the non-biotinylated DNA (cell-free genomic DNA and right arm oligonucleotides), resulting in a purified probe product. Steps 6 to 9 are performed in the same manner as described for Steps 4 to 7 in FIG. 56.

Figure 58A:
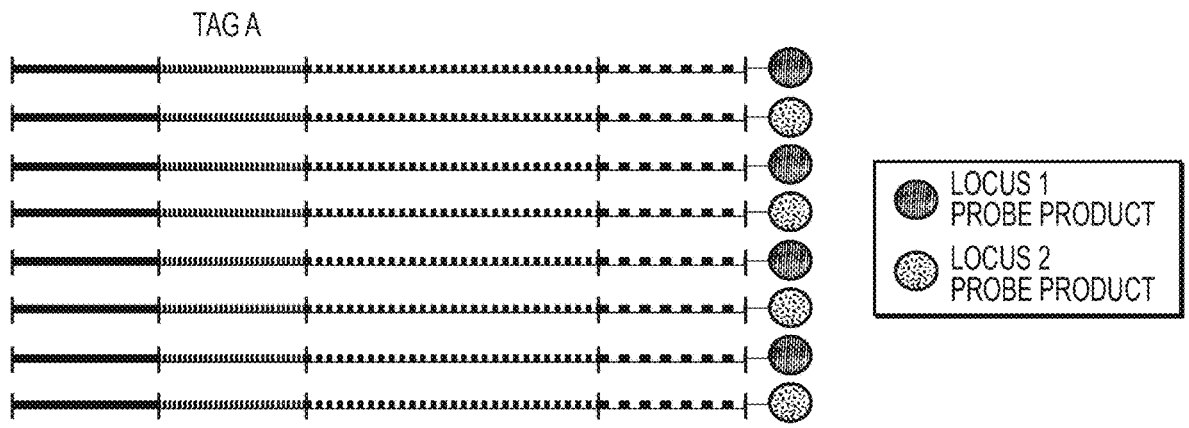
FIGS. 58A, 58B, and 58C provide an example of how probe products for Locus 1 and Locus 2 may be labeled with different label molecules.
Figure 58B:
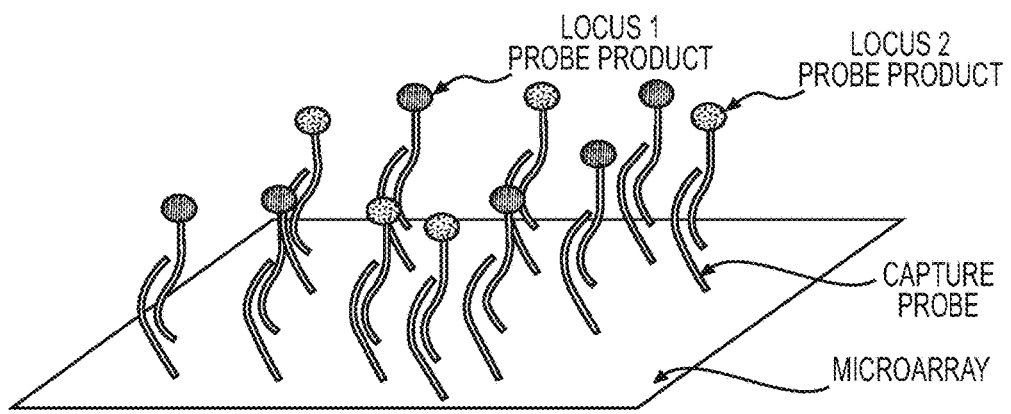
Figure 58C:
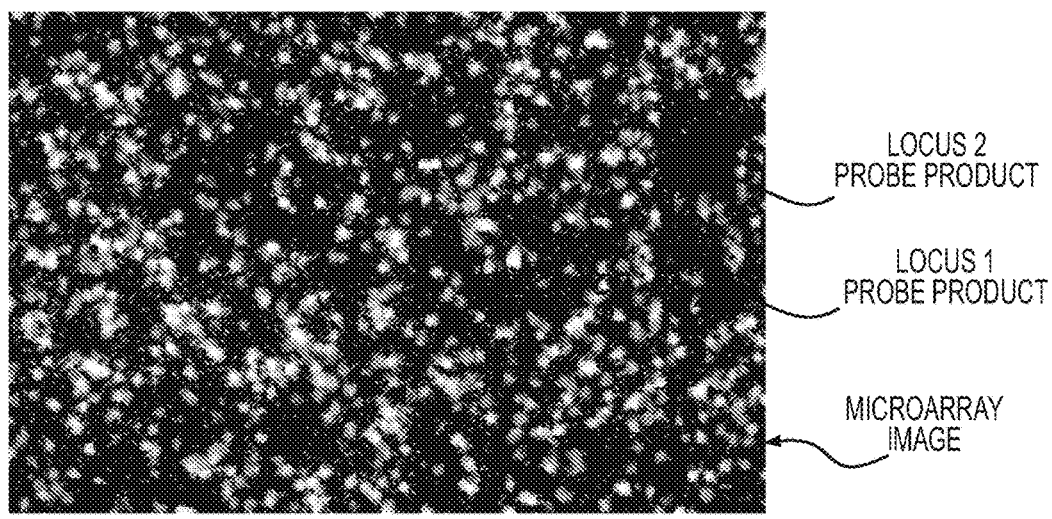

FIGS. 58A, 58B, and 58C provide an example of how probe products for Locus 1 and Locus 2 may be labeled with different label molecules. In FIG. 58A, Locus 1 probe products are labeled with label A (green) and Locus 2 probe products are labeled with label B (red) in one PCR amplification reaction. Probe products for both loci contain affinity tag sequence A. In FIG. 58B, the mixture of differentially labeled probe products is hybridized to a microarray location in which the capture probe sequence is complementary to the affinity tag A sequence. In FIG. 58C, the microarray location is imaged and the number of molecules of label A and label B counted to provide a relative measure of the levels of Locus 1 and Locus 2 present in the sample.

Figure 59:
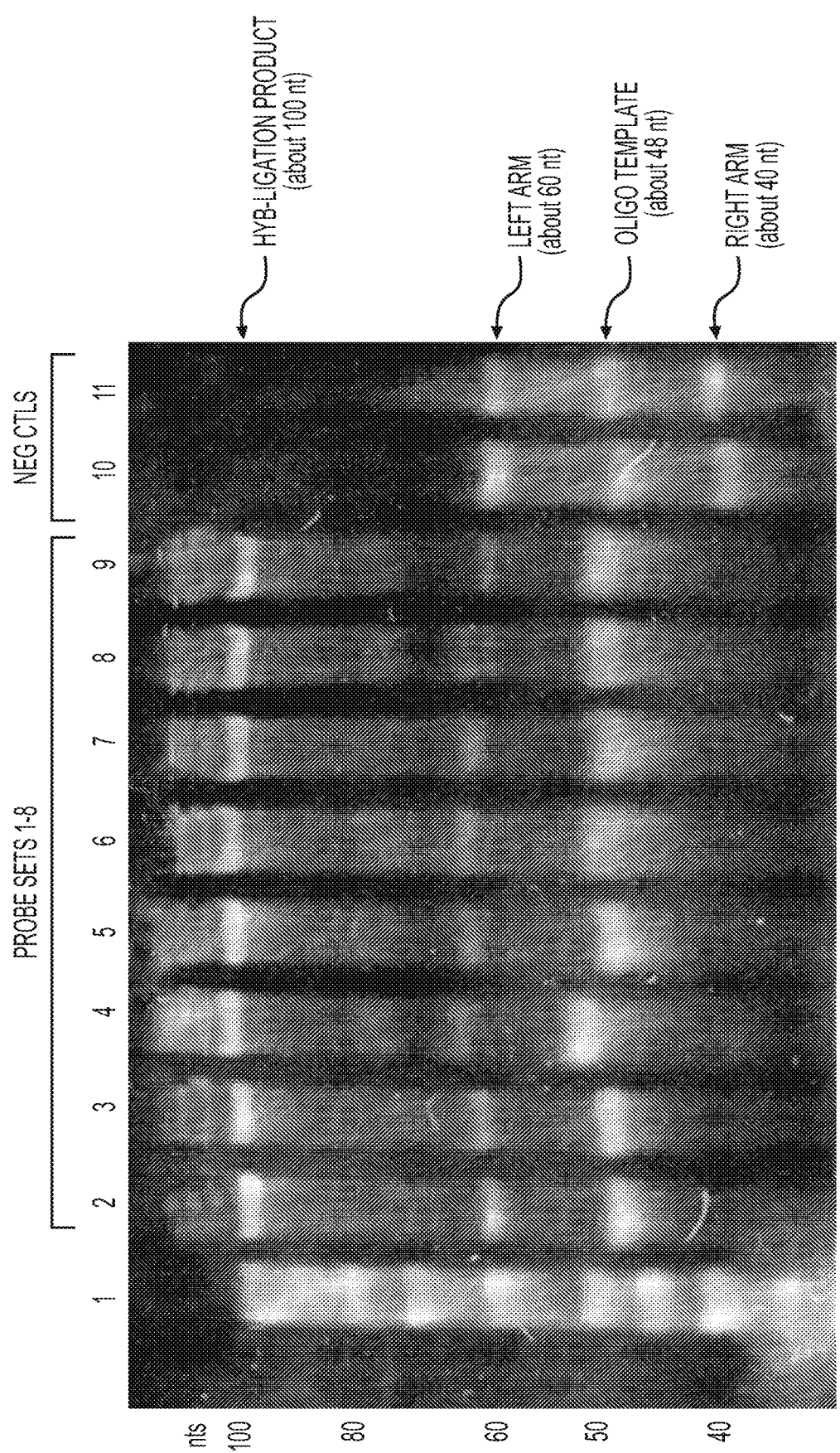
FIG. 59 provides evidence that probe products representing a multitude of genomic locations for one locus may be generated in a ligase enzyme specific manner using the hybridization-ligation process.

FIG. 59 provides evidence that probe products representing a multitude of genomic locations for one locus may be generated in a ligase enzyme specific manner using the hybridization-ligation process. Eight probe sets, each consisting of a left arm and right arm component as described in FIG. 55 and, containing homologs to eight chromosome 18 locations were hybridized to synthetic oligonucleotide templates (about 48 nucleotides) and ligated using a ligase enzyme to join the left and right arms for each. Reaction products were analyzed using denaturing polyacrylamide gel electrophoresis. Gel lane 1 contains a molecular weight ladder to indicate DNA band sizes. Lanes 2 to 9 contain hybridization-ligation reaction products for the eight chromosome 18 probe sets. A DNA band of about 100 nucleotides, representing the probe product of the about 60 nucleotide left arm and the about 40 nucleotide right arm, is present in each of lanes 2 to 9. Lanes 10 and 11 contain negative control reactions to which no ligase enzyme was added. No DNA band of about 100 nucleotides is present in lanes 10 and 11.

Figure 60A:
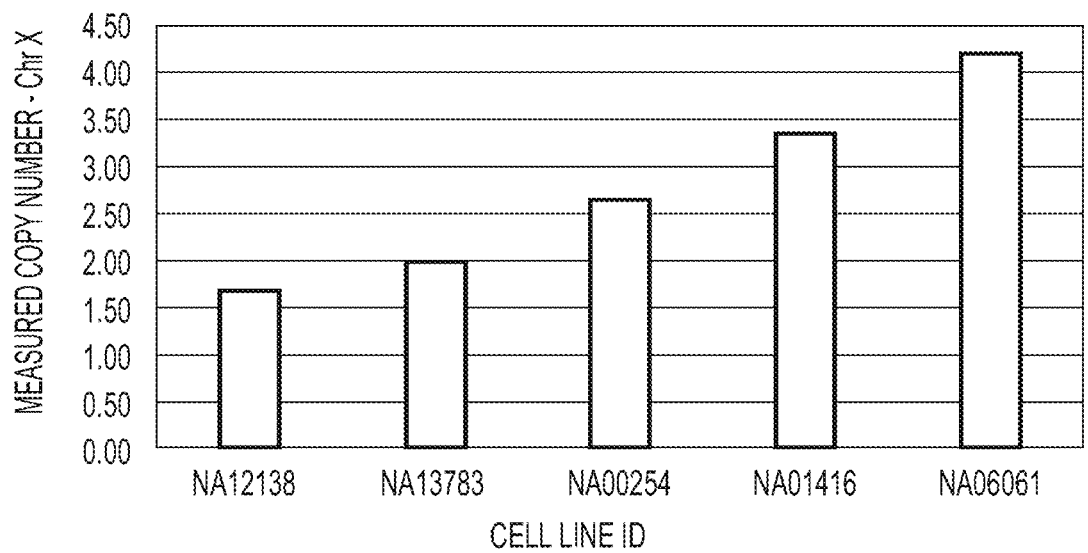
FIGS. 60A and 60B provide data indicating that probe sets may be used to detect relative changes in copy number state.
Figure 60B:
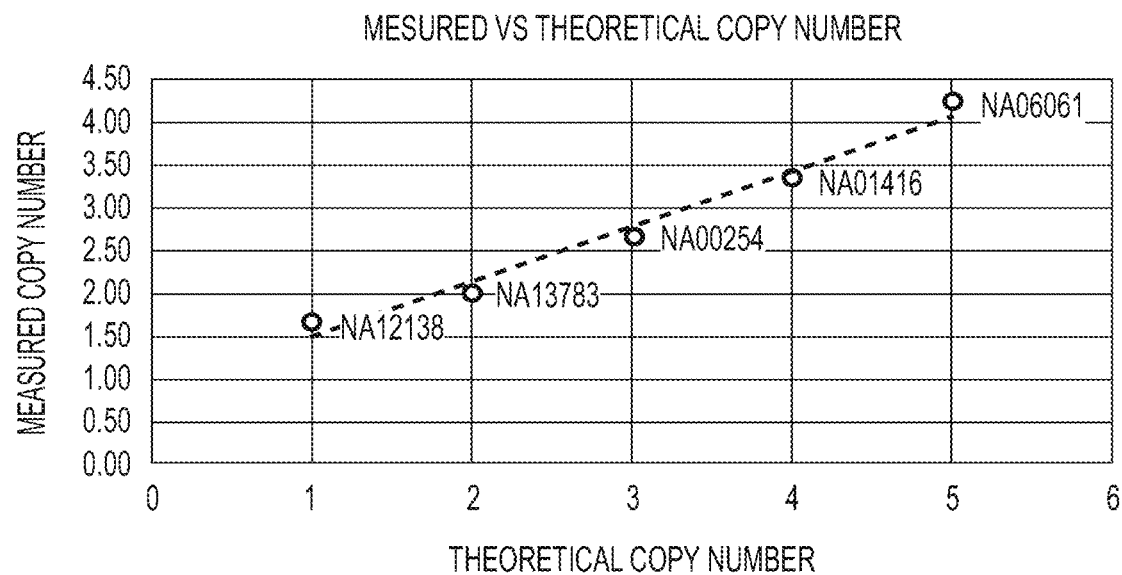

FIGS. 60A and 60B provide provides data indicating that probe sets may be used to detect relative changes in copy number state. A mixture of eight probe sets containing homologs to eight distinct chromosome X locations was used to assay the cell lines containing different numbers of chromosome X indicated in Table 1.

TABLE 1

| Cell lines containing different copy numbers of chromosome X | |
|---|---|
| Coriell Cell Line ID | Number of copies of chromosome X |
| NA12138 | 1 |
| NA13783 | 2 |
| NA00254 | 3 |
| NA01416 | 4 |
| NA06061 | 5 |

Quantitative PCR was used to determine the amount of probe product present for each cell line following the hybridization-ligation and purification processes described in FIG. 57 (Steps 1 to 5). As illustrated by FIG. 60A, the copy number state measured for the various cell lines followed the expected trend indicated in Table 1. For example, qPCR indicated a copy number state of less than two for NA12138, which has one copy of chromosome X. The measured copy number state for NA00254 (three copies of X) was greater than two, for NA01416 (four copies of X) was greater than three, and for NA06061 (five copies of X) was greater than four. The responsiveness of the process in detecting differences in copy number state is further illustrated by FIG. 60B in which the measured copy number state is plotted against the theoretical copy number state.

Figure 61A:
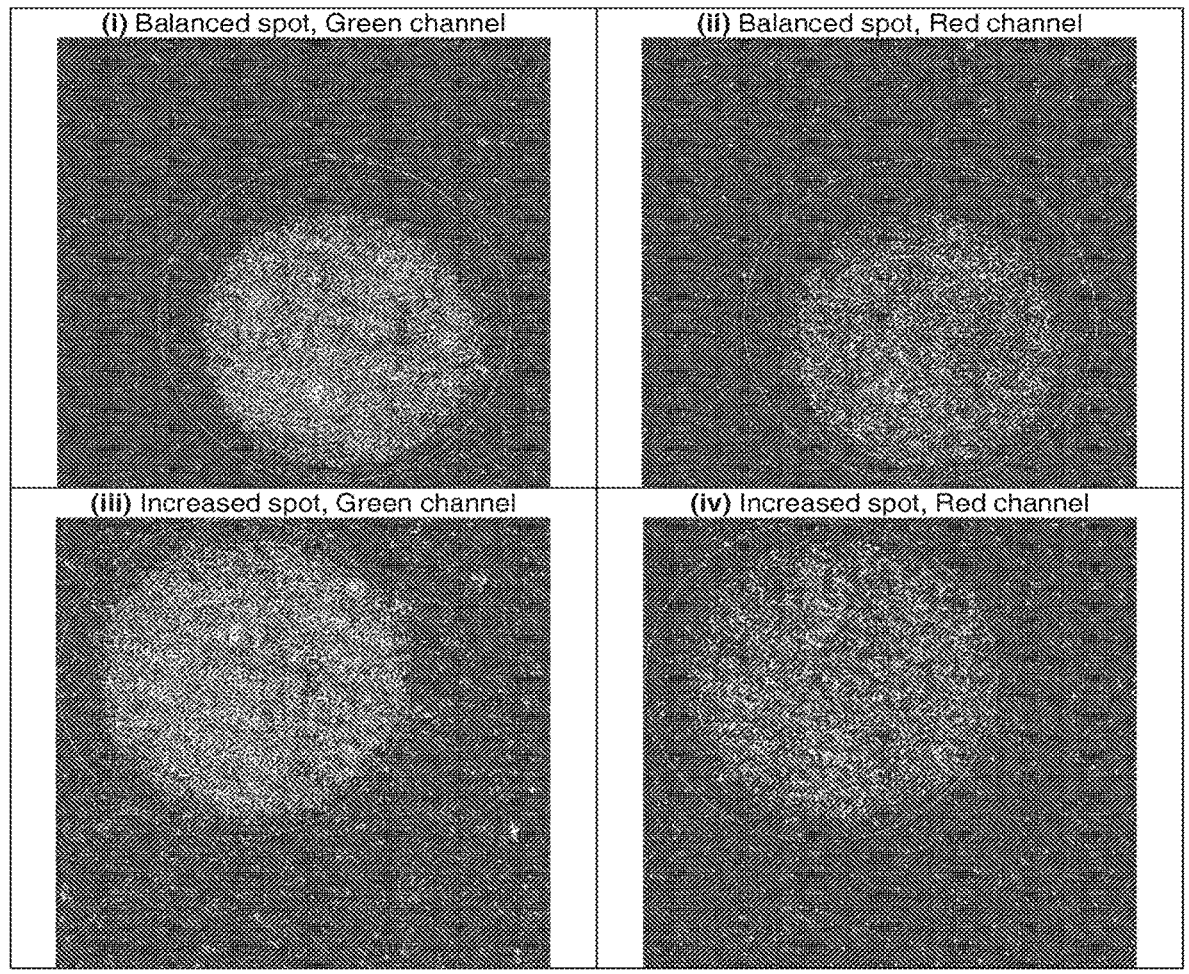
FIGS. 61A, 61B, and 61C provide evidence that mixtures of probe products may be used to generate quantitative microarray data.
Figure 61B:
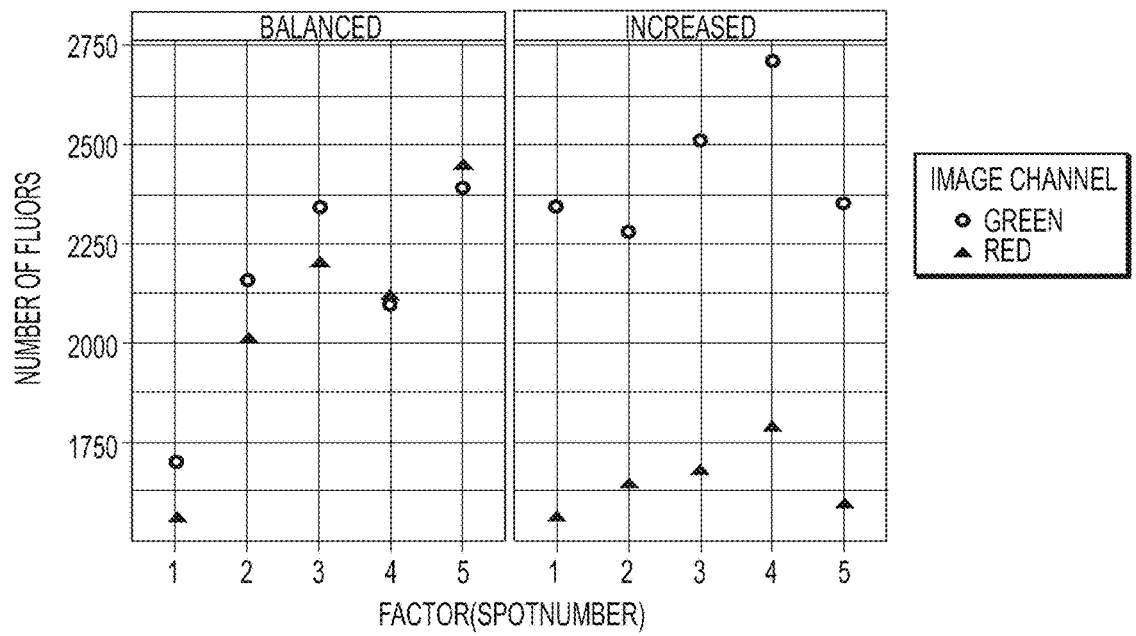
Figure 61C:
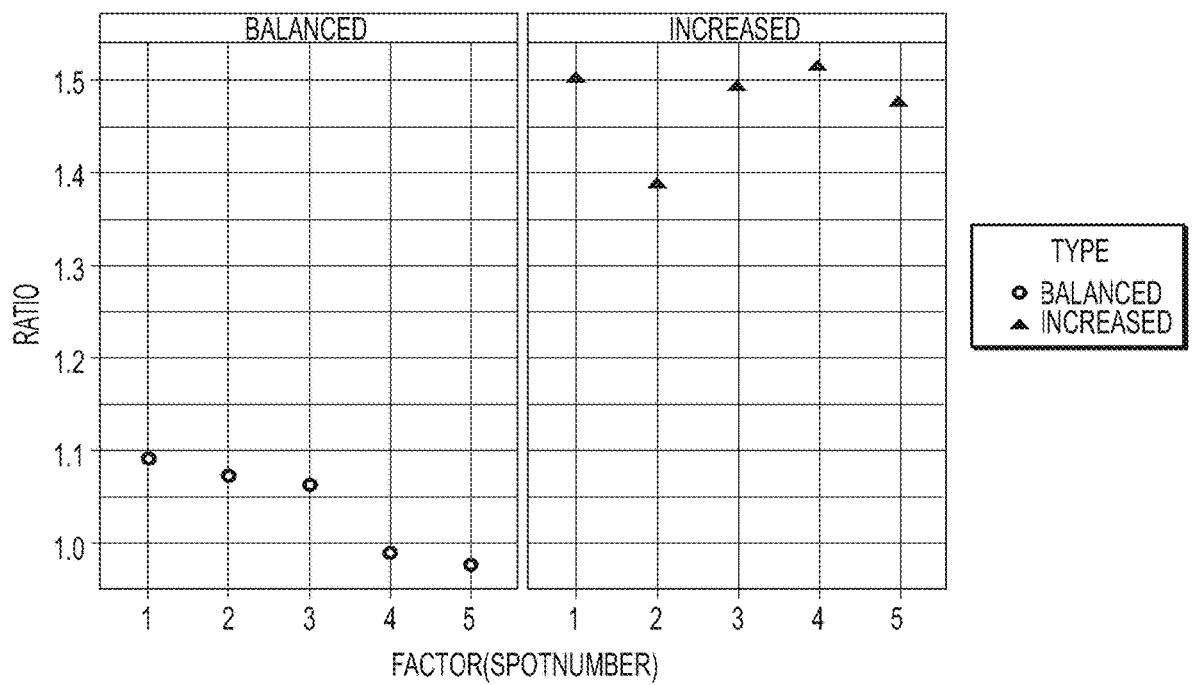

FIGS. 61A, 61B, and 61C provide evidence that mixtures of probe products may be used to generate quantitative microarray data as described in FIGS. 56 and 57.

FIG. 61A depicts representative fluorescence images of two array spots in two orthogonal imaging channels (Alexa 488: green, Alexa 594; red). A region of interest (ROI) is automatically selected (large circle), with any undesired bright contaminants being masked from the image (smaller outlined regions within the ROI). Single fluorophores on single hybridized assay products are visualized as small punctate features within the array spot. (i) A "Balanced" spot (representing genomic targets input at a 1:1 concentration ratio to the assay) imaged in the green channel and (ii) the same spot imaged in the red channel. (iii) An "Increased" spot (representing genomic targets input at a >1:1 concentration ratio to the assay) imaged in the green channel and (iv) the same spot imaged in the red channel.

FIG. 61B presents raw counts of the detected fluorophores in two channels for five spots each of the "Balanced" and "Increased" conditions. Despite some variation in the absolute number of fluors, the numbers in the two channels track closely for the "Balanced" case, but demonstrate clear separation in the "Increased" case.

FIG. 61C presents calculated ratio values for number of fluors in the green channel divided by the number of fluors in the red channel, for the five spots from each of the "Balanced" and "Increased" conditions. The "Balanced" case centers about a ratio of 1.0 and the "Increased" case is at an elevated ratio. Considering the "Balanced" case as comparing two balanced genomic loci and the "Increased" case as one where one locus is increased relative to the other, we may calculate the confidence of separation of the two conditions using an independent, 2-group T-test, yielding a p-value of $8 \times 10^{-14}$.

Figure 62:
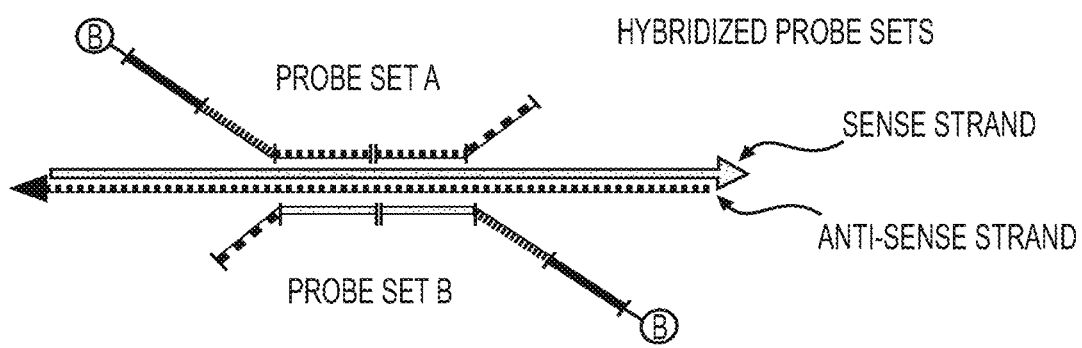
FIGS. 62-64 illustrate modifications of the general procedure described in FIGS. 55, 56, 57, 58A, 58B, and 58C.

FIG. 62 illustrates a modification of the general procedure described in FIGS. 55, 56, 57, 58A, 58B, and 58C. In this embodiment, a second probe set, Probe Set B is designed for each genomic location such that the genome homolog sequences in Probe Set B are a reverse complement of the genome homolog sequences in Probe Set A. Probe Set A will hybridize to the reverse strand of the genomic DNA and Probe Set B will hybridize to the forward strand of the genomic DNA. This embodiment will provide increased sensitivity relative to the embodiment described in FIGS. 55, 56, 57, 58A, 58B, and 58C as it will yield approximately double the number of probe products per locus.

Figure 63:
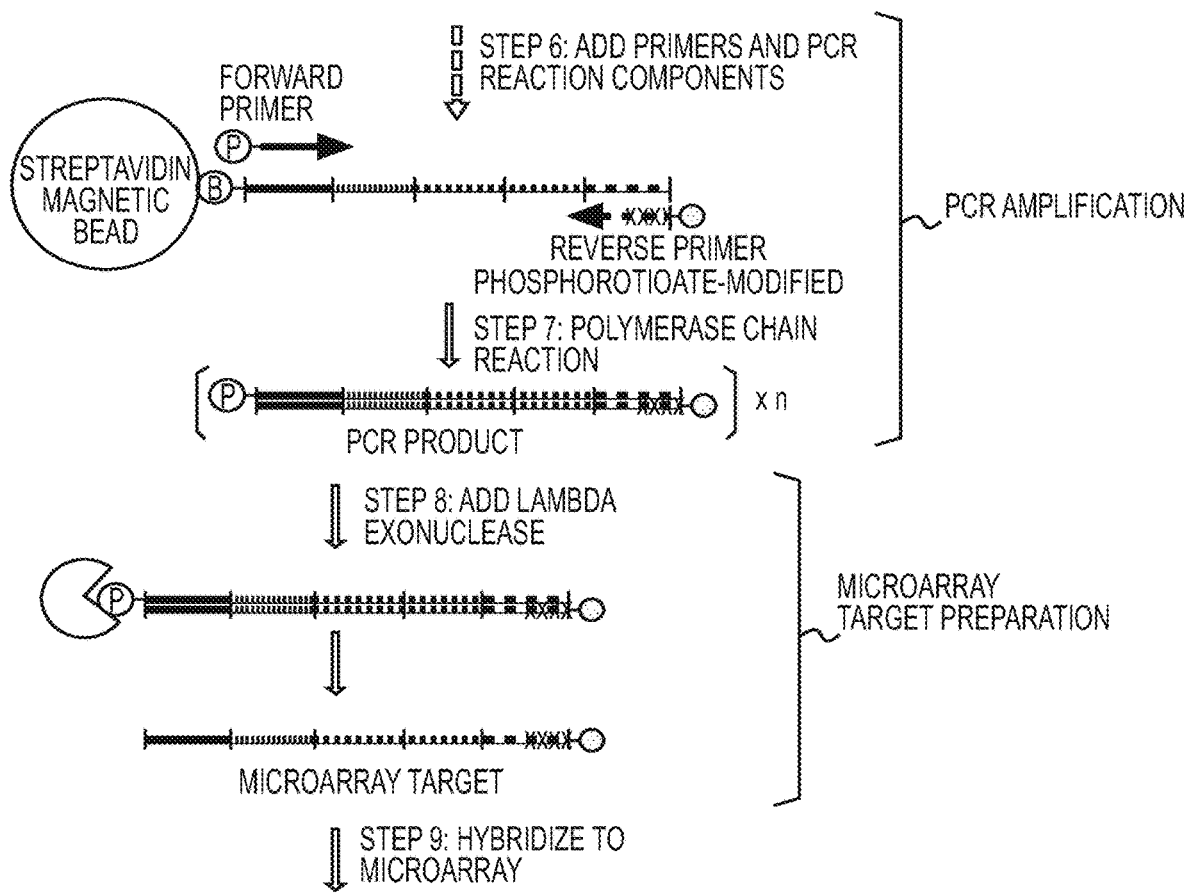

FIG. 63 illustrates a modification to the general procedure described in FIG. 57. In this embodiment, the Reverse Primer used in Step 6 is additionally modified in that the four bonds linking the first five nucleotides in the oligonucleotide sequence are phosphorothioate bonds. This modification will result in all PCR products generated during PCR amplification (Step 7) having a phosphorothioate modification on the 5' end. This modification will protect the reverse strand from any digestion that might occur during the treatment with Lambda exonuclease in Step 8.

Although the 5' phosphate group on the forward strand makes it a preferred template for Lambda exonuclease digestion, the reverse strand may still have some vulnerability to digestion. Phosphorothioate modification of the 5' end of the reverse strand will reduce its vulnerability to Lambda exonuclease digestion.

Figure 64:
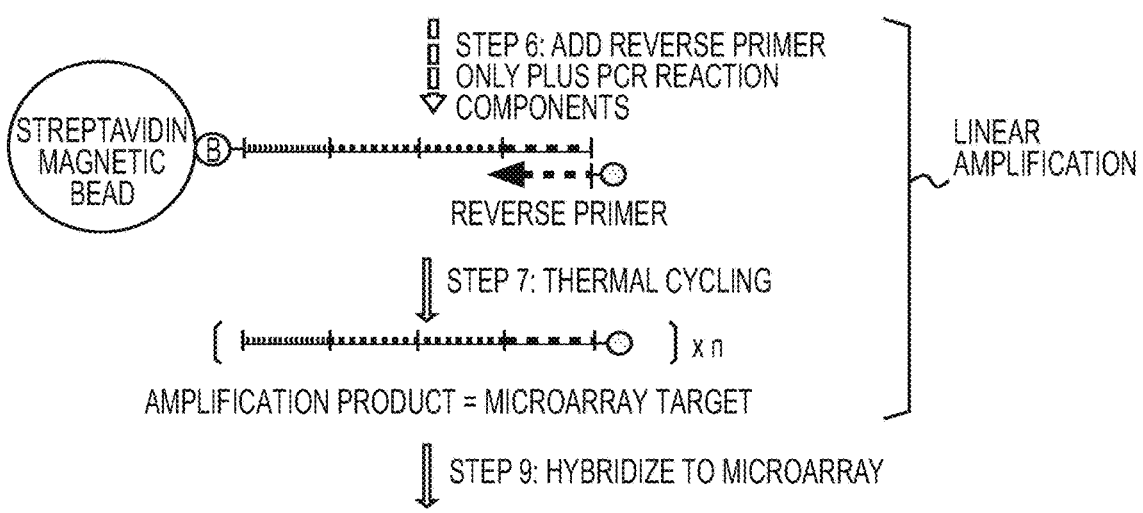

FIG. 64 illustrates a modification of the general procedure described in FIGS. 55, 56, 57, 58A, 58B, and 58C. In this embodiment, PCR amplification of the probe product is replaced with linear amplification by adding the Reverse Primer but no Forward Primer to the amplification reaction in Step 6. If only the Reverse Primer is present the amplification product will be single stranded—the reverse strand with a label of the 5' end. As the amplification product is already single-stranded, it does not require further processing before hybridization to a microarray, i.e., Lambda exonuclease digestion may be omitted. As a forward primer is not used in this embodiment, it is unnecessary for the left arm of the probe set to contain a forward priming sequence. The left arm would consist of an affinity tag sequence and a locus homolog sequence only as illustrated in FIG. 64.

A further embodiment of the general procedure described in FIGS. 55, 56, 57, 58A, 58B, and 58C is one in which the single ligation reaction process in Step 3 is replaced with a cycled ligation reaction process. This is accomplished by replacing the thermolabile ligase enzyme (e.g., T4 ligase) used to catalyze the ligation reaction with a thermostable ligase (e.g., Taq ligase). When a thermostable ligase is used, the hybridization-ligation reaction may be heated to a temperature that will melt all DNA duplexes (e.g., 95° C.) after the initial cycle of hybridization and ligation has occurred. This will make the genomic template DNA fully available for another probe set hybridization and ligation. Subsequent reduction of the temperature (e.g., to 45° C.) will enable this next hybridization and ligation event to occur. Each thermocycling of the hybridization and ligation reaction between a temperature that will melt DNA duplexes and one that will allow hybridization and ligation to occur will linearly increase the amount of probe product yielded from the reaction. If the reaction is exposed to 30 such cycles, up to 30 times the amount of probe product will be yielded than from a process in which a single ligation reaction is used.

Figure 65A:
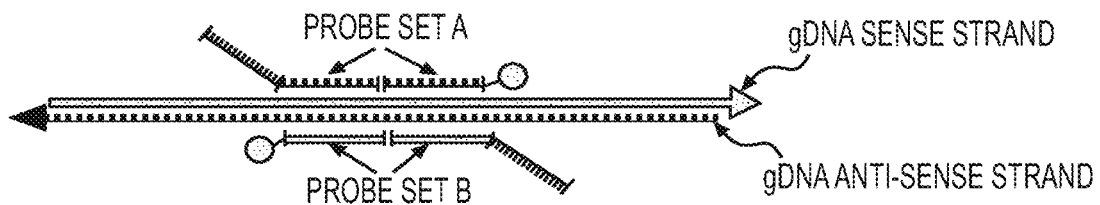
FIGS. 65A and 65B depict further embodiments of the modified procedure described in FIG. 62.
Figure 65B:
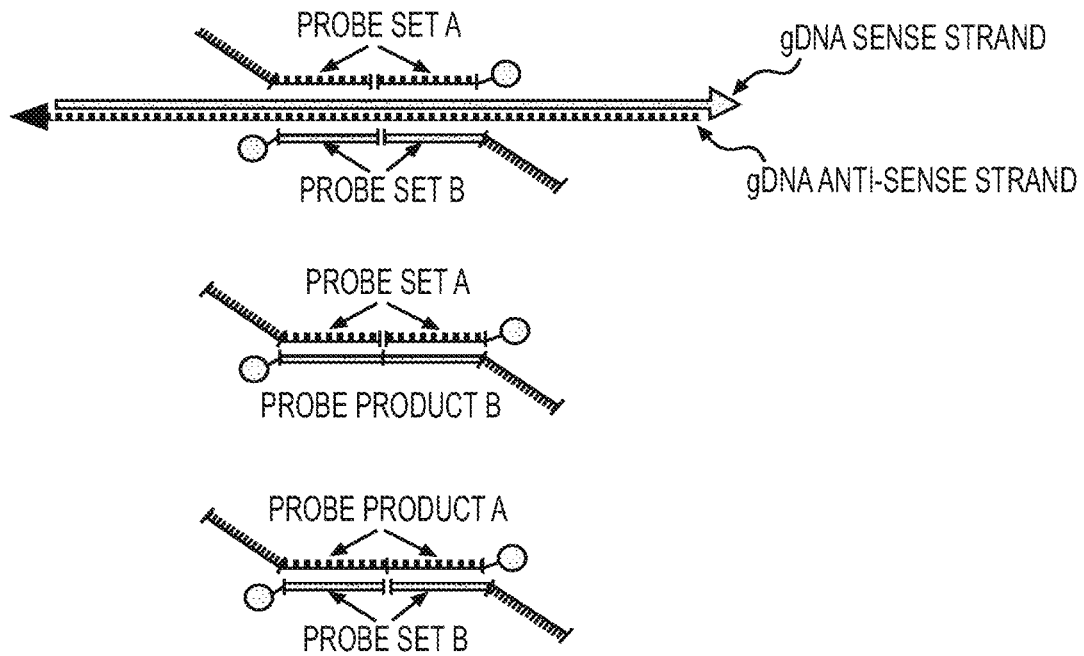

FIGS. 65A and 65B depict further embodiments of the modified procedure described in FIG. 62. This embodiment takes advantage of the ligase chain reaction (LCR) in combining the presence of the reverse complement for each probe set with the use of a thermostable ligase to enable a cycled ligation reaction in which the product is exponentially amplified. FIGS. 65A and 65B depict two probe sets, Probe Set A and Probe Set B for one locus; where the genome homolog sequences in Probe Set B are the reverse complement of the genome homolog sequences in Probe Set A. The 5' arm of each Probe Set consists of an affinity tag sequence and a homolog while the 3' arm of each Probe Set consists of a homolog sequence with a label attached. In the first cycle of a thermocycled reaction, genomic DNA will be the only template available to enable hybridization and ligation to occur to generate a probe product as illustrated in FIG. 65A. However in the second cycle, Probe Product B generated in the first cycle will act as an additional template for Probe Set A and likewise Probe Product A generated in the first cycle will act as an additional template for Probe Set B as illustrated in FIG. 65B. In this same manner, the probe products from each successive cycle will act as template for probe set hybridization and ligation in the next cycle. This process would eliminate the need for PCR amplification of the probe product which may be directly used as microarray target.

Another embodiment of the procedure depicted in FIGS. 65A and 65B is one which employs LCR but uses probe sets that have the structure described in FIG. 55, i.e., both left and right arms are flanked by priming sequences, the left arm contains a biotin molecule and the right arm does not contain a label. After completion of LCR, the probe products are purified using magnetic beads (optional) and then PCR amplified and microarray target prepared as illustrated in FIGS. 56 and 57.

Figure 66A:
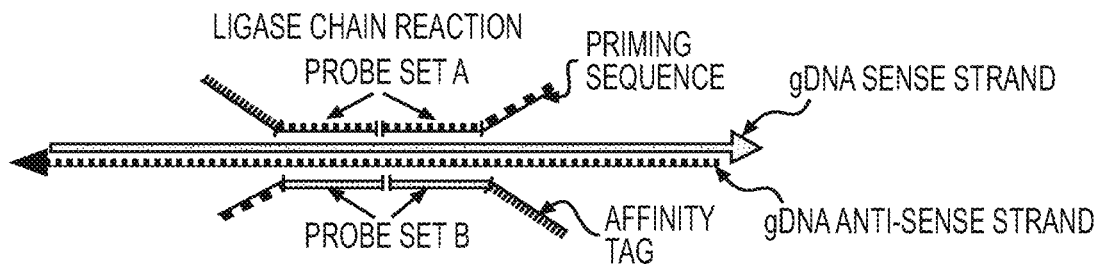
FIGS. 66A, 66B, and 66C depict yet other embodiments of the procedure depicted in FIGS. 65A and 65B.
Figure 66B:
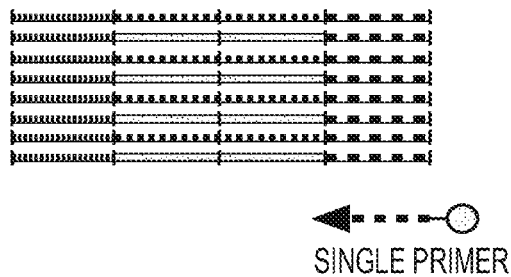
Figure 66C:
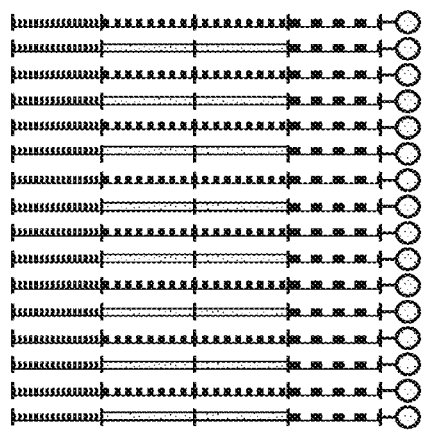

FIGS. 66A, 66B, and 66C depict yet other embodiments of the procedure depicted in FIGS. 65A and 65B. The 5' arm of each Probe Set consists of an affinity tag sequence and a homolog while the 3' arm of each Probe Set consists of a homolog sequence and a priming sequence without a label attached as illustrated in FIG. 66A. After completion of the LCR, the probe product may be purified. The LCR product would then be amplified in a linear manner by the addition of a single primer that has a label attached, along with reaction components (Taq polymerase, dNTPs, and reaction buffer) as illustrated in FIG. 66B. The product of this amplification would be single-stranded (reverse strand only) with a 5' label as illustrated in FIG. 66C. Consequently it would not be necessary to treat it with Lambda exonuclease but rather it could instead be directly used as microarray target.

In another aspect, the genetic variation determined by the methods described herein indicates presence or absence of cancer, pharmacokinetic variability, drug toxicity, transplant rejection, or aneuploidy in the subject. In another aspect, the determined genetic variation indicates presence or absence of cancer. Accordingly, the methods described herein may be performed to diagnose cancer.

A significant challenge in oncology is the early detection of cancer. This is particularly true in cancers that are hard to image or biopsy (e.g., pancreatic cancer, lung cancer). Cell free tumor DNA (tumor cfDNA) in a patient's blood offers a method to non-invasively detect a tumor. These may be solid tumors, benign tumors, micro tumors, liquid tumors, metastasis or other somatic growths. Detection may be at any stage in the tumor development, though ideally early (Stage I or Stage II). Early detection allows intervention (e.g., surgery, chemotherapy, pharmaceutical treatment) that may extend life or lead to remission. Further problems in oncology include the monitoring of the efficacy of treatment, the titration of the dose of a therapeutic agent, the recurrence of a tumor either in the same organ as the primary tumor or at distal locations and the detection of metastasis. The current invention may be used for all these applications.

In some embodiments, the probe sets of the present disclosure may be configured to target known genetic variations associated with tumors. These may include mutations, SNPs, copy number variants (e.g., amplifications, deletions), copy neutral variants (e.g., inversions, translocations), and/or complex combinations of these variants. For example, the known genetic variations associated with tumors include those listed in cancer.sanger.ac.uk/cancergenome/projects/cosmic; nature.com/ng/journal/v45/n10/full/ng.2760.html#supplementary-information; and Tables 2 and 3 below: [B]GENE=p-value from corrected to FDR within peak; [K]Known frequently amplified oncogene or deleted TSG; [P]Putative cancer gene; [E]Epigenetic regulator; [M]Mitochondria-associated gene; **Immediately adjacent to peak region; [T]Adjacent to telomere or centromere of acrocentric chromosome.

TABLE 2

Exemplary genetic variations associated with tumors (Amplification of the gene)

| Peak Name | Rank | Genomic location | Peak region | GISTIC q-value | Gene count | Target(s) | Frequently mutated genes[B] |
|---|---|---|---|---|---|---|---|
| CCND1 | 1 | 11q13.3 | chr11: 69464719-69502928 | 2.05E−278 | 2 | CCND1[K] | CCND1 = 6.6e−08 |
| EGFR | 2 | 7p11.2 | chr7: 55075808-55093954 | 2.30E−240 | 1 | EGFR[K] | EGFR = 2.2e−15 |
| MYC | 3 | 8q24.21 | chr8: 128739772-128762863 | 6.50E−180 | 1 | MYC[K] | |
| TERC | 4 | 3q26.2 | chr3: 169389459-169490555 | 5.40E−117 | 2 | TERC[P] | |
| ERBB2 | 5 | 17q12 | chr17: 37848534-37877201 | 1.59E−107 | 1 | ERBB2[K] | ERBB2 = 1.3e−06 |
| CCNE1 | 6 | 19q12 | chr19: 30306758-30316875 | 4.77E−90 | 1 | CCNE1[K] | |
| MCL1 | 7 | 1q21.3 | chr1: 150496857-150678056 | 1.25E−80 | 6 | MCL1[K] | |
| MDM2 | 8 | 12q15 | chr12: 69183279-69260755 | 2.59E−62 | 1 | MDM2[K] | |
| INTS4 | 9 | 11q14.1 | chr11: 77610143-77641464 | 1.01E−54 | 1 | INTS4 | |
| WHSC1L1 | 10 | 8p11.23 | chr8: 38191804-38260814 | 3.43E−46 | 2 | WHSC1L1[E], LETM2[M] | |
| CDK4 | 11 | 12q14.1 | chr12: 58135797-58156509 | 5.14E−41 | 5 | CDK4[K] | CDK4 = 0.0048 |
| KAT6A | 12 | 8p11.21 | chr8: 41751300-41897859 | 2.97E−39 | 2 | KAT6A[P, E], IKBKB** | |
| SOX2 | 13 | 3q26.33 | chr3: 181151312-181928394 | 1.21E−38 | 2 | SOX2[K] | |
| PDGFRA | 14 | 4q12 | chr4: 54924794-55218386 | 1.08E−37 | 3 | PDGFRA[K] | |
| BDH1 | 15 | 3q29 | chr3: 197212101-197335320 | 1.21E−31 | 1 | BDH1[M] | |
| 1q44 | 16 | 1q44[T] | chr1: 242979907-249250621 | 4.48E−31 | 83 | SMYD3[E] | |
| MDM4 | 17 | 1q32.1 | chr1: 204367383-204548517 | 1.98E−29 | 3 | MDM4[K] | |
| TERT | 18 | 5p15.33 | chr5: 1287704-1300024 | 9.34E−27 | 1 | TERT[K] | |
| KDM5A | 19 | 12p13.33[T] | chr12: 1-980639 | 1.59E−25 | 11 | KDM5A[E] | |
| MYCL1 | 20 | 1p34.2 | chr1: 40317971-40417342 | 3.99E−25 | 2 | MYCL1[K] | |
| IGF1R | 21 | 15q26.3 | chr15: 98667475-100292401 | 8.62E−25 | 9 | IGF1R[K] | |
| PARP10 | 22 | 8q24.3 | chr8: 144925436-145219779 | 5.44E−20 | 15 | PARP10[P, E], CYC1[M] | |
| G6PD | 23 | Xq28 | chrX: 153760870-153767853 | 3.66E−19 | 1 | G6PD | |
| PHF12 | 24 | 17q11.2 | chr17: 27032828-27327946 | 1.75E−16 | 21 | PHF12[E], ERAL1[M] | |
| 20q13.33 | 25 | 20q13.33 | chr20: 62187847-62214354 | 2.96E−16 | 2 | | |
| PAF1 | 26 | 19q13.2 | chr19: 39699366-39945515 | 1.66E−15 | 13 | PAF1[P, E] | IL28A = 0.021, SUPT5H = 0.084 |
| BCL2L1 | 27 | 20q11.21 | chr20: 30179028-30320705 | 2.85E−15 | 4 | BCL2L1[K] | |
| TUBD1 | 28 | 17q23.1 | chr17: 57922443-57946458 | 7.19E−15 | 1 | TUBD1 | TUBD1 = 0.009 |
| [ZNF703] | 29 | 8p11.23 | chr8: 37492669-37527108 | 2.44E−14 | 0 | | |
| 1q23.3 | 30 | 1q23.3 | chr1: 160949115-161115281 | 7.73E−13 | 9 | | |
| 8q22.2 | 31 | 8q22.2 | chr8: 101324079-101652657 | 4.22E−11 | 3 | | SNX31 = 0.015 |
| BRD4 | 32 | 19p13.12 | chr19: 15310246-15428182 | 5.04E−10 | 3 | NOTCH3[P], BRD4[P, E] | |
| KRAS | 33 | 12p12.1 | chr12: 24880663-25722878 | 9.47E−10 | 7 | KRAS[K] | KRAS = 1.5e−14 |
| NKX2-1 | 34 | 14q13.2 | chr14: 35587755-37523513 | 1.33E−09 | 14 | NKX2-1[K] | NFKBIA = 0.0098, RALGAPA1 = 0.027 |
| NFE2L2 | 35 | 2q31.2 | chr2: 178072322-178171101 | 5.48E−09 | 5 | NFE2L2 | NFE2L2 = 3.9e−14 |
| ZNF217 | 36 | 20q13.2 | chr20: 52148496-52442225 | 5.83E−08 | 1 | ZNF217[K] | ZNF217 = 0.0082 |
| 13q34 | 37 | 13q34[T] | chr13: 108818892-115169878 | 6.28E−08 | 45 | ING1[E] | ING1 = 0.00026 |
| KAT6B | 38 | 10q22.2 | chr10: 76497097-77194071 | 1.41E−07 | 9 | KAT6B[E], VDAC2[M] | |
| NSD1 | 39 | 5q35.3 | chr5: 176337344-177040112 | 1.75E−06 | 22 | NSD1[E], PRELID1[M] | NSD1 = 4.9e−10 |
| FGFR3 | 40 | 4p16.3 | chr4: 1778797-1817427 | 2.14E−06 | 2 | FGFR3[P], LETM1[M] | FGFR3 = 0.00018 |
| 9p13.3 | 41 | 9p13.3 | chr9: 35652385-35739486 | 2.55E−06 | 8 | | |
| COX18 | 42 | 4q13.3 | chr4: 73530210-74658151 | 2.68E−06 | 7 | COX18[M] | |
| 7q36.3 | 43 | 7q36.3[T] | chr7: 153768037-159138663 | 3.19E−06 | 30 | PTPRN2[L], DPP6[L] | |
| 18q11.2 | 44 | 18q11.2 | chr18: 23857484-24119078 | 3.83E−06 | 2 | | |
| SOX17 | 45 | 8q11.23 | chr8: 55069781-55384342 | 2.02E−05 | 1 | SOX17 | SOX17 = 0.00092 |
| 11q22.2 | 46 | 11q22.2 | chr11: 102295593-102512085 | 0.00015337 | 3 | | |
| CBX8 | 47 | 17q25.3 | chr17: 77770110-77795534 | 0.00023029 | 1 | CBX8[E] | |
| AKT1 | 48 | 14q32.33 | chr14: 105182581-105333748 | 0.00028451 | 7 | AKT1[K] | AKT1 = 1.1e−14 |
| CDK6 | 49 | 7q21.2 | chr7: 92196092-92530348 | 0.00069831 | 3 | CDK6[K] | |
| 6p21.1 | 50 | 6p21.1 | chr6: 41519930-44297771 | 0.0010459 | 70 | | |
| EHF | 51 | 11p13 | chr11: 34574296-34857324 | 0.0011002 | 1 | EHF | |
| 6q21 | 52 | 6q21 | chr6: 107098934-107359899 | 0.0011806 | 4 | | |

TABLE 2-continued

Exemplary genetic variations associated with tumors (Amplification of the gene)

| Peak Name | Rank | Genomic location | Peak region | GISTIC q-value | Gene count | Target(s) | Frequently mutated genes[B] |
|---|---|---|---|---|---|---|---|
| 19q13.42 | 53 | 19q13.42[T] | chr19: 55524376-59128983 | 0.0013319 | 138 | TRIM28[E], SUV420H2[E] | ZNF471 = 5.4e−05 |
| 17q21.33 | 54 | 17q21.33 | chr17: 47346425-47509605 | 0.0025775 | 2 | | |
| BPTF | 55 | 17q24.2 | chr17: 65678858-66288612 | 0.0028375 | 11 | BPTF[E] | |
| E2F3 | 56 | 6p22.3 | chr6: 19610794-22191922 | 0.0033658 | 7 | E2F3[K] | |
| 19p13.2 | 57 | 19p13.2 | chr19: 10260457-10467501 | 0.0038041 | 12 | MRPL4[M] | DNMT1 = 0.099 |
| 17q25.1 | 58 | 17q25.1 | chr17: 73568926-73594884 | 0.012337 | 2 | | |
| KDM2A | 59 | 11q13.2 | chr11: 67025375-67059633 | 0.012445 | 3 | KDM2A[E] | |
| 8q21.13 | 60 | 8q21.13 | chr8: 80432552-81861219 | 0.020548 | 6 | MRPS28[M] | |
| 2p15 | 61 | 2p15 | chr2: 59143237-63355557 | 0.021056 | 25 | | XPO1 = 1.1e−05 |
| 14q11.2 | 62 | 14q11.2[T] | chr14: 1-21645085 | 0.027803 | 57 | | |
| NEDD9 | 63 | 6p24.2 | chr6: 11180426-11620845 | 0.082606 | 2 | NEDD9[K] | |
| 5p13.1 | 64 | 5p13.1 | chr5: 35459650-50133375 | 0.094657 | 61 | | SLC1A3 = 0.0021, IL7R = 0.0021 |
| LINC00536 | 65 | 8q23.3 | chr8: 116891361-117360815 | 0.095294 | 1 | LINC00536 | |
| 10p15.1 | 66 | 10p15.1 | chr10: 4190059-6130004 | 0.10391 | 21 | | |
| 22q11.21 | 67 | 22q11.21 | chr22: 18613558-23816427 | 0.13213 | 105 | | |
| PHF3 | 68 | 6q12 | chr6: 63883156-64483307 | 0.17851 | 4 | PHF3[E], EYS[L] | PHF3 = 0.051 |
| PAX8 | 69 | 2q13 | chr2: 113990138-114122826 | 0.19717 | 2 | PAX8[K] | |
| 9p24.2 | 70 | 9p24.2[T] | chr9: 1-7379570 | 0.20405 | 45 | SMARCA2[E], KDM4C[E], UHRF2[E], KIAA2026[E] | |

TABLE 3

Exemplary genetic variations associated with tumors (Deletion of the gene)

| Peak Name | Rank | Genomic location | Peak region | GISTIC q-value | Gene count | Target(s) | Frequently mutated genes[B] |
|---|---|---|---|---|---|---|---|
| CDKN2A | 1 | 9p21.3 | chr9: 21865498-22448737 | 0 | 4 | CDKN2A[K] | CDKN2A = 4.4e−15 |
| STK11 | 2 | 19p13.3 | chr19: 1103715-1272039 | 1.46E−238 | 7 | STK11[K] | STK11 = 2.5e−13 |
| PDE4D | 3 | 5q11.2 | chr5: 58260298-59787985 | 2.02E−143 | 3 | PDE4D[L] | |
| PARK2 | 4 | 6q26 | chr6: 161693099-163153207 | 5.85E−137 | 1 | PARK2[L, K] | |
| LRP1B | 5 | 2q22.1 | chr2: 139655617-143637838 | 4.25E−107 | 1 | LRP1B[L] | |
| CSMD1 | 6 | 8p23.2 | chr8: 2079140-6262191 | 2.39E−96 | 1 | CSMD1[L] | |
| 1p36.23 | 7 | 1p36.23 | chr1: 7829287-8925111 | 1.23E−93 | 8 | | |
| ARID1A | 8 | 1p36.11 | chr1: 26900639-27155421 | 5.74E−87 | 2 | ARID1A[K] | ARID1A = 1.5e−14 |
| PTEN | 9 | 10q23.31 | chr10: 89615138-90034038 | 1.12E−79 | 2 | PTEN[K] | PTEN = 2.2e−15 |
| WWOX | 10 | 16q23.1 | chr16: 78109058-79627770 | 8.14E−76 | 1 | WWOX[L] | WWOX = 0.092 |
| RB1 | 11 | 13q14.2 | chr13: 48833767-49064807 | 3.88E−75 | 2 | RB1[K] | RB1 = 1.7e−13 |
| FAM190A | 12 | 4q22.1 | chr4: 90844993-93240505 | 9.26E−75 | 1 | FAM190A[L] | |
| 2q37.3 | 13 | 2q37.3[T] | chr2: 241544527-243199373 | 1.77E−70 | 29 | ING5[E] | |
| 22q13.32 | 14 | 22q13.32[T] | chr22: 48026910-51304566 | 8.20E−65 | 45 | BRD1[E], HDAC10[E] | |
| 11p15.5 | 15 | 11p15.5[T] | chr11: 1-709860 | 1.02E−62 | 34 | SIRT3[E], PHRF1[E] | HRAS = 7.8e−13 |
| LINC00290 | 16 | 4q34.3 | chr4: 178911874-183060693 | 1.21E−55 | 1 | LINC00290 | |
| FHIT | 17 | 3p14.2 | chr3: 59034763-61547330 | 3.01E−55 | 1 | FHIT[L] | |
| RBFOX1 | 18 | 16p13.3 | chr16: 5144019-7771745 | 1.00E−45 | 1 | RBFOX1[L] | |
| PTPRD | 19 | 9p24.1 | chr9: 8310705-12693402 | 3.24E−38 | 1 | PTPRD[L] | |
| 18q23 | 20 | 18q23[T] | chr18: 74979706-78077248 | 1.69E−37 | 12 | | |
| FAT1 | 21 | 4q35.2 | chr4: 187475875-188227950 | 6.81E−36 | 1 | FAT1[K] | FAT1 = 2.4e−15 |
| MPHOSPH8 | 22 | 13q12.11[T] | chr13: 1-20535070 | 2.57E−31 | 10 | MPHOSPH8[E] | |
| 15q15.1 | 23 | 15q15.1 | chr15: 41795901-42068054 | 2.71E−29 | 4 | | MGA = 0.0083, RPAP1 = 0.035 |
| 11q25 | 24 | 11q25[T] | chr11: 133400280-135006516 | 4.93E−26 | 14 | | |
| 1p13.2 | 25 | 1p13.2 | chr1: 110048528-117687124 | 1.69E−25 | 100 | TRIM33[E] | NRAS = 1.8e−13, CD58 = 0.079 |
| NF1 | 26 | 17q11.2 | chr17: 29326736-29722618 | 6.59E−23 | 5 | NF1[K] | NF1 = 3.3e−13 |
| MACROD2 | 27 | 20p12.1 | chr20: 14302876-16036135 | 9.00E−19 | 3 | MACROD2[L] | |
| 7p22.3 | 28 | 7p22.3[T] | chr7: 1-1496620 | 1.04E−17 | 18 | | |
| 6p25.3 | 29 | 6p25.3 | chr6: 1608837-2252425 | 3.01E−17 | 2 | | |
| 21q11.2 | 30 | 21q11.2[T] | chr21: 1-15482604 | 2.34E−14 | 14 | | |
| 9p13.1 | 31 | 9p13.1 | chr9: 38619152-71152237 | 9.75E−14 | 48 | | |
| ZNF132 | 32 | 19q13.43[T] | chr19: 58661582-59128983 | 3.77E−13 | 24 | TRIM28[E], ZNF132 | |
| 5q15 | 33 | 5q15 | chr5: 73236070-114508587 | 8.15E−13 | 156 | APC[K], CHD1[E] | APC = 2.6e−13, RASA1 = 0.0029 |
| MLL3 | 34 | 7q36.1 | chr7: 151817415-152136074 | 9.26E−13 | 1 | MLL3[K, E] | MLL3 = 1.1e−05 |

TABLE 3-continued

Exemplary genetic variations associated with tumors (Deletion of the gene)

| Peak Name | Rank | Genomic location | Peak region | GISTIC q-value | Gene count | Target(s) | Frequently mutated genes[B] |
|---|---|---|---|---|---|---|---|
| 19q13.32 | 35 | 19q13.32 | chr19: 47332686-47763284 | 2.38E−12 | 10 | | |
| 15q12 | 36 | 15q12[T] | chr15: 1-32929863 | 3.40E−11 | 155 | | OTUD7A = 0.027 |
| 12q24.33 | 37 | 12q24.33[T] | chr12: 131692956-133851895 | 1.24E−10 | 27 | | POLE = 3.9e−05, PGAM5 = 0.038 |
| 10q26.3 | 38 | 10q26.3[T] | chr10: 135190263-135534747 | 2.09E−10 | 14 | | |
| 6q21 | 39 | 6q21 | chr6: 86319089-117076132 | 4.56E−10 | 141 | PRDM1[E], HDAC2[E], PRDM13[E] | PRDM1 = 0.00054 |
| PPP2R2A | 40 | 8p21.2 | chr8: 25896447-26250295 | 1.78E−09 | 1 | PPP2R2A | |
| IKZF2 | 41 | 2q34 | chr2: 211542637-214143899 | 3.24E−09 | 4 | IKZF2[K], ERBB4[L] | ERBB4 = 0.00058 |
| CNTN4 | 42 | 3p26.3[T] | chr3: 1-3100786 | 6.44E−09 | 3 | CNTN4[L] | |
| 3p12.2 | 43 | 3p12.2 | chr3: 75363575-86988125 | 1.22E−07 | 12 | ROBO1[L], CADM2[L] | |
| RAD51B | 44 | 14q24.1 | chr14: 68275375-69288431 | 1.38E−07 | 2 | RAD51B[L] | ZFP36L1 = 0.0016 |
| 11q23.1 | 45 | 11q23.1 | chr11: 105849158-117024891 | 5.31E−07 | 84 | ATM[K] | ATM = 1.4e−06, POU2AF1 = 0.082 |
| IMMP2L | 46 | 7q31.1 | chr7: 109599468-111366370 | 5.74E−07 | 2 | IMMP2L[L] | |
| NEGR1 | 47 | 1p31.1 | chr1: 71699756-74522473 | 7.25E−07 | 2 | NEGR1[L] | |
| BRCA1 | 48 | 17q21.31 | chr17: 41178765-41336147 | 7.25E−07 | 2 | BRCA1[K] | BRCA1 = 3.5e−08 |
| 9q34.3 | 49 | 9q34.3 | chr9: 135441810-139646221 | 8.73E−06 | 94 | NOTCH1[K], BRD3[E], GTF3C4[E] | NOTCH1 = 1e−08, RXRA = 2.1e−05, COL5A1 = 0.0022, TSC1 = 0.012 |
| ANKS1B | 50 | 12q23.1 | chr12: 99124001-100431272 | 8.73E−06 | 2 | ANKS1B[L] | |
| DMD | 51 | Xp21.2 | chrX: 30865118-34644819 | 5.15E−05 | 4 | DMD[L] | |
| ZMYND11 | 52 | 10p15.3[T] | chr10: 1-857150 | 7.12E−05 | 4 | ZMYND11[E] | |
| PRKG1 | 53 | 10q11.23 | chr10: 52644085-54061437 | 9.79E−05 | 3 | PRKG1[L] | |
| FOXK2 | 54 | 17q25.3 | chr17: 80443432-80574531 | 0.00019271 | 1 | FOXK2 | |
| AGBL4 | 55 | 1p33 | chr1: 48935280-50514967 | 0.000219 | 2 | AGBL4[L] | |
| CDKN1B | 56 | 12p13.1 | chr12: 12710990-12966966 | 0.00035777 | 5 | CDKN1B[K] | CDKN1B = 2.2e−06 |
| 14q32.33 | 57 | 14q32.33[T] | chr14: 94381429-107349540 | 0.00074358 | 227 | SETD3[E], TDRD9[E] | AKT1 = 2.1e−13, TRAF3 = 9.7e−05 |
| 14q11.2 | 58 | 14q11.2[T] | chr14: 1-30047530 | 0.0010181 | 162 | PRMT5[E], CHD8[E] | CHD8 = 0.034 |
| 2p25.3 | 59 | 2p25.3[T] | chr2: 1-20072169 | 0.0011137 | 86 | MYCN[K] | MYCN = 0.068 |
| 5q35.3 | 60 | 5q35.3[T] | chr5: 153840473-180915260 | 0.0028515 | 212 | NSD1[E], ODZ2[L] | NPM1 = 3.5e−13, NSD1 = 1.9e−09, ZNF454 = 0.0019, UBLCP1 = 0.03, GABRB2 = 0.07 |
| PTTG1IP | 61 | 21q22.3 | chr21: 46230687-46306160 | 0.012227 | 1 | PTTG1IP | |
| 22q11.1 | 62 | 22q11.1[T] | chr22: 1-17960585 | 0.020332 | 15 | | |
| SMAD4 | 63 | 18q21.2 | chr18: 48472083-48920689 | 0.036866 | 3 | SMAD4[K] | SMAD4 = 6.6e−15 |
| 17p13.3 | 64 | 17p13.3[T] | chr17: 1-1180022 | 0.040814 | 16 | | |
| 4p16.3 | 65 | 4p16.3[T] | chr4: 1-1243876 | 0.056345 | 27 | | |
| 9p21.2 | 66 | 9p21.2 | chr9: 27572512-28982153 | 0.091742 | 3 | | |
| 10q25.1 | 67 | 10q25.1 | chr10: 99340084-113910615 | 0.11879 | 137 | HPSE2[L], SMNDC1[E] | SMC3 = 0.00031, GSTO2 = 0.086 |
| SMYD3 | 68 | 1q44 | chr1: 245282267-247110824 | 0.15417 | 8 | SMYD3[E] | |
| 8p11.21 | 69 | 8p11.21 | chr8: 42883855-47753079 | 0.17382 | 4 | | |
| Xp22.33 | 70 | Xp22.33[T] | chrX: 1-11137490 | 0.21462 | 52 | | MXRA5 = 0.031 |

Figure 67A:
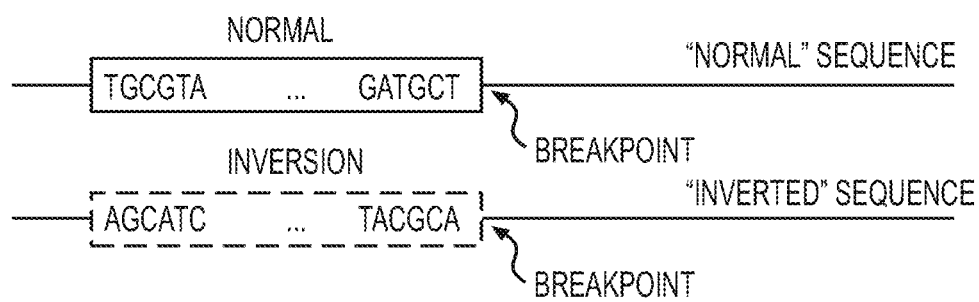
FIGS. 67A, 67B, and 67C depict exemplary probe sets used in methods described herein.
Figure 67B:
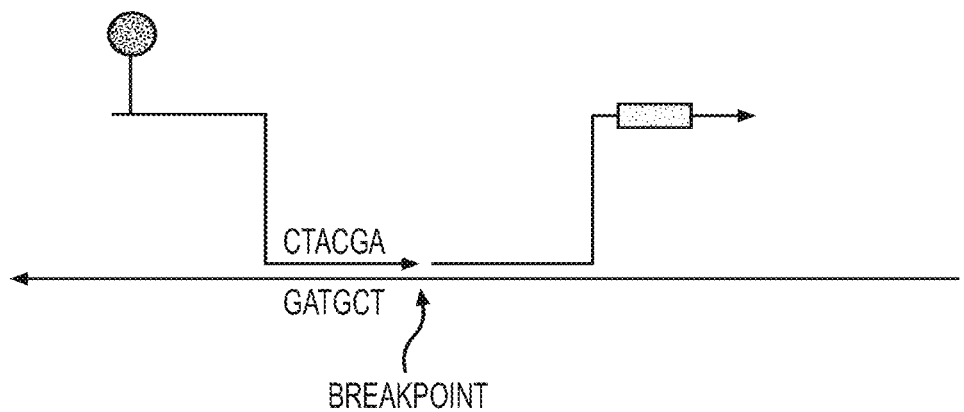
Figure 67C:
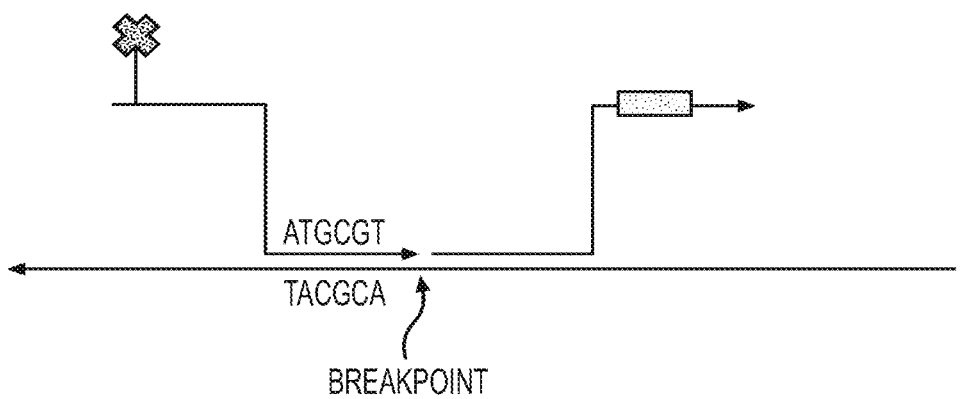

In the method of diagnosing cancer according to some embodiments, inversions that occur at known locations (FIG. 67A) may easily be targeted by designing probes that at least partially overlap the breakpoint in one probe arm. A first probe that binds the "normal" sequence targets non-inverted genomic material (FIG. 67B) and carries a first label type. A second probe that binds the "inverted" target carries a second label type (FIG. 67C). A common right probe arm binds native sequence that is not susceptible to inversion, immediately adjacent the first two probes. This right probe arm further carries a common pull-down tag that localizes the probe products to the same region of an imaging substrate. In this way, the probe pairs may hybridize to the genomic targets, ligate, and be imaged to yield relative counts of the two underlying species.

Figure 68A:
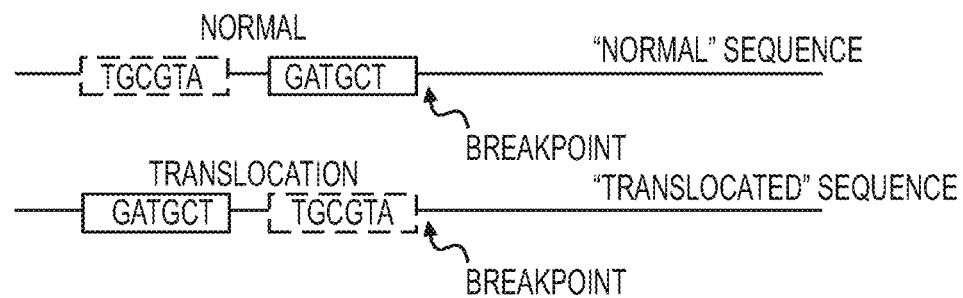
FIGS. 68A, 68B, and 68C depict exemplary probe sets used in methods described herein when translocations that have known breakpoints are assayed.
Figure 68B:
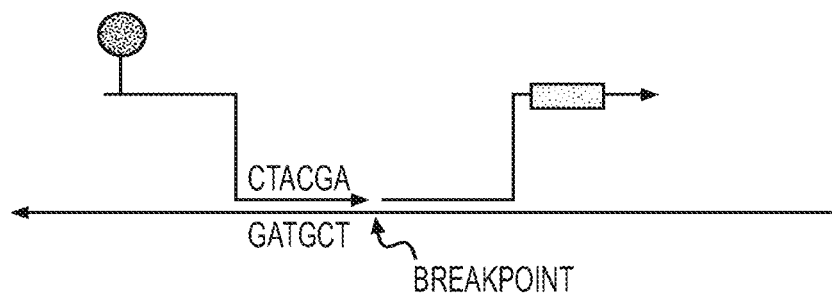
Figure 68C:
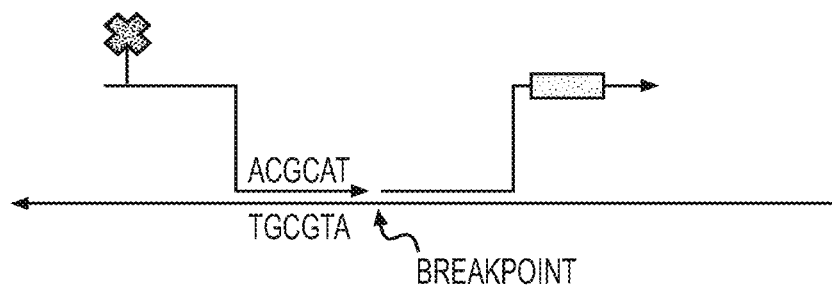

Similarly, translocations that have known breakpoints may also be assayed. FIG. 68A shows two genetic elements that are either in their native order or translocated. Probe arms that at least partially overlap these translocation breakpoints allow differentiation between normal and transposed orders of genetic material. As shown in FIGS. 68B and 68C, by choosing unique labels on the two left arms, the resulting ligated probe products may be distinguished and counted during imaging.

These methods for detecting copy neutral changes (e.g., inversions, translocation) may also be used to detect germ-line variants in cancer or in other disease or conditions.

Figure 69A:
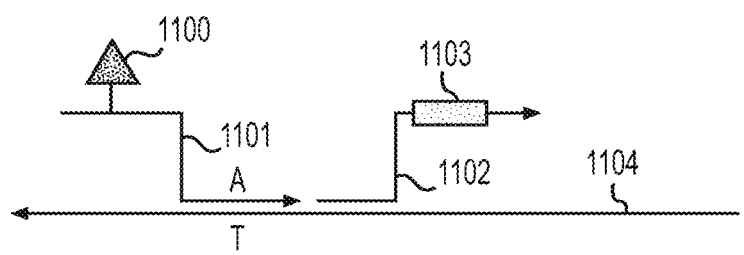
FIGS. 69A and 69B depict exemplary probe sets used in methods described herein when mutations at SNPs are targeted.
Figure 69B:
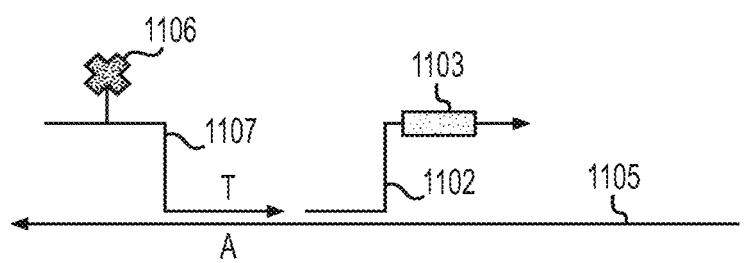

Mutations or SNPs are also implicated in numerous cancers, and are targeted in a similar manner to those that are interrogated in determining fetal fraction in the prenatal diagnostics application. In some embodiments shown in FIGS. 69A and 69B, left probe arms are designed to take advantage of an energetic imbalance caused by one or more mismatched SNPs. This causes one probe arm (1101, carrying one label) to bind more favorably than a second probe arm (1107, carrying a second type of label). Both designs ligate to the same right probe arm (1102) that carries the universal pull-down tag.

A given patient's blood may be probed by one method, or a hybrid of more than one method. Further, in some cases, customizing specific probes for a patient may be valuable. This would involve characterizing tumor features (SNPs, translocations, inversions, etc.) in a sample from the primary tumor (e.g., a biopsy) and creating one or more custom probe sets that is optimized to detect those patient-specific genetic variations in the patient's blood, providing a low-cost, non-invasive method for monitoring. This could have significant value in the case of relapse, where detecting low-level recurrence of a tumor type (identical or related to the original tumor) as early as possible is ideal.

For common disease progression pathways, additional panels may be designed to anticipate and monitor for disease advancement. For example, if mutations tend to accumulate in a given order, probes may be designed to monitor current status and progression "checkpoints," and guide therapy options.

Early detection of cancer: For example, the ALK translocation has been associated with lung cancer. A probe designed to interrogate the ALK translocation may be used to detect tumors of this type via a blood sample. This would be highly advantageous, as the standard method for detecting lung tumors is via a chest x-ray an expensive procedure that may be deleterious to the patient's health and so is not standardly performed.

Detection of recurrence of the primary tumor type: For example, a HER2+ breast tumor is removed by surgery and the patient is in remission. A probe targeting the HER2 gene may be used to monitor for amplifications of the HER2 gene at one or more time points. If these are detected, the patient may have a second HER2+ tumor either at the primary site or elsewhere.

Detection of non-primary tumor types: For example, a HER2+ breast tumor is removed by surgery and the patient is in remission. A probe targeting the EGFR gene may be used to monitor for EGFR+ tumors. If these are detected, the patient may have a second EGFR+ tumor either at the primary site or elsewhere.

Detection of metastasis: For example, the patient has a HER2+ breast tumor. A probe designed to interrogate the ALK translocation may be used to detect tumors of this type via a blood sample. This tumor may not be in the breast and is more likely to be in the lung. If these are detected, the patient may have a metastatic tumor distal to the primary organ.

Determining tumor heterogeneity: Many tumors have multiple clonal populations characterized by different genetic variants. For example, a breast tumor may have one population of cells that are HER2+ and another population of cells that are EGFR+. Using probes designed to target both these variants would allow the identification of this underlying genetic heterogeneity.

Measurement of tumor load: In all the above examples, the quantity of tumor cfDNA may be measured and may be used to determine the size, growth rate, aggressiveness, stage, prognosis, diagnosis and other attributes of the tumor and the patient. Ideally, measurements are made at more than one time point to show changes in the quantity of tumor cfDNA.

Monitoring treatment: For example, a HER2+ breast tumor is treated with Herceptin. A probe targeting the HER2 gene may be used to monitor for quantity of tumor cfDNA, which may be a proxy for the size of the tumor. This may be used to determine if the tumor is changing in size and treatment may be modified to optimize the patient's outcome. This may include changing the dose, stopping treatment, changing to another therapy, combing multiple therapies.

Screening for tumor DNA: There is currently no universal screen for cancer. The present invention offers a way to detect tumors at some or all locations in the body. For example, a panel of probes is developed at a spacing of 100 kb across the genome. This panel may be used as a way to detect genetic variation across the genome. In one example, the panel detects copy number changes of a certain size across the genome. Such copy number changes are associated with tumor cells and so the test detects the presence of tumor cells. Different tumor types may produce different quantities of tumor cfDNA or may have variation in different parts of the genome. As such, the test may be able to identify which organ is affected. Further the quantity of tumor cfDNA measured may indicate the stage or size of the tumor or the location of the tumor. In this way, the test is a whole-genome screen for many or all tumor types.

For all the above tests, in order to mitigate false positives, a threshold may be used to determine the presence or certainty of a tumor. Further, the test may be repeat on multiple sample or at multiple time points to increase the certainty of the results. The results may also be combined with other information or symptoms to provide more information or more certain information on the tumor.

Exemplary probe sets and primers that may be used in the method described herein to measure copy number of nucleic acid regions of interest are listed in Table 4 below. Each of the exemplary probe sets in Table 4 comprises two probes. The first (tagging) probe has a structure including a forward priming site, tag, and homology 1. The second (labeling) probe has structure, including homology 2 and reverse primer site, which is used in labeling. The component sequences of the probes (tag, homology sequence etc.) are also shown.

TABLE 4

| Exemplary probes and primers. | | | | | | | |
|---|---|---|---|---|---|---|---|
| Chromosome ID | Tagging Probe (Forward LocusPrimer + Tag + 5pHom) | Labeling Probe (3'-Hop + Reverse Primer) | Forward primer | Tag | Hom 5p | Hom 3p | Reverse primer |
| 18 | 18-1 GCCCTCATCTTC TTCCCTGCGTTC TCACCACCCTCA CCAAGGAAGAA GTGAGGGCTTCTC (SEQ ID NO: 1) | CGTGCTAATAGTC TCAGGGCTTCCTC CACCGAACGTGT CT (SEQ ID NO: 17) | GCCCTCAT CTTCTTCC CTGC (SEQ ID NO: 33) | GTTCTCA CCACCCT CACCAA (SEQ ID NO: 34) | GGAAGAA GTGAGGG CTTCTC (SEQ ID NO: 35) | CGTGCTA ATAGTCT CAGGGC (SEQ ID NO: 51) | TTCCTCCA CCGAACGT GTCT (SEQ ID NO: 67) |

TABLE 4 -continued

Exemplary probes and primers.

| Chromosome | Locus ID | Tagging Probe (Forward Primer + Tag + 5pHom) | Labeling Probe (3'-Hop + Reverse Primer) | Forward primer | Tag | Hom 5p | Hom 3p | Reverse primer |
|---|---|---|---|---|---|---|---|---|
| 18 | 18-2 | GCCCTCATCTTC TTCCCTGCGTTC TCACCACCCTCA CCAAAAATCAAG GTGACCAGCTCC (SEQ ID NO: 2) | CGACGCTTCATTG CTTCATTTTCCTC CACCGAACGTGT CT (SEQ ID NO: 18) | GCCCTCAT CTTCTTCC CTGC (SEQ ID NO: 33) | GTTCTCA CCACCCT CACCAA (SEQ ID NO: 34) | AAATCAA GGTGACC AGCTCC (SEQ ID NO: 36) | CGACGC TTCATTG CTTCATT (SEQ ID NO: 52) | TTCCTCCA CCGAACGT GTCT (SEQ ID NO: 67) |
| 18 | 18-3 | GCCCTCATCTTC TTCCCTGCGTTC TCACCACCCTCA CCAATCATCTGC CAAGACAGAAG TTC (SEQ ID NO: 3) | CTTGCGCCAAAC AATTGTCTTCCT CCACCGAACGTG TCT (SEQ ID NO: 19) | GCCCTCAT CTTCTTCC CTGC (SEQ ID NO: 33) | GTTCTCA CCACCCT CACCAA (SEQ ID NO: 34) | TCATCTG CCAAGAC AGAAGTT C (SEQ ID NO: 37) | CTTGCGC CAAACA ATTGTCC (SEQ ID NO: 53) | TTCCTCCA CCGAACGT GTCT (SEQ ID NO: 67) |
| 18 | 18-4 | GCCCTCATCTTC TTCCCTGCGTTC TCACCACCCTCA CCAAGCAGGAG AGTCAAAGGTCTG (SEQ ID NO: 4) | GCTGCAGAGTTTG CATTCATTTCCTT CACCGAACGTGT CT (SEQ ID NO: 20) | GCCCTCAT CTTCTTCC CTGC (SEQ ID NO: 33) | GTTCTCA CCACCCT CACCAA (SEQ ID NO: 34) | GCAGGAG AGTCAAA GGTCTG (SEQ ID NO: 38) | GCTGCA GAGTTTG CATTCAT (SEQ ID NO: 54) | TTCCTCCA CCGAACGT GTCT (SEQ ID NO: 67) |
| 18 | 18-5 | GCCCTCATCTTC TTCCCTGCGTTC TCACCACCCTCA CCAAGTTGCCAT GGAGATTGTTGC (SEQ ID NO: 5) | CATACACACAGA CCGAGAGTCTTCC TCCACCGAACGT GTCT (SEQ ID NO: 21) | GCCCTCAT CTTCTTCC CTGC (SEQ ID NO: 33) | GTTCTCA CCACCCT CACCAA (SEQ ID NO: 34) | GTTGCCA TGGAGAT TGTTGC (SEQ ID NO: 39) | CATACA CACAGA CCGAGA GTC (SEQ ID NO: 55) | TTCCTCCA CCGAACGT GTCT (SEQ ID NO: 67) |
| 18 | 18-6 | GCCCTCATCTTC TTCCCTGCGTTC TCACCACCCTCA CCAACAGCTCAG TGATGTCATTGC (SEQ ID NO: 6) | GGATGTCAGCCA GCATAAGTTTCCT CCACCGAACGTG TCT (SEQ ID NO: 22) | GCCCTCAT CTTCTTCC CTGC (SEQ ID NO: 33) | GTTCTCA CCACCCT CACCAA (SEQ ID NO: 34) | CAGCTCA GTGATGT CATTGC (SEQ ID NO: 40) | GGATGT CAGCCA GCATAA GT (SEQ ID NO: 56) | TTCCTCCA CCGAACGT GTCT (SEQ ID NO: 67) |
| 18 | 18-7 | GCCCTCATCTTC TTCCCTGCGTTC TCACCACCCTCA CCAACCTTGACC TCTGCTAATGTGG (SEQ ID NO: 7) | GCAAGTGCCAAA CAGTTCTCTTCCT CCACCGAACGTG TCT (SEQ ID NO: 23) | GCCCTCAT CTTCTTCC CTGC (SEQ ID NO: 33) | GTTCTCA CCACCCT CACCAA (SEQ ID NO: 34) | CCTTGAC CTCTGCT AATGTGG (SEQ ID NO: 41) | GCAAGT GCCAAA CAGTTCT C (SEQ ID NO: 57) | TTCCTCCA CCGAACGT GTCT (SEQ ID NO: 67) |
| 18 | 18-8 | GCCCTCATCTTC TTCCCTGCGTTC TCACCACCCTCA CCAACACCTGTC CAACAGCTACAG (SEQ ID NO: 8) | GATTCCAGCACA CTTGAGTCTTTCC TCCACCGAACGT GTCT (SEQ ID NO: 24) | GCCCTCAT CTTCTTCC CTGC (SEQ ID NO: 33) | GTTCTCA CCACCCT CACCAA (SEQ ID NO: 34) | CACCTGT CCAACAG CTACAG (SEQ ID NO: 42) | GATTCCA GCACAC TTGAGTC T (SEQ ID NO: 58) | TTCCTCCA CCGAACGT GTCT (SEQ ID NO: 67) |
| X | X-1 | GCCCTCATCTTC TTCCCTGCGTTC TCACCACCCTCA CCAAAGAATGTA TCTTCAGGCCTGC (SEQ ID NO: 9) | CCGTTGCAGGTTT AAATGGCGCCCT ATTGCAAGCCCTC TT (SEQ ID NO: 25) | GCCCTCAT CTTCTTCC CTGC (SEQ ID NO: 33) | GTTCTCA CCACCCT CACCAA (SEQ ID NO: 34) | AGAATGT ATCTTCA GGCCTGC (SEQ ID NO: 43) | CCGTTGC AGGTTTA AATGGC (SEQ ID NO: 59) | GCCCTATT GCAAGCCC TCTT (SEQ ID NO: 68) |
| X | X-2 | GCCCTCATCTTC TTCCCTGCGTTC TCACCACCCTCA CCAAAAGTAATC ACTCTGGGTGGC (SEQ ID NO: 10) | CAAGAGTGCTTTA TGGGCCTGCCCTA TTGCAAGCCCTCT T (SEQ ID NO: 26) | GCCCTCAT CTTCTTCC CTGC (SEQ ID NO: 33) | GTTCTCA CCACCCT CACCAA (SEQ ID NO: 34) | AAGTAAT CACTCTG GGTGGC (SEQ ID NO: 44) | CAAGAG TGCTTTA TGGGCCT (SEQ ID NO: 60) | GCCCTATT GCAAGCCC TCTT (SEQ ID NO: 68) |
| X | X-3 | GCCCTCATCTTC TTCCCTGCGTTC TCACCACCCTCA CCAAAGCTCACA GACAACCTTGTG (SEQ ID NO: 11) | GCACTCAAGGAG ATCAGACTGGCC CTATTGCAAGCCC TCTT (SEQ ID NO: 27) | GCCCTCAT CTTCTTCC CTGC (SEQ ID NO: 33) | GTTCTCA CCACCCT CACCAA (SEQ ID NO: 34) | AGCTCAC AGACAAC CTTGTG (SEQ ID NO: 45) | GCACTC AAGGAG ATCAGA CTG (SEQ ID NO: 61) | GCCCTATT GCAAGCCC TCTT (SEQ ID NO: 68) |

TABLE 4 -continued

Exemplary probes and primers.

| Chromosome | Locus ID | Tagging Probe (Forward Primer + Tag + 5pHom) | Labeling Probe (3'-Hop + Reverse Primer) | Forward primer | Tag | Hom 5p | Hom 3p | Reverse primer |
|---|---|---|---|---|---|---|---|---|
| X | X-4 | GCCCTCATCTTC TTCCCTGCGTTC TCACCACCCTCA CCAAGCAATAGA CACCTACAGGCG (SEQ ID NO: 12) | GGCTATCGAACT ACAACCACAGCC CTATTGCAAGCCC TCTT (SEQ ID NO: 28) | GCCCTCAT CTTCTTCC CTGC (SEQ ID NO: 33) | GTTCTCA CCACCCT CACCAA (SEQ ID NO: 34) | GCAATAG ACACCTA CAGGCG (SEQ ID NO: 46) | GGCTATC GAACTA CAACCA CA (SEQ ID NO: 62) | GCCCTATT GCAAGCCC TCTT (SEQ ID NO: 68) |
| X | X-5 | GCCCTCATCTTC TTCCCTGCGTTC TCACCACCCTCA CCAAGCACATTA TCAAAGGCCACG (SEQ ID NO: 13) | GTAGCTGTCTGTG GTGTGATCGCCCT ATTGCAAGCCCTC TT (SEQ ID NO: 29) | GCCCTCAT CTTCTTCC CTGC (SEQ ID NO: 33) | GTTCTCA CCACCCT CACCAA (SEQ ID NO: 34) | GCACATT ATCAAAG GCCACG (SEQ ID NO: 47) | GTAGCT GTCTGTG GTGTGAT C (SEQ ID NO: 63) | GCCCTATT GCAAGCCC TCTT (SEQ ID NO: 68) |
| X | X-6 | GCCCTCATCTTC TTCCCTGCGTTC TCACCACCCTCA CCAACAACGACC TAAAGCATGTGC (SEQ ID NO: 14) | CAAGAAACTTCG AGCCTTAGCAGC CCTATTGCAAGCC CTCTT (SEQ ID NO: 30) | GCCCTCAT CTTCTTCC CTGC (SEQ ID NO: 33) | GTTCTCA CCACCCT CACCAA (SEQ ID NO: 34) | CAACGAC CTAAAGC ATGTGC (SEQ ID NO: 48) | CAAGAA ACTTCGA GCCTTAG CA (SEQ ID NO: 64) | GCCCTATT GCAAGCCC TCTT (SEQ ID NO: 68) |
| X | X-7 | GCCCTCATCTTC TTCCCTGCGTTC TCACCACCCTCA CCAAGACATACA TGGCTTTGGCAG (SEQ ID NO: 15) | GTGAACCAGTCC GAGTGAAAGCCC TATTGCAAGCCCT CTT (SEQ ID NO: 31) | GCCCTCAT CTTCTTCC CTGC (SEQ ID NO: 33) | GTTCTCA CCACCCT CACCAA (SEQ ID NO: 34) | GACATAC ATGGCTT TGGCAG (SEQ ID NO: 49) | GTGAAC CAGTCC GAGTGA AA (SEQ ID NO: 65) | GCCCTATT GCAAGCCC TCTT (SEQ ID NO: 68) |
| X | X-8 | GCCCTCATCTTC TTCCCTGCGTTC TCACCACCCTCA CCAAGAGATACT GCCACTTATGCACG (SEQ ID NO: 16) | GCAAATGATGTTC AGCACCACGCCC TATTGCAAGCCCT CTT (SEQ ID NO: 32) | GCCCTCAT CTTCTTCC CTGC (SEQ ID NO: 33) | GTTCTCA CCACCCT CACCAA (SEQ ID NO: 34) | GAGATAC TGCCACT TATGCAC G (SEQ ID NO: 50) | GCAAAT GATGTTC AGCACC AC (SEQ ID NO: 66) | GCCCTATT GCAAGCCC TCTT (SEQ ID NO: 68) |

Exemplary probe sets and primers that may be used in the method described herein to detect a polymorphism at a SNP site are listed in Table 5 below. Each of the exemplary probe sets in Table 5 comprises three probes, two allele specific probes (that are used for labeling) and a tagging probe. In these examples, the two allele specific probes have homology sequences that are different at one or more nucleotides. The structure of the first allelic probe includes a Forward Primer Site Allele 1 and Homology Allele 1; and the structure of the second allelic probe includes a Forward Primer Site Allele 2 and Homology Allele 2. In practice, labeled primers may be used with different labels on the two primers (so the labels are allele specific). In these examples, there also is a universal 3' probe which includes a homology region (without any SNP), the tagging sequence and a reverse primer site. The component sequences of the probes (tag, homology sequence etc.) are also shown.

TABLE 5

Exemplary probes and primers.

| Chromosome | Labeling Probe-Allele 1 (Forward Primer Hom 5p Allele 1) | Labeling Probe-Allele 2 (Forward Primer Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr21 | TTCCTCCACC GAACGTGTCT AGACCAGCAC AACTTACTcg (SEQ ID NO: 69) | GCCCTATTGCA AGCCCTCTTAG ACCAGCACAAC TTACTta (SEQ ID NO: 112) | CACTTGACAA AGTTCTCACG CGCCGAAGTT CTCCGAAGGA TGCCCTCATC TTCTTCCCTGC (SEQ ID NO: 155) | TTCCTC CACCGA ACGTGT CT (SEQ ID NO: 67) | GCCCTAT TGCAAG CCCTCTT (SEQ ID NO: 68) | AGACCA GCACAA CTTACTc g (SEQ ID NO: 198) | AGACC AGCAC AACTT ACTta (SEQ ID NO: 241) | CACTT GACA AAGTT CTCAC GC (SEQ ID NO: 284) | GCCGA AGTTC TCCGA AGGAT (SEQ ID NO: 327) | GCCCT CATCT TCTTC CCTGC (SEQ ID NO: 33) |
| chr3 | TTCCTCCACC GAACGTGTCT CCAAATgCAC CTGCCtg (SEQ ID NO: 70) | GCCCTATTGCA AGCCCCTCTTCCA AATtCACCTGCC ca (SEQ ID NO: 113) | CATTAGGGAT TAACGGCTTG GGACAGACTG ACGGAGCTTC AGCCCTCATC TTCTTCCCTGC (SEQ ID NO: 156) | TTCCTC CAC CGA ACGTGT CT (SEQ ID NO: 67) | GCCCTAT TGCAAG CCCTCTT (SEQ ID NO: 68) | CCAAAT gCACCT GCCtg (SEQ ID NO: 199) | CCAAA TtCACC TGCCca (SEQ ID NO: 242) | CATTA GGGAT TAACG GCTTG G (SEQ ID NO: 285) | GACA GACTG ACGG AGCTT CA (SEQ ID NO: 328) | GCCCT CATCT TCTTC CCTGC (SEQ ID NO: 33) |
| chr13 | TTCCTCCACC GAACGTGTCT AGTTTGGACA AAGGCaATTCg (SEQ ID NO: 71) | GCCCTATTGCA AGCCCTCTTAGT TGGACAAAGG CgATTta (SEQ ID NO: 114) | CACACGTTAA GAAGACTTTC TGCTGACTCT GCCGCACATG ATCGCCTCA TCTTCTTCCCT GC (SEQ ID NO: 157) | TTCCTC CACCGA ACGTGT CT (SEQ ID NO: 67) | GCCCTAT TGCAAG CCCTCTT (SEQ ID NO: 68) | AGTTTG GACAAA GGCaAT Tcg (SEQ ID NO: 200) | AGTTT GGACA AAGGC gATTta (SEQ ID NO: 243) | CACAC GTTAA GAAG ACTTT CTGC (SEQ ID NO: 286) | TGACT CTGCC GCACA TGATC (SEQ ID NO: 329) | GCCCT CATCT TCTTC CCTGC (SEQ ID NO: 33) |
| chr3 | TTCCTCCACC GAACGTGTCT TGAGCTTAGC CAATATCaAAGg (SEQ ID NO: 72) | GCCCTATTGCA AGCCCTCTTTGA GCTTAGCCAAT ATCAACaAGa (SEQ ID NO: 115) | CTAAGTGCCC TCCATGAGAA AGGATCCGAT AGCCCTGC AGGCCCTCAT CTTCTTCCCTG C (SEQ ID NO: 158) | TTCCTC CACCGA ACGTGT CT (SEQ ID NO: 67) | GCCCTAT TGCAAG CCCTCTT (SEQ ID NO: 68) | TGAGCT TAGCCA ATATCA AgAAGg (SEQ ID NO: 201) | TGAGC TTAGC CAATA TCAAcA AGa (SEQ ID NO: 244) | CTAAG TGCCC TCCAT GAGA AAG (SEQ ID NO: 287) | GATCC GATAG CCCTC TGCAG (SEQ ID NO: 330) | GCCCT CATCT TCTTC CCTGC (SEQ ID NO: 33) |
| chr9 | TTCCTCCACC GAACGTGTCT ACGTGAACTT TCCTTGTGTAcA | GCCCTATTGCA AGCCCTCTTAC GTGAACTTTCCT TGGTAAt (SEQ | GCACAGATTT CCCACACTCT CAACAGGCCT GCTAAACACC | TTCCTC CACCGA ACGTGT CT (SEQ | GCCCTAT TGCAAG CCCTCTT (SEQ ID | ACGTGA ACTTTC CTTGGT AcAc | ACGTG AACTT TCCTTG GTAAt | GCACA GATTT CCCAC ACTCT | CAACA GGCCT GCTAA ACACC | GCCCT CATCT TCTTC CCTGC |

TABLE 5 -continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | TTCCTCCACC GAACGTGTCT TGAAGATGTT CTAATACCTT GCcg (SEQ ID NO: 73) | (SEQ ID NO: 116) | GCCCTCATCT TCTTCCCTGC (SEQ ID NO: 159) | TTCCTC CACCGA ACGTGT CT (SEQ ID NO: 67) | GCCCTAT TGCAAG CCCTCTT (SEQ ID NO: 68) | (SEQ ID NO: 202) | (SEQ ID NO: 245) | (SEQ ID NO: 288) | (SEQ ID NO: 331) | GCCCT CATCT TCTTC CCTGC (SEQ ID NO: 33) |
| chr3 | TTCCTCCACC GAACGTGTCT TGAAGATGTT CTAATACCTT GCcg (SEQ ID NO: 74) | GCCCTATTGCA AGCCCTCTTGA AGATGTTCTAA TACCTTGCta (SEQ ID NO: 117) | CTTACAGGAG GTCTGCAAGC AGGTCAACAA CCGAGGGACT CGCCCTCATC TTCTTCCCTGC (SEQ ID NO: 160) | TTCCTC CACCGA ACGTGT CT (SEQ ID NO: 67) | GCCCTAT TGCAAG CCCTCTT (SEQ ID NO: 68) | TGAAGA TGTTCT AATACC TTGCcg (SEQ ID NO: 203) | TGAAAG ATGTTC TAAT ACCTT GCta (SEQ ID NO: 246) | CTTAC AGGA GGTCT GCCAT CA (SEQ ID NO: 289) | GGTCA ACAAC CGAG GGACT C (SEQ ID NO: 332) | GCCCT CATCT TCTTC CCTGC (SEQ ID NO: 33) |
| chr17 | TTCCTCCACC GAACGTGTCT CAGTGTGGAG ACtGAACg (SEQ ID NO: 75) | GCCCTATTGCA AGCCCTCTTCA GTGTGGAGACC GAACa (SEQ ID NO: 118) | CCACAATGAG AAGGCAGAGT TGTCATTAAT GCTGGCGGCG CCCTTCATCTTC TTCCCTGC (SEQ ID NO: 161) | TTCCTC CACCGA ACGTGT CT (SEQ ID NO: 67) | GCCCTAT TGCAAG CCCTCTT (SEQ ID NO: 68) | CAGTGT GGAGAC tGAACg (SEQ ID NO: 204) | CAGTG TGGAG ACCGA ACa (SEQ ID NO: 247) | CCACA ATGAG AAGG CAGA G (SEQ ID NO: 290) | TTGTC ATTAA TGCTG GCGGC (SEQ ID NO: 333) | GCCCT CATCT TCTTC CCTGC (SEQ ID NO: 33) |
| chr16 | TTCCTCCACC GAACGTGTCT AGGCAGGGTA GATTGTCATGAA aTg (SEQ ID NO: 76) | GCCCTATTGCA AGCCCTCTTAG GCAGGGTAATG TCATGAAgTt (SEQ ID NO: 119) | GCTGTGGCAT AGTACACTC CGGTGACGGT TTGCAACTTT GCCCTCATCT TCTTCCCTGC (SEQ ID NO: 162) | TTCCTC CACCGA ACGTGT CT (SEQ ID NO: 67) | GCCCTAT TGCAAG CCCTCTT (SEQ ID NO: 68) | AGGCAG GGTAAT GTCATG AAaTg (SEQ ID NO: 205) | AGGCA GGGTA ATGTC ATGAA gTt (SEQ ID NO: 248) | GCTGT GGCAT AGCTA CACTC (SEQ ID NO: 291) | CGGTG ACGGT TTGCA ACTTT (SEQ ID NO: 334) | GCCCT CATCT TCTTC CCTGC (SEQ ID NO: 33) |
| chr21 | TTCCTCCACC GAACGTGTCT GATTGTCTGGAG AGcGCTg (SEQ ID NO: 77) | GCCCTATTGCA AGCCCTCTTGAT GTGGGTCTGGAGggC Tc (SEQ ID NO: 120) | CAGGGTAATT TGTGGGTCTG GTCCAGCAGT TAAGGGCTC GCCCTCATCT TCTTCCCTGC (SEQ ID NO: 163) | TTCCTC CACCGA ACGTGT CT (SEQ ID NO: 67) | GCCCTAT TGCAAG CCCTCTT (SEQ ID NO: 68) | GATTGT CTGGAG cGCTg (SEQ ID NO: 206) | GATTG TCTGG AGggC Tc (SEQ ID NO: 249) | CAGG GTAAT TTGTG GTCT G (SEQ ID NO: 292) | GTCCG GCAGT TAAGG GTCTC (SEQ ID NO: 335) | GCCCT CATCT TCTTC CCTGC (SEQ ID NO: 33) |
| chr2 | TTCCTCCACC GAACGTGTCT AGGGAGCAAT AGGCcg (SEQ | GCCCTATTGCA AGCCCTCTTAG GGAGCAATAAG GGAGCAATAAG Cta (SEQ ID NO: | GGGCTATCCA GAAAGATAAG AATACTCACA AACGACTGCG | TTCCTC CACCGA ACGTGT CT (SEQ | GCCCTAT TGCAAG CCCTCTT (SEQ ID | AGGGAG CAATAG GCcg (SEQ ID | AGGGA GCAAT AGGCta (SEQ ID | GGGCT ATCCA GAAA GATAA | TACTC ACAA ACGAC TGCGC | GCCCT CATCT TCTTC CCTGC |

TABLE 5-continued

Exemplary probes and primers.

| Chromosome | Labeling Probe-Allele 1 (Forward Primer + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | ID NO: 78) | 121) | CAGCCCTCAT CTTCTTCCCTG C (SEQ ID NO: 164) | TTCCTC CACCGA ACGTGT CT (SEQ ID NO: 67) | GCCCTAT TGCAAG CCCTCTT (SEQ ID NO: 68) | NO: 207) | NO: 250) | GAA (SEQ ID NO: 293) | A (SEQ ID NO: 336) | GCCCT CATCT TCTTC CCTGC (SEQ ID NO: 33) |
| chr2 | TTCCTCCACC GAACGTGTCT CTGCAGGGTA CAAcACg (SEQ ID NO: 79) | GCCCTATTGCA AGCCCTCTTCTG CAGGGTACAAG ACa (SEQ ID NO: 122) | CATAACTGGT GGAGTATTTC ACTCGTATAT GGCCGACTGG AGGGCCCTCA TCTTCTTCCCT GC (SEQ ID NO: 165) | TTCCTC CACCGA ACGTGT CT (SEQ ID NO: 67) | GCCCTAT TGCAAG CCCTCTT (SEQ ID NO: 68) | CTGCAG GGTACA AcACg (SEQ ID NO: 208) | CTGCA GGGTA CAAgA Ca (SEQ ID NO: 251) | CATAA CTGGT GGAGT ATTTC ACT (SEQ ID NO: 294) | CGTAT ATGGC CGACT GGAG (SEQ ID NO: 337) | GCCCT CATCT TCTTC CCTGC (SEQ ID NO: 33) |
| chr19 | TTCCTCCACC GAACGTGTCT CGTATCTGGG AAGAcGc (SEQ ID NO: 80) | GCCCTATTGCA AGCCCTCTTCGT ATCTGGGAAGAt GGg (SEQ ID NO: 123) | CTTCAAGGAA GAAATTCAAC AGGTAGGGT TTGCGGCGAT AAGGGCCCTC ATCTTCTTCCC TGC (SEQ ID NO: 166) | TTCCTC CACCGA ACGTGT CT (SEQ ID NO: 67) | GCCCTAT TGCAAG CCCTCTT (SEQ ID NO: 68) | CGTATC TGGGAA GAcGGc (SEQ ID NO: 209) | CGTAT CTGGG AAGAtG Gg (SEQ ID NO: 252) | CTTCA AGGA AGAA ATTCA ACAG GG (SEQ ID NO: 295) | TAGGG TTTGC GGCG ATAAG G (SEQ ID NO: 338) | GCCCT CATCT TCTTC CCTGC (SEQ ID NO: 33) |
| chr9 | TTCCTCCACC GAACGTGTCT CCTGTAATCC CTTGcAATgc (SEQ ID NO: 81) | GCCCTATTGCA AGCCCTCTTCCT GTAATCCCTTGC AATaa (SEQ ID NO: 124) | CATGGATTCA ACACAGCAAA CACCAAGTCA ACCACCCGAG ACGCCCTCAT CTTCTTCCCTG C (SEQ ID NO: 167) | TTCCTC CACCGA ACGTGT CT (SEQ ID NO: 67) | GCCCTAT TGCAAG CCCTCTT (SEQ ID NO: 68) | CCTGTA ATCCCT TGCAAT gc (SEQ ID NO: 210) | CCTGT AATCC CTTGC AATaa (SEQ ID NO: 253) | CATGG ATTCA ACACA GCAA ACA (SEQ ID NO: 296) | CCAAG TCAAC CACCC GAGA C (SEQ ID NO: 339) | GCCCT CATCT TCTTC CCTGC (SEQ ID NO: 33) |
| chr16 | TTCCTCCACC GAACGTGTCT GGTCTCAGCA CGGtCTg (SEQ ID NO: 82) | GCCCTATTGCA AGCCCTCTTGGT CTCAGCACGTG CTt (SEQ ID NO: 125) | CTCTGACCTC CTTCACTCTTA CACTTCCTTG GCCTTCCCTTC TCTTCCCTGC (SEQ ID NO: 168) | TTCCTC CACCGA ACGTGT CT (SEQ ID NO: 67) | GCCCTAT TGCAAG CCCTCTT (SEQ ID NO: 68) | GGTCTC AGCACG GTtCTg (SEQ ID NO: 211) | GGTCT CAGCA CGGtCC Tt (SEQ ID NO: 254) | CTCTG ACCTC CTTCA CTCTT AC (SEQ ID NO: 297) | ACTTC CTGG CCTTC CTTCT (SEQ ID NO: 340) | GCCCT CATCT TCTTC CCTGC (SEQ ID NO: 33) |
| chr9 | TTCCTCCACC GAACGTGTCT GCACCTCCCT | GCCCTATTGCA AGCCCTCTTGC ACCTCCCTAtCA | GCTTTCATTTG TGCTAAACCT CGCTTGGGTC | TTCCTC CACCGA ACGTGT | GCCCTAT TGCAAG CCCTCTT | GCACCT CCCTAc CACAc | GCACC TCCCT AtCACA | GTTTG CATTT GTGCT | GCTTG GGTCC TCTCC | GCCCT CATCT TCTTC |

TABLE 5 -continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | TTCCTCCACC GAACGTGTCT GCCTAGTCT AGAGAGAAGt c (SEQ ID NO: 84) | CAt (SEQ ID NO: 126) | CTCTCCTGAA CGCCCTCATC TTCTTCCCTGC (SEQ ID NO: 169) | TTCCTC CACCGA ACGTGT CT (SEQ ID NO: 67) | GCCCTAT TGCAAG CCCTCTT (SEQ ID NO: 68) | (SEQ ID NO: 212) | t (SEQ ID NO: 255) | AAACC TC (SEQ ID NO: 298) | TGAAC (SEQ ID NO: 341) | GCCCT CATCT TCTTC CCTGC (SEQ ID NO: 33) |
| chr3 | TTCCTCCACC GAACGTGTCT GCCTAGTCT AGAGAGAAGt c (SEQ ID NO: 84) | GCCCTATTGCA AGCCCTTTGCC TCTAGTAGAG AGAAGcg (SEQ ID NO: 127) | CATCCCAGAT GCCCTCATAA CGTCCGAACC ACAATGCTGC CCTCATCTTCT TCCCTGC (SEQ ID NO: 170) | TTCCTC CACCGA ACGTGT CT (SEQ ID NO: 67) | GCCCTAT TGCAAG CCCTCTT (SEQ ID NO: 68) | GCCTCT AGCTAG AGAGAA Gtc (SEQ ID NO: 213) | GCCTC TAGCT AGAGA AGAGcg (SEQ ID NO: 256) | CATCC CAGAT GCCCT CAT (SEQ ID NO: 299) | AACGT CCGAA CCACA ATGCT (SEQ ID NO: 342) | GCCCT CATCT TCTTC CCTGC (SEQ ID NO: 33) |
| chr20 | TTCCTCCACC GAACGTGTCT CTGGCAGTCT AGCgTTAc (SEQ ID NO: 85) | GCCCTATTGCA AGCCCTCTTCTG GCAGTCTAGCCa TTAt (SEQ ID NO: 128) | GTAGAAATCC CAAGGCAATC AGCTCCTGCC ATCCAACAGT CGGCCCTCAT CTTCTTCCCTG C (SEQ ID NO: 171) | TTCCTC CACCGA ACGTGT CT (SEQ ID NO: 67) | GCCCTAT TGCAAG CCCTCTT (SEQ ID NO: 68) | CTGGCA GTCTAG CCgTTAc (SEQ ID NO: 214) | CTGGC AGTCT AGCCaT TAt (SEQ ID NO: 257) | GTAGA AATCC CAAG GCAAT CAG (SEQ ID NO: 300) | CTCTT CGCAT CCAAC AGTCG (SEQ ID NO: 343) | GCCCT CATCT TCTTC CCTGC (SEQ ID NO: 33) |
| chrX | TTCCTCCACC GAACGTGTCT TGTCTTAGAA TTTGGCAACTg Gc (SEQ ID NO: 86) | GCCCTATTGCA AGCCCTCTTTGT CTTAGAATTTG GCAACTaGt (SEQ ID NO: 129) | GAACAACTAA CTCCACAGAA CCCCCACCGT AGCACTCCTT CTTGCCTCA TCTTCTTCCCT GC (SEQ ID NO: 172) | TTCCTC CACCGA ACGTGT CT (SEQ ID NO: 67) | GCCCTAT TGCAAG CCCTCTT (SEQ ID NO: 68) | TGTCTT AGAATT TGGCAA CTgGc (SEQ ID NO: 215) | TGTCTT AGAAT TTGGC AACTaG t (SEQ ID NO: 258) | GAAC AACTA ACTCC ACAG AACCC (SEQ ID NO: 301) | CCACC GTAGC ACTCC TTCTT (SEQ ID NO: 344) | GCCCT CATCT TCTTC CCTGC (SEQ ID NO: 33) |
| chr7 | TTCCTCCACC GAACGTGTCT GGGAAAAGC CTAcTGAAc (SEQ ID NO: 87) | GCCCTATTGCA AGCCCTCTTGC AGGAAAGCCTAa TGAAt (SEQ ID NO: 130) | GTGCAGAGGA CAGGAAGAAC GGAGCGTCGG TAGTGTAAAG CCCTCATCTTC TTCCCTGC (SEQ ID NO: 173) | TTCCTC CACCGA ACGTGT CT (SEQ ID NO: 67) | GCCCTAT TGCAAG CCCTCTT (SEQ ID NO: 68) | GCAGGA AAGCCT AcTGAA c (SEQ ID NO: 216) | GCAGG AAAGC CTAtTG AAt (SEQ ID NO: 259) | GTGCA GAGG ACAG GAAG AA (SEQ ID NO: 302) | CGGA GCGTC GGTAG TGTAA A (SEQ ID NO: 345) | GCCCT CATCT TCTTC CCTGC (SEQ ID NO: 33) |
| chr3 | TTCCTCCACC GAACGTGTCT GGGAGCCAGA AATtCt (SEQ ID | GCCCTATTGCA AGCCCTCTTGG GAGCCAGAGA ATtTCt (SEQ ID | GGTGCTTCAA GACATACACC TTAACAACTC GACGAACCTA | TTCCTC CACCGA ACGTGT CT (SEQ | GCCCTAT TGCAAG CCCTCTT (SEQ ID | GGGAGC CAGAGA AATgTCc (SEQ ID | GGGAG CCAGA GAAATt TCt | GGTGC TTCAA TTCAA GACAT ACACC | ACAAC TCGAC GAACC TACCG | GCCCT CATCT TCTTC |

TABLE 5 -continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | TTCCTCCACC GAACGTGTCT TGTCCCAGT TCCACTTCATt TAg (SEQ ID NO: 89) | GCCCTATTGCA AGCCCTCTTGT CTCCAGTTCCAC TTCATgTAa (SEQ ID NO: 132) | CCGGCCCTCA TCTTCTTCCCT GC (SEQ ID NO: 174) | TTCCTC CACCGA ACGTGT CT (SEQ ID NO: 67) | GCCCTAT TGCAAG CCCTCTT (SEQ ID NO: 68) | NO: 217) | (SEQ ID NO: 260) | TTA (SEQ ID NO: 303) | (SEQ ID NO: 346) | (SEQ ID NO: 33) |
| chr2 | TTCCTCCACC GAACGTGTCT TGTCCCAGT TCCACTTCATt TAg (SEQ ID NO: 89) | GCCCTATTGCA AGCCCTTTGT CTCCAGTTGGA TGGCCCATCC TTATGTGCTG GCCCTCATCT TCTTCCCTGC (SEQ ID NO: 175) | GGAACCTCTG TGACCTTGGA TGGCCCATCC TTATGTGCTG GCCCTCATCT TCTTCCCTGC (SEQ ID NO: 175) | TTCCTC CACCGA ACGTGT CT (SEQ ID NO: 67) | GCCCTAT TGCAAG CCCTCTT (SEQ ID NO: 68) | TGTCTC CAGTTC CACTTC ATtTAg (SEQ ID NO: 218) | TGTCTC CAGTTC CCACT TCATgT Aa (SEQ ID NO: 261) | GGAA CCTCT GTGAC CTTGG A (SEQ ID NO: 304) | TGGCC CATCC TTATG TGCTG (SEQ ID NO: 347) | GCCCT CATCT TCTTC CCTGC (SEQ ID NO: 33) |
| chr15 | TTCCTCCACC GAACGTGTCT CCGGTTAATT GCCTACTcg (SEQ ID NO: 90) | GCCCTATTGCA AGCCCTCTTCCC GTTAATTGCCTA tTta (SEQ ID NO: 133) | CCCAGTGGTA CCTTCTGAAG GTCGTTATTG CCAAGCCCG CCCTTCATCTTC TTCCCTG (SEQ ID NO: 176) | TTCCTC CACCGA ACGTGT CT (SEQ ID NO: 67) | GCCCTAT TGCAAG CCCTCTT (SEQ ID NO: 68) | CCCGTT AATTGC CTACTcg (SEQ ID NO: 219) | CCCGT TAATT GCCTA tTta (SEQ ID NO: 262) | CCCAG TGGTA CCTTC TGAA (SEQ ID NO: 305) | GGTCG TTATT GCTCA AGCCC (SEQ ID NO: 348) | GCCCT CATCT TCTTC CCTGC (SEQ ID NO: 33) |
| chr15 | TTCCTCCACC GAACGTGTCT CTCGGTTCCCA CTGGaAAg (SEQ ID NO: 91) | GCCCTATTGCA AGCCCTCTTCTC GGTCCCACTGGg AAa (SEQ D NO: 134) | CTTCTGTTGCT TATTTGGGTA ACTTGATTCT GGCCCTCCCA TCGCCTCAT CTTCTTCCCTG C (SEQ ID NO: 177) | TTCCTC CACCGA ACGTGT CT (SEQ ID NO: 67) | GCCCTAT TGCAAG CCCTCTT (SEQ ID NO: 68) | CTCGGT CCCACT GGaAAg (SEQ ID NO: 220) | CTCGG TCCCA CTGGg AAa (SEQ ID NO: 263) | CTTCT GTTGC TTATT TGGGT AAC (SEQ ID NO: 306) | TTGAT TCTGG CCCTC CCATC (SEQ ID NO: 349) | GCCCT CATCT TCTTC CCTGC (SEQ ID NO: 33) |
| chr2 | TTCCTCCACC GAACGTGTCT ACACCATGA TTCAGTTACtg (SEQ ID NO: 92) | GCCCTATTGCA AGCCCTCTTAC ACCATGATTC AGTTACca (SEQ ID NO: 135) | CCCACTGGAT GCCTCCCTCA CGCCAGCTAT TTAGTGCCC TCATCTTCTTC CCTGC (SEQ ID NO: 178) | TTCCTC CACCGA ACGTGT CT (SEQ ID NO: 67) | GCCCTAT TGCAAG CCCTCTT (SEQ ID NO: 68) | ACACCC ATGATT CAGTTA Ctg (SEQ ID NO: 221) | ACACC CATGA TTCAG TTACca (SEQ ID NO: 264) | CCCAC TGGAT GCCTC C (SEQ ID NO: 307) | CTCAC GCCGG CTATT TAGGT (SEQ ID NO: 350) | GCCCT CATCT TCTTC CCTGC (SEQ ID NO: 33) |
| chr9 | TTCCTCCACC GAACGTGTCT GCTAGTATGA ACATCACAgGc (SEQ ID NO: 93) | GCCCTATTGCA AGCCCTCTTGCT AGTATGAACAT CACAaGt (SEQ ID NO: 136) | CGGAGAGACG CATCTGAAAG TCTGGGTAGG TGGAGGACGC CCTCATCTTCT (SEQ ID NO: 178) | TTCCTC CACCGA ACGTGT CT (SEQ ID NO: 67) | GCCCTAT TGCAAG CCCTCTT (SEQ ID NO: 68) | GCTAGT ATGAAC ATCACA gGc (SEQ ID NO: | GCTAG TATGA ACATC ACAaGt (SEQ ID | CGGA GAGA CGCAT CTGAA (SEQ | AGTCT GGGTA GGTGG AGGA C (SEQ | GCCCT CATCT TCTTC CCTGC (SEQ |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | | | TCCCTGC (SEQ ID NO: 179) | TTCCTC CACCGA ACGTGT CT (SEQ ID NO: 67) | | NO: 222) | NO: 265) | ID NO: 308) | ID NO: 351) | ID NO: 33) |
| chr7 | TTCCTCCACC GAACGTGTCT GATAAGGAGT AGAGACGAG Tcg (SEQ ID NO: 94) | GCCCTATTGCA AGCCCTCTTAC AAATGAGTAAG AAGCGAGTta (SEQ ID NO: 137) | CAGGATTCC AGCTTACAGG GCGACTGAGC CACATCCAAC TGCCCTCATC TTCTTCCCTGC (SEQ ID NO: 180) | TTCCTC CACCGA ACGTGT CT (SEQ ID NO: 67) | GCCCTAT TGCAAG CCCTCTT (SEQ ID NO: 68) | ACAAAT GAGTAA GAAGCG AGTcg (SEQ ID NO: 223) | ACAAA TGAGT AAGAA GCGAG Tta (SEQ ID NO: 266) | CAGG ATTTC CAGCT TACAG GG (SEQ ID NO: 309) | CGACT GAGCC ACATC CAACT (SEQ ID NO: 352) | GCCCT CATCT TCTTC CCTGC (SEQ ID NO: 33) |
| chr20 | TTCCTCCACC GAACGTGTCT GATGACCA CCATGCACCA GCTACc (SEQ ID NO: 95) | GCCCTATTGCA AGCCCTCTTGAT AAGGGTTGCTC TaCa (SEQ ID NO: 138) | CTTGCAAGAT GTGCCTCTTA GAGCCTCAGC CGGAATTGAA GCCCTCATCT TCTTCCCTGC (SEQ ID NO: 181) | TTCCTC CACCGA ACGTGT CT (SEQ ID NO: 67) | GCCCTAT TGCAAG CCCTCTT (SEQ ID NO: 68) | GATAAG GGTTGC TCTgCg (SEQ ID NO: 224) | GATAA GGGTT GCTCTa ca (SEQ ID NO: 267) | CTTGC AAGAT GTGCC TCTTA (SEQ ID NO: 310) | GAGCC TCAGC CGGA ATTGA A (SEQ ID NO: 353) | GCCCT CATCT TCTTC CCTGC (SEQ ID NO: 33) |
| chr20 | TTCCTCCACC GAACGTGTCT CCATGCACCA GCTACc (SEQ ID NO: 96) | GCCCTATTGCA AGCCCTCTTCCA TGCACCAGCTA Cta (SEQ ID NO: 139) | GGGTGGTTTC TCTAAACACA AATTGCCAAT CTGCACCAAT GCGCCCTCAT CTTCTTCCCTG C (SEQ ID NO: 182) | TTCCTC CACCGA ACGTGT CT (SEQ ID NO: 67) | GCCCTAT TGCAAG CCCTCTT (SEQ ID NO: 68) | CCATGC ACCACC TACcc (SEQ ID NO: 225) | CCATG CACCA GCTAct a (SEQ ID NO: 268) | GGGTG GTTTC TCTAA ACACA AA (SEQ ID NO: 311) | TTGCC ATTCT GCACC AATGC (SEQ ID NO: 354) | GCCCT CATCT TCTTC CCTGC (SEQ ID NO: 33) |
| chr1 | TTCCTCCACC GAACGTGTCT AACTGTACCC TACTCCCAgc (SEQ ID NO: 97) | GCCCTATTGCA AGCCCTCTTAA CTGTACCCTACT CCCAat (SEQ ID NO: 140) | GCAGGGTATT GAGAGAAGG ATCTATTGGT GTTCGCGGCT GATGCCCTCA TCTTCTTCCCT GC (SEQ ID NO: 183) | TTCCTC CACCGA ACGTGT CT (SEQ ID NO: 67) | GCCCTAT TGCAAG CCCTCTT (SEQ ID NO: 68) | AACTGT ACCCTA CTCCCA gc (SEQ ID NO: 226) | AACTG TACCC TACTC CCAat (SEQ ID NO: 269) | GCAG GGTAT TGAGA GAAG GATC (SEQ ID NO: 312) | TATTG GTGTT GCGCG GCTGAT (SEQ ID NO: 355) | GCCCT CATCT TCTTC CCTGC (SEQ ID NO: 33) |
| chr2 | TTCCTCCACC GAACGTGTCT AGGACCAAGG GACCAGTTAg (SEQ ID NO: 98) | GCCCTATTGCA AGCCCTCTTAG GACCAAGGGAC CAGTTcAc (SEQ ID NO: 141) | GTGCACATTT CTTGATGAAG GGATGGGCGT AACAGGAGGA CTGCCCTCAT CTTCTTCCCTG (SEQ ID NO: | TTCCTC CACCGA ACGTGT CT (SEQ ID NO: 67) | GCCCTAT TGCAAG CCCTCTT (SEQ ID NO: 68) | AGGACC AAGGGA CCAGTTt Ag (SEQ ID NO: 227) | AGGAC CAAGG GACCA GTTcAc (SEQ ID NO: 270) | GTGCA CATTT CTTGA TGAAG GG (SEQ ID NO: | ATGGG CGTAA CAGG AGGA CT (SEQ | GCCCT CATCT TCTTC CCTGC (SEQ ID NO: |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| chr7 | TTCCTCCACC GAACGTGTCT GAGAGTTCCTC CAAGAAATTG CAGCCCTCAT cg (SEQ ID NO: 99) | GCCCTATTGCA AGCCCTCTTAG AGTTCCTCCAA GAAATTGta (SEQ ID NO: 142) | GAGCAATGCC TGTTTCATGA GAGGAATGGC CTAACCTGCAT GAAATTGta CTTCTTCCCTG C (SEQ ID NO: 185) | TTCCTC CACCGA ACGTGT CT (SEQ ID NO: 67) | GCCCTAT TGCAAG CCCTCTT (SEQ ID NO: 68) | AGAGTT CCTCCA AGAAAT TGcg (SEQ ID NO: 228) | AGAGT TCCTCC AAGAA ATTGta (SEQ ID NO: 271) | GAGC AATGC CTGTT TCATG AGA (SEQ ID NO: 313) | GGAAT GGCCT ACCTG CATCA (SEQ ID NO: 356) | GCCCT CATCT TCTTC CCTGC (SEQ ID NO: 33) |
| chr5 | TTCCTCCACC GAACGTGTCT ACATTATACA GCATGCTGGT TAtc (SEQ ID NO: 100) | GCCCTATTGCA AGCCCTCTTAC ATTATACAGCA TGCTGGtTAga (SEQ ID NO: 143) | GTTAACATTA TACAGCATGG TGGCCCCGTT GTTGTCATCG CATGCCCCTC ATCTTCTTCCC TGC (SEQ ID NO: 186) | TTCCTC CACCGA ACGTGT CT (SEQ ID NO: 67) | GCCCTAT TGCAAG CCCTCTT (SEQ ID NO: 68) | ACATTA TACAGC ATGCTG GcTAtc (SEQ ID NO: 229) | ACATT ATACA GCATG CTGGtT Aga (SEQ ID NO: 272) | GTTAA CATTA TACAG CATGG TGGC (SEQ ID NO: 314) | CCCGT TGTTG TCATC GCATC (SEQ ID NO: 357) | GCCCT CATCT TCTTC CCTGC (SEQ ID NO: 33) |
| chr2 | TTCCTCCACC GAACGTGTCT GAGGAAGAA AGTGAGgTTT Gc (SEQ ID NO: 101) | GCCCTATTGCA AGCCCTCTTCA GGAAGAAAGTG AGaTTTGt (SEQ ID NO: 144) | GCAGAACATG TCCTGAAGCG TTCGATGAGT CCCATGAGTG CCCTCATCTTC TTCCCTGC (SEQ ID NO: 187) | TTCCTC CACCGA ACGTGT CT (SEQ ID NO: 67) | GCCCTAT TGCAAG CCCTCTT (SEQ ID NO: 68) | GAGGAA GAAAGT GAGGTT TGc (SEQ ID NO: 230) | GAGGAA AGAAA GTGAG aTTTGt (SEQ ID NO: 273) | GCAG AACAT GTCTC GAAG C (SEQ ID NO: 315) | GTTCG ATGCG TCCCA TGAGT (SEQ ID NO: 358) | GCCCT CATCT TCTTC CCTGC (SEQ ID NO: 33) |
| chr15 | TTCCTCCACC GAACGTGTCT CTGAATTATG TGCTTACCAaG AGc (SEQ ID NO: 102) | GCCCTATTGCA AGCCCTCTCTG AATTATGTGCTT ACCAgGAgT (SEQ ID NO: 145) | CAGCTTGTTC CCAAACCCAT CAACCCGCGT AGATGTTCCT GCCCTCATCT TCTTCCCTGC (SEQ ID NO: 274) | TTCCTC CACCGA ACGTGT CT (SEQ ID NO: 67) | GCCCTAT TGCAAG CCCTCTT (SEQ ID NO: 68) | CTGAAT TATGTG CTTACC AaGAGc (SEQ ID NO: 231) | CTGAA TTATGT GCTTA CCAgG AGt (SEQ ID NO: 316) | CAGCT TGTTC CCAAA CCCAT (SEQ ID NO: 317) | CAACC CGCGT AGATG TTCCT (SEQ ID NO: 359) | GCCCT CATCT TCTTC CCTGC (SEQ ID NO: 33) |
| chr9 | TTCCTCCACC GAACGTGTCT TGGGTTCTGA TAACCTTATC AAgc (SEQ ID NO: 146) | GCCCTATTGCA AGCCCTCTTGG GTTCTGATAAC CTTATCAAct (SEQ ID NO: 188) | CAAAGTGTGG AAGTTGCTTC CGCCAGCTCA AGAGTGTAGC CGCCCTCATC | TTCCTC CACCGA ACGTGT CT (SEQ ID NO: | GCCCTAT TGCAAG CCCTCTT (SEQ ID NO: 68) | TGGGTT CTGATA ACCTTA TCAAgc (SEQ ID | TGGGT TCTGA TAACC TTATC AAct | CAAA GTGTG GAAGT TGCTT CC | GCCAG CTCAA GAGTG TAGCC | GCCCT CATCT TCTTC CCTGC (SEQ |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | NO: 103) | | TTCTTCCCTGC (SEQ ID NO: 189) | TTCCTC CACCGA ACGTGT CT (SEQ ID NO: 67) | | NO: 232) | (SEQ ID NO: 275) | (SEQ ID NO: 318) | TTCTT GATCC (SEQ ID NO: 361) | GCCCT CATCT TCTTC CCTGC (SEQ ID NO: 33) |
| chr2 | TTCCTCCACC GAACGTGTCT GGTTAGTCAA ACATGcTGc (SEQ ID NO: 104) | GCCCTATTGCA AGCCCCTTGGT TAGTCAAACAT GtTGt (SEQ ID NO: 147) | GGTGACTTT GTCCATCCTT CTTGCATGCA CGCGATGTGC CCTCATCTTCT TCCCTGC (SEQ ID NO: 190) | TTCCTC CACCGA ACGTGT CT (SEQ ID NO: 67) | GCCCTAT TGCAAG CCCTCTT (SEQ ID NO: 68) | GGTTAG TCAAAC ATGcTGc (SEQ ID NO: 233) | GGTTA GTCAA ACATGt TGt (SEQ ID NO: 276) | GGTCG ACTTT GTCCA TCC (SEQ ID NO: 319) | TTCTT GATCC TGCGC GATGT (SEQ ID NO: 362) | GCCCT CATCT TCTTC CCTGC (SEQ ID NO: 33) |
| chr17 | TTCCTCCACC GAACGTGTCT GACACTGGCA GAATCAAAtC Ac (SEQ ID NO: 105) | GCCCTATTGCA AGCCCCTCTTGA CACTGGCAGAA TCAAAcCAa (SEQ ID NO: 148) | CTCTGTTGCCT GTGGACTCAT CGCAGGCAGT CCCTATACGC CCTCATCTTCT TCCCTGC (SEQ ID NO: 191) | TTCCTC CACCGA ACGTGT CT (SEQ ID NO: 67) | GCCCTAT TGCAAG CCCTCTT (SEQ ID NO: 68) | GACACT GGCAGA ATCAAA tCAc (SEQ ID NO: 234) | GACAC TGGCA GAATC AAAcC Aa (SEQ ID NO: 277) | CTCTG TTGCC TGTGG ACTC C (SEQ ID NO: 320) | ATCGC AGGC GTTCC CTATA (SEQ ID NO: 363) | GCCCT CATCT TCTTC CCTGC (SEQ ID NO: 33) |
| chr6 | TTCCTCCACC GAACGTGTCT AGAGTTACAC CTTTAGCTAA CcAc (SEQ ID NO: 106) | GCCCTATTGCA AGCCCCTCTTAG AGTTACACCTTT AGCTAActAg (SEQ ID NO: 149) | CTAACTAGAA TTAGTCTGCC TGCCTATTGG ACCTCCGACA ACGAGCCCTC ATCTTCTTCCC TGC (SEQ ID NO: 192) | TTCCTC CACCGA ACGTGT CT (SEQ ID NO: 67) | GCCCTAT TGCAAG CCCTCTT (SEQ ID NO: 68) | AGAGTT ACACCT TTAGCT AACAc (SEQ ID NO: 235) | AGAGT TACAC CTTTA GCTAA CtAg (SEQ ID NO: 278) | CTAAC TAGAA TTAGT TGCC TGCC (SEQ ID NO: 321) | TATTG GACCT CCGAC CACGA (SEQ ID NO: 364) | GCCCT CATCT TCTTC CCTGC (SEQ ID NO: 33) |
| chr7 | TTCCTCCACC GAACGTGTCT CCAGGAGTTC AAGAaGCg (SEQ ID NO: 107) | GCCCTATTGCA AGCCCCTCTTCCA GGAGTTCAAGg AGCa (SEQ ID NO: 150) | GTGAGCCATA ATCGTGTCAA GCCACCATTT AGATCCGGCG CCCTCATCTTC TTCCCTGC (SEQ ID NO: 193) | TTCCTC CACCGA ACGTGT CT (SEQ ID NO: 67) | GCCCTAT TGCAAG CCCTCTT (SEQ ID NO: 68) | CCAGGA GTTCAA GaAgGCg (SEQ ID NO: 236) | CCAGG AGTTC AAGgA GCa (SEQ ID NO: 279) | GTGAG CCATA ATCGT GTCA (SEQ ID NO: 322) | AGCCA CCATT TAGAT CCGCG (SEQ ID NO: 365) | GCCCT CATCT TCTTC CCTGC (SEQ ID NO: 33) |
| chr4 | TTCCTCCACC GAACGTGTCT ACCACTCCTT TCTCCCaTCTc (SEQ ID NO: 108) | GCCCTATTGCA AGCCCCTCTTACC ACTCCTTTCTC CgTCTt (SEQ ID NO: 151) | GAGAATTAAT GCTCCCTTC CTGGACCAGT AGAAGTCTGC CCGGCCCTCA TCTTCTTCCCT GC (SEQ ID | TTCCTC CACCGA ACGTGT CT (SEQ ID NO: 67) | GCCCTAT TGCAAG CCCTCTT (SEQ ID NO: 68) | ACCACT CCTTTC TCCcaTC Tc (SEQ ID NO: 237) | ACCAC TCCTTT CTCCCg TCTt (SEQ ID NO: 280) | GAGA ATTAA TGCTC CCTG (SEQ ID NO: 323) | GACCA GTAGA AGTCT GCCCG (SEQ ID NO: 366) | GCCCT CATCT TCTTC CCTGC (SEQ ID NO: 33) |

TABLE 5-continued

Exemplary probes and primers.

| Chromosome | Labeling Probe-Allele 1 (Forward Primer Allele 1 + Hom 5p Allele 1) | Labeling Probe-Allele 2 (Forward Primer Allele 2 + Hom 5p Allele 2) | Tagging Probe (Hom 3p + Tag + Reverse Primer) | Primer-Allele 1 | Forward Primer-Allele 2 | Hom 5p-Allele 1 | Hom 5p-Allele 2 | Hom 3p | Tag | Reverse Primer |
|---|---|---|---|---|---|---|---|---|---|---|
| | | | | | | | | 323) | | |
| chr2 | TTCCTCCACC GAACGTGTCT GTCTTATGGG ACAATGGTtG ATAg (SEQ ID NO: 109) | GCCCTATTGCA AGCCCTCTTGTC TTATGGACAA TGGTcGATAt (SEQ ID NO: 152) | GTGGTCTGCT GTTGACCAAT TTCAGAATGG CCGAGCTGTG CCCTCATCTTC TTCCCTGC (SEQ ID NO: 195) | TTCCTC CACCGA ACGTGT CT (SEQ ID NO: 67) | GCCCTAT TGCAAG CCCTCTT (SEQ ID NO: 68) | GTCTTA TGGGAC AATGGT tGATAg (SEQ ID NO: 238) | GTCTT ATGGG ACAAT GGTcG ATAt (SEQ ID NO: 281) | GTGGT CTGCT GTTGA CCAA (SEQ ID NO: 324) | TTTCA GAATG GCCGA GCTGT (SEQ ID NO: 367) | GCCCT CATCT TCTTC CCTGC (SEQ ID NO: 33) |
| chr17 | TTCCTCCACC GAACGTGTCT CTACCCTCAA CCCTgTc (SEQ ID NO: 110) | GCCCTATTGCA AGCCCTCTTCTA CCCTCAACCCTC aTt (SEQ ID NO: 153) | GGTTGCAACT GCTAATCTAT AGGTGACCTT CTTGTACGCC GCCCTCATCT TCTTCCCTGC (SEQ ID NO: 196) | TTCCTC CACCGA ACGTGT CT (SEQ ID NO: 67) | GCCCTAT TGCAAG CCCTCTT (SEQ ID NO: 68) | CTACCC TCAACC CTCgTc (SEQ ID NO: 239) | CTACC CTCAA CCCTCa Tt (SEQ ID NO: 282) | GGTTG CAACT GCTGA TCTAT (SEQ ID NO: 325) | AGGTG ACCTT CTTGT ACGCC (SEQ ID NO: 368) | GCCCT CATCT TCTTC CCTGC (SEQ ID NO: 33) |
| chr7 | TTCCTCCACC GAACGTGTCT CCAAGAGACTGA TCATGCcg (SEQ ID NO: 111) | GCCCTATTGCA AGCCCTCTTCCA AGACTGATCAT GCta (SEQ ID NO: 154) | CTTTCCCAGT CAAGGCAGGG CGCGTCCTTA TTTCCATCGC CCTCATCTTCT TCCCTGC (SEQ ID NO: 197) | TTCCTC CACCGA ACGTGT CT (SEQ ID NO: 67) | GCCCTAT TGCAAG CCCTCTT (SEQ ID NO: 68) | CCAAGA CTGATC ATGCcg (SEQ ID NO: 240) | CCAAG ACTGA TCATG Cta (SEQ ID NO: 283) | CTTTC CCAGT CAAG GCAG (SEQ ID NO: 326) | GGCGC GTCCT TATTT CCATC (SEQ ID NO: 369) | GCCCT CATCT TCTTC CCTGC (SEQ ID NO: 33) |

EXAMPLES

The following protocol describes the processing of up to 24 cell-free DNA samples through hybridization-ligation, purification, amplification, microarray target preparation, microarray hybridization and microarray washing.

The following materials were prepared or obtained: Cell-free DNA (cfDNA) in a volume of 20 µL water; Probe Mix: mixture of all Tagging and Labeling probe oligonucleotides at a concentration of 2 nM each; Taq Ligase (40 U/µL); Magnetic Beads: MyOne Streptavidin C1 Dynabeads; Bead Binding and Washing Buffer, 1× and 2× concentrations; Forward amplification primer, 5' phosphate modified; Reverse amplification primer, labeled; AmpliTaq Gold Enzyme (5 U/µL); dNTP Mix; Lambda Exonuclease (5 U/µL); Hybridization Buffer, 1.25×; Hybridization control oligonucleotides; Microarray Wash Buffer A; Microarray Wash Buffer B; Microarray Wash Buffer C Hybridization-ligation Reaction: The cfDNA samples (20 µL) were added to wells A3-H3 of a 96-well reaction plate. The following reagents were added to each cfDNA sample for a total reaction volume of 50 µL, and mixed by pipetting up and down 5-8 times.

| Component | Volume |
| --- | --- |
| H$_2$O | 19.33 µL |
| Probe Mix | 5 µL |
| 10X Taq Ligase Buffer | 5 µL |
| Taq Ligase | 0.67 µL |

The plate was placed in a thermal cycler and ligate using the following cycling profile: (i) 95° C. for 5 minutes; (ii) 95° C. for 30 seconds; (iii) 45° C. for 25 minutes; (iv) Repeat steps b to c 4 times; and (v) 4° C. hold.

Hybridization-ligation Product Purification:

Wash Dynabeads: a vial of Dynabeads was vortexted at highest setting for 30 seconds. 260 µL beads were transferred to a 1.5 mL tube. 900 µL of 2× Bead Binding and Washing Buffer and mix beads were mixed by pipetting up and down 5-8 times. The tube was placed on a magnetic stand for 1 min, and the supernatant was discarded. The tube from the magnetic stand was removed and resuspended the washed magnetic beads in 900 µL of 2× Bead Binding and Washing Buffer by pipetting up and down 5-8 times. The tube was placed on the magnetic stand for 1 min and discard the supernatant. The tube was removed from the magnetic stand and add 1,230 µL of 2× Bead Binding and Washing Buffer. The beads were resuspended by pipetting up and down 5-8 times.

Immobilize HL Products: 50 µL of washed beads was transferred to each hybridization-ligation reaction product in the 96-well reaction plate and mix by pipetting up and down 8 times, was incubated for 15 min at room temperature, mixed on a plate magnet twice during the incubation time. The beads were separated with on a plate magnet for 3 min and then remove and discard the supernatant. The plate was removed from the plate magnet, 200 µL 1× Bead Binding and Washing Buffer were added, and the beads were resuspended by pipetting up and down 5-8 times. The plate was placed on the plate magnet for 1 min, and the supernatant was discarded. The plate was removed from the plate magnet, 180 µL 1×SSC was added, and the beads were resuspended by pipetting up and down 5-8 times. The plate was placed on the plate magnet for 1 min, and the supernatant was discarded.

Purify Hyb-Ligation Products: 50 µL of freshly prepared 0.15 M NaOH was added to each well and, the beads were resuspended by pipetting up and down 5-8 times, and incubated at room temperature for 10 minutes. The plate was placed on the plate magnet for 2 minutes and then was removed, and the supernatant was discarded. The plate was removed from the plate magnet, 200 µL of freshly prepared 0.1 M NaOH was added, and the beads were resuspended by pipetting up and down 5-8 times. The plate was placed on the plate magnet for 1 min, and the supernatant was discarded. The plate was removed from the plate magnet, and 180 µL 0.1 M NaOH was added, and the beads were resuspended by pipetting up and down 5-8 times. The plate was placed on the plate magnet for 1 min, and the supernatant was discarded. The plate was removed from the plate magnet, 200 µL of 1× Binding and Wash Buffer were added, and the beads were resuspended by pipetting up and down 5-8 times. Place the plate on the plate magnet for 1 min and discard the supernatant. Remove the plate from the plate magnet, add 180 µL TE, and the beads were resuspended by pipetting up and down 5-8 times. The plate was placed on the plate magnet for 1 min, and the supernatant was discarded. 20 µL water was added to each well and the beads were resuspended by pipetting up and down 5-8 times. The plate was sealed and store at 4° C. until used in subsequent steps.

Amplification: The following reagents were added to each hybridization-ligation reaction product in the 96-well reaction plate for a total reaction volume of 50 µL.

| Component | Volume |
| --- | --- |
| H2O | 17.25 µL |
| Forward Primer, 10 µM | 2.5 µL |
| Reverse Primer, 10 µM | 2.5 µL |
| 4 mM dNTP Mix (L/N 052114) | 2.5 µL |
| 10X AmpliTaq Gold Buffer | 5 µL |
| AmpliTaq Gold Enzyme | 0.25 µL |

The plate was placed in a thermal cycler, and the probes were ligated using the following cycling profile: (i) 95° C. for 5 minutes; (ii) 95° C. for 30 seconds; (iii) 45° C. for 25 minutes; (iv) Repeat steps b to c 4 times; and (v) 4° C. hold.

Hybridization-Ligation Product Purification: the reagents were mixed by pipetting up and down 5-8 times. The plate was placed in a thermal cycler, and the probes were amplified using the following cycling profile: (i) 95° C. for 5 minutes; (ii) 95° C. for 30 seconds; (iii) 54° C. for 30 seconds; (iv) 72° C. for 60 seconds, (v) Repeat steps b to d 29 times; (vi) 72° C. for 5 minutes; (vii) Repeat steps b to c 4 times; and (v) 4° C. hold.

Microarray Target Preparation (Single Strand Digestion): the following reagents were added to each amplified reaction product in the 96-well reaction plate for a total reaction volume of 60 µL.

| Component | Volume |
| --- | --- |
| H$_2$O | 3 µL |
| 10X Lambda Exonuclease Buffer | 6 µL |
| Lambda Exonuclease Enzyme | 1 µL |

The reagents were mixed by pipetting up and down 5-8 times. The plate was placed in a thermal cycler, and the probes were digested using the following cycling profile: (i) 37° C. for 60 minutes; (ii) 80° C. for 30 minutes; (iii) 4° C.

hold. The plate was placed in Speed-vac and dry down samples using medium heat setting for about 60 minutes or until all liquid has evaporated. Samples were stored at 4° C. in the dark until used in subsequent steps.

Microarray Hybridization: the following reagents were added to each dried Microarray Target in the 96-well reaction plate for a total reaction volume of 20 µL.

| Component | Volume |
|---|---|
| H₂O | 3 µL |
| 1.25X Hybridization Buffer | 16 µL |
| Hybridization control oligonucleotides | 1 µL |

The reagents were mixed by pipetting up and down 10-20 times to be resuspended and were spun briefly to bring contents to the bottoms of the plate wells. The plate was placed in a thermal cycler, and the probes were denatured using the following cycling profile: (i) 70° C. for 3 minutes; (ii) 42° C. hold. The barcode of the microarray to be used was recorded for each sample in the Tracking Sheet. A hybridization chamber containing a Lifter Slip for each microarray to be processed is prepared. For each sample, 15 µL of Microarray Target was added to the center of a Lifter Slip in a hybridization chamber, and the appropriate microarray was immediately placed onto the target fluid by placing the top edge down onto the lifter slip and slowly letting it fall down flat. The hybridization chambers were closed and incubated them at 42° C. for 60 minutes. The hybridization chambers were opened, and each microarray was removed from the Lifter Slips and placed into a rack immersed in Microarray Wash Buffer A. Once all the microarrays were in the rack, the rack was stirred at 650 rpm for 5 minutes. The rack of microarrays was removed from Microarray Wash Buffer A, excess liquid on a clean room wipe was tapped off, and the rack were quickly placed into Microarray Wash Buffer B. The rack was stirred at 650 rpm for 5 minutes. The rack of microarrays was removed from Microarray Wash Buffer B, excess liquid was tapped off on a clean room wipe, and the rack was quickly placed into Microarray Wash Buffer C. The rack was stirred at 650 rpm for 5 minutes. Immediately upon completion of the 5 minute wash in Microarray Wash Buffer C, the rack of microarrays was slowly removed from the buffer. This took 5-10 seconds to maximize the sheeting of the wash buffer from the cover slip surface. Excess liquid was tapped off on a clean room wipe. A vacuum aspirator was used to remove any remaining buffer droplets present on either surface of each microarray. The microarrays were stored in a slide rack under nitrogen and in the dark until the microarrays were analyzed.

The invention claimed is:

1. A method of detecting nucleic acid copy numbers in a genetic sample obtained from a subject, comprising
   contacting first and second probe sets to the genetic sample, wherein the first probe set comprises a first labeling probe and a first tagging probe, and the second probe set comprises a second labeling probe and a second tagging probe;
   hybridizing at least parts of probes of the first and second probe sets to first and second nucleic acid regions of interest in nucleotide molecules present in the genetic sample to produce first and second probe products, respectively, wherein the first and second probe products are circular molecules;
   amplifying the first and second probe products to form first and second amplified probe products;
   labeling the first and second amplified probe products with first and second labels to produce first and second labeled amplified probe products;
   immobilizing at least parts of probes of the first and second labeled amplified probe products to a substrate at a density in which the first and second labeled probe products are optically resolvable after immobilization; and
   detecting (i) a first number of the first labeled amplified probe products, and (ii) a second number of the second labeled amplified probe products to detect the nucleic acid copy numbers.

2. The method according to claim 1, wherein the first probe set further comprises a first gap probe, and the second probe set further comprises a second gap probe.

3. The method according to claim 2, wherein each of the first and second gap probes comprises an artificial nucleotide sequence.

4. The method according to claim 2, wherein
   in the first probe set, the first gap probe, the first labeling probe, and the first tagging probe are adjacent to each other, and
   in the second probe set, the second gap probe, the second labeling probe, and the second tagging probe are adjacent to each other.

5. The method according to claim 2, further comprising, after the hybridizing before the amplifying, (i) ligating the first gap probe, the first labeling probe, and the first tagging probe in the first probe set, and (ii) ligating the second gap probe, the second labeling probe, and the second tagging probe in the second probe set.

6. The method according to claim 1, further ligating probes in each of the first and second probe sets after the hybridizing before the amplifying.

7. The method according to claim 1, wherein the amplifying comprises linear amplification.

8. The method according to claim 1, further immobilizing probe products to a well.

9. The method according to claim 1, wherein each of the first and second labeling probes and the first and second tagging probes independently comprises a naturally-occurring nucleotide sequence.

10. The method according to claim 1, wherein the amplifying and labeling comprise amplifying and labeling the first and second probe products with first and second labels by using labelled first and second primers.

11. The method according to claim 1, wherein the labeling further comprises labeling the first and second amplified probe products with first and second affinity tags.

12. The method according to claim 1, wherein the labeling further comprises labeling the first and second amplified probe products with third and fourth labels, respectively.

13. The method according to claim 1, wherein each of the circular molecules comprises a naturally-occurring oligonucleotide and a non-naturally occurring oligonucleotide.

14. The method according to claim 1, wherein the said at least parts of probes of the first and second labeled amplified probe products are covalently immobilized to the substrate via biotin-Strepatavidin.

15. A method of detecting nucleic acid copy numbers in a genetic sample obtained from a subject, comprising
   contacting first and second probe sets to the genetic sample, wherein the first probe set comprises a first labeling probe and a first tagging probe, and the second probe set comprises a second labeling probe and a second tagging probe;
   hybridizing at least parts of probes of the first and second probe sets to first and second nucleic acid regions of interest in nucleotide molecules present in the genetic sample to produce first and second probe products, respectively, wherein the first and second probe products are circular molecules;
   amplifying the first and second probe products to form first and second amplified probe products;
   immobilizing at least parts of probes of the first and second amplified probe products to a substrate at a density in which the first and second probe products are optically resolvable after immobilization to produce first and second immobilized amplified probe products;
   labeling the first and second immobilized amplified probe products with first and second labels to produce first and second labeled amplified probe products; and
   detecting (i) a first number of the first labeled amplified probe products, and (ii) a second number of the second labeled amplified probe products to detect the nucleic acid copy numbers.

16. The method according to claim 15, wherein the first probe set further comprises a first gap probe, and the second probe set further comprises a second gap probe.

17. The method according to claim 16, wherein each of the first and second gap probes comprises an artificial nucleotide sequence.

18. The method according to claim 16, wherein
in the first probe set, the first gap probe, the first labeling probe, and the first tagging probe are adjacent to each other, and
in the second probe set, the second gap probe, the second labeling probe, and the second tagging probe are adjacent to each other.

19. The method according to claim 16, further comprising, after the hybridizing before the amplifying, (i) ligating the first gap probe, the first labeling probe, and the first tagging probe in the first probe set, and (ii) ligating the second gap probe, the second labeling probe, and the second tagging probe in the second probe set.

20. The method according to claim 15, further ligating probes in each of the first and second probe sets after the hybridizing before the amplifying.

21. The method according to claim 15, wherein the amplifying comprises linear amplification.

22. The method according to claim 15, further immobilizing probe products to a well.

23. The method according to claim 15, wherein each of the first and second labeling probes and the first and second tagging probes independently comprises a naturally-occurring nucleotide sequence.

24. The method according to claim 15, wherein the amplifying and labeling comprise amplifying and labeling the first and second probe products with first and second labels by using labelled first and second primers.

25. The method according to claim 15, wherein the labeling further comprises labeling the first and second amplified probe products with first and second affinity tags.

26. The method according to claim 15, wherein the labeling further comprises labeling the first and second amplified probe products with third and fourth labels, respectively.

27. The method according to claim 15, wherein each of the circular molecules comprises a naturally-occurring oligonucleotide and a non-naturally occurring oligonucleotide.

28. The method according to claim 15, wherein the said at least parts of probes of the first and second labeled amplified probe products are covalently immobilized to the substrate via biotin-Strepatavidin.

* * * * *